United States Patent
Yamashita et al.

(10) Patent No.: US 10,723,742 B2
(45) Date of Patent: Jul. 28, 2020

(54) BIPHENYL COMPOUND OR SALT THEREOF

(71) Applicant: TAIHO PHARMACEUTICAL CO., LTD., Tokyo (JP)

(72) Inventors: Satoshi Yamashita, Tsukuba (JP); Takahiro Ogawa, Tsukuba (JP); Hideya Komatani, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 15/776,548

(22) PCT Filed: Nov. 25, 2016

(86) PCT No.: PCT/JP2016/085067
§ 371 (c)(1),
(2) Date: May 16, 2018

(87) PCT Pub. No.: WO2017/090756
PCT Pub. Date: Jun. 1, 2017

(65) Prior Publication Data
US 2018/0354960 A1 Dec. 13, 2018

(30) Foreign Application Priority Data

Nov. 27, 2015 (JP) .................... 2015-232009
Jun. 13, 2016 (JP) .................... 2016-117454

(51) Int. Cl.

| | | |
|---|---|---|
| C07D 487/10 | (2006.01) |
| C07D 405/10 | (2006.01) |
| C07D 471/08 | (2006.01) |
| C07D 211/58 | (2006.01) |
| C07D 207/14 | (2006.01) |
| C07D 207/04 | (2006.01) |
| C07D 487/08 | (2006.01) |
| C07D 471/10 | (2006.01) |
| C07D 451/04 | (2006.01) |
| C07D 451/00 | (2006.01) |
| C07D 417/10 | (2006.01) |
| C07D 413/10 | (2006.01) |
| C07D 403/10 | (2006.01) |
| C07D 401/10 | (2006.01) |
| A61P 35/00 | (2006.01) |
| A61K 31/538 | (2006.01) |
| A61K 31/4995 | (2006.01) |
| A61K 31/437 | (2006.01) |
| A61K 31/416 | (2006.01) |
| A61K 31/404 | (2006.01) |
| A61K 31/4184 | (2006.01) |
| A61K 31/40 | (2006.01) |
| A61K 31/407 | (2006.01) |
| A61K 31/4439 | (2006.01) |
| A61K 31/4196 | (2006.01) |
| A61K 31/445 | (2006.01) |
| A61K 31/428 | (2006.01) |
| A61K 31/439 | (2006.01) |

(Continued)

(52) U.S. Cl.
CPC ............ *C07D 487/10* (2013.01); *A61K 31/40* (2013.01); *A61K 31/404* (2013.01); *A61K 31/407* (2013.01); *A61K 31/416* (2013.01); *A61K 31/4184* (2013.01); *A61K 31/4196* (2013.01); *A61K 31/424* (2013.01); *A61K 31/428* (2013.01); *A61K 31/437* (2013.01); *A61K 31/438* (2013.01); *A61K 31/439* (2013.01); *A61K 31/445* (2013.01); *A61K 31/4439* (2013.01); *A61K 31/46* (2013.01); *A61K 31/4995* (2013.01); *A61K 31/538* (2013.01); *A61P 35/00* (2018.01); *C07D 207/04* (2013.01); *C07D 207/14* (2013.01); *C07D 211/58* (2013.01); *C07D 401/10* (2013.01); *C07D 403/10* (2013.01); *C07D 405/10* (2013.01); *C07D 413/10* (2013.01); *C07D 417/10* (2013.01); *C07D 451/00* (2013.01); *C07D 451/04* (2013.01); *C07D 471/08* (2013.01); *C07D 471/10* (2013.01); *C07D 487/08* (2013.01)

(58) Field of Classification Search
None
See application file for complete search history.

(56) References Cited

U.S. PATENT DOCUMENTS

2012/0142028 A1 6/2012 Richardson et al.
2012/0201832 A1 8/2012 Eckhardt et al.
(Continued)

FOREIGN PATENT DOCUMENTS

EP 3381896 A1 10/2018
JP 2012-506238 A 3/2012
(Continued)

OTHER PUBLICATIONS

Wu et al., "3-(Piperidin-4-ylmethoxy)pyridine Containing Compounds are Potent Inhibitors of lysine Specific Demethylase 1", Journal of Medicinal Chemistry, 2016, vol. 59, No. 1, pp. 253-263.
(Continued)

*Primary Examiner* — Alicia L Otton
(74) *Attorney, Agent, or Firm* — Rothwell, Figg, Ernst & Manbeck, P.C.

(57) ABSTRACT

A compound or a salt thereof represented by Formula (I). An LSD1 inhibitor containing the compound or a salt thereof as an active ingredient. A pharmaceutical composition containing the compound or salt thereof. An antitumor agent containing the compound or a salt thereof as an active ingredient.

10 Claims, No Drawings

(51) Int. Cl.
    *A61K 31/424*    (2006.01)
    *A61K 31/438*    (2006.01)
    *A61K 31/46*     (2006.01)

(56) References Cited

U.S. PATENT DOCUMENTS

| | | |
|---|---|---|
| 2013/0035377 A1 | 2/2013 | Minucci et al. |
| 2013/0231342 A1 | 9/2013 | Munoz et al. |
| 2016/0257662 A1 | 9/2016 | McCall et al. |

FOREIGN PATENT DOCUMENTS

| | | |
|---|---|---|
| JP | 2012-524280 A | 10/2012 |
| JP | 2013-525318 A | 6/2013 |
| JP | 2013-535460 A | 9/2013 |
| JP | 2016-531121 A | 10/2016 |
| WO | 2010077624 A1 | 7/2010 |
| WO | 2014151761 A1 | 9/2014 |
| WO | 2015089192 A1 | 6/2015 |
| WO | 2015103060 A1 | 7/2015 |
| WO | 2015168466 A1 | 11/2015 |
| WO | 2016/007727 A1 | 1/2016 |
| WO | 2016/029262 A1 | 3/2016 |
| WO | 2016/037005 A1 | 3/2016 |
| WO | 2017/013061 A1 | 1/2017 |
| WO | 2017/090756 A1 | 6/2017 |
| WO | 2018216795 A1 | 11/2018 |
| WO | 2018216800 A1 | 11/2018 |
| WO | 2018221555 A1 | 12/2018 |

OTHER PUBLICATIONS

Singh et al., "Inhibition of LSD1 sensitizes glioblastoma cells to histone deacetylase inhibitors", Neuro-Oncology, 2011, vol. 13, No. 8, pp. 894-903.
Fiskus et al., "Highly effective combination of LSD (KDM1A) antagonist and pan-histone deacetylase inhibitor against human AML cells", Leukemia, 2014, vol. 28, No. 11, pp. 2155-2164.
Rosenbaum, "A Novel Immunohistochemical and Molecular Marker for Neuroendocrine and Neuroepithelial Neoplasms", American Journal of Clinical Pathlogy, 2015, vol. 144, No. 4, pp. 579-591.
Takagi, "LSD1 Inhibitor T-3775440 Inhibits SCLC Cell Proliferation by Disrupting LSD1 Interactions with Snag Domain Proteins INSM1 and GFI1B", Cancer Research, 2017, vol. 77, No. 17, pp. 4652-4662.
Ye et al., "The LSD1 inhibitor INCB059872 is synergistic with ATRA in models of non-APL acute myelogenous eukemia", Cancer Research 71(14 Suppl), Abstract 4696, 2016, 4 pages.
Breslin et al., "Neuroendocrine differentiation factor, IA-1, is a trascriptional repressor and contains a specific DNA-binding domain: identification of consensus IA-1 binding sequence", Nucleic Acids Research, 2002, vol. 30, No. 4, pp. 1038-1045.

Lan et al., "Structure, expression, and biological function of INSM1 transcription factor in neuroendocrine differentiation", FASEB Journal, 2009, 23(7): 2024-2033 (Abstract).
Lin et al., "Requirement of the Histone Demethylase LSD1 in Snail-mediated Transcriptoinal Repression during Epithelial-Mesenchymal Transition", Oncogene, 2010, 29(35): 4896-4904.
Saleque et al., "Epigenetic Regulation of Hematopoietic Differentiation by Gfi-1 and Gfi-1 b is Mediated by the Cofactors CoREST and LSD1", Molecular Cell, 2007, 27, 562-572.
Welcker et al., "Insm1 controls development of pituitary endocrine cells and requires a SNAG domain for function and for recruitment of histone-modifying factors", Development, 2013, 140(24), 4947-4958.
Lan et al., "IA-1, a New Marker for Neuroendocrine Differentiation in Human Lung Cancer Cell Lines", Cancer Research, 1993, 53(18), 4169-4171.
Amente et al., "The histone LSD1 demethylase in stemness and cancer transcription programs", Biochimica et Biophysica Acta, 2013, vol. 1829, No. 10, pp. 981-986.
Maes et al., "KDM1 histone lysine demethylases as targets for treatments of oncological and neurodegenerative disease", Epigenomics, 2015, vol. 7, No. 4, pp. 609-626.
Harris et al., "The Histone Demethylase KDM1A Sustains the Oncogenic Potential of MLL-AF9 Leukemia Stem Cells", Cancer Cell, 2012, vol. 21, No. 4, pp. 473-487.
Mohammad et al., A DNA Hypomethylation Signature Predicts Antitumor Activity of LSD1 Inhibitors in SCLC, Cancer Cell, 2015, vol. 28, No. 1, pp. 57-69.
Hill et al., "Inhibition of LSD1 reduces herpesvirus infection, shedding, and recurrence by promoting epigenetic suppression of viral genomes", Science Translational Medicine, 2014, vol. 6, No. 265, 265ra169.
Shi et al., "Lysine-specific demethylase 1 is a therapeutic target for fetal hemoglobin induction", Nature Medicine, 2013, vol. 19, No. 3, pp. 291-294.
Kawagishi et al., "TPC-144, a novel reversible LSD1 inhibitor, exhibited strong antitumor activity in preclinical models of AML and SCLC", The European Journal of Cancer , 2016, vol. 68, Supplment 1, pp. S86-S987, 258.
International Search Report cited in PCT/JP206/085067 dated Jan. 31, 2017, 4 pages.
Crombie et al., "Synthesis and evaluation of azabicyclo [3.2. 1] octane derivatives as potent mixed vasopressin antagonists", Bioorganic & Medicinal Chemistry Letters, 20(12), 2010, pp. 3742-3745.
First Examination Report dated Jul. 29, 2019 for the corresponding IN patent application No. 201817022113, 6 pgs.
Maiques-Diaz et al., "LSD1: Biolojic roles and therapeutic targeting", Epigenobics, 2016, 8(8), pp. 1103-16.
Wang et al., "Identification of an INSMI-bindingsite in the insulinoter:negative regulation of the insulin gene scription", J. Endocrinol 2008, 198(1), pp. 29-39.
Official Action of the corresponding RU Patent Applincation No. 2019144056, Apr. 21, 2020, 14 pages.

BIPHENYL COMPOUND OR SALT THEREOF

CROSS-REFERENCE TO RELATED APPLICATIONS

The present application is a 35 U.S.C. 371 National Phase Entry Application from PCT/JP2016/085067, filed Nov. 25, 2016, which Claims priority to Japanese Patent Application No. 2015-232009 filed on Nov. 27, 2015, and Japanese Patent Application No. 2016-117454 filed on Jun. 13, 2016, which are incorporated herein by reference in their entirety.

TECHNICAL FIELD

Histone methylation modification is one of the epigenetic mechanisms, which regulate gene expressions. Histone methylation modification regulates various processes including cellular maintenance, growth, and differentiation.

LSD1 (KDM1A), one of the enzymes that regulate histone methylation modification, is an FAD (flavin adenine dinucleotide)-dependent histone demethylase, and mainly demethylates the lysine residue at position 4 (K4) and the lysine residue at position 9 (K9) on histone H3 (Non-patent Literature (NPL) 1). With such functions, LSD1 is believed to positively or negatively regulate various gene transcriptions, and regulate stem cell self-renewal and cell differentiation in each normal tissue.

In general, abnormalities in cell self-renewal capacity or differentiation are believed to lead to cell cancerization. Thus, aberrant control of LSD1, which plays a key role in these processes, can possibly cause cell cancerization. In fact, in terms of various solid and blood cancers, many reports have been made regarding the correlation of over-expression of LSD1 and their prognosis (NPL 2). Further, in cell lines from carcinomas or in non-clinical models, LSD1 inhibition has been reported to have resulted in induction of cellular differentiation, growth inhibition, and an in vivo antitumor effect (NPL 3 and NPL 4), which strongly suggests that LSD1 serves as one of the important target molecules in cancer therapy. These carcinomas in which LSD1 is involved, such as SCLC and AML, have an extremely short lifetime, and existing therapeutic methods cannot achieve a satisfactory therapeutic effect.

Accordingly, LSD1 inhibitory drugs are expected to provide effective therapeutic means based on novel mechanisms to treat intractable cancers, for which no therapeutic methods currently exist.

Further, according to some reports, LSD1, which is involved in neuron programs and functions, can also possibly serve as a target in the treatment of diseases other than cancers, such as Alzheimer's disease, Huntington's disease, Rett syndrome, and other cranial nerve diseases (NPL 2); Herpesvirus infections, in which LSD1 function has been implicated (NPL 5); and sickle cell diseases (NPL 6).

Therefore, an object of the present invention is to provide a useful novel compound that exhibits selective and strong inhibitory activity for LSD1, and that is used for the treatment of cancers and other LSD1-related diseases.

CITATION LIST

Patent Literature

PTL 1: WO 2015/089192
PTL 2: WO 2015/168466
PTL 3: WO 2015/103060
PTL 4: WO 2010/077624

Non-Patent Literature

NPL 1: Biochim. Biophys. Acta, 1829 (10), pp. 981-986 (2013)
NPL 2: Epigenomics, 7 (4), pp. 609-626 (2015)
NPL 3: Cancer Cell, 21 (4), pp. 473-487 (2012)
NPL 4: Cancer Cell, 28 (1), pp. 57-69 (2015)
NPL 5: Sci. Transl. Med., 6 (265), 265ra169 (2014)
NPL 6: Nat. Med., 19 (3), pp. 291-294 (2013)

SUMMARY OF INVENTION

Technical Problem

The compound of the present invention is a novel biphenyl compound having excellent LSD1 inhibitory activity. More specifically, as shown in Formula (I), the compound of the present invention is a novel biphenyl compound comprising
(i) a benzene ring having an amide or thioamide group formed together with cyclic amino,
(ii) the benzene ring having, at the meta position relative to the amide or thioamide group, a benzene ring having 4-nitro or 4-cyano,
(iii) the benzene ring further having, at the para-position relative to the amide or thioamide group, an unsaturated hydrocarbon ring or an unsaturated heterocyclic ring.

PTL 1 and PTL 2 disclose a substituted heterocyclic compound as a compound having LSD1 inhibitory activity. Specifically, PTL 1 and PTL 2 disclose, for example, a cyanobenzene-containing pyrimidine compound, a cyanobenzene-containing pyrazole compound, or a 6-oxo-1,6-dihydro-pyrimidine compound containing cyanobenzene etc. However, all of these compounds are clearly different from the compound of the present invention because the compound of the present invention contains a phenyl ring having an amide or thioamide group formed together with cyclic amino, whereas the compounds of PTL 1 and PTL 2 contain a pyrimidine ring, a pyrazole ring, 6-oxo-1,6-dihydro-pyrimidine, or the like. As shown below in the Comparative Examples, neither compounds in which the benzene ring of the compound of the present invention is replaced with a pyrimidine ring or a pyrazole ring (Comparative Examples 1, 2, and 3), nor a compound that does not have an amide or thioamide group formed together with cyclic amino (Comparative Example 1), showed LSD1 inhibitory activity. Even when a phenyl compound had an amide or thioamide group formed together with cyclic amino, the compound, if not having an unsaturated hydrocarbon ring or an unsaturated heterocyclic ring at the para position relative to the amide or thioamide group (Comparative Example 4), also did not show LSD1 inhibitory activity.

Additionally, for example, PTL 3 also discloses a compound in which the phenyl moiety of the compound of the present invention is a 5-membered heterocyclic ring; however, PTL 3 nowhere discloses LSD1 inhibitory activity, and such a compound of PTL 3 does not have LSD1 inhibitory activity, as stated above with reference to the Comparative Examples. Further, the compound specifically disclosed in this international publication, i.e., a compound in which the 4-nitro- or 4-cyano-containing benzene ring of the compound of the present invention is replaced with a 4-trifluoromethyl-containing benzene ring, did not have LSD1 inhibitory activity, as shown below in Comparative Example 5.

Further, for example, PTL 4 discloses a phenyl ring having an amide group formed when cyclic amino and carbonyl are taken together; however, PTL 4 nowhere discloses LSD1 inhibitory activity. Further, the compound of PTL 4 is clearly different from the compound of the present invention, since the moiety corresponding to R3 in Formula (I) is a heterocyclic ring bonded directly or via a linker to cyclic amino. As shown later in the Comparative Examples, a compound in which a heterocyclic ring is bonded to cyclic amino (Comparative Example 6) did not show LSD1 inhibitory activity.

Solution to Problem

To solve the above problems, the present inventors conducted extensive research, and found that the biphenyl compound according to the present invention has excellent LSD1 inhibitory activity and cancer-cell-growth inhibitory activity, has low toxicity, and is useful as an orally administrable pharmaceutical preparation for treating cancers. The present invention has thus been accomplished.

More specifically, the present invention provides the following:

Item 1. A compound represented by Formula (I) or a salt thereof:

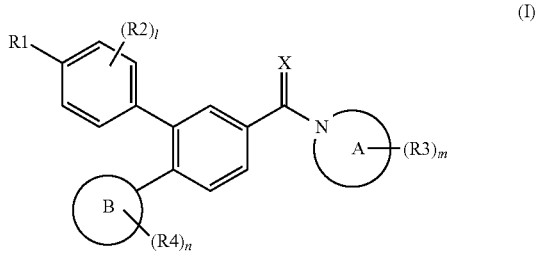

wherein
ring A represents a monocyclic, bridged cyclic, or spirocyclic nitrogen-containing saturated heterocyclic group,
ring B represents monocyclic or bicyclic unsaturated hydrocarbon or a monocyclic or bicyclic unsaturated heterocyclic group that may be substituted with oxo,
X represents O or S,
R1 represents nitro or cyano,
R2 represents halogen,
R3 represents substituted or unsubstituted amino, C1-C6 alkyl, halogen, cyano, oxo, hydroxy, carbamoyl, sulfo, C1-C6 alkoxy, or amino (C1-C6 alkyl),
R4 represents halogen, hydroxy, nitro, cyano, amino, carboxy, (C2-C7 acyl)amino, (C2-C7 acyl)oxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, substituted or unsubstituted carbamoyl, substituted or unsubstituted C2-C6 alkynyl, substituted or unsubstituted (C1-C6 alkyl)carbonyl, substituted or unsubstituted 4- to 14-membered nitrogen-containing saturated heterocyclic group, or substituted or unsubstituted C6-C14 aromatic hydrocarbon,
l is an integer of 0 to 2,
m is an integer of 0 to 2, and
n is an integer of 0 to 5,
wherein when l is 2, two R2s may be identical or different, when m is 2, two R3s may be identical or different, and when n is 2 to 5, two to five R4s may be identical or different.

Item 2. The compound or a salt thereof according to Item 1, which satisfies the following conditions in Formula (I):
ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms,
ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen,
R3 represents amino, mono- or di(C1-C6 alkyl)amino, (C3-C7 cycloalkyl)amino, or C1-C6 alkyl, and
R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl,
wherein when at least one R4 represents substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl)oxy, amino that may be substituted with C1-C6 alkyl or C2-C7 acyl, C3-C7 cycloalkyl that may be substituted with hydroxy, or (C1-C6 alkoxy)(C1-C6 alkyl), and when two or more of the substituents are present, the substituents may be identical or different.

Item 3. The compound or a salt thereof according to Item 1 or 2, which satisfies the following conditions in Formula (I):
ring A represents pyrrolidinyl, piperidinyl, piperazinyl, azepanyl, diazepanyl,

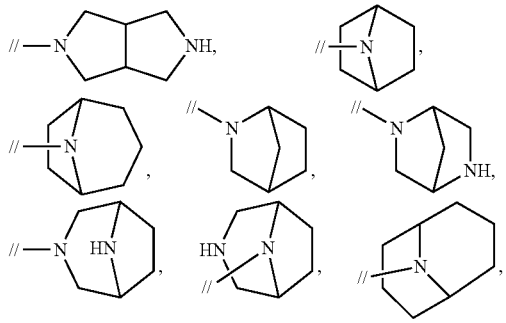

2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[4.5]decanyl, or 9-oxa-diazaspiro[3.5]nonanyl, and
R3 represents amino, methylamino, ethylamino, isopropylamino, dimethylamino, cyclobutylamino, or methyl, wherein when two or more R3s are present, R3s may be identical or different.

Item 4. The compound or a salt thereof according to any one of Items 1 to 3, which satisfies the following conditions in Formula (I):

R4 represents halogen, nitro, cyano, carboxy, C1-C8 alkyl that may be substituted with halogen, amino, hydroxy, carboxy, carbamoyl, (C1-C6 alkyl) carbamoyl, (C1-C6 alkyl)carbonylamino, C1-C6 alkoxy, (C1-C6 alkyl)carbonyl, C3-C7 cycloalkyl, hydroxy(C3-C7 cycloalkyl), or (C1-C6 alkyl)carbonyloxy, C2-C6 alkenyl, C1-C6 alkoxy that may be substituted with hydroxy or monocyclic 5- to 10-membered unsaturated hydrocarbon, C3-C7 cycloalkyl that may be substituted with hydroxy, hydroxy (C1-C4 alkyl), (C1-C4 alkoxy) (C1-C4 alkyl), hydroxy (C3-C7 cycloalkyl), or (C6-C14 aromatic hydrocarbon)-substituted carbamoyl, mono- or di(C1-C6 alkyl)amino, or carbamoyl that may be substituted with C1-C6 alkyl, wherein when two or more R4s are present, R4s may be identical or different.

Item 5. The compound represented by Formula (I) or a salt thereof according to any one of Items 1 to 4, wherein
ring A represents pyrrolidinyl, piperidinyl, piperazinyl, azepanyl, diazepanyl,

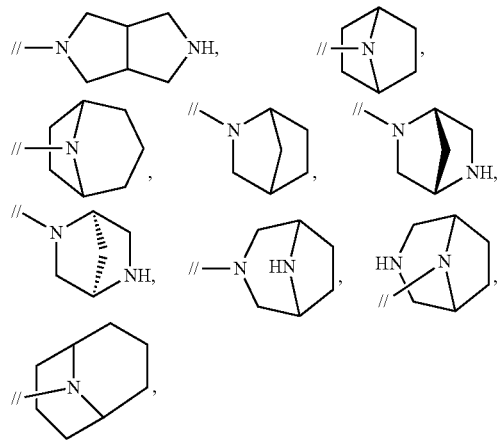

2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[4.5]decanyl, or 9-oxa-diazaspiro[3.5]nonanyl,
ring B represents phenyl, naphthyl, pyridyl, pyrazolopyridyl, pyrazolopyrimidinyl, indolyl, indolinyl, 2-oxo-indolinyl, indazolyl, benzoimidazolyl, benzoisoxazolyl, benzothiazolyl, benzotriazolyl, imidazopyridinyl, quinolinyl, isoquinolinyl, quinazolinyl, quinoxalinyl, phthalazinyl, 2-oxo-2,3-dihydrobenzo[d]oxazolyl, 1,3-dihydroisobenzofuranyl, dihydrobenzooxazinyl, benzodioxolyl, dihydrobenzodioxynyl, or 2-oxo-2,3-dihydrobenzo[d]thiazolyl,
X represents O or S,
R1 represents nitro or cyano,
R2 represents fluorine, and is present at the ortho position relative to R1 on the phenyl,
R3 represents amino, methylamino, ethylamino, isopropylamino, dimethylamino, cyclobutylamino, or methyl, wherein when two or more R3s are present, R3s may be identical or different, and
R4 represents fluorine, chlorine, bromine, iodine, nitro, cyano, carboxy, methyl, ethyl, n-propyl, isopropyl, tert-butyl, difluoromethyl, trifluoromethyl, fluoroethyl, aminoethyl, hydroxymethyl, hydroxyethyl, hydroxypropyl, hydroxydimethylethyl, hydroxymethylpropyl, hydroxymethylbutyl, hydroxyethylbutyl, carboxymethyl, carbamoylmethyl, methylcarbamoylmethyl, dimethylcarbamoylmethyl, acetylaminoethyl, methoxyethyl, hydroxycyclopropylmethyl, hydroxycyclopropylethyl, hydroxycyclobutylmethyl, methylcarbonyloxyethyl, isobutenyl, methoxy, hydroxypropoxy, cyclopropyl, hydroxymethyl cyclopropyl, methoxymethyl cyclopropyl, hydroxycyclopropyl cyclopropyl, phenylcarbamoyl cyclopropyl, benzyloxy, dimethylamino, carbamoyl, methylcarbamoyl, or dimethylcarbamoyl, wherein when two or more R4s are present, R4s may be identical or different, and
n is an integer of 0 to 3, wherein when n is 2 to 3, two to three R4s may be identical or different.

Item 6. Compounds according to any one of the following (1) to (24) or a salt of the compounds according to any one of the following (1) to (24);
(1) 4-[5-[(3-exo)-3-amino-8-azabicyclo[3.2.1]octane-8-carbonyl]-2-[2-fluoro-4-(2-hydroxy-2-methyl-propyl)phenyl]phenyl]-2-fluoro-benzonitrile,
(2) 4-[5-[(3S)-3-aminopyrrolidine-1-carbonyl]-2-[2-fluoro-4-(2-hydroxy-2-methyl-propyl)phenyl]phenyl]-2-fluoro-benzonitrile,
(3) 4-[5-[(3-endo)-3-amino-8-azabicyclo[3.2.1]octane-8-carbonyl]-2-[2-fluoro-4-(2-hydroxy-2-methyl-propyl) phenyl]phenyl]-2-fluoro-benzonitrile,
(4) (S)-5'-(3-aminopyrrolidine-1-carbonyl)-3-fluoro-2'-(6-fluoro-1-(2-hydroxy-2-methylpropyl)-1H-indol-5-yl)-[1,1'-biphenyl]-4-carbonitrile,
(5) 5'-((3-endo)-3-amino-8-azabicyclo[3.2.1]octane-8-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile,
(6) 5'-((1S,2S,4R)-rel-2-amino-7-azabicyclo[2.2.1]heptane-7-carbonyl)-2'',3-difluoro-4''-(2-hydroxy-2-methylpropyl)-[1,1':2',1''-terphenyl]-4-carbonitrile-isomer-B,
(7) 5'-((1S,2S,4R)-rel-2-amino-7-azabicyclo[2.2.1]heptane-7-carbonyl)-2'-(6,7-difluoro-1-methyl-1H-benzo[d][1,2,3]triazol-5-yl)-3-fluoro-[1,1'-biphenyl]-4-carbonitrile-isomer-B,
(8) 5'-((1S,2S,4R)-rel-2-amino-7-azabicyclo[2.2.1]heptane-7-carbonyl)-3-fluoro-2'-(6-fluoro-1-(2-hydroxy-2-methylpropyl)-1H-indazol-5-yl)-[1,1'-biphenyl]-4-carbonitrile-isomer-B,
(9) 5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-B,
(10) 5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile,
(11) 5'-((1S,2S,4R)-rel-2-amino-7-azabicyclo[2.2.1]heptane-7-carbonyl)-2'-(7-chloro-6-fluoro-1-(2-hydroxy-2-methylpropyl)-1H-benzo[d][1,2,3]triazol-5-yl)-3-fluoro-[1,1'-biphenyl]-4-carbonitrile-isomer-X,
(12) 5'-((1S,2S,4R)-rel-2-amino-7-azabicyclo[2.2.1]heptane-7-carbonyl)-2'-(7-chloro-6-fluoro-1-(2-hydroxy-2-methylpropyl)-1H-benzo[d][1,2,3]triazol-5-yl)-3-fluoro-[1,1'-biphenyl]-4-carbonitrile,
(13) 5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile-isomer-X,
(14) 5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile,

(15) (S)-5'-(3-aminopyrrolidine-1-carbonyl)-3-fluoro-2'-(5-fluoro-3-(2-hydroxy-2-methylpropyl)benzo[d]isoxazol-6-yl)-[1,1'-biphenyl]-4-carbonitrile,
(16) 5'-((1S,2S,4R)-rel-2-amino-7-azabicyclo[2.2.1]heptane-7-carbonyl)-2'-(7-(difluoromethyl)-6-fluoro-1-(2-hydroxy-2-methylpropyl)-1H-benzo[d][1,2,3]triazol-5-yl)-3-fluoro-[1,1'-biphenyl]-4-carbonitrile-isomer-X,
(17) 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-(2-hydroxy-2-methylpropyl)-1H-benzo[d][1,2,3]triazole-7-carbonitrile-isomer-X,
(18) 5'-((1S,2S,4R)-rel-2-amino-7-azabicyclo[2.2.1]heptane-7-carbonyl)-2'-(7-(difluoromethyl)-6-fluoro-1-(2-hydroxy-2-methylpropyl)-1H-benzo[d][1,2,3]triazol-5-yl)-3-fluoro-[1,1'-biphenyl]-4-carbonitrile,
(19) 5'-((3-endo)-3-amino-8-azabicyclo[3.2.1]octane-8-carbonyl)-2'-(7-chloro-6-fluoro-1-((1-hydroxycyclobutyl)methyl)-1H-benzo[d][1,2,3]triazol-5-yl)-3-fluoro-[1,1'-biphenyl]-4-carbonitrile,
(20) 5'-((3-endo)-3-amino-8-azabicyclo[3.2.1]octane-8-carbonyl)-2'-(7-(difluoromethyl)-6-fluoro-1-((1-hydroxycyclobutyl)methyl)-1H-benzo[d][1,2,3]triazol-5-yl)-3-fluoro-[1,1'-biphenyl]-4-carbonitrile,
(21) 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-((1-hydroxycyclobutyl)methyl)-1H-benzo[d][1,2,3]triazole-7-carbonitrile-isomer-X,
(22) 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-((1-hydroxycyclobutyl)methyl)-1H-benzo[d][1,2,3]triazole-7-carbonitrile,
(23) 5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile-isomer-X,
(24) 5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile.

Item 7. An LSD1 inhibitor comprising the compound or a salt thereof according to any one of Items 1 to 6, as an active ingredient.

Item 8. A pharmaceutical composition comprising the compound or a salt thereof according to any one of Items 1 to 6.

Item 9. The pharmaceutical composition according to Item 8, which is an orally administered composition.

Item 10. An antitumor agent comprising the compound or a salt thereof according to any one of Items 1 to 6, as an active ingredient.

Item 11. A method for treating a cancer patient, the method comprising administering an effective amount of the compound or a salt thereof according to any one of items 1 to 6 to the patient.

Item 12. The compound or a salt thereof according to any one of Items 1 to 6, for use in the treatment of a cancer patient.

Item 13. Use of the compound or a salt thereof according to any one of Items 1 to 6 in the manufacture of an antitumor agent.

Advantageous Effects of Invention

The present invention provides a novel compound represented by Formula (I) above or a salt thereof, both of which are useful as an LSD1 inhibitor.

It has been revealed that the compound of the present invention or a salt thereof has excellent LSD1 inhibitory activity and a cancer cell growth inhibitory effect, has low toxicity, and is orally administrable. Therefore, the compound of the present invention or a salt thereof is useful as an agent for preventing and/or treating cancer.

DESCRIPTION OF EMBODIMENTS

The compound represented by Formula (I) of the present invention is a novel biphenyl compound comprising (i) a benzene ring having an amide or thioamide group formed together with cyclic amino, (ii) the benzene ring having, at the meta position relative to the amide or thioamide group, a benzene ring having 4-nitro or 4-cyano, (iii) the benzene ring further having, at the para position relative to the amide or thioamide group, an unsaturated hydrocarbon ring or an unsaturated heterocyclic ring.

In the present specification, unless otherwise specified, examples of the "substituent" include halogen, hydroxy, cyano, nitro, alkyl, hydroxyalkyl, halogenoalkyl, cycloalkyl, hydroxycycloalkyl, cycloalkyl-alkyl, aralkyl, alkenyl, alkynyl, alkoxy, halogenoalkoxy, cycloalkoxy, cycloalkyl-alkoxy, unsaturated hydrocarbon ring-alkoxy, alkylthio, cycloalkyl-alkylthio, amino, mono- or di-alkylamino, cycloalkylamino, cycloalkyl-alkylamino, acyl, acyloxy, oxo, carboxy, alkoxycarbonyl, aralkyloxycarbonyl, carbamoyl that may be substituted with an unsaturated hydrocarbon ring, saturated or unsaturated heterocyclic group, unsaturated hydrocarbon ring (e.g., aromatic hydrocarbon), saturated heterocyclic oxy, and the like. The number of the substituents, when present, is typically one, two, or three.

In the present specification, examples of the "halogen" include fluorine, chlorine, bromine, iodine, and the like, with fluorine, chlorine, bromine, or iodine being preferable, and fluorine or chlorine being more preferable.

In the present specification, the "alkyl" may be straight or branched. Examples include C1-C6 alkyl, such as methyl, ethyl, n-propyl, isopropyl, n-butyl, isobutyl, sec-butyl, tert-butyl, n-pentyl, isopentyl, tert-pentyl, and n-hexyl.

In the present specification, examples of the "hydroxyalkyl" include the above-listed alkyl groups that have at least one hydroxy group (e.g., one or two hydroxy groups). Specific examples include hydroxymethyl, 2-hydroxyethyl, 1-hydroxyethyl, 3-hydroxypropyl, 2-hydroxypropyl, 1-methyl-2-hydroxyethyl, 4-hydroxybutyl, isobutyl, 2,2-dimethyl-2-hydroxyethyl, 5-hydroxypentyl, 3,3-dimethyl-3-hydroxypropyl, 6-hydroxyhexyl, dihydroxymethyl, 1,2-dihydroxyethyl, 2,3-dihydroxypropyl, 3,4-dihydroxybutyl, 4,5-dihydroxypentyl, 5,6-dihydroxyhexyl, and the like, with hydroxyalkyl having one hydroxy group being preferable.

In the present specification, the "halogenoalkyl" is straight or branched C1-C6 alkyl having 1 to 13 halogen atoms (halogeno C1-C6 alkyl). Examples include halogeno C1-C6 alkyl, such as fluoromethyl, difluoromethyl, trifluoromethyl, trichloromethyl, fluoroethyl, 1,1,1-trifluoroethyl, monofluoro-n-propyl, perfluoro-n-propyl, and perfluoroisopropyl, with halogeno C1-C4 alkyl being preferable, and halogeno C1-C4 alkyl having 1 to 7 halogen atoms being more preferable.

In the present specification, specific examples of the "cycloalkyl" include C3-C7 cycloalkyl, such as cyclopropyl, cyclobutyl, cyclopentyl, cyclohexyl, and cycloheptyl.

In the present specification, examples of the "hydroxycycloalkyl" include the above-listed C3-C7 cycloalkyl groups that have at least one hydroxy group (e.g., one or two hydroxy groups). Specific examples include 1-hydroxycyclopropyl, 2-hydroxycyclopropyl, 1-hydroxycyclobutyl, 3-hydroxycyclobutyl, 1-hydroxycyclopentyl, 3,4-dihydroxycyclopentyl, 1-hydroxycyclohexyl, 4-hydroxycyclohexyl, 1-hydroxycycloheptyl, and the like, with hydroxycycloalkyl having one hydroxy group being preferable.

In the present specification, examples of the "cycloalkylalkyl" include C3-C7 cycloalkyl substituted C1-C4 alkyl, such as cyclopropylmethyl, cyclobutylmethyl, cyclopentylmethyl, cyclohexylmethyl, and cycloheptylmethyl.

In the present specification, examples of the "aralkyl" include C7-C13 aralkyl, such as benzyl, phenethyl, naphthylmethyl, and fluorenylmethyl.

In the present specification, the "alkenyl" may be straight, branched, or cyclic, and refers to unsaturated hydrocarbon having at least one double bond (e.g., one or two double bonds). Examples include C2-C6 alkenyl, such as vinyl, allyl, 1-propenyl, 2-methyl-2-propenyl, isopropenyl, 1-butenyl, 2-butenyl, 3-butenyl, isobutenyl, 2-pentenyl, 3-pentenyl, 4-pentenyl, 2-methyl-2-butenyl, 3-methyl-2-butenyl, 5-hexenyl, 1-cyclopentenyl, 1-cyclohexenyl, and 3-methyl-3-butenyl.

In the present specification, the "alkynyl" may be straight, branched, or cyclic, and refers to unsaturated hydrocarbon having at least one triple bond (e.g., one or two triple bonds). Examples include C2-C6 alkynyl, such as ethynyl, 1-propynyl, 2-propynyl, 1-butynyl, 2-butynyl, 3-butynyl, and 1-methyl-2-propynyl.

In the present specification, the "alkoxy" may be straight or branched. Examples include C1-C6 alkoxy, such as methoxy, ethoxy, n-propoxy, isopropoxy, n-butoxy, isobutoxy, sec-butoxy, tert-butoxy, pentyloxy, isopentyloxy, and hexyloxy.

In the present specification, the "halogenoalkoxy" refers to straight or branched C1-C6 alkoxy having 1 to 13 halogen atoms (halogeno C1-C6 alkoxy). Examples include halogeno C1-C6 alkoxy, such as fluoromethoxy, difluoromethoxy, trifluoromethoxy, trichloromethoxy, fluoroethoxy, 1,1,1-trifluoroethoxy, monofluoro-n-propoxy, perfluoro-n-propoxy, and perfluoro-isopropoxy, with halogeno C1-C4 alkoxy being preferable, and halogeno C1-C4 alkoxy having 1 to 7 halogen atoms being more preferable.

In the present specification, examples of the "cycloalkoxy" include C3-C7 cycloalkoxy, such as cyclopropoxy, cyclobutoxy, cyclopentyloxy, cyclohexyloxy, and cycloheptyloxy.

In the present specification, examples of the "cycloalkylalkoxy" include C3-C7 cycloalkyl substituted C1-C4 alkoxy, such as cyclopropylmethoxy, cyclobutylmethoxy, cyclopentylmethoxy, cyclohexylmethoxy, and cycloheptylmethoxy.

In the present specification, the "alkylthio" may be straight or branched. Examples include C1-C6 alkylthio, such as methylthio, ethylthio, n-propylthio, isopropylthio, n-butylthio, isobutylthio, tert-butylthio, n-pentylthio, isopentylthio, and hexylthio.

In the present specification, examples of the "cycloalkylalkylthio" include C3-C7 cycloalkyl-substituted C1-C4 alkylthio, such as cyclopropylmethylthio, cyclobutylmethylthio, cyclopentylmethylthio, cyclohexylmethylthio, and cycloheptylmethylthio.

In the present specification, examples of the "monoalkylamino" include amino monosubstituted with straight or branched C1-6 alkyl, such as methylamino, ethylamino, n-propylamino, isopropylamino, n-butylamino, isobutylamino, tert-butylamino, n-pentylamino, isopentylamino, and hexylamino.

In the present specification, examples of the "dialkylamino" include amino disubstituted with the same or different straight or branched C1-C6 alkyl groups, such as dimethylamino, diethylamino, di(n-propyl)amino, diisopropylamino, di(n-butyl)amino, diisobutylamino, di(tert-butyl)amino, di(n-pentyl)amino, diisopentylamino, dihexylamino, methylethylamino, and methylisopropylamino.

In the present specification, examples of the "cycloalkylamino" include amino having one or two cycloalkyl groups mentioned above. Specific examples include N-cyclopropylamino, N,N-dicyclopropylamino, N-cyclobutylamino, N-cyclopentylamino, N-cyclohexylamino, N-cycloheptylamino, and the like.

In the present specification, examples of the "cycloalkylalkylamino" include C3-C7 cycloalkyl-substituted C1-C4 alkylamino, such as cyclopropylmethylamino, cyclobutylmethylamino, cyclopentylmethylamino, cyclohexylmethylamino, and cycloheptylmethylamino.

In the present specification, the "acyl" refers to alkylcarbonyl or arylcarbonyl.

In the present specification, examples of the "alkylcarbonyl" include straight or branched (C1-C6 alkyl)carbonyl, such as methylcarbonyl, ethylcarbonyl, n-propylcarbonyl, isopropylcarbonyl, n-butylcarbonyl, isobutylcarbonyl, tert-butylcarbonyl, n-pentylcarbonyl, isopentylcarbonyl, and hexylcarbonyl.

In the present specification, examples of the "arylcarbonyl" include (C6-C13 aryl)carbonyl, such as phenylcarbonyl, naphthylcarbonyl, fluorenylcarbonyl, anthrylcarbonyl, biphenylylcarbonyl, tetrahydronaphthylcarbonyl, chromanylcarbonyl, 2,3-dihydro-1,4-dioxanaphthalenylcarbonyl, indanylcarbonyl, and phenanthrylcarbonyl.

In the present specification, the "acylamino" refers to alkylcarbonylamino or arylcarbonylamino.

In the present specification, examples of the "alkylcarbonylamino" include straight or branched (C1-C6 alkyl)carbonylamino, such as methylcarbonylamino, ethylcarbonylamino, n-propylcarbonylamino, isopropylcarbonylamino, n-butylcarbonylamino, isobutylcarbonylamino, tert-butylcarbonylamino, n-pentylcarbonylamino, isopentylcarbonylamino, and hexylcarbonylamino.

In the present specification, examples of the "arylcarbonylamino" include (C6-C13 aryl)carbonylamino, such as phenylcarbonylamino, naphthylcarbonylamino, fluorenylcarbonylamino, anthrylcarbonylamino, biphenylylcarbonylamino, tetrahydronaphthylcarbonylamino, chromanylcarbonylamino, 2,3-dihydro-1,4-dioxanaphthalenylcarbonylamino, indanylcarbonylamino, and phenanthrylcarbonylamino.

In the present specification, the "acyloxy" refers to alkylcarbonyloxy or arylcarbonyloxy.

In the present specification, examples of the "alkylcarbonyloxy" include straight or branched (C1-C6 alkyl)carbonyloxy, such as methylcarbonyloxy, ethylcarbonyloxy, n-propylcarbonyloxy, isopropylcarbonyloxy, n-butylcarbonyloxy, isobutylcarbonyloxy, tert-butylcarbonyloxy, n-pentylcarbonyloxy, isopentylcarbonyloxy, and hexylcarbonyloxy.

In the present specification, examples of the "arylcarbonyloxy" include (C6-C13 aryl)carbonyloxy, such as phenylcarbonyloxy, naphthylcarbonyloxy, fluorenylcarbonyloxy, anthrylcarbonyloxy, biphenylylcarbonyloxy, tetrahydronaphthylcarbonyloxy, chromanylcarbonyloxy, 2,3-dihydro-1,4-dioxanaphthalenylcarbonyloxy, indanylcarbonyloxy, and phenanthrylcarbonyloxy.

In the present specification, the "alkoxycarbonyl" may be straight or branched. Examples include (C1-C6 alkoxy) carbonyl, such as methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, isopentyloxycarbonyl, and hexyloxycarbonyl.

In the present specification, examples of the "aralkyloxycarbonyl" include (C7-C13 aralkyl)oxycarbonyl, such as benzyloxycarbonyl, phenethyloxycarbonyl, naphthylmethyloxycarbonyl, and fluorenylmethyloxycarbonyl.

In the present specification, the "saturated heterocyclic group" refers to a monocyclic or polycyclic saturated heterocyclic group having one or more (preferably 1 to 3) heteroatoms selected from nitrogen, oxygen, and sulfur. Specific examples include morpholinyl, pyrrolidinyl, piperidinyl, piperazinyl, azepanyl, diazepanyl, tetrahydrofuranyl, tetrahydropyranyl, tetrahydrothiophenyl, thiazolidinyl, oxazolidinyl, and the like.

In the present specification, the "unsaturated heterocyclic group" refers to a monocyclic or polycyclic, completely or partially unsaturated heterocyclic group having one or more (preferably 1 to 3) heteroatoms selected from nitrogen, oxygen, and sulfur. Specific examples include imidazolyl, thienyl, furyl, pyrrolyl, oxazolyl, isoxazolyl, triazolyl, isothiazolyl, thiadiazolyl, pyrazolyl, triazolyl, tetrazolyl, pyridyl, pyrazyl, pyrimidinyl, pyridazinyl, pyrazolopyridyl, pyrazolopyrimidinyl, indolyl, isoindolyl, indazolyl, triazolopyridyl, benzoimidazolyl, benzoxazolyl, benzoisoxazolyl, benzothiazolyl, benzothienyl, benzofuranyl, 1,3-dihydroisobenzofuranyl, purinyl, benzotriazolyl, imidazopyridinyl, quinolinyl, isoquinolinyl, quinazolinyl, quinoxalinyl, phthalazinyl, methylenedioxyphenyl, ethylenedioxyphenyl, dihydrobenzofuranyl, and the like.

In the present specification, examples of the "unsaturated hydrocarbon" include a monocyclic or polycyclic C5-14 hydrocarbon ring having at least one unsaturated bond (e.g., 1 to 8 unsaturated bonds), and the like. The "unsaturated hydrocarbon" is preferably aromatic hydrocarbon, or monocyclic or bicyclic 5- to 14-membered unsaturated hydrocarbon.

In the present specification, examples of the "aromatic hydrocarbon" include C6-C14 aromatic hydrocarbons, such as phenyl, naphthyl, anthracenyl, phenanthryl, fluorenyl, and tetrahydronaphthyl.

In the present specification, examples of the "monocyclic or bicyclic 5- to 14-membered unsaturated hydrocarbon" include cyclopentadienyl, phenyl, naphthyl, tetrahydronaphthyl, azulenyl, heptalenyl, and the like.

In the present specification, examples of the "monocyclic 5- to 10-membered unsaturated hydrocarbon" include cyclopentadienyl, phenyl, cyclooctatetraenyl, and the like.

In the present specification, the "saturated heterocyclic oxy" refers to saturated heterocyclic oxy having a heteroatom selected from nitrogen, oxygen, and sulfur. Specific examples include morpholinyloxy, 1-pyrrolidinyloxy, piperidinyloxy, piperazinyloxy, 4-methyl-1-piperazinyloxy, tetrahydrofuranyloxy, tetrahydropyranyloxy, tetrahydrothiophenyloxy, thiazolidinyloxy, and oxazolidinyloxy, with saturated heterocyclic oxy having 1 to 3 heteroatoms selected from nitrogen, oxygen, and sulfur being preferable.

In the present specification, the term "CA-CB" used in the description of a group indicates that the group has A- to B-number of carbon atoms. For example, "C1-C6 alkyl" refers to alkyl having 1 to 6 carbon atoms, and "C6-C14 aromatic hydrocarbon oxy" refers to oxy to which C6-C14 aromatic hydrocarbon is bonded. Further, the term "A- to B-membered" indicates that the number of atoms (number of ring members) that constitute a ring is A to B. For example, "4- to 10-membered nitrogen-containing saturated heterocyclic group" refers to a nitrogen-containing saturated heterocyclic group containing 4 to 10 ring members.

In the compound represented by Formula (I) of the present invention, ring A refers to a nitrogen-containing saturated heterocyclic group that may be crosslinked or spirocyclic. As shown in Formula (1) above, the nitrogen on ring A is bonded to carbonyl or carbothionyl.

Examples of the monocyclic nitrogen-containing saturated heterocyclic group in the "monocyclic, bridged cyclic, or spirocyclic nitrogen-containing saturated heterocyclic group" represented by ring A include monocyclic nitrogen-containing saturated heterocyclic groups, such as pyrrolidinyl, piperidinyl, piperazinyl, azepanyl, diazepanyl, and the like. The monocyclic nitrogen-containing saturated heterocyclic group is preferably a monocyclic nitrogen-containing saturated heterocyclic group having 1 to 3 nitrogen atoms, 0 to 1 sulfur atoms, and 0 to 2 oxygen atoms as heteroatoms, more preferably a monocyclic nitrogen-containing saturated heterocyclic group having 1 to 2 nitrogen atoms as heteroatoms, more preferably a monocyclic 4- to 10-membered nitrogen-containing saturated heterocyclic group having 1 to 2 nitrogen atoms as heteroatoms, more preferably pyrrolidinyl, piperidinyl, piperazinyl, azepanyl, or diazepanyl, still furthermore preferably pyrrolidinyl, piperidinyl, azepanyl, or diazepanyl, more preferably pyrrolidinyl or diazepanyl, and more preferably pyrrolidinyl.

Examples of the bridged cyclic nitrogen-containing saturated heterocyclic group in the "monocyclic, bridged cyclic, or spirocyclic nitrogen-containing saturated heterocyclic group" represented by ring A include

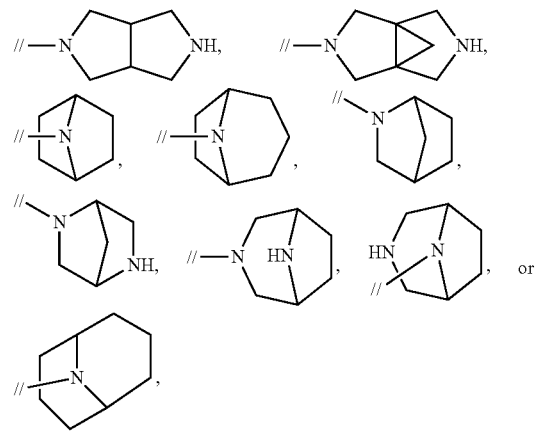

and the like. The bridged cyclic nitrogen-containing saturated heterocyclic group is preferably

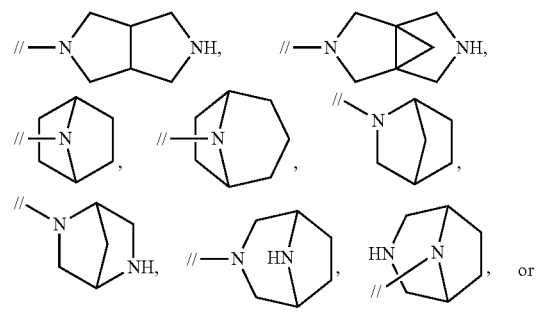

-continued

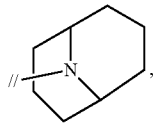

more preferably

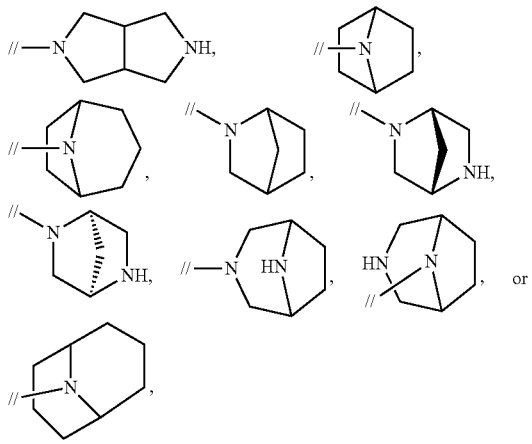

more preferably

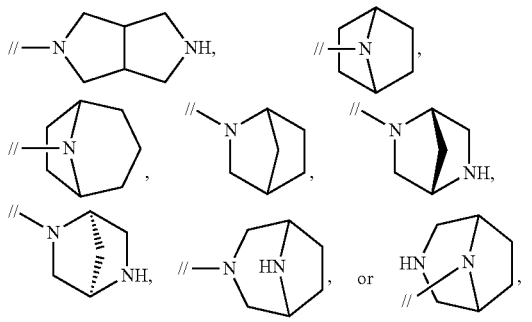

more preferably

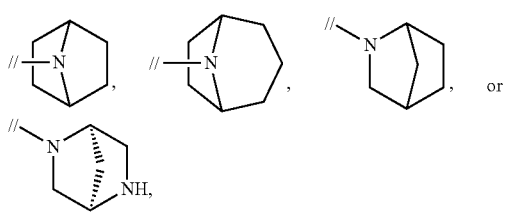

and more preferably

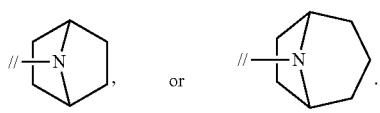

Examples of the spirocyclic nitrogen-containing saturated heterocyclic group in the "monocyclic, bridged cyclic, or spirocyclic nitrogen-containing saturated heterocyclic group" represented by ring A include spirocyclic groups having 0 to 2 oxygen atoms in which any two of 4- to 7-membered nitrogen-containing saturated heterocyclic groups are bonded to each other. The spirocyclic nitrogen-containing saturated heterocyclic group is preferably a 7- to 12-membered spirocyclic group having 2 nitrogen atoms and 0 to 1 oxygen atoms in which any two of 4- to 7-membered nitrogen-containing saturated heterocyclic groups are bonded to each other, more preferably diazaspiroheptanyl, diazaspirooctanyl, diazaspirononanyl, diazaspirodecanyl, diazaspiroundecanyl, oxadiazaspiroheptanyl, oxadiazaspirooctanyl, oxadiazaspirononanyl, oxadiazaspirodecanyl, or oxadiazaspiroundecanyl, more preferably diazaspirooctanyl, diazaspirononanyl, diazaspirodecanyl, or oxadiazaspirononanyl, more preferably 2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[3.5]decanyl, or 9-oxa-diazaspiro[3.5]nonanyl, more preferably 2,7-diazaspiro[3.4]octanyl, 3,7-diazaspiro[3.4]octanyl, 2,7-diazaspiro[3.5]nonanyl, 2,8-diazaspiro[3.5]nonanyl, or 9-oxa-diazaspiro[3.5]nonanyl, more preferably 2,7-diazaspiro[3.4]octanyl, 3,7-diazaspiro[3.4]octanyl, or 2,8-diazaspiro[3.5]nonanyl, and more preferably 2,8-diazaspiro[3.5]nonanyl.

The "monocyclic, bridged cyclic, or spirocyclic nitrogen-containing saturated heterocyclic group" represented by ring A is preferably a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms, more preferably a monocyclic 4- to 10-membered nitrogen-containing saturated heterocyclic group having 1 to 2 nitrogen atoms as heteroatoms, a bridged cyclic nitrogen-containing saturated heterocyclic group, such as

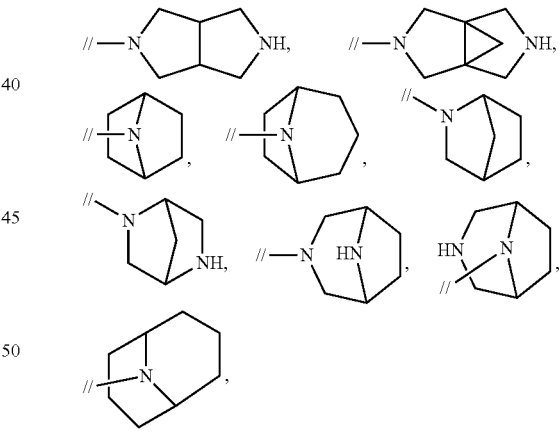

or a spirocyclic group having 0 to 2 oxygen atoms in which any two of 4- to 7-membered nitrogen-containing saturated heterocyclic groups are bonded to each other, more preferably a monocyclic 4- to 10-membered nitrogen-containing saturated heterocyclic group having 1 to 2 nitrogen atoms as heteroatoms, a bridged cyclic nitrogen-containing saturated heterocyclic group, such as

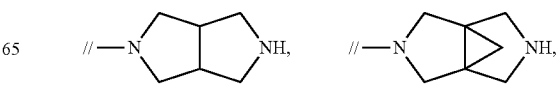

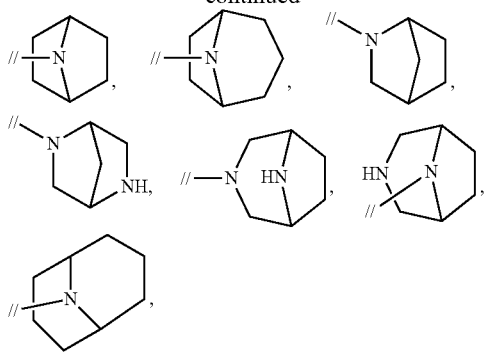

or a 7- to 12-membered spirocyclic group having 2 nitrogen atoms and 0 to 1 oxygen atoms in which any two of 4- to 7-membered nitrogen-containing saturated heterocyclic rings are bonded to each other, more preferably pyrrolidinyl, piperidinyl, piperazinyl, azepanyl, diazepanyl,

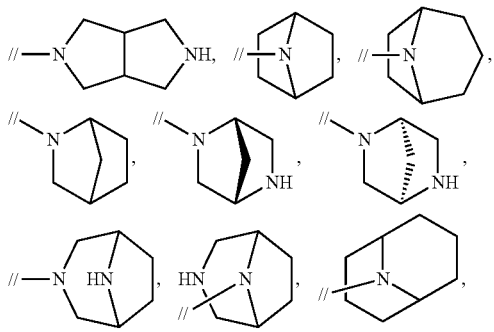

2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[4.5]decanyl, or 9-oxa-diazaspiro[3.5]nonanyl, more preferably pyrrolidinyl, piperidinyl, azepanyl, diazepanyl,

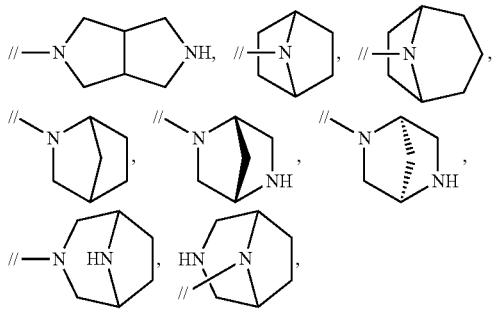

2,7-diazaspiro[3.4]octanyl, 3,7-diazaspiro[3.4]octanyl, 2,7-diazaspiro[3.5]nonanyl, 2,8-diazaspiro[3.5]nonanyl, or 9-oxa-diazaspiro[3.5]nonanyl, more preferably pyrrolidinyl,

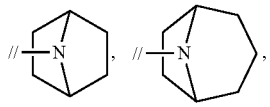

or 2,8-diazaspiro[3.5]nonanyl, more preferably pyrrolidinyl,

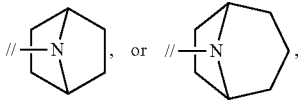

In the compound represented by Formula (I) of the present invention, ring B represents monocyclic or bicyclic unsaturated hydrocarbon, or a monocyclic or bicyclic unsaturated heterocyclic group.

The "monocyclic or bicyclic unsaturated hydrocarbon" represented by ring B is preferably monocyclic or bicyclic 5- to 14-membered unsaturated hydrocarbon, more preferably phenyl or naphthyl, and more preferably phenyl.

The "monocyclic or bicyclic unsaturated heterocyclic group" represented by ring B refers to a monocyclic or bicyclic, completely or partially unsaturated heterocyclic group having a heteroatom selected from nitrogen, oxygen, and sulfur, preferably a 5- to 14-membered unsaturated heterocyclic group having 0 to 4 nitrogen atoms, 0 to 2 sulfur atoms, and 0 to 3 oxygen atoms as heteroatoms and having at least one of nitrogen, sulfur, and oxygen, and more preferably imidazolyl, thienyl, furyl, pyrrolyl, oxazolyl, isoxazolyl, thiazolyl, isothiazolyl, thiadiazolyl, pyrazolyl, triazolyl, tetrazolyl, pyridyl, pyrazyl, pyrimidinyl, pyridazinyl, pyrazolopyridyl, pyrazolopyrimidinyl, indolyl, isoindolyl, indolinyl, indazolyl, triazolopyridyl, benzoimidazolyl, benzoxazolyl, benzoisoxazolyl, benzothiazolyl, benzotriazolyl, benzothienyl, benzofuranyl, purinyl, imidazopyridinyl, quinolinyl, isoquinolinyl, quinazolinyl, quinoxalinyl, phthalazinyl, methylenedioxyphenyl, ethylenedioxyphenyl, dihydrobenzofuranyl, 1,3-dihydroisobenzofuranyl, dihydrobenzoxazolyl (e.g., 2,3-dihydrobenzo[d]oxazolyl), dihydrobenzoxazinyl (e.g., 3,4-dihydro-2H-benzo[b][1,4]oxazinyl), benzodioxolyl (e.g., benzo[d][1,3]dioxolyl), dihydrobenzodioxynyl (e.g., 2,3-dihydrobenzo[b][1,4]dioxynyl), or dihydrobenzothiazolyl (e.g., 2,3-dihydrobenzo[d]thiazolyl), more preferably pyridyl, pyrazolopyridyl, pyrazolopyrimidinyl, indolyl, indolinyl, indazolyl, benzoimidazolyl, benzoisoxazolyl, benzothiazolyl, benzotriazolyl, imidazopyridinyl, quinolinyl, isoquinolinyl, quinoxalinyl, quinazolinyl, phthalazinyl, dihydrobenzoxazolyl, 1,3-dihydroisobenzofuranyl, dihydrobenzooxazinyl, benzodioxolyl, dihydrobenzodioxynyl, or dihydrobenzothiazolyl, more preferably pyridyl, pyrazolopyridyl, indolyl, indolinyl, indazolyl, benzoimidazolyl, benzoisoxazolyl, benzotriazolyl, quinolinyl, dihydrobenzoxazolyl, 1,3-dihydroisobenzofuranyl, dihydrobenzooxazinyl, or dihydrobenzothiazolyl, and more preferably indolyl, indazolyl, benzoisoxazolyl, or benzotriazolyl. The monocyclic or bicyclic unsaturated heterocyclic group represented by ring B may be substituted with oxo. Examples of the monocyclic or bicyclic unsaturated heterocyclic group that is substituted with oxo include 2-oxo-indolinyl,

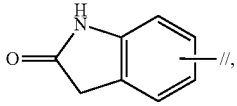

2-oxo-2,3-dihydrobenzo[d]oxazolyl,

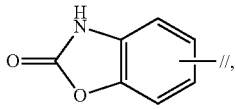

2-oxo-2,3-dihydrobenzo[d]thiazolyl,

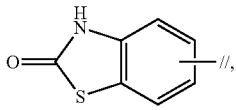

and the like. The monocyclic or bicyclic unsaturated heterocyclic group that is substituted with oxo is preferably 2-oxo-indolinyl, 2-oxo-2,3-dihydrobenzo[d]oxazolyl, or 2-oxo-2,3-dihydrobenzo[d]thiazolyl, and more preferably 2-oxo-2,3-dihydrobenzo[d]oxazolyl or 2-oxo-2,3-dihydrobenzo[d]thiazolyl.

Ring B is preferably monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen, more preferably phenyl, naphthyl, pyridyl, pyrazolopyridyl, pyrazolopyrimidinyl, indolyl, indolinyl, 2-oxoindolinyl, indazolyl, benzoimidazolyl, benzoisoxazolyl, benzothiazolyl, benzotriazolyl, imidazopyridinyl, quinolinyl, isoquinolinyl, quinazolinyl, quinoxalinyl, phthalazinyl, 2-oxo-2,3-dihydrobenzo[d]oxazolyl, 1,3-dihydroisobenzofuranyl, dihydrobenzooxazinyl, benzodioxolyl, dihydrobenzodioxynyl, or 2-oxo-2,3-dihydrobenzo[d]thiazolyl, more preferably phenyl, naphthyl, pyridyl, pyrazolopyridyl, indolyl, indolinyl, indazolyl, benzoimidazolyl, benzoisoxazolyl, benzotriazolyl, quinolinyl, 2-oxo-2,3-dihydrobenzo[d]oxazolyl, 1,3-dihydroisobenzofuranyl, dihydrobenzooxazinyl, or 2-oxo-2,3-dihydrobenzo[d]thiazolyl, and more preferably phenyl, indolyl, indazolyl, benzoisoxazolyl, or benzotriazolyl.

In the compound represented by Formula (I) of the present invention, X represents oxygen or sulfur, and preferably oxygen.

In the compound represented by Formula (I) of the present invention, R1 represents nitro or cyano, and preferably cyano.

In the compound represented by Formula (I) of the present invention, R2 represents halogen, and preferably fluorine. When two or more R2s are present, R2s may be identical or different.

In the compound represented by Formula (I) of the present invention, 1 is an integer of 0 to 2, and preferably an integer of 0 to 1.

In the compound represented by Formula (I) of the present invention, R3 represents substituted or unsubstituted amino, C1-C6 alkyl, halogen, cyano, oxo, hydroxy, carbamoyl, sulfo, C1-C6 alkoxy, or amino (C1-C6 alkyl). When two or more R3s are present, R3s may be identical or different.

The "C1-C6 alkyl" represented by R3 may be straight or branched. Examples include methyl, ethyl, n-propyl, isopropyl, n-butyl, isobutyl, tert-butyl, n-pentyl, isopentyl, hexyl, and the like, with C1-C4 alkyl being preferable, and methyl being more preferable.

Examples of the "mono(C1-C6 alkyl)amino" represented by R3 include methylamino, ethylamino, n-propylamino, isopropylamino, n-butylamino, isobutylamino, tert-butylamino, n-pentylamino, isopentylamino, hexylamino, and the like, with mono(C1-C4 alkyl)amino being preferable, and methylamino, ethylamino, or isopropylamino being more preferable.

Examples of the "di(C1-C6 alkyl)amino" represented by R3 include dimethylamino, diethylamino, di(n-propyl) amino, diisopropylamino, di(n-butyl)amino, diisobutylamino, di(tert-butyl)amino, di(n-pentyl)amino, diisopentylamino, dihexylamino, methylethylamino, methylisopropylamino, and the like. The "di(C1-C6 alkyl) amino" is preferably dimethylamino, diethylamino, di(n-propyl)amino, diisopropylamino, di(n-butyl)amino, diisobutylamino, di(tert-butyl)amino, di(n-pentyl)amino, diisopentylamino, dihexylamino, methylethylamino, or methylisopropylamino, more preferably di(C1-C4 alkyl) amino, and more preferably dimethylamino.

Examples of the "(C3-C7 cycloalkyl)amino" represented by R3 include (C3-C7 cycloalkyl)amino, such as cyclopropylamino, cyclobutylamino, cyclopentylamino, cyclohexylamino, and cycloheptylamino. The "(C3-C7 cycloalkyl) amino" is preferably cyclopropylamino, cyclobutylamino, cyclopentylamino, cyclohexylamino, or cycloheptylamino, and more preferably cyclobutylamino.

R3 is preferably substituted or unsubstituted amino, C1-C6 alkyl, halogen, cyano, oxo, hydroxy, carbamoyl, sulfo, C1-C6 alkoxy, or amino(C1-C6 alkyl), more preferably amino that may be substituted with one to two C1-C6 alkyl or C3-C7 cycloalkyl groups, C1-C6 alkyl, halogen, cyano, oxo, hydroxy, carbamoyl, sulfo, C1-C6 alkoxy, or amino(C1-C6 alkyl), more preferably amino, mono- or di(C1-C6 alkyl)amino, (C3-C7 cycloalkyl)amino, or C1-C6 alkyl, more preferably amino, methylamino, ethylamino, isopropylamino, dimethylamino, cyclobutylamino, or methyl, more preferably amino or methyl, and more preferably amino.

In the compound represented by Formula (I) of the present invention, m is an integer of 0 to 2, and preferably an integer of 0 to 1.

In the compound represented by Formula (I) of the present invention, R4 represents halogen, hydroxy, nitro, cyano, amino, carboxy, (C2-C7 acyl)amino, (C2-C7 acyl) oxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, substituted or unsubstituted carbamoyl, substituted or unsubstituted C2-C6 alkynyl, substituted or unsubstituted (C1-C6 alkyl)carbonyl, substituted or unsubstituted 4- to 14-membered nitrogen-containing saturated heterocyclic group, or substituted or unsubstituted C6-C14 aromatic hydrocarbon. When two or more R4s are present, R4s may be identical or different.

In the present invention, when at least one R4 represents substituted C1-C8 alkyl, substituted C2-C6 alkenyl, substituted C1-C6 alkoxy, substituted C3-C7 cycloalkyl, or substituted carbamoyl, examples of the substituents include halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic 5- to 10-membered unsaturated hydrocarbon, (C2-C7 acyl)oxy, amino that may be substituted with C1-C6 alkyl or C2-C7 acyl, C3-C7 cycloalkyl that may be substituted with hydroxy, (C1-C6 alkoxy)(C1-C6 alkyl), and the like. When two or more of the substituents are present, the substituents may be identical or different.

The "C1-C8 alkyl" in the "substituted or unsubstituted C1-C8 alkyl" represented by R4 is preferably methyl, ethyl, n-propyl, isopropyl, n-butyl, isobutyl, sec-butyl, tert-butyl, pentyl, hexyl, heptyl, or octyl, more preferably C1-C6 alkyl, more preferably methyl, ethyl, n-propyl, isopropyl, n-butyl, isobutyl, sec-butyl, tert-butyl, pentyl, or hexyl, and more preferably methyl, ethyl, n-propyl, isopropyl, n-butyl, isobutyl, sec-butyl, or tert-butyl.

The substituent in the "substituted or unsubstituted C1-C8 alkyl" represented by R4 may be, for example, the substituents mentioned above, preferably halogen, amino, hydroxy, carboxy, carbamoyl, alkylcarbamoyl, acylamino, alkoxy, hydroxycycloalkyl, or acyloxy, more preferably halogen, amino, hydroxy, carboxy, carbamoyl, (C1-C6 alkyl)carbamoyl, (C2-C7 acyl)amino, C1-C6 alkoxy, C3-C7 cycloalkyl, hydroxy(C3-C7 cycloalkyl), or (C2-C7 acyl)oxy, more preferably halogen, amino, hydroxy, carboxy, carbamoyl, (C1-C6 alkyl)carbamoyl, (C1-C6 alkyl)carbonylamino, C1-C6 alkoxy, C3-C7 cycloalkyl, hydroxy(C3-C7 cycloalkyl), or (C1-C6 alkyl)carbonyloxy, and more preferably fluorine, amino, hydroxy, carboxy, carbamoyl, methylcarbamoyl, dimethylcarbamoyl, acetylamino, methoxy, hydroxycyclopropyl, or methylcarbonyloxy.

The "substituted or unsubstituted C1-C8 alkyl" represented by R4 is preferably unsubstituted C1-C8 alkyl, or C1-C8 alkyl that may be substituted with halogen, amino, hydroxy, carboxy, carbamoyl, (C1-C6 alkyl)carbamoyl, (C1-C6 alkyl)carbonylamino, C1-C6 alkoxy, C3-C7 cycloalkyl, hydroxy(C3-C7 cycloalkyl), or (C1-C6 alkyl)carbonyloxy, more preferably methyl, ethyl, n-propyl, isopropyl, tert-butyl, difluoromethyl, trifluoromethyl, fluoroethyl, aminoethyl, hydroxymethyl, hydroxyethyl, hydroxypropyl, hydroxydimethylethyl, hydroxymethylpropyl, hydroxymethylbutyl, hydroxyethylbutyl, carboxymethyl, carbamoylmethyl, methylcarbamoylmethyl, dimethylcarbamoylmethyl, acetylaminoethyl, methoxyethyl, hydroxycyclopropylmethyl, hydroxycyclopropylethyl, hydroxycyclobutylmethyl, or methylcarbonyloxyethyl, more preferably methyl, ethyl, n-propyl, tert-butyl, difluoromethyl, hydroxyethyl, hydroxymethylpropyl, hydroxymethylbutyl, hydroxyethylbutyl, carbamoylmethyl, methylcarbamoylmethyl, dimethylcarbamoylmethyl, methoxyethyl, hydroxycyclopropylmethyl, hydroxycyclobutylmethyl, or methylcarbonyloxyethyl, more preferably methyl, difluoromethyl, hydroxymethylpropyl, hydroxymethylbutyl, hydroxycyclobutylmethyl, methoxyethyl, or hydroxycyclobutylmethyl, and more preferably methyl, difluoromethyl, hydroxymethylpropyl, hydroxyethylbutyl, or hydroxycyclobutylmethyl.

The "substituted or unsubstituted C2-C6 alkenyl" represented by R4 is preferably unsubstituted C2-C6 alkenyl, more preferably vinyl, allyl, 1-propenyl, 2-methyl-2-propenyl, isopropenyl, 1-, 2- or 3-butenyl, isobutenyl, 2-, 3-, or 4-pentenyl, 2-methyl-2-butenyl, 3-methyl-2-butenyl, 5-hexenyl, 1-cyclopentenyl, 1-cyclohexenyl, or 3-methyl-3-butenyl, and more preferably isobutenyl.

Examples of the "C2-C6 alkynyl" in the "substituted or unsubstituted C2-C6 alkynyl" represented by R4 include ethynyl, 1- or 2-propynyl, 1-, 2- or 3-butynyl, 1-methyl-2-propynyl, and the like. The "substituted or unsubstituted C2-C6 alkynyl" is preferably unsubstituted C2-C6 alkynyl.

The "C1-C6 alkoxy" in the "substituted or unsubstituted C1-C6 alkoxy" represented by R4 is preferably methoxy, ethoxy, n-propoxy, isopropoxy, n-butoxy, isobutoxy, sec-butoxy, tert-butoxy, pentyloxy, or hexyloxy, and more preferably methoxy, ethoxy, n-propoxy, isopropoxy, n-butoxy, isobutoxy, sec-butoxy, and tert-butoxy.

The substituent in the "substituted or unsubstituted C1-C6 alkoxy" represented by R4 may be, for example, those mentioned above, and is preferably hydroxy or 5- to 14-membered unsaturated hydrocarbon, more preferably hydroxy or monocyclic 5- to 10-membered unsaturated hydrocarbon, and more preferably hydroxy or phenyl.

The "substituted or unsubstituted C1-C6 alkoxy" represented by R4 is preferably C1-C6 alkoxy that may be substituted with hydroxy or 5- to 14-membered unsaturated hydrocarbon, more preferably C1-C6 alkoxy that may be substituted with hydroxy or monocyclic 5- to 10-membered unsaturated hydrocarbon, more preferably C1-C6 alkoxy that may be substituted with hydroxy or phenyl, and more preferably methoxy, hydroxypropoxy, or benzyloxy.

The "substituted or unsubstituted C3-C7 cycloalkyl" represented by R4 is preferably C3-C7 cycloalkyl that may be substituted with hydroxyalkyl, alkoxyalkyl, hydroxycycloalkyl, or unsaturated hydrocarbon carbamoyl, more preferably C3-C7 cycloalkyl that may be substituted with hydroxy(C1-C4 alkyl), (C1-C4 alkoxy)(C1-C4 alkyl), hydroxy(C3-C7 cycloalkyl), or (C6-C14 aromatic hydrocarbon)carbamoyl, more preferably C3-C7 cycloalkyl that may be substituted with hydroxy(C1-C4 alkyl), (C1-C4 alkoxy)(C1-C4 alkyl), hydroxy(C3-C7 cycloalkyl), or phenylcarbamoyl, more preferably cyclopropyl, hydroxymethyl cyclopropyl, methoxymethyl cyclopropyl, hydroxycyclopropyl cyclopropy, or phenylcarbamoyl cyclopropyl, more preferably cyclopropyl or hydroxymethyl cyclopropyl, and more preferably cyclopropyl.

The "mono- or di(C1-C6 alkyl)amino" represented by R4 is preferably methylamino, ethylamino, n-propylamino, isopropylamino, n-butylamino, isobutylamino, tert-butylamino, n-pentylamino, isopentylamino, hexylamino, dimethylamino, diethylamino, di(n-propyl)amino, diisopropylamino, di(n-butyl)amino, diisobutylamino, di(tert-butyl)amino, di(n-pentyl)amino, diisopentylamino, dihexylamino, methylethylamino, or methylisopropylamino, more preferably methylamino, ethylamino, n-propylamino, isopropylamino, and n-butylamino, isobutylamino, tert-butylamino, dimethylamino, diethylamino, di(n-propyl)amino, diisopropylamino, di(n-butyl)amino, diisobutylamino, di(tert-butyl)amino, methylethylamino, or methylisopropylamino, and more preferably dimethylamino.

The "substituted or unsubstituted carbamoyl" represented by R4 is preferably carbamoyl that may be substituted with alkyl, more preferably carbamoyl that may be substituted with C1-C6 alkyl, and more preferably carbamoyl, methylcarbamoyl, or dimethylcarbamoyl.

Examples of the alkylcarbonyl in the "substituted or unsubstituted (C1-C6 alkyl)carbonyl" represented by R4 include straight or branched (C1-C6 alkyl)carbonyl, such as methylcarbonyl, ethylcarbonyl, n-propylcarbonyl, isopropylcarbonyl, n-butylcarbonyl, isobutylcarbonyl, tert-butylcarbonyl, n-pentylcarbonyl, isopentylcarbonyl, and hexylcarbonyl.

Examples of the "nitrogen-containing saturated heterocyclic group" in the "substituted or unsubstituted 4- to 14-membered nitrogen-containing saturated heterocyclic group" represented by R4 include morpholinyl, azetidinyl, pyrrolidinyl, piperidinyl, piperazinyl, and the like.

Examples of the "substituted or unsubstituted C6-C14 aromatic hydrocarbon" represented by R4 include C6-C14 aromatic hydrocarbon that may be substituted with methyl, such as phenyl, toluyl, xylyl, naphthyl, anthracenyl, phenanthryl, fluorenyl, and tetrahydronaphthyl.

R4 is preferably halogen, hydroxy, nitro, cyano, amino, carboxy, (C2-C7 acyl)amino, (C2-C7 acyl)oxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, substituted or unsubstituted carbamoyl, substituted or unsubstituted C2-C6 alkynyl, substituted or unsubstituted (C1-C6 alkyl)carbonyl, substituted or unsubstituted 4- to 14-membered nitrogen-containing saturated heterocyclic group, or substituted or unsubstituted C6-C14 aromatic hydrocarbon, more preferably halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl, more preferably halogen, nitro, cyano, carboxy, C1-C6 alkyl that may be substituted with halogen, amino, hydroxy, carboxy, carbamoyl, (C1-C6 alkyl)carbamoyl, (C1-C6 alkyl)carbonylamino, C1-C6 alkoxy, C3-C7 cycloalkyl, hydroxy(C3-C7 cycloalkyl), or (C1-C6 alkyl)carbonyloxy, C2-C6 alkenyl, C1-C6 alkoxy that may be substituted with hydroxy or monocyclic 5- to 10-membered unsaturated hydrocarbon, C3-C7 cycloalkyl that may be substituted with hydroxy, hydroxy(C1-C4 alkyl), (C1-C4 alkoxy)(C1-C4 alkyl), hydroxy(C3-C7 cycloalkyl), or (C6-C14 aromatic hydrocarbon)-substituted carbamoyl, mono- or di(C1-C6 alkyl) amino, or carbamoyl that may be substituted with C1-C6 alkyl, more preferably fluorine, chlorine, bromine, iodine, nitro, cyano, carboxy, methyl, ethyl, n-propyl, isopropyl, tert-butyl, difluoromethyl, trifluoromethyl, fluoroethyl, aminoethyl, hydroxymethyl, hydroxyethyl, hydroxypropyl, hydroxydimethylethyl, hydroxymethylpropyl, hydroxymethylbutyl, hydroxyethylbutyl, carboxymethyl, carbamoylmethyl, methylcarbamoylmethyl, dimethylcarbamoylmethyl, acetylaminoethyl, methoxyethyl, hydroxycyclopropylmethyl, hydroxycyclopropylethyl, hydroxycyclobutylmethyl, methylcarbonyloxyethyl, isobutenyl, methoxy, hydroxypropoxy, cyclopropyl, hydroxymethyl cyclopropyl, methoxymethyl cyclopropyl, hydroxycyclopropyl cyclopropy, phenylcarbamoyl cyclopropyl, benzyloxy, dimethylamino, carbamoyl, methylcarbamoyl, or dimethylcarbamoyl, more preferably fluorine, chlorine, bromine, nitro, cyano, carboxy, methyl, ethyl, n-propyl tert-butyl, difluoromethyl, hydroxyethyl, hydroxymethylpropyl, hydroxymethylbutyl, hydroxyethylbutyl, carbamoylmethyl, methylcarbamoylmethyl, dimethylcarbamoylmethyl, methoxyethyl, hydroxycyclopropylmethyl, hydroxycyclobutylmethyl, methylcarbonyloxyethyl, methoxy, cyclopropyl, hydroxymethyl cyclopropyl, dimethylamino, carbamoyl, methylcarbamoyl, or dimethylcarbamoyl, more preferably fluorine, chlorine, bromine, cyano, methyl, difluoromethyl, hydroxymethylpropyl, hydroxymethylbutyl, hydroxyethylbutyl, methoxyethyl, hydroxycyclobutylmethyl, or cyclopropyl, and more preferably fluorine, chlorine, bromine, cyano, methyl, difluoromethyl, hydroxymethylpropyl, hydroxyethylbutyl, or hydroxycyclobutylmethyl.

In the compound represented by Formula (I) of the present invention, n is an integer of 0 to 5, and preferably an integer of 0 to 3.

As the compound of the present invention, preferred is a compound represented by Formula (I) or a salt thereof, wherein ring A represents a monocyclic, bridged cyclic, or spirocyclic nitrogen-containing saturated heterocyclic group, ring B represents a monocyclic or bicyclic unsaturated hydrocarbon, or a monocyclic or bicyclic unsaturated heterocyclic group that may be substituted with oxo, X represents O or S, R1 represents nitro or cyano, R2 represents halogen, R3 represents substituted or unsubstituted amino, C1-C6 alkyl, halogen, cyano, oxo, hydroxy, carbamoyl, sulfo, C1-C6 alkoxy, or amino(C1-C6 alkyl), R4 represents halogen, hydroxy, nitro, cyano, amino, carboxy, (C2-C7 acyl)amino, (C2-C7 acyl)oxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, substituted or unsubstituted carbamoyl, substituted or unsubstituted C2-C6 alkynyl, substituted or unsubstituted (C1-C6 alkyl)carbonyl, substituted or unsubstituted 4- to 14-membered nitrogen-containing saturated heterocyclic group, or substituted or unsubstituted C6-C14 aromatic hydrocarbon, l is an integer of 0 to 2, m is an integer of 0 to 2, and n is an integer of 0 to 5, wherein when l is 2, two R2s may be identical or different, when m is 2, two R3s may be identical or different, and when n is 2 to 5, two to five R4s may be identical or different.

More preferred is a compound represented by Formula (I) or a salt thereof, wherein ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms, ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen, X represents O or S, R1 represents nitro or cyano, R2 represents halogen, R3 represents amino, mono- or di(C1-C6 alkyl)amino, (C3-C7 cycloalkyl)amino, or C1-C6 alkyl, R4 represents halogen, hydroxy, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl, wherein when at least one R4 is substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, monocyclic 5- to 10-membered unsaturated hydrocarbon, carbamoyl that may be substituted with C1-C6 alkyl or monocyclic, 5- to 10-membered unsaturated hydrocarbon, (C2-C7 acyl) oxy, amino that may be substituted with C1-C6 alkyl or C2-C7 acyl, C3-C7 cycloalkyl that may be substituted with hydroxy, or (C1-C6 alkoxy)(C1-C6 alkyl), wherein when two or more of the substituents are present, the substituents may be identical or different, l is an integer of 0 to 2, m is an integer of 0 to 2, and n is an integer of 0 to 5, wherein when l is 2, two R2s may be identical or different, when m is 2, two R3s may be identical or different, and when n is 2 to 5, two to five R4s may be identical or different.

More preferred is a compound represented by Formula (I) or a salt thereof, wherein ring A represents pyrrolidinyl, piperidinyl, piperazinyl, azepanyl, diazepanyl,

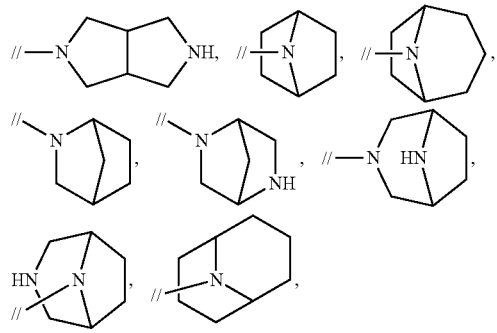

2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[4.5]decanyl, or 9-oxa-diazaspiro[3.5]nonanyl, ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen, X represents O or S, R1 represents nitro or cyano, R2 represents halogen, R3 represents amino, methylamino, ethylamino, isopropylamino, dimethylamino, cyclobutylamino, or methyl, R4 represents halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, or substituted or unsubstituted carbamoyl, wherein when at least one R4 is substituted C1-C8 alkyl, substituted C2-C6 alkenyl, substituted C1-C6 alkoxy, substituted C3-C7 cycloalkyl, or substituted carbamoyl, the substituent is halogen, carboxy, C1-C6 alkoxy, hydroxy, C1-C6 alkyl that may be substituted with hydroxy, a monocyclic 5- to 10-membered unsaturated hydrocarbon, carbamoyl that may be substituted with C1-C6 alkyl or monocyclic 5- to 10-membered unsaturated hydrocarbon, C2-C7 acyl, amino that may be substituted with C1-C6 alkyl or C2-C7 acyl, C3-C7 cycloalkyl that may be substituted with hydroxy, or (C1-C6 alkoxy) (C1-C6 alkyl), wherein when two or more of the substituents are present, the substituents may be identical or different, l is an integer of 0 to 2,
m is an integer of 0 to 2, and
n is an integer of 0 to 5, wherein when l is 2, two R2s may be identical or different, when m is 2, two R3s may be identical or different, and when n is 2 to 5, two to five R4s may be identical or different.

More preferred is a compound represented by Formula (I) or a salt thereof, wherein ring A represents pyrrolidinyl, piperidinyl, piperazinyl, azepanyl, and diazepanyl,

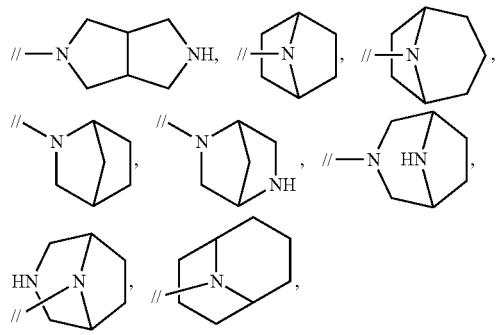

2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[4.5]decanyl, or 9-oxa-diazaspiro[3.5]nonanyl, ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen, X represents O or S, R1 represents nitro or cyano, R2 represents halogen, R3 represents amino, methylamino, ethylamino, isopropylamino, dimethylamino, cyclobutylamino, or methyl, R4 represents halogen, nitro, cyano, carboxy, C1-C8 alkyl that may be substituted with halogen, amino, hydroxy, carboxy, carbamoyl, (C1-C6 alkyl) carbamoyl, (C1-C6 alkyl)carbonylamino, C1-C6 alkoxy, (C1-C6 alkyl)carbonyl, C3-C7 cycloalkyl, hydroxy(C3-C7 cycloalkyl), or (C1-C6 alkyl)carbonyloxy, C2-C6 alkenyl, C1-C6 alkoxy that may be substituted with hydroxy or monocyclic 5- to 10-membered unsaturated hydrocarbon, C3-C7 cycloalkyl that may be substituted with hydroxy, hydroxy (C1-C4 alkyl), (C1-C4 alkoxy) (C1-C4 alkyl), hydroxy (C3-C7 cycloalkyl), or (C6-C14 aromatic hydrocarbon)-substituted carbamoyl, mono- or di(C1-C6 alkyl)amino, or carbamoyl that may be substituted with C1-C6 alkyl, l is an integer of 0 to 2,
m is an integer of 0 to 2, and
n is an integer of 0 to 5, wherein when l is 2, two R2s may be identical or different, when m is 2, two R3s may be identical or different, and when n is 2 to 5, two to five R4s may be identical or different.

More preferred is a compound represented by Formula (I) or a salt thereof, wherein ring A represents pyrrolidinyl, piperidinyl, piperazinyl, azepanyl, diazepanyl,

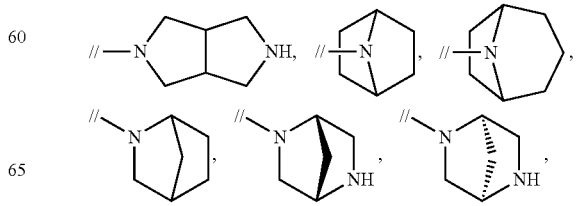

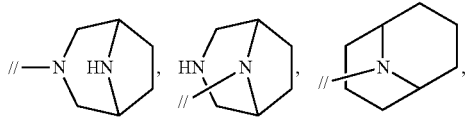

2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[4.5]decanyl, or 9-oxa-diazaspiro[3.5]nonanyl, ring B represents phenyl, naphthyl, pyridyl, pyrazolopyridyl, pyrazolopyrimidinyl, indolyl, indolinyl, 2-oxoindolinyl, indazolyl, benzoimidazolyl, benzoisoxazolyl, benzothiazolyl, benzotriazolyl, imidazopyridinyl, quinolinyl, isoquinolinyl, quinoxalinyl, quinazolinyl, phthalazinyl, 2-oxo-2,3-dihydrobenzo[d]oxazolyl, 1,3-dihydroisobenzofuranyl, dihydrobenzooxazinyl, benzodioxolyl, dihydrobenzodioxynyl, or 2-oxo-2,3-dihydrobenzo[d]thiazolyl, X represents O or S, R1 represents nitro or cyano, R2 represents fluorine, and is present at the ortho position relative to R1 on the phenyl, R3 represents amino, methylamino, ethylamino, isopropylamino, dimethylamino, cyclobutylamino, or methyl (wherein when two or more R3s are present, R3s may be identical or different), R4 represents fluorine, chlorine, bromine, iodine, nitro, cyano, carboxy, methyl, ethyl, n-propyl, isopropyl, tert-butyl, difluoromethyl, trifluoromethyl, fluoroethyl, aminoethyl, hydroxymethyl, hydroxyethyl, hydroxypropyl, hydroxydimethylethyl, hydroxymethylpropyl, hydroxymethylbutyl, hydroxyethylbutyl, carboxymethyl, carbamoylmethyl, methylcarbamoylmethyl, dimethylcarbamoylmethyl, acetylaminoethyl, methoxyethyl, hydroxycyclopropylmethyl, hydroxycyclopropylethyl, hydroxycyclobutylmethyl, methylcarbonyloxyethyl, isobutenyl, methoxy, hydroxypropoxy, cyclopropyl, hydroxymethyl cyclopropyl, methoxymethyl cyclopropyl, hydroxycyclopropyl cyclopropyl, phenylcarbamoyl cyclopropyl, benzyloxy, dimethylamino, carbamoyl, methylcarbamoyl, or dimethylcarbamoyl, l is an integer of 0 to 2,
m is an integer of 0 to 2, and
n is an integer of 0 to 3,
wherein when m is 2, two R3s may be identical or different, and
when n is 2 to 3, two to three R4s may be identical or different.

More preferred is a compound represented by Formula (I) or a salt thereof, wherein
ring A represents pyrrolidinyl, piperidinyl, azepanyl, diazepanyl,

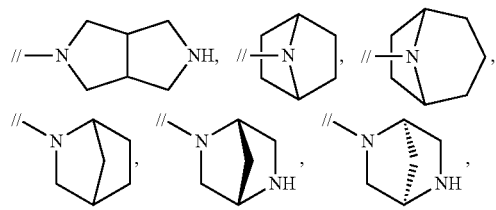

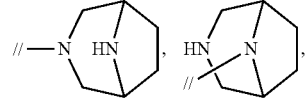

2,7-diazaspiro[3.4]octanyl, 3,7-diazaspiro[3.4]octanyl, 2,7-diazaspiro[3.5]nonanyl, 2,8-diazaspiro[3.5]nonanyl, or 9-oxa-diazaspiro[3.5]nonanyl, ring B represents phenyl, naphthyl, pyridyl, pyrazolopyridyl, indolyl, indolinyl, indazolyl, benzoimidazolyl, benzoisoxazolyl, benzotriazolyl, quinolinyl, 2-oxo-2,3-dihydrobenzo[d]oxazolyl, 1,3-dihydroisobenzofuranyl, dihydrobenzooxazinyl, or 2-oxo-2,3-dihydrobenzo[d]thiazolyl, X represents O or S, R1 represents cyano, R2 represents fluorine, and is present at the ortho position relative to R1 on the phenyl, R3 represents amino, methylamino, ethylamino, isopropylamino, dimethylamino, cyclobutylamino, or methyl (wherein when two or more R3s are present, R3s may be identical or different), R4 represents fluorine, chlorine, bromine, nitro, cyano, carboxy, methyl, ethyl, n-propyl, tert-butyl, difluoromethyl, hydroxyethyl, hydroxymethylpropyl, hydroxymethylbutyl, hydroxyethylbutyl, carbamoylmethyl, methylcarbamoylmethyl, dimethylcarbamoylmethyl, methoxyethyl, hydroxycyclopropylmethyl, hydroxycyclobutylmethyl, methylcarbonyloxyethyl, methoxy, cyclopropyl, hydroxymethylcyclopropyl, dimethylamino, carbamoyl, methylcarbamoyl, or dimethylcarbamoyl, l is an integer of 0 to 2,
m is an integer of 0 to 2, and
n is an integer of 0 to 3,
wherein when m is 2, two R3s may be identical or different, and
when n is 2 to 3, two to three R4s may be identical or different.

More preferred is a compound represented by Formula (I) or a salt thereof, wherein
ring A represents pyrrolidinyl,

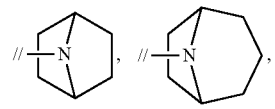

or 2,8-diazaspiro[3.5]nonanyl,
ring B represents phenyl, indolyl, indazolyl, benzoisoxazolyl, or benzotriazolyl, X represents O, R1 represents cyano, R2 represents fluorine, and is present at the ortho position relative to R1 on the phenyl, R3 represents amino or methyl (wherein when two or more R3s are present, R3s may be identical or different), R4 represents fluorine, chlorine, bromine, cyano, methyl, difluoromethyl, hydroxymethylpropyl, hydroxymethylbutyl, hydroxyethylbutyl, methoxyethyl, hydroxycyclobutylmethyl, or cyclopropyl, l is an integer of 0 to 2,
m is an integer of 0 to 2, and
n is an integer of 0 to 3, wherein when m is 2, two R3s may be identical or different, and when n is 2 to 3, two to three R4s may be identical or different.

More preferred is a compound represented by Formula (I) or a salt thereof, wherein ring A represents pyrrolidinyl,

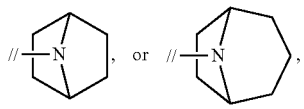

ring B represents phenyl, indolyl, indazolyl, benzoisoxazolyl, or benzotriazolyl,
X represents O,
R1 represents cyano,
R2 represents fluorine, and is present at the ortho position relative to R1 on the phenyl,
R3 represents amino (wherein when two or more R3s are present, R3s may be identical or different),
R4 represents fluorine, chlorine, bromine, cyano, methyl, difluoromethyl, hydroxymethylpropyl, hydroxyethylbutyl, or hydroxycyclobutylmethyl,
l is an integer of 0 to 2,
m is an integer of 0 to 2, and
n is an integer of 0 to 3,
wherein when m is 2, two R3s may be identical or different, and
when n is 2 to 3, two to three R4s may be identical or different.

Specific examples of the compounds of the present invention include, but are not limited to, the compounds produced in the Examples below.

The following are examples of preferable compounds of the present invention:
4-[5-[(3-exo)-3-amino-8-azabicyclo[3.2.1]octane-8-carbonyl]-2-[2-fluoro-4-(2-hydroxy-2-methyl-propyl)phenyl]phenyl]-2-fluoro-benzonitrile;
4-[5-[(3S)-3-aminopyrrolidine-1-carbonyl]-2-[2-fluoro-4-(2-hydroxy-2-methyl-propyl)phenyl]phenyl]-2-fluoro-benzonitrile;
4-[5-[(3-endo)-3-amino-8-azabicyclo[3.2.1]octane-8-carbonyl]-2-[2-fluoro-4-(2-hydroxy-2-methyl-propyl)phenyl]phenyl]-2-fluoro-benzonitrile;
(S)-5'-(3-aminopyrrolidine-1-carbonyl)-3-fluoro-2'-(6-fluoro-1-(2-hydroxy-2-methylpropyl)-1H-indol-5-yl)-[1,1'-biphenyl]-4-carbonitrile;
5'-((3-endo)-3-amino-8-azabicyclo[3.2.1]octane-8-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile;
5'-((1S,2S,4R)-rel-2-amino-7-azabicyclo[2.2.1]heptane-7-carbonyl)-2",3-difluoro-4"-(2-hydroxy-2-methylpropyl)-[1,1':2',1"-terphenyl]-4-carbonitrile-isomer-B;
5'-((1S,2S,4R)-rel-2-amino-7-azabicyclo[2.2.1]heptane-7-carbonyl)-2'-(6,7-difluoro-1-methyl-1H-benzo[d][1,2,3]triazol-5-yl)-3-fluoro-[1,1'-biphenyl]-4-carbonitrile-isomer-B;
5'-((1S,2S,4R)-rel-2-amino-7-azabicyclo[2.2.1]heptane-7-carbonyl)-3-fluoro-2'-(6-fluoro-1-(2-hydroxy-2-methylpropyl)-1H-indazol-5-yl)-[1,1'-biphenyl]-4-carbonitrile-isomer-B;
5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-B;
5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile;
5'-((1S,2S,4R)-rel-2-amino-7-azabicyclo[2.2.1]heptane-7-carbonyl)-2'-(7-chloro-6-fluoro-1-(2-hydroxy-2-methylpropyl)-1H-benzo[d][1,2,3]triazol-5-yl)-3-fluoro-[1,1'-biphenyl]-4-carbonitrile-isomer-X;
5'-((1S,2S,4R)-rel-2-amino-7-azabicyclo[2.2.1]heptane-7-carbonyl)-2'-(7-chloro-6-fluoro-1-(2-hydroxy-2-methylpropyl)-1H-benzo[d][1,2,3]triazol-5-yl)-3-fluoro-[1,1'-biphenyl]-4-carbonitrile;
5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile-isomer-X;
5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile;
(S)-5'-(3-aminopyrrolidine-1-carbonyl)-3-fluoro-2'-(5-fluoro-2-hydroxy-2-methylpropyl)benzo[d]isoxazol-6-yl)-[1,1'-biphenyl]-4-carbonitrile;
5'-((1S,2S,4R)-rel-2-amino-7-azabicyclo[2.2.1]heptane-7-carbonyl)-2'-(7-(difluoromethyl)-6-fluoro-1-(2-hydroxy-2-methylpropyl)-1H-benzo[d][1,2,3]triazol-5-yl)-3-fluoro-[1,1'-biphenyl]-4-carbonitrile-isomer-X;
5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-(2-hydroxy-2-methylpropyl)-1H-benzo[d][1,2,3]triazole-7-carbonitrile-isomer-X;
5'-((1S,2S,4R)-rel-2-amino-7-azabicyclo[2.2.1]heptane-7-carbonyl)-2'-(7-(difluoromethyl)-6-fluoro-1-(2-hydroxy-2-methylpropyl)-1H-benzo[d][1,2,3]triazol-5-yl)-3-fluoro-[1,1'-biphenyl]-4-carbonitrile;
5'-((3-endo)-3-amino-8-azabicyclo[3.2.1]octane-8-carbonyl)-2'-(7-chloro-6-fluoro-1-((1-hydroxycyclobutyl)methyl)-1H-benzo[d][1,2,3]triazol-5-yl)-3-fluoro-[1,1'-biphenyl]-4-carbonitrile;
5'-((3-endo)-3-amino-8-azabicyclo[3.2.1]octane-8-carbonyl)-2'-(7-(difluoromethyl)-6-fluoro-1-((1-hydroxycyclobutyl)methyl)-1H-benzo[d][1,2,3]triazol-5-yl)-3-fluoro-[1,1'-biphenyl]-4-carbonitrile;
5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-((1-hydroxycyclobutyl)methyl)-1H-benzo[d][1,2,3]triazole-7-carbonitrile-isomer-X;
5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-((1-hydroxycyclobutyl)methyl)-1H-benzo[d][1,2,3]triazole-7-carbonitrile;
5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile-isomer-X;
5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile.

Next, the methods for producing the compounds of the present invention are described.

Compound (I) of the present invention may be produced, for example, through the production methods below or the methods described in the Examples. However, the methods for producing Compound (I) of the present invention are not limited to these reaction examples.

In steps 1 to 5, in the formulas, L1, L2, and L3 each individually represent a leaving group, NH$_2$, or OH, W represents hydroxy, C1-C6 alkoxy, or

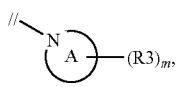

Q1 represents L1 or

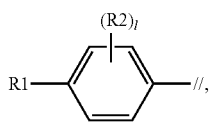

Q2 represents L2 or

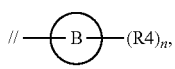

and E1 represents hydrogen or substituted or unsubstituted C1-C6 alkyl, wherein when E1 is substituted or unsubstituted C1-C6 alkyl, E1, taken together with the BOO, may form a ring. X, ring A, ring B, R1, R2, R3, R4, l, m, and n are as defined above.

Step 1: Suzuki Reaction

This step represents a method for producing a compound represented by Formula (IV) through a Suzuki reaction using a compound represented by Formula (II).

This step may be performed in accordance with a commonly known method (e.g., the method disclosed in Chemical Reviews, Vol. 95, p. 2457, 1995). Protection of a substituent, removal or conversion of the protecting group, and conversion of leaving groups L1, L2, and L3 can be suitably performed.

Examples of the leaving groups represented by L1, L2, and L3 include halogen, such as chlorine, bromine, and iodine; organic sulfonyloxy groups, such as trifluoromethylsulfonyloxy and p-tolylsulfonyloxy; and the like.

The amount of the aromatic boronic acid or aromatic boronic acid ester (III) used may be 0.5 to 10 moles, and preferably 0.8 to 3 moles, per mole of the compound represented by Formula (II).

Examples of transition metal catalysts include palladium catalysts, such as palladium acetate, tetrakis(triphenylphosphine)palladium, 1,1'-bis(diphenylphosphino)ferrocene-palladium(II) dichloride bis(dibenzylideneacetone)dipalladium (0), and tris(dibenzylideneacetone)dipalladium(0); nickel catalysts, such as nickel chloride; and the like.

As necessary, a ligand may be added. Examples of ligands include triphenylphosphine, tricyclohexylphosphine, (diphenylphosphino)ferrocene, 2-dicyclohexylphosphino-2',4', 6'-triisopropylbiphenyl, Silica-SMAP, and the like. The amount of the transition metal catalyst used varies depending on the type of catalyst. The amount of the transition metal catalyst used is usually 0.0001 to 1 mole, and pref-

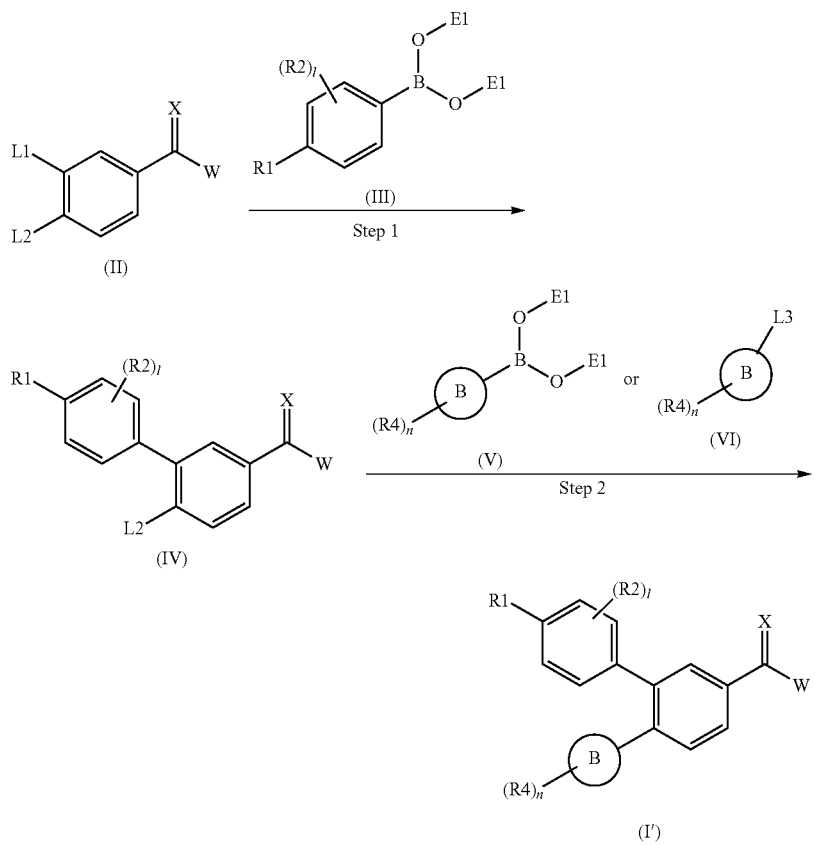

erably 0.001 to 0.5 moles, per mole of the compound represented by Formula (II). The amount of the ligand used is usually 0.0001 to 4 moles, and preferably 0.01 to 2 moles, per mole of the compound represented by Formula (II).

Examples of bases include organic amines, such as triethylamine; alkali metal salts, such as sodium carbonate, potassium carbonate, cesium carbonate, sodium phosphate, tripotassium phosphate, sodium hydroxide, and potassium hydroxide; alkali metal alkoxides, such as sodium methoxide, sodium ethoxide, sodium tert-butoxide, and potassium tert-butoxide; and the like. The amount of the base used is usually 0.1 to 10 moles, and preferably 1 to 5 moles, per mole of the compound represented by Formula (II).

The solvent is not limited as long as it does not adversely affect the reaction. Examples include toluene, acetonitrile, 1,2-dimethoxyethane, tetrahydrofuran, 1,4-dioxane, ethanol, N,N-dimethylformamide, water, mixed solvents thereof, and the like. The reaction time is 0.1 to 7 days, and preferably 0.5 to 24 hours. The reaction temperature is 0° C. to the boiling temperature of the solvent, and preferably 20° C. to 160° C.

The thus-obtained compound represented by Formula (IV) can be subjected to the subsequent step after or without isolation or purification by known isolation and purification means, such as concentration, vacuum concentration, crystallization, solvent extraction, reprecipitation, and chromatography.

It is also possible to first perform a reaction for converting L2 into

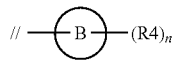

by reacting the compound represented by Formula (V) or (VI) with the compound represented by Formula (II), as in step 2 described below.

Step 2: Suzuki Reaction

This step represents a method for producing a compound represented by Formula (I') through a Suzuki reaction using the compound represented by Formula (IV).

This step can be performed as in step 1. When L2 (if the reaction for converting L2 into

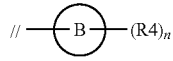

is performed first, then L1) is a boronic acid or a boronic acid ester derivative, compound (VI) is used for the reaction.

L3 in (VI) is the same as L1 and L2 in step 1, and the amount of (VI) used is usually 1 to 10 moles, and preferably 1 to 5 moles, per mole of the compound represented by Formula (IV).

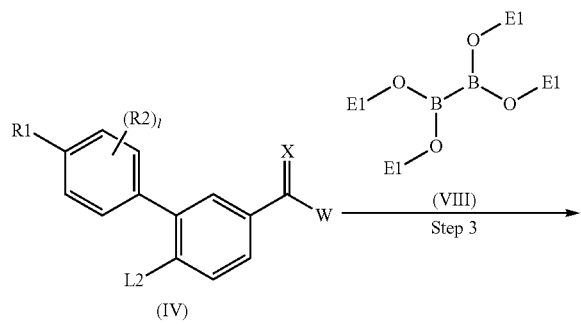

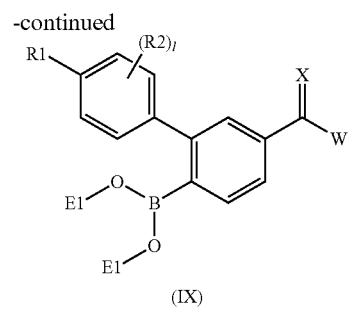

Step 3: Boronic Acid Esterification Reaction

This step represents a method for producing a compound represented by Formula (IX), in which L2 has been converted into a boronic acid ester through a boronic acid esterification reaction, using a compound represented by Formula (IV) and diborane compound (VIII) in the presence of a transition metal catalyst, and a base, optionally using a ligand.

The amount of diborane compound (VIII) used is 1 to 10 moles, and preferably 1 to 5 moles, per mole of the compound represented by Formula (IV).

The transition metal catalyst may be the same as in step 1.

As a base, potassium acetate, sodium acetate, and the like may be used, in addition to those mentioned in step 1.

The ligand may be the same as in step 1, with Silica-SMAP being preferable.

The solvent may be the same as in step 1.

The reaction temperature is usually 0 to 200° C., and preferably 50 to 160° C. The reaction time is usually 5 minutes to 3 days, preferably 5 minutes to 10 hours.

Before performing step 3, it is possible to first introduce

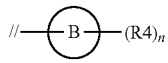

into a compound represented by Formula (II); afterward, a boronic acid esterification reaction with respect to L1 may be performed as in step 3.

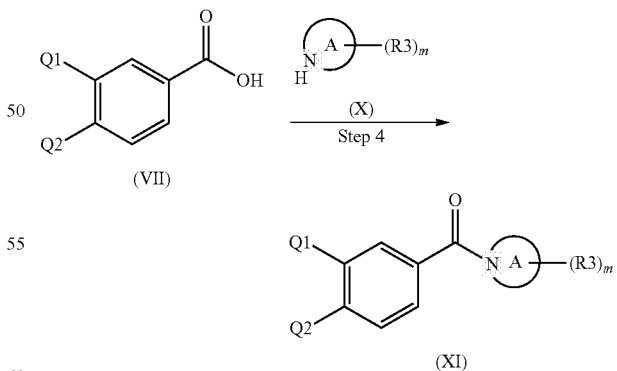

Step 4: Amidation Reaction

This step represents a method for producing a compound represented by Formula (XI) through an amidation reaction using a carboxylic acid compound represented by Formula (VII), an amine compound represented by Formula (X), and a condensation agent.

The amount of amine compound (X) used is 0.5 to 10 moles, and preferably 0.8 to 5 moles, per mole of the compound represented by Formula (VII).

Examples of condensation agents include benzotriazol-1-yloxy-trisdimethylaminophoshonium salts, 4-(4,6-dimethoxy-1,3,5-triazin-2-yl)-4-methylmorpholinium chloride, a combination of 1-ethyl-3-(3-dimethylaminopropyl)carbodiimide and 1-hydroxybenzotriazole, O-(7-azabenzotriazol-1-yl)-N,N,N',N'-tetramethyluronium fluorophosphate, and the like. The amount added is usually 1 to 100 moles, and preferably 1 to 5 moles, per mole of the compound represented by Formula (VII).

A base is optionally added during the above reaction. Examples of bases include organic bases, such as triethylamine, diisopropylethylamine, and pyridine; and inorganic bases, such as potassium carbonate. The amount added is usually 1 to 100 moles, preferably 1 to 10 moles, per mole of the compound represented by Formula (VII).

The solvent is not particularly limited, and any solvent that does not adversely affect the reaction can be used. Examples of the solvent include toluene, chloroform, tetrahydrofuran, N,N-dimethylformamide, dimethylacetamide, N-methylpyrrolidin-2-one, mixtures thereof, and the like.

The reaction temperature is usually −78 to 200° C., and preferably 0 to 50° C. The reaction time is usually 5 minutes to 3 days, preferably 5 minutes to 10 hours.

The thus-obtained compound represented by Formula (XI) can be subjected to the subsequent step after or without isolation or purification by known isolation and purifiction means, such as concentration, vacuum concentration, crystallization, solvent extraction, reprecipitation, and chromatography.

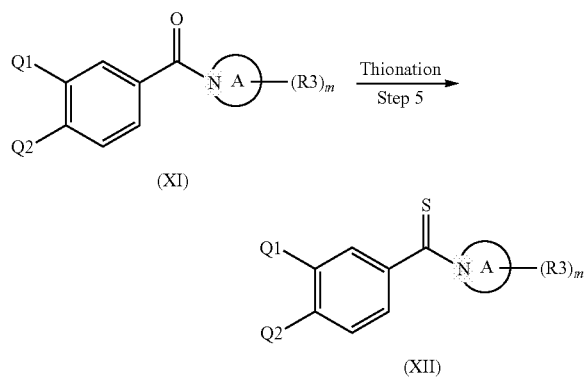

Step 5: Thionation Reaction

This step represents a method for producing a thioamide compound represented by Formula (XII) through a reaction that uses a compound represented by Formula (XI) and a thionation reagent.

Examples of thionation reagents include Lawesson's reagent and the like. The amount of this reagent added may be 1 to 10 moles, and preferably 1 to 5 moles, per mole of the compound represented by Formula (XI).

The solvent may be the same as in step 1.

The reaction temperature is usually 0 to 200° C., and preferably 0 to 100° C. The reaction time is usually 5 minutes to 3 days, and preferably 5 minutes to 10 hours.

The thus-obtained compound represented by Formula (XII) can be subjected to the subsequent step after or without isolation or purification by known isolation and purification means, such as concentration, vacuum concentration, crystallization, solvent extraction, reprecipitation, and chromatography.

The conversion of substituents W and X, and leaving groups L1, L2, and L3, may be suitably performed.

In any of steps 1 to 5, protection of a substituent, and removal or conversion of the protecting group, can be suitably performed. For example, for functional groups such as amino, imino, hydroxy, carboxy, carbonyl, and amide groups, as well as functional groups having an active proton, such as indole, protected reagents can be used, or a protecting group can be introduced into such a functional group according to a usual method; afterward, the protecting group can be removed in an appropriate step in each production method.

The protecting group of an amino group or protecting group of an imino group is not particularly limited, insofar as it has a protecting function. Examples of such protecting groups include aralkyl groups, such as benzyl, p-methoxybenzyl, 3,4-dimethoxybenzyl, o-nitrobenzyl, p-nitrobenzyl, benzhydryl, trityl, and cumyl; lower alkanoyl groups, such as formyl, acetyl, propionyl, butyryl, pivaloyl, trifluoroacetyl, and trichloroacetyl; benzoyl; arylalkanoyl groups, such as phenylacetyl and phenoxyacetyl; lower alkoxycarbonyl groups, such as methoxycarbonyl, ethoxycarbonyl, propyloxycarbonyl, and tert-butoxycarbonyl; aralkyloxycarbonyl groups, such as p-nitrobenzyloxycarbonyl and phenethyloxycarbonyl; lower alkylsilyl groups, such as trimethylsilyl and tert-butyldimethylsilyl; tetrahydropyranyl; trimethylsilylethoxymethyl; lower alkylsulfonyl groups, such as methylsulfonyl, ethylsulfonyl, and tert-butylsulfonyl; lower alkylsulfinyl groups, such as tert-butylsulfinyl; arylsulfonyl groups, such as benzenesulfonyl and toluenesulfonyl; and imido groups, such as phthalimido. In particular, trifluoroacetyl, acetyl, tert-butoxycarbonyl, benzyloxycarbonyl, trimethylsilylethoxymethyl, cumyl, and the like are preferable.

The protecting group of a hydroxy group is not particularly limited insofar as it has a protecting function. Examples of such protecting groups include lower alkyl groups, such as methyl, ethyl, propyl, isopropyl, and tert-butyl; lower alkylsilyl groups, such as trimethylsilyl and tert-butyldimethylsilyl; lower alkoxymethyl groups, such as methoxymethyl and 2-methoxyethoxymethyl; tetrahydropyranyl; trimethylsilylethoxymethyl; aralkyl groups, such as benzyl, p-methoxybenzyl, 2,3-dimethoxybenzyl, o-nitrobenzyl, p-nitrobenzyl, and trityl; and acyl groups, such as formyl, acetyl, and trifluoroacetyl. In particular, methyl, methoxymethyl, tetrahydropyranyl, trimethylsilylethoxymethyl, tert-butyldimethylsilyl, and acetyl are preferable.

The protecting group of a carboxy group is not particularly limited insofar as it has a protecting function. Examples of such protecting groups include lower alkyl groups, such as methyl, ethyl, propyl, isopropyl, and tert-butyl; halo-lower-alkyl groups, such as 2,2,2-trichloroethyl; lower alkenyl groups, such as allyl; trimethylsilylethoxymethyl; and aralkyl groups, such as benzyl, p-methoxybenzyl, p-nitrobenzyl, benzhydryl, and trityl. In particular, methyl, ethyl, tert-butyl, allyl, benzyl, p-methoxybenzyl, trimethylsilylethoxymethyl, and the like are preferable.

The protecting group of a carbonyl group is not particularly limited insofar as it has a protecting function. Examples of such protecting groups include ethylene ketal, trimethylene ketal, dimethyl ketal, ethylene acetal, trimethylene acetal, dimethyl acetal, and like ketals and acetals.

The protecting group of an amide group or the protecting group of a functional group having an active proton, such as indole, is not particularly limited, insofar as it has a protecting function. Examples of such protecting groups include lower alkyl groups, such as methyl, ethyl, propyl, isopropyl, and tert-butyl; lower alkylsilyl groups, such as trimethylsilyl and tert-butyldimethylsilyl; lower alkoxymethyl groups, such as methoxymethyl and 2-methoxyethoxymethyl; tetrahydropyranyl; trimethylsilylethoxymethyl; aralkyl groups, such as benzyl, p-methoxybenzyl, 2,3-dimethoxybenzyl, o-nitrobenzyl, p-nitrobenzyl, and trityl; and acyl groups, such as formyl, acetyl, and trifluoroacetyl. In particular, methyl, methoxymethyl, tetrahydropyranyl, trimethylsilylethoxymethyl, tert-butyldimethylsilyl, and acetyl are preferable.

The method for removing such a protecting group may vary depending on the type of protecting group, stability of the target compound (I), etc. For example, the following methods can be used: solvolysis using an acid or a base according to the method disclosed in a publication (Protective Groups in Organic Synthesis, third edition, T. W. Green, John Wiley & Sons (1999)) or a similar method, i.e., a method comprising reacting with 0.01 moles or a large excess of an acid, preferably trifluoroacetic acid, formic acid, or hydrochloric acid, or an equimolar to large excessive molar amount of a base, preferably potassium hydroxide or calcium hydroxide; chemical reduction using a metal hydride complex etc.; or catalytic reduction using a palladium-carbon catalyst, Raney nickel catalyst, etc.

The compound of the present invention can be easily isolated and purified by common isolation and purification means. Examples of such means include solvent extraction, recrystallization, preparative reversed-phase high-performance liquid chromatography, column chromatography, preparative thin-layer chromatography, and the like.

When the compound of the present invention has isomers such as optical isomers, stereoisomers, rotational isomers, and tautomers, any of the isomers and mixtures thereof is included within the scope of the compound of the present invention, unless otherwise specified. For example, when the compound of the present invention has optical isomers, the optical isomer separated from a racemic mixture is also included within the scope of the compound of the present invention, unless otherwise specified. Each of such isomers can be obtained as a single compound by known synthesis and separation means (e.g., concentration, solvent extraction, and column chromatography, recrystallization).

As stated above, unless otherwise specified, the compound of the present invention includes all of the enantiomers and mixtures thereof. The compound of the present invention may be a mixture of R and S enantiomers. Such a mixture may be a mixture comprising 90% or more, 95% or more, or 99% or more of R enantiomer; a mixture comprising 90% or more, 95% or more, or 99% or more of S enantiomer; or the like.

Methods for chiral resolution include, for example: a diastereomer method of causing a chiral resolving agent to act on the compound of the present invention to form a salt, and resolving one of the enantiomers using a solubility difference etc. of the obtained salt; a preferential crystallization method of adding one of the enantiomers to a supersaturated solution of a racemate as a seed for crystallization; and column chromatography such as HPLC using a chiral column. A chiral resolving agent that can be used in the diastereomer method can be appropriately selected from, for example, acid resolving agents such as tartaric acid, malic acid, lactic acid, mandelic acid, 10-camphorsulfonic acid, and derivatives thereof; and basic resolving agents such as brucine, strychnine, quinine, and like alkaloid compounds, amino acid derivatives, cinchonidine, and α-methylbenzylamine. One of the enantiomers of the compound of the present invention alone can be obtained not only by obtaining the compound of the present invention as a mixture of enantiomers and then conducting chiral resolution as above, but also by obtaining one enantiomer of the compound of the present invention through chiral resolution as above or by other methods, and using it as a synthetic raw material of the compound of the present invention. Furthermore, methods for obtaining one of the enantiomers of the compound of the present invention or its raw material compound include a method of preferentially obtaining one of the enantiomers by adjusting reaction conditions for a catalyst or the like in a reaction step of generating asymmetric carbon.

The compound of the present invention or a salt thereof may be in the form of crystals. Single crystals and polymorphic crystal mixtures are included within the scope of the compound of the present invention or a salt thereof. Such crystals can be produced by crystallization according to a crystallization method known per se in the art. The compound of the present invention or a salt thereof may be a solvate (e.g., a hydrate) or a non-solvate. Any of such forms are included within the scope of the compound of the present invention or a salt thereof. Compounds labeled with an isotope (e.g., 3H, 14C, 35S, and 125I) are also included within the scope of the compound of the present invention or a salt thereof.

The salts of the compounds of the present invention or of the intermediates thereof refer to common salts used in the field of organic chemistry. Examples of such salts include base addition salts to a carboxy group when the compound has a carboxy group, and acid addition salts to an amino or basic heterocyclic group when the compound has an amino or basic heterocyclic group.

Examples of base addition salts include alkali metal salts, such as sodium salts and potassium salts; alkaline earth metal salts, such as calcium salts and magnesium salts; ammonium salts; and organic amine salts, such as trimethylamine salts, triethylamine salts, dicyclohexylamine salts, ethanolamine salts, diethanolamine salts, triethanolamine salts, procaine salts, and N,N'-dibenzylethylenediamine salts.

Examples of acid addition salts include inorganic acid salts, such as hydrochloride, sulfate, nitrate, phosphate, and perchlorate; organic acid salts, such as acetate, formate, maleate, fumarate, tartrate, citrate, ascorbate, and trifluoroacetate; and sulfonates such as methanesulfonate, isethionate, benzenesulfonate, and p-toluenesulfonate.

Due to their excellent LSD1 inhibitory activity, the compounds of the present invention or salts thereof are useful as a pharmaceutical preparation for preventing and treating LSD1-related diseases.

Examples of the "LSD1-related diseases" include diseases whose incidence can be reduced, and whose symptoms can be remitted, relieved, and/or completely cured by eliminating, suppressing, and/or inhibiting LSD1 function. Examples of such diseases include, but are not limited to, malignant tumors etc. The type of malignant tumor to be treated by the compound or a salt thereof of the present invention is not particularly limited. Examples of such malignant tumors include head and neck cancers, esophagus cancer, gastric cancer, colon cancer, rectum cancer, liver cancer, gallbladder cancer, cholangiocarcinoma, biliary tract cancer, pancreatic cancer, lung cancer, breast cancer, ovarian cancer, cervical cancer, endometrial cancer, renal cancer, bladder cancer, prostate cancer, testicular tumor, osteosarcoma, soft-tissue sarcoma, leukemia, myelodysplastic syndrome, chronic myeloproliferative disease, malignant lymphoma, multiple myeloma, skin cancer, brain tumor, mesothelioma, and the like. Preferable examples include lung cancers (e.g., non-small cell lung cancer and small cell lung cancer), leukemia, and myelodysplastic syndromes.

When the compound of the present invention or a salt thereof is used as a pharmaceutical preparation, a pharmaceutical carrier can be added, if required, thereby forming a suitable dosage form according to prevention and treatment purposes. Examples of the dosage form include oral preparations, injections, suppositories, ointments, patches, and the like. Of these, oral preparations are preferable. Such dosage forms can be formed by methods conventionally known to persons skilled in the art.

As the pharmaceutical carrier, various conventional organic or inorganic carrier materials used as preparation materials may be blended as an excipient, binder, disintegrant, lubricant, or colorant in solid preparations; or as a solvent, solubilizing agent, suspending agent, isotonizing agent, buffer, or soothing agent in liquid preparations. Moreover, pharmaceutical preparation additives, such as antiseptics, antioxidants, colorants, sweeteners, and stabilizers, may also be used, if required.

Oral solid preparations are prepared as follows. After an excipient is added optionally with an excipient, a binder, disintegrant, lubricant, colorant, taste-masking or flavoring agent, etc., to the compound of the present invention, the resulting mixture is formulated into tablets, coated tablets, granules, powders, capsules, or the like by ordinary methods.

Examples of excipients include lactose, sucrose, D-mannitol, glucose, starch, calcium carbonate, kaolin, microcrystalline cellulose, and silicic acid anhydride. Examples of binders include water, ethanol, 1-propanol, 2-propanol, simple syrup, liquid glucose, liquid a-starch, liquid gelatin, D-mannitol, carboxymethyl cellulose, hydroxypropyl cellulose, hydroxypropyl starch, methyl cellulose, ethyl cellulose, shellac, calcium phosphate, polyvinylpyrrolidone, and the like. Examples of disintegrators include dry starch, sodium alginate, powdered agar, sodium hydrogen carbonate, calcium carbonate, sodium lauryl sulfate, stearic acid monoglyceride, lactose, and the like. Examples of lubricants include purified talc, stearic acid salt sodium, magnesium stearate, borax, polyethylene glycol, and the like. Examples of colorants include titanium oxide, iron oxide, and the like. Examples of taste-masking or flavoring agents include sucrose, bitter orange peel, citric acid, tartaric acid, and the like.

When a liquid preparation for oral administration is prepared, a taste-masking agent, a buffer, a stabilizer, a flavoring agent, and the like may be added to the compound of the present invention; and the resulting mixture may be formulated into an oral liquid preparation, syrup, elixir, etc., according to an ordinary method.

In this case, the same taste-masking or flavoring agent as those mentioned above may be used. Examples of the buffer include sodium citrate and the like, and examples of the stabilizer include tragacanth, gum arabic, gelatin, and the like. As necessary, these preparations for oral administration may be coated according to methods known in the art with an enteric coating or other coating for the purpose of, for example, persistence of effects. Examples of such coating agents include hydroxypropyl methylcellulose, ethyl cellulose, hydroxymethyl cellulose, hydroxypropyl cellulose, polyoxyethylene glycol, and Tween 80 (registered trademark).

When an injection is prepared, a pH adjuster, a buffer, a stabilizer, an isotonizing agent, a topical anesthetic, and the like may be added, as necessary, to the compound of the present invention; and the resulting mixture may be formulated into subcutaneous, intramuscular, and intravenous injections according to an ordinary method.

Examples of usable pH adjusters and buffers include sodium citrate, sodium acetate, sodium phosphate, and the like. Examples of usable stabilizers include sodium pyrosulfite, EDTA, thioglycolic acid, and thiolactic acid. Examples of usable topical anesthetics include procaine hydrochloride, lidocaine hydrochloride, and the like. Examples of usable isotonizing agents include sodium chloride, glucose, D-mannitol, glycerin, and the like.

The amount of the compound of the present invention to be incorporated in each of such dosage unit forms depends on the condition of the patient to whom the compound is administered, the dosage form, etc. In general, in the case of an oral agent, an injection, and a suppository, the amount of the compound of the present invention is preferably 0.05 to 1000 mg, 0.01 to 500 mg, and 1 to 1000 mg, respectively, per dosage unit form.

The daily dose of the medicine in such a dosage form depends on the condition, body weight, age, gender, etc., of the patient, and cannot be generalized. For example, the daily dose of the compound of the present invention for an adult (body weight: 50 kg) may be usually 0.05 to 5000 mg, and preferably 0.1 to 1000 mg; and is preferably administered in one dose, or in two to three divided doses, per day.

EXAMPLES

The present invention is described below in more detail with reference to Examples. However, the scope of the present invention is not limited to these Examples. The present invention is fully described below by way of Examples; however, it is understood that various changes and modifications by a skilled artisan are possible. Therefore, such changes and modifications are included in the present invention as long as they do not depart from the scope of the invention.

The various reagents used in the Examples were obtained from commercial suppliers, unless otherwise specified. For silica gel column chromatography, a SNAP-Ultra (registered trademark) silica prepacked column produced by Biotage was used. Alternatively, for basic silica gel column chromatography, a KP-NH (registered trademark) prepacked column produced by Biotage was used. NMR spectra were measured by using an AL400 (400 MHz; produced by JEOL), a Mercury 400 (400 MHz; produced by Agilent Technologies, Inc.), or a 500-MHz Bruker Avance III HD NMR Spectrometer (500 MHz; Bruker). When the deuterated solvent contained tetramethylsilane, tetramethylsilane was used as the internal reference. Otherwise, an NMR solvent was used as the internal reference. All of the δ values are shown in ppm. The microwave reaction was performed using an Initiator produced by Biotage.

LCMS spectra were measured using an Acquity SQD (quadrupole) produced by Waters Corporation under the following conditions.
Column: Acquity UPLC (registered trademark) BEH C18, 2.1×50 mm,
1.7 μm (produced by Waters Corporation)
MS detection: ESI positive
UV detection: 254 and 280 nm Column flow rate: 0.5 mL/min
Mobile phase: Water/acetonitrile (0.1% formic acid)
Injection volume: 1 μL

TABLE 1

| | Gradient | |
|---|---|---|
| Time (min) | Water | Acetonitrile |
| 0 | 95 | 5 |
| 0.1 | 95 | 5 |
| 2.1 | 5 | 95 |
| 3.0 | STOP | |

Preparative reversed-phase HPLC purification was performed under the following conditions using a preparative separation system available from Gilson, Inc.
Column: Xselect CSH Prep C18 5 μm OBD (19×50 mm)+ (19×100 mm), produced by Waters Corporation
UV detection: 254 nm
Column flow rate: 18 mL/min
Mobile phase: Water/acetonitrile (0.1% formic acid)
Injection volume: 0.1 to 0.5 mL
The symbols stand for the following.
s: Singlet
d: Doublet
t: Triplet
q: Quartet
dd: Double doublet
dt: Double triplet
td: Triple doublet
tt: Triple triplet
ddd: Double double doublet
ddt: Double double triplet
dtd: Double triple doublet
tdd: Triple double doublet
m: Multiplet
br: Broad
brs: Broad singlet
THF: Tetrahydrofuran
DMF: N,N-dimethylformamide
DME: 1,2-Dimethoxyethane
DMSO: Dimethylsulfoxide
HATU: O-(7-azabenzotriazol-1-yl)-N,N,N',N'-tetramethyluronium fluorophosphate
TEA: Triethylamine
WSC HCl: 1-Ethyl-3-(3-dimethylaminopropyl)carbodiimide hydrochloride
t-BuOH: Tertiary butanol
DMAP: N,N-dimethylaminopyridine
Pd(PPh$_3$)$_4$: Tetrakis(triphenylphosphine)palladium(0)
Pd(dba)$_2$: Bis(dibenzylideneacetone)palladium(0)
PCy$_3$: Tricyclohexylphosphine
TFA: Trifluoroacetic acid
Pd(OAc)$_2$: Palladium acetate
KOAc: Potassium acetate
PdCl$_2$(dPIDf): [1,1'-Bis(diphenylphosphino)ferrocene]palladium(II) dichloride
PdCl$_2$(dppf)CH$_2$Cl$_2$: [1,1'-Bis(diphenylphosphino)ferrocene]palladium(II) dichloride dichloromethane complex
DMEAD: Di-2-methoxyethyl azodicarboxylate
PPh$_3$: Triphenylphosphine
DMA: Dimethylacetamide
MeMgBr: Methylmagnesium bromide
EtMgBr: Ethylmagnesium bromide
MTBE: Methyltertiary-butyl ether
DCM: Dichloromethane
Boc$_2$O: Di-tert-butyl dicarbonate
NBS: N-bromosuccinimide
X-phos: 2-dicyclohexylphosphino-2',4',6'-triisopropylbiphenyl
MeOH: Methanol
EtOH: Ethanol
IPE: Diisopropyl ether
TBAF: Tetrabutylammonium fluoride Example 1: Synthesis of 4-[5-[(3S)-3-aminopyrrolidine-1-carbonyl]-2-(p-tolyl)phenyl]benzonitrile Step 1
3-Bromo-4-chloro-benzoic acid (19 g) was dissolved in DMF (160 mL). At 25° C., DMAP (20 g) and WSC HCl (31 g) were added thereto, followed by the addition of t-BuOH (38 mL). The resulting mixture was stirred at room temperature overnight. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl 3-bromo-4-chloro-benzoate.

Step 2
The tert-butyl 3-bromo-4-chloro-benzoate (1.3 g) obtained in step 1 above was dissolved in 1,4-dioxane (8.7 mL). At room temperature, (4-cyanophenyl)boronic acid (768 mg), Pd(PPh$_3$)$_4$ (151 mg), and a 2 M Na CO$_3$ aqueous solution (5.4 mL) were added thereto, and the reaction solution was stirred in a microwave reactor at 120° C. for 30 minutes. The reaction solution was then vacuum-concentrated, and the residue was purified by silica gel column chromatography (mobile phase: hexane/ethyl acetate) to give tert-butyl 4-chloro-3-(4-cyanophenyl)benzoate.

Step 3
The tert-butyl 4-chloro-3-(4-cyanophenyl)benzoate (1.1 g) obtained in step 2 above was dissolved in 1,4-dioxane (17 mL). At room temperature, p-tolylboronic acid (932 mg), Pd(dba)$_2$ (157 mg), tripotassium phosphate (1.5 g), and a solution of 1 M PCy$_3$ in THF (0.57 mL) were added thereto, and the reaction solution was stirred in a microwave reactor at 160° C. for 30 minutes. After the addition of chloroform, the insoluble matter was filtered off, and the solvent was distilled off. The residue was purified by silica gel column chromatography (mobile phase: hexane/ethyl acetate), and the solvent was distilled off. The residue was dissolved in TFA (2 mL). The solvent was distilled off. Ethyl acetate was added thereto, and the mixture was washed sequentially with water and saturated brine. After the organic layer was dried over anhydrous sodium sulfate, the solvent was distilled off to give 3-(4-cyanophenyl)-4-(p-tolyl)benzoic acid.

Step 4
The 3-(4-cyanophenyl)-4-(p-tolyl)benzoic acid (10 mg) obtained in step 3 above, tert-butyl N-[(3S)-pyrrolidin-3-yl]carbamate (6 mg), and HATU (24 mg) were dissolved in THF (0.5 mL). At room temperature, TEA (0.013 mL) was added thereto, followed by stirring at 50° C. overnight. The reaction solution was vacuum-concentrated, and the solvent was distilled off. The residue was purified by silica gel column chromatography (mobile phase: hexane/ethyl acetate) to give tert-butyl N-[(3S)-1-[3-(4-cyanophenyl)-4-(p-tolyl)benzoyl]pyrrolidin-3-yl]carbamate.

Step 5
The tert-butyl N-[(3S)-1-[3-(4-cyanophenyl)-4-(p-tolyl)benzoyl]pyrrolidin-3-yl]carbamate (15 mg) obtained in step 4 above was dissolved in TFA (0.3 mL), and the progress of the reaction was confirmed by LCMS, followed by vacuum concentration. The residue was purified by reversed-phase HPLC (mobile phase: water/acetonitrile) to give the title compound.

Example 2: Synthesis of 4-[5-[(3S)-3-aminopyrrolidine-1-carbothioyl]-2-(p-tolyl)phenyl]benzonitrile The 4-[5-[(3S)-3-aminopyrrolidine-1-carbonyl]-2-(p-tolyl)phenyl]benzonitrile (6 mg) obtained in Example 1 (step 5) was dissolved in THF (0.8 mL). At room temperature, Lawesson's reagent (3.8 mg) was added thereto, followed by stirring at room temperature for 30 minutes. Chloroform was added thereto, and the mixture was partitioned with sodium bicarbonate water. After the organic layer was dried over anhydrous sodium sulfate, the solvent was distilled off. The residue was purified by reversed-phase HPLC (mobile phase: water/acetonitrile) to give the title compound.

Example 3: Synthesis of 4-[5-(4-aminopiperidine-1-carbonyl)-2-(p-tolyl)phenyl]benzonitrile Step 1

The 3-(4-cyanophenyl)-4-(p-tolyl)benzoic acid (20 mg) obtained in Example 1 (step 3) was dissolved in THF (1 mL). At room temperature, tert-butyl N-(4-piperidyl)carbamate (13 mg), HATU (49 mg), and TEA (0.027 mL) were added thereto, followed by stirring at 50° C. overnight. The reaction solution was vacuum-concentrated, and the solvent was distilled off. The residue was purified by silica gel column chromatography (mobile phase: hexane/ethyl acetate) to give tert-butyl N-[1-[3-(4-cyanophenyl)-4-(p-tolyl)benzoyl]-4-piperidyl]carbamate.

Step 2

The tert-butyl N-[1-[3-(4-cyanophenyl)-4-(p-tolyl)benzoyl]-4-piperidyl]carbamate (30 mg) obtained in step 1 above was dissolved in TFA (0.3 mL), and the progress of the reaction was confirmed by LCMS, followed by vacuum concentration. The residue was purified by reversed-phase HPLC (mobile phase: water/acetonitrile) to give the title compound.

Example 4: Synthesis of 4-[5-(2,8-diazaspiro[3.5]nonane-2-carbonyl)-2-(p-tolyl)phenyl]benzonitrile The procedure of steps 1 to 5 in Example 1 was repeated using tert-butyl 2,8-diazaspiro[3.5]nonane-8-carboxylate hydrochloride instead of tert-butyl N-[(3S)-pyrrolidin-3-yl]carbamate to give the title compound.

Example 5: Synthesis of 4-[5-(2,7-diazaspiro[3.4]octane-7-carbonyl)-2-(p-tolyl)phenyl]benzonitrile The procedure of steps 1 to 5 in Example 1 was repeated using tert-butyl 2,7-diazaspiro[3.4]octane-2-carboxylate instead of tert-butyl N-[(3S)-pyrrolidin-3-yl]carbamate to give the title compound.

Example 6: Synthesis of 4-[5-(3,8-diazaspiro[4.4]nonane-8-carbonyl)-2-(p-tolyl)phenyl]benzonitrile The procedure of steps 1 to 5 in Example 1 was repeated using tert-butyl 3,8-diazaspiro[4.4]nonane-8-carboxylate instead of tert-butyl N-[(3S)-pyrrolidin-3-yl]carbamate to give the title compound.

Example 7: Synthesis of 4-[5-[(3-exo)-3-amino-8-azabicyclo[3.2.1]octane-8-carbonyl]-2-(p-tolyl)phenyl]benzonitrile Step 1

3-Bromo-4-chloro-benzoic acid (500 mg) was dissolved in DMA (5.3 mL). At room temperature, HATU (1 g), TEA (0.59 mL), and tert-butyl N-[(3-exo)-8-azabicyclo[3.2.1]octan-3-yl]carbamate (480 mg) were added thereto, followed by stirring at room temperature for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3-exo)-8-(3-bromo-4-chloro-benzoyl)-8-azabicyclo[3.2.1]octan-3-yl]carbamate.

Step 2

The tert-butyl N-[(3-exo)-8-(3-bromo-4-chloro-benzoyl)-8-azabicyclo[3.2.1]octan-3-yl]carbamate (200 mg) obtained in step 1 above was dissolved in 1,4-dioxane (2.3 mL). At room temperature, (4-cyanophenyl)boronic acid (60 mg), Pd(PPh$_3$)$_4$ (16 mg), and a 2 M Na CO$_3$ aqueous solution (1.1 mL) were added thereto, and the reaction solution was stirred in a microwave reactor at 120° C. for 30 minutes. The solvent was distilled off, and the residue was purified by silica gel column chromatography (mobile phase: hexane/ethyl acetate) to give tert-butyl N-[(3-exo)-8-[4-chloro-3-(4-cyanophenyl)benzoyl]-8-azabicyclo[3.2.1]octan-3-yl]carbamate.

Step 3

The tert-butyl N-[(3-exo)-8-[4-chloro-3-(4-cyanophenyl)benzoyl]-8-azabicyclo[3.2.1]octan-3-yl]carbamate (15 mg) obtained in step 2 above was dissolved in 1,4-dioxane (0.322 mL). At room temperature, p-tolylboronic acid (5.3 mg), Pd(dba)$_2$ (0.93 mg), a solution of 1 M PCy$_3$ in THF (0.003 mL), and tripotassium phosphate (21 mg) were added thereto, and the reaction solution was stirred in a microwave reactor at 160° C. for 30 minutes. The solvent was distilled off, and the residue was purified by silica gel column chromatography (mobile phase: hexane/ethyl acetate) to give tert-butyl N-[(3-exo)-8-[3-(4-cyanophenyl)-4-(p-tolyl)benzoyl]-8-azabicyclo[3.2.1]octan-3-yl]carbamate.

Step 4

The tert-butyl N-[(3-exo)-8-[3-(4-cyanophenyl)-4-(p-tolyl)benzoyl]-8-azabicyclo[3.2.1]octan-3-yl]carbamate (15 mg) obtained in step 3 above was dissolved in TFA (0.3 mL), and the progress of the reaction was confirmed by LCMS, followed by vacuum concentration. The residue was purified by reversed-phase HPLC (mobile phase: water/acetonitrile) to give the title compound.

Example 8: Synthesis of 4-[5-[(3S)-3-amino-3-methyl-pyrrolidine-1-carbonyl]-2-(p-tolyl)phenyl]benzonitrile The procedure of steps 1 to 5 in Example 1 was repeated using tert-butyl N-[(3S)-3-methylpyrrolidin-3-yl]carbamate instead of tert-butyl N-[(3S)-pyrrolidin-3-yl]carbamate to give the title compound.

Example 9: Synthesis of 4-[5-[(3S)-3-aminopyrrolidine-1-carbonyl]-2-(2-chloro-4-methyl-phenyl)phenyl]benzonitrile Step 1

3-Bromo-4-chloro-benzoic acid (10 g) was dissolved in DMA (85 mL). At room temperature, HATU (24 g), TEA (12 mL), and tert-butyl N-[(3S)-pyrrolidin-3-yl]carbamate (8.7 g) were added thereto, followed by stirring at room temperature for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3S)-1-(3-bromo-4-chloro-benzoyl)pyrrolidin-3-yl]carbamate.

Step 2

The tert-butyl N-[(3S)-1-(3-bromo-4-chloro-benzoyl)pyrrolidin-3-yl]carbamate (2.2 g) obtained in step 1 above was dissolved in 1,4-dioxane (13.6 mL). At room temperature, 4-(4,4,5,5-tetramethyl-1,3,2-dioxaborolan-2-yl)benzonitrile (1.5 g), Pd(PPh$_3$)$_4$ (189 mg), and a 2 M Na CO$_3$ aqueous solution (6.8 mL) were added thereto, and the reaction solution was stirred in a microwave reactor at 120° C. for 30 minutes. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3S)-1-[4-chloro-3-(4-cyanophenyl)benzoyl]pyrrolidin-3-yl]carbamate.

Step 3

The tert-butyl N-[(3S)-1-[4-chloro-3-(4-cyanophenyl)benzoyl]pyrrolidin-3-yl]carbamate (500 mg) obtained in step 2 above was dissolved in 1,4-dioxane (9.8 mL). At room temperature, Pd(OAc)$_2$ (26 mg), KOAc (346 mg), bis(pinacolato)diboron (596 mg), and Silica-SMAP (150 mg) were added thereto, followed by stirring at 160° C. overnight. The mixture was passed through Celite, and the filtrate was vacuum-concentrated. The residue was purified by silica gel column chromatography (mobile phase: hexane/ethyl acetate) to give tert-butyl N-[(3S)-1-[3-(4-cyanophenyl)-4-(4,4,5,5-tetramethyl-1,3,2-dioxaborolan-2-yl)benzoyl]pyrrolidin-3-yl]carbamate.

Step 4

The tert-butyl N-[(3S)-1-[3-(4-cyanophenyl)-4-(4,4,5,5-tetramethyl-1,3,2-dioxaborolan-2-yl)benzoyl]pyrrolidin-3-yl]carbamate (15 mg) obtained in step 3 above, 1-bromo-2-chloro-4-methyl-benzene (12 mg), and Pd(PPh$_3$)$_4$ (1.7 mg) were suspended in 1,4-dioxane (1.5 mL). At room temperature, a 2 M Na CO$_3$ aqueous solution (0.7 mL) was added thereto, followed by stirring at 120° C. for 30 minutes. After the reaction solution was filtered, the solvent was distilled off to give tert-butyl N-[(3S)-1-[4-(2-chloro-4-methyl-phenyl)-3-(4-cyanophenyl)benzoyl]pyrrolidin-3-yl]carbamate.

Step 5

The tert-butyl N-[(3S)-1-[4-(2-chloro-4-methyl-phenyl)-3-(4-cyanophenyl)benzoyl]pyrrolidin-3-yl]carbamate (15 mg) obtained in step 4 above was dissolved in TFA (0.3 mL), and the progress of the reaction was confirmed by LCMS, followed by vacuum concentration. The residue was purified by reversed-phase HPLC (mobile phase: water/acetonitrile) to give the title compound.

Example 10: Synthesis of 4-[5-[(3S)-3-aminopyrrolidine-1-carbonyl]-2-(3-chloro-4-methyl-phenyl)phenyl]benzonitrile The procedure of steps 1 to 5 in Example 9 was repeated using 4-bromo-2-chloro-1-methyl-benzene instead of 1-bromo-2-chloro-4-methyl-benzene to give the title compound.

Example 11: Synthesis of 4-[5-[(3S)-3-aminopyrrolidine-1-carbonyl]-2-[3-fluoro-4-(trifluoromethyl)phenyl]phenyl]benzonitrile The procedure of steps 1 to 5 in Example 9 was repeated using 4-bromo-2-fluoro-1-(trifluoromethyl)benzene instead of 1-bromo-2-chloro-4-methyl-benzene to give the title compound.

Example 12: Synthesis of 4-[5-[(3S)-3-aminopyrrolidine-1-carbonyl]-2-(4-methyl-2-nitro-phenyl)phenyl]benzonitrile Step 1

The tert-butyl N-[(3S)-1-[4-chloro-3-(4-cyanophenyl)benzoyl]pyrrolidin-3-yl]carbamate (15 mg) obtained in Example 9 (step 2), 4-methyl-2-nitrophenylboronic acid pinacol ester (18 mg), Pd(dba)$_2$ (1.6 mg), a solution of 1 M PCy$_3$ in THF (0.003 mL), and tripotassium phosphate (15 mg) were added thereto, and the reaction solution was stirred in a microwave reactor at 160° C. for 30 minutes. The solvent was distilled off, and the residue was purified by silica gel column chromatography (mobile phase: hexane/ethyl acetate) to give tert-butyl N-[(3S)-1-[3-(4-cyanophenyl)-4-(4-methyl-2-nitro-phenyl)benzoyl]pyrrolidin-3-yl]carbamate.

Step 2

The tert-butyl N-[(3S)-1-[3-(4-cyanophenyl)-4-(4-methyl-2-nitro-phenyl)benzoyl]pyrrolidin-3-yl]carbamate (10 mg) obtained in step 1 above was dissolved in TFA (0.3 mL), and the progress of the reaction was confirmed by LCMS, followed by vacuum concentration. The residue was purified by reversed-phase HPLC (mobile phase: water/acetonitrile) to give the title compound.

Example 13: Synthesis of 4-[5-[(3S)-3-aminopyrrolidine-1-carbonyl]-2-[4-(difluoromethyl)phenyl]phenyl]benzonitrile The procedure of steps 1 to 5 in Example 9 was repeated using 1-bromo-4-(difluoromethyl)benzene instead of 1-bromo-2-chloro-4-methyl-benzene to give the title compound.

Example 14: Synthesis of 4-[5-[(3S)-3-aminopyrrolidine-1-carbonyl]-2-[4-(trifluoromethyl)phenyl]phenyl]benzonitrile The procedure of steps 1 to 2 in Example 12 was repeated using [4-(trifluoromethyl)phenyl]boronic acid instead of 4-methyl-2-nitrophenylboronic acid pinacol ester to give the title compound.

Example 15: Synthesis of 4-[5-[(3S)-3-aminopyrrolidine-1-carbonyl]-2-(2-fluoro-4-methyl-phenyl)phenyl]benzonitrile Step 1

The tert-butyl N-[(3S)-1-[4-chloro-3-(4-cyanophenyl)benzoyl]pyrrolidin-3-yl]carbamate (1.7 g) obtained in Example 9 (step 2) was dissolved in 1,4-dioxane (20 mL). At room temperature, (2-fluoro-4-methyl-phenyl)boronic acid (980 mg), Pd(dba)$_2$ (110 mg), a solution of 1 M PCy$_3$ in THF (0.4 mL), and tripotassium phosphate (2.5 g) were added thereto, and the reaction solution was stirred in a microwave reactor at 160° C. for 45 minutes. The mixture was purified by NH-silica gel and washed with methanol/ethyl acetate, and the solvent was distilled off to give tert-butyl N-[(3S)-1-[3-(4-cyanophenyl)-4-(2-fluoro-4-methyl-phenyl)benzoyl]pyrrolidin-3-yl]carbamate.

Step 2

The tert-butyl N-[(3S)-1-[3-(4-cyanophenyl)-4-(2-fluoro-4-methyl-phenyl)benzoyl]pyrrolidin-3-yl]carbamate (1.7 g) obtained in step 1 above was dissolved in TFA (44 mL), followed by stirring for 10 minutes. The solvent was distilled off, and the residue was purified by reversed-phase HPLC (mobile phase: water/acetonitrile) to give the title compound.

Example 16: Synthesis of 4-[5-[(3S)-3-aminopyrrolidine-1-carbonyl]-2-(p-tolyl)phenyl]-2-fluoro-benzonitrile Step 1

The tert-butyl N-[(3S)-1-(3-bromo-4-chloro-benzoyl)pyrrolidin-3-yl]carbamate (14 g) obtained in Example 9 (step 1) was dissolved in 1,4-dioxane (87 mL). At room temperature, (4-cyano-3-fluoro-phenyl)boronic acid (6.3 g), Pd(PPh$_3$)$_4$ (1.2 g), and a 2 M Na$_2$CO$_3$ aqueous solution (44 mL) were added thereto, followed by stirring at 90° C. overnight. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3S)-1-[4-chloro-3-(4-cyano-3-fluoro-phenyl)benzoyl]pyrrolidin-3-yl]carbamate.

Step 2

The tert-butyl N-[(3S)-1-[4-chloro-3-(4-cyano-3-fluoro-phenyl)benzoyl]pyrrolidin-3-yl]carbamate (48 mg) obtained in step 1 above was dissolved in 1,4-dioxane (0.5 mL). At room temperature, p-tolylboronic acid (29 mg), Pd(dba)$_2$ (3.1 mg), a solution of 1 M PCy$_3$ in THF (0.005 mL), and tripotassium phosphate (68 mg) were added thereto, and the reaction solution was stirred in a microwave reactor at 160° C. for 45 minutes. The mixture was purified by NH-silica gel and washed with methanol/ethyl acetate, and the solvent was distilled off to give tert-butyl N-[(3S)-1-[3-(4-cyano-3-fluoro-phenyl)-4-(p-tolyl)benzoyl]pyrrolidin-3-yl]carbamate.

Step 3

TFA (1.2 mL) was added to the tert-butyl N-((3S)-1-[3-(4-cyano-3-fluoro-phenyl)-4-(p-tolyl)benzoyl]pyrrolidin-3-yl]carbamate (48 mg) obtained in step 2 above, followed by stirring for 10 minutes. The solvent was distilled off, and the residue was purified by reversed-phase HPLC (mobile phase: water/acetonitrile) to give the title compound.

Example 17: Synthesis of 4-[5-[(3-endo)-3-amino-8-azabicyclo[3.2.1]octane-8-carbonyl]-2-(p-tolyl)phenyl]-2-fluoro-benzonitrile Step 1

3-Bromo-4-chloro-benzoic acid (700 mg) was dissolved in THF (15 mL). At room temperature, HATU (1.2 g), TEA (0.83 mL), and tert-butyl N-[(3-endo)-8-azabicyclo[3.2.1]octan-3-yl]carbamate (700 mg) were added thereto, followed by stirring at 50° C. for 1 hour. The solvent was distilled off, and the residue was purified by silica gel column chromatography (mobile phase: hexane/ethyl acetate) to give tert-butyl N-[(3-endo)-8-(3-bromo-4-chloro-benzoyl)-8-azabicyclo[3.2.1]octan-3-yl]carbamate.

Step 2

The tert-butyl N-[(3-endo)-8-(3-bromo-4-chloro-benzoyl)-8-azabicyclo[3.2.1]octan-3-yl]carbamate (1.2 g) obtained in step 1 above was dissolved in 1,4-dioxane (6.7 mL). At room temperature, (4-cyano-3-fluoro-phenyl)boronic acid (461 mg), PdCl$_2$(dppf) (58 mg), and a 2 M Na$_2$CO$_3$ aqueous solution (3.3 mL) were added thereto, followed by stirring at 95° C. overnight. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3-endo)-8-[4-chloro-3-(4-cyano-3-fluoro-phenyl)benzoyl]-8-azabicyclo[3.2.1]octan-3-yl]carbamate.

Step 3

The tert-butyl N-[(3-endo)-8-[4-chloro-3-(4-cyano-3-fluoro-phenyl)benzoyl]-8-azabicyclo[3.2.1]octan-3-yl]carbamate (17 mg) obtained in step 2 above was dissolved in 1,4-dioxane (0.5 mL). At room temperature, p-tolylboronic acid (9.6 mg), Pd(dba)$_2$ (1.6 mg), tripotassium phosphate (15 mg), and a solution of 1 M PCy$_3$ in THF (0.004 mL) were added thereto, and the mixture was stirred in a microwave reactor at 160° C. for 30 minutes. The reaction solution was filtered through NH-silica gel, and the solvent of the filtrate was distilled off to give tert-butyl N-[(3-endo)-8-[3-(4-cyano-3-fluoro-phenyl)-4-(p-tolyl)benzoyl]-8-azabicyclo[3.2.1]octan-3-yl]carbamate.

Step 4

The tert-butyl N-[(3-endo)-8-[3-(4-cyano-3-fluoro-phenyl)-4-(p-tolyl)benzoyl]-8-azabicyclo[3.2.1]octan-3-yl]carbamate (15 mg) obtained in step 3 above was dissolved in TFA (0.3 mL), and the progress of the reaction was confirmed by LCMS, followed by vacuum concentration. The residue was purified by reversed-phase HPLC (mobile phase: water/acetonitrile) to give the title compound.

Example 18: Synthesis of 4-[5-[(3-exo)-3-amino-8-azabicyclo[3.2.1]octane-8-carbonyl]-2-(1-methylindol-5-yl)phenyl]-2-fluoro-benzonitrile Step 1

The tert-butyl N-[(3-exo)-8-(3-bromo-4-chloro-benzoyl)-8-azabicyclo[3.2.1]octan-3-yl]carbamate (300 mg) obtained in Example 7 (step 1) was dissolved in 1,4-dioxane (1.7 mL). At room temperature, (4-cyano-3-fluoro-phenyl)boronic acid (123 mg), PdCl$_2$(dppf) (17 mg), and a 2 M Na$_2$CO$_3$ aqueous solution (0.85 mL) were added thereto, and the reaction solution was stirred in a microwave reactor at 120° C. for 30 minutes. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3-exo)-8-[4-chloro-3-(4-cyano-3-fluoro-phenyl)benzoyl]-8-azabicyclo[3.2.1]octan-3-yl]carbamate.

Step 2

The tert-butyl N-[(3-exo)-8-[4-chloro-3-(4-cyano-3-fluoro-phenyl)benzoyl]-8-azabicyclo[3.2.1]octan-3-yl]carbamate (10 mg) obtained in step 1 above was dissolved in 1,4-dioxane (0.5 mL). At room temperature, (1-methylindol-5-yl)boronic acid (7.2 mg), Pd(dba)$_2$ (0.9 mg), tripotassium phosphate (8.8 mg), and a solution of 1 M PCy$_3$ in THF (0.002 mL) were added thereto, and the reaction solution was stirred in a microwave reactor at 160° C. for 30 minutes. The reaction solution was filtered through NH-silica gel, and the solvent of the filtrate was distilled off. The residue was purified by silica gel column chromatography (mobile phase: hexane/ethyl acetate) to give tert-butyl N-[(3-exo)-8-[3-(4-cyano-3-fluoro-phenyl)-4-(1-methylindol-5-yl)benzoyl]-8-azabicyclo[3.2.1]octan-3-yl]carbamate.

Step 3

The tert-butyl N-[(3-exo)-8-[3-(4-cyano-3-fluoro-phenyl)-4-(1-methylindol-5-yl)benzoyl]-8-azabicyclo[3.2.1]octan-3-yl]carbamate (15 mg) obtained in step 2 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 19: Synthesis of 4-[5-[(3S)-3-aminopyrrolidine-1-carbonyl]-2-(p-tolyl)phenyl]-2,6-difluoro-benzonitrile Step 1

4-Bromo-3-chloro-benzoic acid (2 g) was dissolved in DMA (17 mL). At room temperature, HATU (4.8 g), TEA (2.4 mL), and tert-butyl N-[(3S)-pyrrolidin-3-yl]carbamate (1.7 g) were added thereto, followed by stirring at room temperature for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3S)-1-(4-bromo-3-chloro-benzoyl)pyrrolidin-3-yl]carbamate.

Step 2

The tert-butyl N-[(3S)-1-(4-bromo-3-chloro-benzoyl)pyrrolidin-3-yl]carbamate obtained in step 1 above was dissolved in 1,4-dioxane (10.6 mL). At room temperature, Pd(PPh$_3$)$_4$ (147 mg), a 2 M Na CO$_3$ aqueous solution (5.3 mL), and p-tolylboronic acid (693 mg) were added thereto, and the reaction solution was stirred in a microwave reactor at 120° C. for 30 minutes. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl N-[(3S)-1-[3-chloro-4-(p-tolyl)benzoyl]pyrrolidin-3-yl]carbamate.

Step 3

The tert-butyl N-[(3S)-1-[3-chloro-4-(p-tolyl)benzoyl]pyrrolidin-3-yl]carbamate (666 mg) obtained in step 2 above was dissolved in 1,4-dioxane (16 mL). At room temperature, Pd(OAc)$_2$ (36 mg), KOAc (473 mg), bis(pinacolato)diboron (815 mg), and a solution of 1 M PCy$_3$ in THF (0.24 mL) were added thereto. After degassing and nitrogen substitution, the mixture was stirred at 80° C. overnight. The reaction solution was passed through Celite, and the solvent of the filtrate was distilled off. The residue was purified by silica gel column chromatography (mobile phase: hexane/ethyl acetate) to give tert-butyl N-[(3S)-1-[4-(p-tolyl)-3-(4,4,5,5-tetramethyl-1,3,2-dioxaborolan-2-yl)benzoyl]pyrrolidin-3-yl]carbamate.

Step 4

The tert-butyl N-[(3S)-1-[4-(p-tolyl)-3-(4,4,5,5-tetramethyl-1,3,2-dioxaborolan-2-yl)benzoyl]pyrrolidin-3-yl]carbamate (15 mg) obtained in step 3 above, 4-bromo-2,6-difluoro-benzonitrile (12.9 mg), and Pd(PPh$_3$)$_4$ (1.7 mg) were suspended in 1,4-dioxane (1.5 mL). At room temperature, a 2 M Na CO$_3$ aqueous solution (0.7 mL) was added thereto, and the reaction solution was stirred in a microwave reactor at 120° C. for 30 minutes. The reaction solution was filtrated, and the solvent was distilled off to give tert-butyl N-[(3S)-1-[3-(4-cyano-3,5-difluoro-phenyl)-4-(p-tolyl)benzoyl]pyrrolidin-3-yl]carbamate.

Step 5

The tert-butyl N-[(3S)-1-[3-(4-cyano-3,5-difluoro-phenyl)-4-(p-tolyl)benzoyl]pyrrolidin-3-yl]carbamate (15 mg) obtained in step 4 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 20: Synthesis of 4-[5-[(3S)-3-aminopyrrolidine-1-carbonyl]-2-[2-fluoro-4-(2-methoxyethyl)phenyl]phenyl]-2-fluoro-benzonitrile Step 1

1-Bromo-2-fluoro-4-(2-methoxyethyl)benzene (4.5 g) was suspended in 1,4-dioxane (48 mL), followed by stirring. Then, bis(pinacolato)diboron (7.4 g), KOAc (3.8 g), and PdCl$_2$(dppf) (0.71 g) were added thereto, followed by stirring at 90° C. overnight. Ethyl acetate was added thereto, the mixture was passed through Celite, and the filtrate was washed sequentially with water and saturated brine. After the organic layer was dried over anhydrous sodium sulfate, the solvent was distilled off. The residue was purified by silica gel column chromatography (mobile phase: hexane/ethyl acetate) to give 2-[2-fluoro-4-(2-methoxyethyl)phenyl]-4,4,5,5-tetramethyl-1,3,2-dioxaborolane.

Step 2

The tert-butyl N-[(3S)-1-[4-chloro-3-(4-cyano-3-fluoro-phenyl)benzoyl]pyrrolidin-3-yl]carbamate (150 mg) obtained in Example 16 (step 1), the 2-[2-fluoro-4-(2-methoxyethyl)phenyl]-4,4,5,5-tetramethyl-1,3,2-dioxaborolane (189 mg) obtained in step 1 above, Pd(dba)$_2$ (15 mg), tripotassium phosphate (144 mg), and a solution of 1 M PCy$_3$ in THF (0.034 mL) were dissolved in 1,4-dioxane (3.8 mL). The reaction solution was stirred in a microwave reactor at 160° C. for 45 minutes. The reaction solution was filtered through NH-silica gel, and the solvent of the filtrate was distilled off. The residue was purified by silica gel column chromatography (mobile phase: hexane/ethyl acetate) to give tert-butyl N-[(3S)-1-[3-(4-cyanophenyl)-4-[2-fluoro-4-(2-methoxyethyl)phenyl]benzoyl]pyrrolidin-3-yl]carbamate.

Step 3

The tert-butyl N-[(3S)-1-[3-(4-cyanophenyl)-4-[2-fluoro-4-(2-methoxyethyl)phenyl]benzoyl]pyrrolidin-3-yl]carbamate (150 mg) obtained in step 2 above was dissolved in TFA (10 mL), and the progress of the reaction was confirmed with LCMS, followed by vacuum concentration. The residue was purified by reversed-phase HPLC (mobile phase: water/acetonitrile) to give the title compound.

Example 21: Synthesis of 4-[5-[(3-endo)-3-amino-8-azabicyclo[3.2.1]octane-8-carbonyl]-2-(2-fluoro-4-methyl-phenyl)phenyl]-2-fluoro-benzonitrile The procedure of steps 1 to 4 in Example 17 was repeated using (2-fluoro-4-methyl-phenyl)boronic acid instead of p-tolylboronic acid to give the title compound.

Example 22: Synthesis of 4-[5-[(3-endo)-3-amino-8-azabicyclo[3.2.1]octane-8-carbonyl]-2-[2-fluoro-4-(2-methoxyethyl)phenyl]phenyl]-2-fluoro-benzonitrile Step 1
The tert-butyl 3-bromo-4-chloro-benzoate (1.00 g) obtained in Example 1 (step 1) was dissolved in 1,4-dioxane (8.6 mL). At room temperature, (4-cyano-3-fluoro-phenyl) boronic acid (509 mg), Pd(PPU4 (119 mg), and a 2 M Na$_2$CO$_3$ aqueous solution (4.3 mL) were added thereto, and the reaction solution was stirred in a microwave reactor at 120° C. for 30 minutes. The reaction solution was filtrated, and the solvent was distilled off. The residue was purified by silica gel column chromatography (mobile phase: hexane/ethyl acetate) to give tert-butyl 4-chloro-3-(4-cyano-3-fluoro-phenyl)benzoate.
Step 2
The tert-butyl 4-chloro-3-(4-cyano-3-fluoro-phenyl)benzoate (1.00 g) obtained in step 1 above was dissolved in 1,4-dioxane (15 mL). At room temperature, the 2-[2-fluoro-4-(2-methoxyethyl)phenyl]-4,4,5,5-tetramethyl-1,3,2-dioxaborolane (1.69 g) obtained in Example 20 (step 1), Pd(dba)$_2$ (138 mg), tripotassium phosphate (1.28 g), and a solution of 1 M PCy$_3$ in THF (0.30 mL) were added thereto, and the reaction solution was stirred in a microwave reactor at 160° C. for 30 minutes. After the addition of chloroform, the insoluble matter was filtered off, and the solvent was distilled off. The residue was purified by silica gel column chromatography (mobile phase: hexane/ethyl acetate), and the solvent was distilled off. The residue was dissolved in TFA (2 mL), and the solvent was distilled off. Ethyl acetate was added thereto, and the mixture was washed sequentially with water and saturated brine. After the organic layer was dried over anhydrous sodium sulfate, the solvent was distilled off to give 3-(4-cyano-3-fluoro-phenyl)-4-[2-fluoro-4-(2-methoxyethyl)phenyl]benzoic acid.
Step 3
The 3-(4-cyano-3-fluoro-phenyl)-4-[2-fluoro-4-(2-methoxyethyl)phenyl]benzoic acid (10 mg) obtained in step 2 above, tert-butyl N-[(3-endo)-8-azabicyclo[3.2.1]octan-3-yl]carbamate (5.8 mg), and HATU (19 mg) were dissolved in THF (0.5 mL). At room temperature, TEA (0.007 mL) was added thereto, followed by stirring at 50° C. overnight. The reaction solution was vacuum-concentrated, and the solvent was distilled off. The residue was purified by silica gel column chromatography (mobile phase: hexane/ethyl acetate) to give tert-butyl N-[(3-endo)-8-[3-(4-cyano-3-fluoro-phenyl)-4-[2-fluoro-4-(2-methoxyethyl)phenyl]benzoyl]-8-azabicyclo[3.2.1]octan-3-yl]carbamate.
Step 4
The tert-butyl N-[(3-endo)-8-[3-(4-cyano-3-fluoro-phenyl)-4-[2-fluoro-4-(2-methoxyethyl)phenyl]benzoyl]-8-azabicyclo[3.2.1]octan-3-yl]carbamate (10.9 mg) obtained in step 3 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 23: Synthesis of 4-[5-[(3-exo)-3-amino-8-azabicyclo[3.2.1]octane-8-carbonyl]-2-(6-fluoro-1-methyl-indol-5-yl)phenyl]-2-fluoro-benzonitrile Step 1
The tert-butyl N-[(3-exo)-8-[4-chloro-3-(4-cyano-3-fluoro-phenyl)benzoyl]-8-azabicyclo[3.2.1]octan-3-yl]carbamate (270 mg) obtained in Example 18 (step 1) was dissolved in 1,4-dioxane (2.8 mL). At room temperature, Pd(OAc)$_2$ (2.5 mg), KOAc (164 mg), bis(pinacolato)diboron (283 mg), and Silica-SMAP (4.6 mg) were added thereto, followed by stirring at 150° C. overnight. The mixture was passed through Celite, and the filtrate was vacuum-concentrated. The residue was purified by silica gel column chromatography (mobile phase: hexane/ethyl acetate) to give tert-butyl N-[(3-exo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate.
Step 2
The tert-butyl N-[(3-exo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate (10 mg) obtained in step 1 above, 5-bromo-6-fluoro-1-methyl-indole (4.8 mg), and PdCl$_2$(dppf) (0.71 mg) were suspended in 1,4-dioxane (0.5 mL). At room temperature, tripotassium phosphate (11 mg) was added thereto, followed by stirring at 125° C. for 45 minutes. After the reaction solution was filtrated, the solvent was distilled off to give tert-butyl N-[(3-exo)-8-[3-(4-cyano-3-fluoro-phenyl)-4-(6-fluoro-1-methyl-indol-5-yl)benzoyl]-8-azabicyclo[3.2.1]octan-3-yl]carbamate.
Step 3
The tert-butyl N-[(3-exo)-8-[3-(4-cyano-3-fluoro-phenyl)-4-(6-fluoro-1-methyl-indol-5-yl)benzoyl]-8-azabicyclo[3.2.1]octan-3-yl]carbamate (8 mg) obtained in step 2 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 24: Synthesis of 4-[5-[(3-exo)-3-amino-8-azabicyclo[3.2.1]octane-8-carbonyl]-2-(6-fluoro-1-methyl-indazol-5-yl)phenyl]-2-fluoro-benzonitrile Step 1
The tert-butyl N-[(3-exo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate (10 mg) obtained in Example 23 (step 1) was dissolved in 1,4-dioxane (0.5 mL). At room temperature, 5-bromo-6-fluoro-1-methyl-indazole (4.8 mg), PdCl$_2$(dppf) (0.71 mg), and tripotassium phosphate (11 mg) were added thereto, and the mixture was stirred in a microwave reactor at 125° C. for 45 minutes. The reaction solution was filtrated, and the solvent was distilled off to give tert-butyl N-[(3-exo)-8-[3-(4-cyano-3-fluoro-phenyl)-4-(6-fluoro-1-methyl-indazol-5-yl)benzoyl]-8-azabicyclo[3.2.1]octan-3-yl]carbamate.
Step 2
The tert-butyl N-[(3-exo)-8-[3-(4-cyano-3-fluoro-phenyl)-4-(6-fluoro-1-methyl-indazol-5-yl)benzoyl]-8-azabicyclo[3.2.1]octan-3-yl]carbamate (15 mg) obtained in step 1 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 25: Synthesis of 4-[5-[(3S)-3-amino-3-methyl-pyrrolidine-1-carbonyl]-2-[2-fluoro-4-(2-methoxyethyl)phenyl]phenyl]-2-fluoro-benzonitrile Step 1

The 3-(4-cyano-3-fluoro-phenyl)-4-[2-fluoro-4-(2-methoxyethyl)phenyl]benzoic acid (10 mg) obtained in Example 22 (step 2) and tert-butyl N-[(3S)-3-methylpyrrolidin-3-yl]carbamate (5.1 mg) were dissolved in THF (0.5 mL). At room temperature, TEA (0.011 mL) and HATU (19 mg) were added thereto, followed by stirring at 50° C. overnight. The reaction solution was vacuum-concentrated, and the solvent was distilled off to give tert-butyl N-[(3S)-1-[3-(4-cyano-3-fluoro-phenyl)-4-[2-fluoro-4-(2-methoxyethyl)phenyl]benzoyl]-3-methyl-pyrrolidin-3-yl]carbamate Step 2

The tert-butyl N-[(3S)-1-[3-(4-cyano-3-fluoro-phenyl)-4-[2-fluoro-4-(2-methoxyethyl)phenyl]benzoyl]-3-methyl-pyrrolidin-3-yl]carbamate (15 mg) obtained in step 1 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 26: Synthesis of 4-[5-[(3-exo)-3-amino-8-azabicyclo[3.2.1]octane-8-carbonyl]-2-[2-fluoro-4-(2-methoxyethyl)phenyl]phenyl]-2-fluoro-benzonitrile Step 1

The 3-(4-cyano-3-fluoro-phenyl)-4-[2-fluoro-4-(2-methoxyethyl)phenyl]benzoic acid (10 mg) obtained in Example 22 (step 2), and tert-butyl N-[(3-exo)-8-azabicyclo[3.2.1]octan-3-yl]carbamate (5.8 mg) were dissolved in THF (0.5 mL). At room temperature, TEA (0.011 mL) and HATU (19 mg) were added thereto, followed by stirring at 50° C. overnight. The reaction solution was vacuum-concentrated, and the solvent was distilled off to give tert-butyl N-[(3-exo)-8-[3-(4-cyano-3-fluoro-phenyl)-4-[2-fluoro-4-(2-methoxyethyl)phenyl]benzoyl]-8-azabicyclo[3.2.1]octan-3-yl]carbamate.

Step 2

The tert-butyl N-[(3-exo)-8-[3-(4-cyano-3-fluoro-phenyl)-4-[2-fluoro-4-(2-methoxyethyl)phenyl]benzoyl]-8-azabicyclo[3.2.1]octan-3-yl]carbamate (15 mg) obtained in step 1 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 27: Synthesis of 4-[5-(3,8-diazabicyclo[3.2.1]octane-8-carbonyl]-2-[2-fluoro-4-(2-methoxyethyl)phenyl]phenyl]-2-fluoro-benzonitrile The procedure of steps 1 to 4 in Example 22 was repeated using tert-butyl 3,8-diazabicyclo[3.2.1]octane-3-carboxylic acid instead of tert-butyl N-[(3-endo)-8-azabicyclo[3.2.1]octan-3-yl]carbamate to give the title compound.

Example 28: Synthesis of 4-[5-[(3-exo)-3-amino-8-azabicyclo[3.2.1]octane-8-carbonyl]-2-[2-fluoro-4-(2-hydroxy-2-methyl-propyl)phenyl]phenyl]-2-fluoro-benzonitrile Step 1

Methyl 2-(4-bromo-3-fluoro-phenyl)acetate (500 mg) was dissolved in THF (2.2 mL). At −30° C., a solution of 3 M MeMgBr in ether (5.40 mL) was added thereto dropwise, followed by stirring at room temperature overnight. The reaction solution was introduced into an aqueous ammonium chloride solution, ethyl acetate was added thereto, and the mixture was washed sequentially with water and saturated brine. After the organic layer was dried over anhydrous sodium sulfate, the solvent was distilled off. The residue was purified by silica gel column chromatography (mobile phase: ethyl acetate/hexane=10%→50%) to give 1-(4-bromo-3-fluoro-phenyl)-2-methyl-propan-2-ol.

Step 2

The tert-butyl N-[(3-exo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate (68 mg) obtained in Example 23 (step 1), the 1-(4-bromo-3-fluoro-phenyl)-2-methyl-propan-2-ol (107 mg) obtained in step 1 above, and Pd(PPh$_3$)$_4$ (6.42 mg) were suspended in 1,4-dioxane (0.93 mL). At room temperature, a 2 M Na$_2$CO$_3$ aqueous solution (0.46 mL) was added thereto, followed by stirring at 125° C. for 45 minutes. After the reaction solution was filtrated, the solvent was distilled off to give tert-butyl N-[(3-exo)-8-[3-(4-cyano-3-fluoro-phenyl)-4-[2-fluoro-4-(2-hydroxy-2-methyl-propyl)phenyl]benzoyl]-8-azabicyclo[3.2.1]octan-3-yl]carbamate.

Step 3

The tert-butyl N-[(3-exo)-8-[3-(4-cyano-3-fluoro-phenyl)-4-[2-fluoro-4-(2-hydroxy-2-methyl-propyl)phenyl]benzoyl]-8-azabicyclo[3.2.1]octan-3-yl]carbamate (90 mg) obtained in step 2 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 29: Synthesis of 4-[5-[(3S)-3-aminopyrrolidine-1-carbonyl]-2-[4-(hydroxymethyl)phenyl]phenyl]benzonitrile Step 1

[4-(4,4,5,5-Tetramethyl-1,3,2-dioxaborolan-2-yl)phenyl]methanol (500 mg) and DMAP (26 mg) were dissolved in THF (7.1 mL), followed by the addition of TEA (0.74 mL). At room temperature, acetylchloride (0.23 mL) was added thereto, followed by stirring for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give [4-(4,4,5,5-tetramethyl-1,3,2-dioxaborolan-2-yl)phenyl]methyl acetate.

Step 2

The tert-butyl N-[(3S)-1-[4-chloro-3-(4-cyanophenyl)benzoyl]pyrrolidin-3-yl]carbamate (100 mg) obtained in Example 9 (step 2) and the [4-(4,4,5,5-tetramethyl-1,3,2-dioxaborolan-2-yl)phenyl]methyl acetate (130 mg) obtained in step 1 above were dissolved in 1,4-dioxane (1.2 mL). At room temperature, Pd(dba)$_2$ (6.8 mg), tripotassium phosphate (100 mg), and a solution of 1 M PCy$_3$ in THF (0.02 mL) were added thereto, and the mixture was stirred in a microwave reactor at 160° C. for 1 hour. The reaction solution was filtered through NH-silica gel, and the solvent of the filtrate was distilled off. The residue was purified by silica gel column chromatography (mobile phase: ethyl acetate/hexane=30%→100%) to give [4-[4-[(3S)-3-(tert-butoxycarbonylamino)pyrrolidine-1-carbonyl]-2-(4-cyanophenyl)phenyl]phenyl]methyl acetate.

Step 3

The [4-[4-[(3S)-3-(tert-butoxycarbonylamino)pyrrolidine-1-carbonyl]-2-(4-cyanophenyl)phenyl]phenyl]methyl acetate (100 mg) obtained in step 2 above was dissolved in MeOH (2 mL). At room temperature, $K_2CO_3$ (65 mg) was added thereto, followed by stirring at room temperature for 30 minutes. Chloroform was added thereto, the mixture was washed sequentially with a saturated aqueous ammonium chloride solution and saturated brine, and dried over anhydrous sodium sulfate, and the solvent was distilled off. The residue was purified by silica gel column chromatography (mobile phase: ethyl acetate/hexane=40%→100%) to give tert-butyl N-[(3S)-1-[3-(4-cyanophenyl)-4-[4-(hydroxymethyl)phenyl]benzoyl]pyrrolidin-3-yl]carbamate.

Step 4

The tert-butyl N-[(3S)-1-[3-(4-cyanophenyl)-4-[4-(hydroxymethyl)phenyl]benzoyl]pyrrolidin-3-yl]carbamate (15 mg) obtained in step 3 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 30: Synthesis of 4-[5-[(3S)-3-aminopyrrolidine-1-carbonyl]-2-[4-(2-methoxyethyl)phenyl]phenyl]benzonitrile Step 1

1-Bromo-4-(2-methoxyethyl)benzene (450 mg) was dissolved in 1,4-dioxane (5.2 mL). Then, bis(pinacolato)diboron (797 mg), KOAc (411 mg), and $PdCl_2(dppf)$ (77 mg) were added thereto, followed by stirring at 90° C. overnight. Ethyl acetate was added thereto, the mixture was passed through Celite, and the filtrate was washed sequentially with water and saturated brine. After the organic layer was dried over anhydrous sodium sulfate, the solvent was distilled off. The residue was purified by silica gel column chromatography (mobile phase: ethyl acetate/hexane=2%→20%) to give 2-[4-(2-methoxyethyl)phenyl]-4,4,5,5-tetramethyl-1,3,2-dioxaborolane.

Step 2

The tert-butyl N-[(3S)-1-[4-chloro-3-(4-cyanophenyl)benzoyl]pyrrolidin-3-yl]carbamate (300 mg) obtained in Example 9 (step 2) and the 2-[4-(2-methoxyethyl)phenyl]-4,4,5,5-tetramethyl-1,3,2-dioxaborolane (369 mg) obtained in step 1 above were dissolved in 1,4-dioxane (2 mL). At room temperature, $Pd(dba)_2$ (32 mg), tripotassium phosphate (300 mg), and a solution of 1 M $PCy_3$ in THF (0.07 mL) were added thereto, and the mixture was stirred in a microwave reactor at 160° C. for 45 minutes. The reaction solution was passed through Celite, and the solvent of the filtrate was distilled off. The residue was purified by reversed-phase HPLC (mobile phase: water/acetonitrile) to give tert-butyl N-[(3S)-1-[3-(4-cyanophenyl)-4-[4-(2-methoxyethyl)phenyl]benzoyl]pyrrolidin-3-yl]carbamate.

Step 3

The tert-butyl N-[(3S)-1-[3-(4-cyanophenyl)-4-[4-(2-methoxyethyl)phenyl]benzoyl]pyrrolidin-3-yl]carbamate (15 mg) obtained in step 2 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 31: Synthesis of 4-[5-[(3S)-3-aminopyrrolidine-1-carbonyl]-2-[4-(2-hydroxyethyl)phenyl]phenyl]benzonitrile The procedure of steps 1 to 4 in Example 29 was repeated using 2-[4-(4,4,5,5-tetramethyl-1,3,2-dioxaborolan-2-yl)phenyl]ethanol instead of [4-(4,4,5,5-tetramethyl-1,3,2-dioxaborolan-2-yl)phenyl]methanol to give the title compound.

Example 32: Synthesis of 4-[5-[(3S)-3-aminopyrrolidine-1-carbonyl]-2-[4-(3-hydroxypropyl)phenyl]phenyl]benzonitrile The procedure of steps 1 to 4 in Example 29 was repeated using 3-[4-(4,4,5,5-tetramethyl-1,3,2-dioxaborolan-2-yl)phenyl]propan-1-ol instead of [4-(4,4,5,5-tetramethyl-1,3,2-dioxaborolan-2-yl)phenyl]methanol to give the title compound.

Example 33: Synthesis of 4-[5-[(3S)-3-aminopyrrolidine-1-carbonyl]-2-[4-[1-(hydroxymethyl)cyclopropyl]phenyl]phenyl]benzonitrile The procedure of steps 1 to 5 in Example 9 was repeated using (1-(4-bromophenyl)cyclopropyl)methanol instead of 1-bromo-2-chloro-4-methyl-benzene to give the title compound.

Example 34: Synthesis of 4-[5-[(3S)-3-aminopyrrolidine-1-carbonyl]-2-[4-(2-hydroxy-2-methyl-propyl)phenyl]phenyl]benzonitrile The procedure of steps 1 to 5 in Example 9 was repeated using 1-(4-bromophenyl)-2-methylpropan-2-ol instead of 1-bromo-2-chloro-4-methyl-benzene to give the title compound.

Example 35: Synthesis of 4-[5-[(3S)-3-aminopyrrolidine-1-carbonyl]-2-[4-(2-hydroxypropoxy)phenyl]phenyl]benzonitrile Step 1

The procedure of step 1 in Example 12 was repeated using (4-benzyloxyphenyl)boronic acid instead of 4-methyl-2-nitrophenylboronic acid pinacol ester to give tert-butyl N-[(3S)-1-[4-(4-benzyloxyphenyl)-3-(4-cyanophenyl)benzoyl]pyrrolidin-3-yl]carbamate.

Step 2

The tert-butyl N-[(3S)-1-[4-(4-benzyloxyphenyl)-3-(4-cyanophenyl)benzoyl]pyrrolidin-3-yl]carbamate (800 mg) obtained in step 1 above and palladium hydroxide-carbon (160 mg) were suspended in EtOH (20 mL), and hydrogen substitution was carried out, followed by stirring at room temperature for 6 hours. The reaction solution was passed through Celite, and the solvent was distilled off. The residue was purified by silica gel column chromatography (mobile phase: hexane/ethyl acetate) to give tert-butyl N-[(3S)-1-[3-(4-cyanophenyl)-4-(4-hydroxyphenyl)benzoyl]pyrrolidin-3-yl]carbamate.

Step 3

The tert-butyl N-[(3S)-1-[3-(4-cyanophenyl)-4-(4-hydroxyphenyl)benzoyl]pyrrolidin-3-yl]carbamate (15 mg) obtained in step 2 above was dissolved in DMF (0.5 mL). At room temperature, K₂CO₃ (6.4 mg) and 2-methyloxirane (5.4 mg) were added thereto, followed by stirring at 120° C. for 2 hours. Ethyl acetate was added thereto, the resulting mixture was washed sequentially with water and saturated brine, and dried over anhydrous sodium sulfate, and the solvent was distilled off. The residue was purified by silica gel column chromatography (mobile phase: hexane/ethyl acetate) to give tert-butyl N-[(3S)-1-[3-(4-cyanophenyl)-4-[4-(2-hydroxypropoxy)phenyl]benzoyl]pyrrolidin-3-yl]carbamate.

Step 4

The tert-butyl N-[(3S)-1-[3-(4-cyanophenyl)-4-[4-(2-hydroxypropoxy)phenyl]benzoyl]pyrrolidin-3-yl]carbamate (15 mg) obtained in step 3 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 36: Synthesis of 4-[5-[(3S)-3-aminopyrrolidine-1-carbonyl]-2-(2-fluoro-4-methyl-phenyl)phenyl]-2-fluoro-benzonitrile The procedure of steps 1 to 3 in Example 16 was repeated using (2-fluoro-4-methyl-phenyl)boronic acid instead of p-tolylboronic acid to give the title compound.

Example 37: Synthesis of 4-[5-[(3S)-3-aminopyrrolidine-1-carbonyl]-2-[2-fluoro-4-(2-hydroxy-2-methyl-propyl)phenyl]phenyl]-2-fluoro-benzonitrile Step 1

The tert-butyl N-[(3S)-1-[4-chloro-3-(4-cyano-3-fluorophenyl)benzoyl]pyrrolidin-3-yl]carbamate (4 g) obtained in Example 16 (step 1) was dissolved in 1,4-dioxane (45 mL). At room temperature, Pd(OAc)₂ (0.40 g), KOAc (2.7 g), bis(pinacolato)diboron (4.6 g), and Silica-SMAP (0.72 g) were added thereto, followed by stirring at 150° C. for 18 hours. The reaction solution was filtrated, and the solvent was distilled off. The residue was purified by silica gel column chromatography (mobile phase: hexane/ethyl acetate) to give tert-butyl N-[(3S)-1-[3-(4-cyano-3-fluorophenyl)-4-(4,4,5,5-tetramethyl-1,3,2-dioxaborolan-2-yl)benzoyl]pyrrolidin-3-yl]carbamate.

Step 2

The tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate (30 mg) obtained in step 1 above and the 1-(4-bromo-3-fluoro-phenyl)-2-methyl-propan-2-ol (28 mg) obtained in Example 28 (step 1) were dissolved in 1,4-dioxane (0.8 mL). At room temperature, Pd(PPh₃)₄ (3.2 mg) and a 2 M Na₂CO₃ aqueous solution (0.4 mL) were added thereto, and the mixture was stirred in a microwave reactor at 120° C. for 30 minutes. The reaction solution was filtrated, and the solvent was distilled off. Ethyl acetate was added thereto, the resulting mixture was washed sequentially with water and saturated brine, and dried over anhydrous sodium sulfate, and the solvent was distilled off. The residue was purified by silica gel column chromatography (mobile phase: chloroform/methanol) to give tert-butyl N-[(3S)-1-[3-(4-cyano-3-fluoro-phenyl)-4-[2-fluoro-4-(2-hydroxy-2-methyl-propyl)phenyl]benzoyl]pyrrolidin-3-yl]carbamate.

Step 3

The tert-butyl N-[(3S)-1-[3-(4-cyano-3-fluoro-phenyl)-4-[2-fluoro-4-(2-hydroxy-2-methyl-propyl)phenyl]benzoyl]pyrrolidin-3-yl]carbamate (20 mg) obtained in step 2 above was dissolved in MeOH (1 mL). At room temperature, a 12 M HCl aqueous solution (1 mL) was added thereto, followed by stirring at room temperature for 30 minutes. The reaction solution was neutralized by the addition of water (1 mL) and a 2 M aqueous sodium hydroxide solution (6 mL). Chloroform was added thereto, the mixture was washed sequentially with water and saturated brine, and dried over anhydrous sodium sulfate. Thereafter, the solvent was distilled off to give the title compound.

Example 38: Synthesis of 2-fluoro-4-[2-[2-fluoro-4-(2-methoxyethyl)phenyl]-5-(9-oxa-2,6-diazaspiro[3.5]nonane-2-carbonyl)phenyl]benzonitrile The procedure of steps 1 to 4 in Example 22 was repeated using tert-butyl 9-oxa-2,6-diazaspiro[3.5]nonane-6-carboxylic acid instead of tert-butyl N-[(3-endo)-8-azabicyclo[3.2.1]octan-3-yl]carbamate to give the title compound.

Example 39: Synthesis of 4-[5-(2,3,3a,4,6,6a-hexahydro-1H-pyrrolo[3,4-c]pyrrole-5-carbonyl)-2-[2-fluoro-4-(2-methoxyethyl)phenyl]phenyl]-2-fluoro-benzonitrile The procedure of steps 1 to 4 in Example 22 was repeated using tert-butyl 2,3,3a,4,6,6a-hexahydro-1H-pyrrolo[3,4-c]pyrrole-5-carboxylic acid instead of tert-butyl N-[(3-endo)-8-azabicyclo[3.2.1]octan-3-yl]carbamate to give the title compound.

Example 40: 4-[5-[(3S)-3-aminopyrrolidine-1-carbonyl]-2-[4-(2-hydroxy-2-methyl-propyl)phenyl]phenyl]-2-fluoro-benzonitrile The procedure of steps 1 to 3 in Example 37 was repeated using 1-(4-bromophenyl)-2-methylpropan-2-ol instead of 1-(4-bromo-3-fluoro-phenyl)-2-methyl-propan-2-ol to give the title compound.

Example 41: Synthesis of 4-[5-[(3-endo)-3-amino-8-azabicyclo[3.2.1]octane-8-carbonyl]-2-[2-fluoro-4-(2-hydroxy-2-methyl-propyl)phenyl]phenyl]-2-fluoro-benzonitrile Step 1

The tert-butyl 4-chloro-3-(4-cyano-3-fluoro-phenyl)benzoate (300 mg) obtained in Example 22 (step 1) was dissolved in 1,4-dioxane (5 mL). At room temperature, Pd(OAc)₂ (40 mg), KOAc (300 mg), bis(pinacolato)diboron (500 mg), and Silica-SMAP (50 mg) were added thereto, followed by stirring at 100° C. for 26 hours. The reaction solution was filtrated, and the solvent was distilled off. The residue was purified by silica gel column chromatography (mobile phase: hexane/ethyl acetate) to give tert-butyl 3-(4-cyano-3-fluoro-phenyl)-4-(4,4,5,5-tetramethyl-1,3,2-dioxaborolan-2-yl)benzoate.

Step 2

The tert-butyl 3-(4-cyano-3-fluoro-phenyl)-4-(4,4,5,5-tetramethyl-1,3,2-dioxaborolan-2-yl)benzoate (100 mg) obtained in step 1 above was dissolved in DCM (1.2 mL). At room temperature, TFA (1.00 mL) was added thereto, followed by stirring at room temperature for 30 minutes. The reaction solution was vacuum-concentrated, and the solvent was distilled off. Chloroform was added thereto, the mixture was washed with water and dried over anhydrous sodium sulfate, and the solvent was distilled off to give 3-(4-cyano-3-fluoro-phenyl)-4-(4,4,5,5-tetramethyl-1,3,2-dioxaborolan-2-yl)benzoic acid.

Step 3

The 3-(4-cyano-3-fluoro-phenyl)-4-(4,4,5,5-tetramethyl-1,3,2-dioxaborolan-2-yl)benzoic acid (500 mg) obtained in step 2 above and tert-butyl N-[(3-endo)-8-azabicyclo[3.2.1]octan-3-yl]carbamate (308 mg) were dissolved in THF (4.5 mL). At room temperature, TEA (0.57 mL) and HATU (1 g) were added thereto, followed by stirring at 50° C. for 1 hour. The reaction solution was vacuum-concentrated, and the residue was purified by silica gel column chromatography (mobile phase: hexane/ethyl acetate) to give tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate.

Step 4

The tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate (30 mg) obtained in step 3 above and the 1-(4-bromo-3-fluoro-phenyl)-2-methyl-propan-2-ol (19 mg) obtained in Example 28 (step 1) were dissolved in 1,4-dioxane (0.5 mL). At room temperature, Pd(PPh$_3$)$_4$ (18 mg) and a 2 M Na CO$_3$ aqueous solution (0.3 mL) were added thereto, and the mixture was stirred in a microwave reactor at 120° C. for 30 minutes. The supernatant of the reaction solution was collected and filtered through NH-silica gel, and the solvent was distilled off to give tert-butyl-N-[(3-endo)-8-[3-(4-cyano-3-fluoro-phenyl)-4-[2-fluoro-4-(2-hydroxy-2-methyl-propyl)phenyl]benzoyl]-8-azabicyclo[3.2.1]octan-3-yl]carbamate.

Step 5

The tert-butyl-N-[(3-endo)-8-[3-(4-cyano-3-fluoro-phenyl)-4-[2-fluoro-4-(2-hydroxy-2-methyl-propyl)phenyl]benzoyl]-8-azabicyclo[3.2.1]octan-3-yl]carbamate (15 mg) obtained in step 4 above was dissolved in MeOH (0.5 mL). At room temperature, a 12 M HCl aqueous solution (0.5 mL) was added thereto, followed by stirring at room temperature for 30 minutes. Then, water and a 2 M aqueous sodium hydroxide solution (3 mL) were added thereto, and the mixture was partitioned and extracted with chloroform. After the organic layer was dried over anhydrous sodium sulfate, the solvent was distilled off. The residue was purified by reversed-phase HPLC (mobile phase: water/acetonitrile) to give the title compound.

Example 42: Synthesis of 4-[5-[(3S)-3-(methylamino)pyrrolidine-1-carbonyl]-2-(p-tolyl)phenyl]benzonitrile The procedure of steps 1 to 5 in Example 1 was repeated using (S)-tert-butyl methyl(pyrrolidin-3-yl)carbamate instead of tert-butyl N-[(3S)-pyrrolidin-3-yl]carbamate to give the title compound.

Example 43: Synthesis of 4-[5-[(3S)-3-aminopyrrolidine-1-carbonyl]-2-(4-benzyloxyphenyl)phenyl]benzonitrile The procedure of steps 1 to 5 in Example 9 was repeated using 1-(benzyloxy)-4-bromobenzene instead of 1-bromo-2-chloro-4-methyl-benzene to give the title compound.

Example 44: Synthesis of 1-[4-[4-[(3S)-3-aminopyrrolidine-1-carbonyl]-2-(4-cyanophenyl)phenyl]phenyl]-N-phenylcyclopropanecarboxamide The procedure of steps 1 to 5 in Example 9 was repeated using 1-(4-bromophenyl)-N-phenylcyclopropanecarboxamide instead of 1-bromo-2-chloro-4-methyl-benzene to give the title compound.

Example 45: Synthesis of 2-[4-[4-[(3S)-3-aminopyrrolidine-1-carbonyl]-2-(4-cyanophenyl)phenyl]phenyl]ethyl acetate Step 1

The procedure of step 1 in Example 29 was repeated using 2-(4-(4,4,5,5-tetramethyl-1,3,2-dioxaborolan-2-yl)phenyl)ethanol instead of [4-(4,4,5,5-tetramethyl-1,3,2-dioxaborolan-2-yl)phenyl]methanol to give 4-(4,4,5,5-tetramethyl-1,3,2-dioxaborolan-2-yl)phenethyl acetate.

Step 2

The procedure of steps 1 to 2 in Example 12 was repeated using the 4-(4,4,5,5-tetramethyl-1,3,2-dioxaborolan-2-yl)phenethyl acetate obtained in step 1 above instead of 4-methyl-2-nitrophenylboronic acid pinacol ester to give the title compound.

Example 46: Synthesis of 4-[2-[4-(2-hydroxyethyl)phenyl]-5-[(3S)-3-(methylamino)pyrrolidine-1-carbonyl]phenyl]benzonitrile Step 1

The procedure of steps 1 to 5 in Example 1 was repeated using the 4-(4,4,5,5-tetramethyl-1,3,2-dioxaborolan-2-yl)phenethyl acetate obtained in Example 45 (step 1) instead of p-tolylboronic acid, and using (S)-tert-butyl methyl(pyrrolidin-3-yl)carbamate instead of tert-butyl N-[(3S)-pyrrolidin-3-yl]carbamate to give 2-[4-[2-(4-cyanophenyl)-4-[(3S)-3-(methylamino)pyrrolidine-1-carbonyl]phenyl]phenyl]ethyl acetate.

Step 2

The procedure of step 3 in Example 29 was repeated using the 2-[4-[2-(4-cyanophenyl)-4-[(3S)-3-(methylamino)pyrrolidine-1-carbonyl]phenyl]phenyl]ethyl acetate obtained in step 1 above instead of [4-[4-[(3S)-3-(tert-butoxycarbonylamino)pyrrolidine-1-carbonyl]-2-(4-cyanophenyl)phenyl]phenyl]methyl acetate to give the title compound.

Example 47: Synthesis of 4-[2-[4-(2-methoxyethyl)phenyl]-5-[(3S)-3-(methylamino)pyrrolidine-1-carbonyl]phenyl]benzonitrile Step 1

The procedure of steps 1 to 5 in Example 1 was repeated using (4-(2-methoxyethyl)phenyl)boronic acid instead of p-tolylboronic acid, and using (S)-tert-butyl methyl(pyrrolidin-3-yl)carbamate instead of tert-butyl N-[(3S)-pyrrolidin-3-yl]carbamate to give the title compound.

Example 48: Synthesis of 4-[5-[(3S)-3-(dimethylamino)pyrrolidine-1-carbonyl]-2-[4-[1-(hydroxymethyl)cyclopropyl]phenyl]phenyl]benzonitrile The procedure of steps 1 to 4 in Example 1 was repeated using [4-[1-(hydroxymethyl)cyclopropyl]phenyl]boronic acid instead of p-tolylboronic acid, and using (S)-N,N- dimethylpyrrolidin-3-amine instead of tert-butyl N-[(3S)-pyrrolidin-3-yl]carbamate to give the title compound.

Example 49: Synthesis of 4-[5-[(3S)-3-aminopyrrolidine-1-carbonyl]-2-(3-fluoro-4-methyl-phenyl)phenyl]benzonitrile The procedure of steps 1 to 2 in Example 12 was repeated using (3-fluoro-4-methyl-phenyl)boronic acid instead of 4-methyl-2-nitrophenylboronic acid pinacol ester to give the title compound.

Example 50: Synthesis of 4-[5-[(3S)-3-aminopyrrolidine-1-carbonyl]-2-(4-chlorophenyl)phenyl]benzonitrile The procedure of steps 1 to 5 in Example 9 was repeated using 1-bromo-4-chloro-benzene instead of 1-bromo-2-chloro-4-methyl-benzene to give the title compound.

Example 51: Synthesis of 4-[5-[(3S)-3-aminopyrrolidine-1-carbonyl]-2-(4-bromophenyl)phenyl]benzonitrile The procedure of steps 1 to 5 in Example 9 was repeated using 1,4-dibromobenzene instead of 1-bromo-2-chloro-4-methyl-benzene to give the title compound.

Example 52: Synthesis of 5'-((1S,4S)-2,5-diazabicyclo[2.2.1]heptane-2-carbonyl)-4''-methyl-[1,1':2',1''-terphenyl]-4-carbonitrile The procedure of steps 1 to 5 in Example 1 was repeated using tert-butyl (1S,4S)-2,5-diazabicyclo[2.2.1]heptane-2-carboxylate instead of tert-butyl N-[(3S)-pyrrolidin-3-yl]carbamate to give the title compound.

Example 53: Synthesis of 4-[2-[4-(2-aminoethyl)phenyl]-5-[(3S)-3-aminopyrrolidine-1-carbonyl]phenyl]benzonitrile Step 1
The tert-butyl N-[(3S)-1-[3-(4-cyanophenyl)-4-(4,4,5,5-tetramethyl-1,3,2-dioxaborolan-2-yl)benzoyl]pyrrolidin-3-yl]carbamate (50 mg) obtained in Example 9 (step 3) was dissolved in 1,4-dioxane (0.48 mL). At room temperature, 2-(4-bromophenyl)ethanamine (29 mg), Pd(PPh$_3$)$_4$ (3.4 mg), and a 2 M Na CO$_3$ aqueous solution (0.24 mL) were added thereto, and the mixture was stirred in a microwave reactor at 120° C. for 30 minutes. The residue was purified by silica gel column chromatography (mobile phase: hexane/ethyl acetate) to give tert-butyl N-[(3S)-1-[4-[4-(2-aminoethyl)phenyl]-3-(4-cyanophenyl)benzoyl]pyrrolidin-3-yl]carbamate.
Step 2
The tert-butyl N-[(3S)-1-[4-[4-(2-aminoethyl)phenyl]-3-(4-cyanophenyl)benzoyl]pyrrolidin-3-yl]carbamate (15 mg) obtained in step 1 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 54: Synthesis of 4-[5-[(3S)-3-aminopyrrolidine-1-carbonyl]-2-(4-iodophenyl)phenyl]benzonitrile The procedure of steps 1 to 5 in Example 9 was repeated using 1,4-diiodobenzene instead of 1-bromo-2-chloro-4-methyl-benzene to give the title compound.

Example 55: Synthesis of N-[2-[4-[4-[(3S)-3-aminopyrrolidine-1-carbonyl]-2-(4-cyanophenyl)phenyl]phenyl]ethyl]acetamide The tert-butyl N-[(3S)-1-[4-[4-(2-aminoethyl)phenyl]-3-(4-cyanophenyl)benzoyl]pyrrolidin-3-yl]carbamate (15 mg) obtained in Example 53 (step 1) was dissolved in THF. At room temperature, TEA (0.02 mL) and then acetylchloride (4.6 mg) were added thereto, followed by stirring at room temperature for 1 hour. TFA was added to the residue, and the progress of the reaction was confirmed with LCMS, followed by vacuum concentration. The residue was purified by reversed-phase HPLC (mobile phase: water/acetonitrile) to give the title compound.

Example 56: Synthesis of 4-[5-[(3S)-3-aminopyrrolidine-1-carbonyl]-2-(4-propylphenyl)phenyl]benzonitrile The procedure of steps 1 to 2 in Example 12 was repeated using (4-propylphenyl)boronic acid instead of 4-methyl-2-nitrophenylboronic acid pinacol ester to give the title compound.

Example 57: Synthesis of 4-[5-[(3S)-3-aminopyrrolidine-1-carbonyl]-2-(2-naphthyl)phenyl]benzonitrile The procedure of steps 1 to 2 in Example 12 was repeated using 2-naphthyl boronic acid instead of 4-methyl-2-nitrophenylboronic acid pinacol ester to give the title compound.

Example 58: Synthesis of 4-[2-[4-[1-(hydroxymethyl)cyclopropyl]phenyl]-5-[(3S)-3-(methylamino)pyrrolidine-1-carbonyl]phenyl]benzonitrile The procedure of steps 1 to 5 in Example 1 was repeated using [4-[1-(hydroxymethyl)cyclopropyl]phenyl]boronic acid instead of p-tolylboronic acid, and using (S)-tert-butyl methyl(pyrrolidin-3-yl)carbamate instead of tert-butyl N-[(3S)-pyrrolidin-3-yl]carbamate to give the title compound.

Example 59: Synthesis of 4-[5-[(3S)-3-aminopyrrolidine-1-carbonyl]-2-[4-[(1-hydroxycyclopropyl)methyl]phenyl]phenyl]benzonitrile The procedure of steps 1 to 5 in Example 9 was repeated using 1-[(4-bromophenyl)methyl]cyclopropanol instead of 1-bromo-2-chloro-4-methyl-benzene to give the title compound.

Example 60: Synthesis of 4-[5-[(3S)-3-aminopyrrolidine-1-carbonyl]-2-[4-(2-methylprop-1-enyl)phenyl]phenyl]benzonitrile The procedure of steps 1 to 5 in Example 9 was repeated using 1-bromo-4-(2-methylprop-1-enyl)benzene instead of 1-bromo-2-chloro-4-methyl-benzene to give the title compound.

Example 61: Synthesis of 4-[5-[(3S)-3-aminopyrrolidine-1-carbonyl]-2-[4-(3-hydroxy-3-methyl-butyl)phenyl]phenyl]benzonitrile The procedure of steps 1 to 5 in Example 9 was repeated using 4-(4-bromophenyl)-2-methyl-butan-2-ol instead of 1-bromo-2-chloro-4-methyl-benzene to give the title compound.

Example 62: Synthesis of 4-[5-[(3S)-3-aminopyrrolidine-1-carbonyl]-2-[4-[2-(1-hydroxycyclopropyl)ethyl]phenyl]phenyl]benzonitrile The procedure of steps 1 to 5 in Example 9 was repeated using 1-[2-(4-bromophenyl)ethyl]cyclopropanol instead of 1-bromo-2-chloro-4-methyl-benzene to give the title compound.

Example 63: Synthesis of 4-[5-[(3S)-3-aminopyrrolidine-1-carbonyl]-2-[4-(2-hydroxyethyl)phenyl]phenyl]-2-fluoro-benzonitrile The procedure of steps 1 to 3 in Example 37 was repeated using 2-(4-bromophenyl)ethanol instead of 1-(4-bromo-3-fluoro-phenyl)-2-methyl-propan-2-ol to give the title compound.

Example 64: Synthesis of 4-[5-[(3S)-3-aminopyrrolidine-1-carbonyl]-2-[2-fluoro-4-(2-hydroxy-2-methyl-propyl)phenyl]phenyl]benzonitrile The procedure of steps 1 to 5 in Example 9 was repeated using the 1-(4-bromo-3-fluoro-phenyl)-2-methyl-propan-2-ol obtained in Example 28 (step 1) instead of 1-bromo-2-chloro-4-methyl-benzene to give the title compound.

Example 65: Synthesis of 4-[5-[(3S)-3-aminopyrrolidine-1-carbonyl]-2-[4-(3-hydroxy-3-methyl-butyl)phenyl]phenyl]-2-fluoro-benzonitrile The procedure of steps 1 to 3 in Example 16 was repeated using 2-methyl-4-[4-(4,4,5,5-tetramethyl-1,3,2-dioxaborolan-2-yl)phenyl]butan-2-ol instead of p-tolylboronic acid to give the title compound.

Example 66: Synthesis of 4-[5-[(3S)-3-aminopyrrolidine-1-carbonyl]-2-[4-[1-(methoxymethyl)cyclopropyl]phenyl]phenyl]benzonitrile The procedure of steps 1 to 5 in Example 9 was repeated using 1-bromo-4-[1-(methoxymethyl)cyclopropyl]benzene instead of 1-bromo-2-chloro-4-methyl-benzene to give the title compound.

Example 67: Synthesis of 4-[5-[(3S)-3-aminopyrrolidine-1-carbonyl]-2-[2-fluoro-4-[(1-hydroxycyclopropyl)methyl]phenyl]benzonitrile Step 1
Methyl-2-(4-bromo-3-fluoro-phenyl)acetate (500 mg) and titanium isopropoxide (0.84 mL) were dissolved in THF (5 mL). At 0° C., a solution of 3 M EtMgBr in diethyl ether (1.9 mL) was added thereto dropwise, followed by stirring at room temperature overnight. Ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give 1-[(4-bromo-3-fluoro-phenyl)methyl]cyclopropanol.
Step 2
The procedure of steps 1 to 5 in Example 9 was repeated using the 1-[(4-bromo-3-fluoro-phenyl)methyl]cyclopropanol obtained in step 1 above instead of 1-bromo-2-chloro-4-methyl-benzene to give the title compound.

Example 68: Synthesis of 4-[5-[(3S)-3-aminopyrrolidine-1-carbonyl]-2-[4-[1-(1-hydroxycyclopropyl)cyclopropyl]phenyl]phenyl]benzonitrile Step 1
The procedure of step 1 in Example 67 was repeated using methyl 1-(4-bromophenyl)cyclopropanecarboxylic acid instead of methyl-2-(4-bromo-3-fluoro-phenyl)acetate to give 1-[1-(4-bromophenyl)cyclopropyl]cyclopropanol.
Step 2
The procedure of steps 1 to 5 in Example 9 was repeated using the 1-[1-(4-bromophenyl)cyclopropyl]cyclopropanol obtained in step 1 above instead of 1-bromo-2-chloro-4-methyl-benzene to give the title compound.

Example 69: Synthesis of 4-[5-[(3S)-3-aminopyrrolidine-1-carbonyl]-2-[4-(2-methoxyethyl)phenyl]phenyl]-2-fluoro-benzonitrile The procedure of steps 1 to 3 in Example 16 was repeated using the 2-[4-(2-methoxyethyl)phenyl]-4,4,5,5-tetramethyl-1,3,2-dioxaborolane obtained in Example 30 (step 1) instead of p-tolylboronic acid to give the title compound.

Example 70: Synthesis of 4-[5-[(3S)-3-aminopyrrolidine-1-carbonyl]-2-[2-fluoro-4-(2-hydroxyethyl)phenyl]phenyl]benzonitrile The procedure of steps 1 to 5 in Example 9 was repeated using 2-(4-bromo-3-fluoro-phenyl)ethanol instead of 1-bromo-2-chloro-4-methyl-benzene to give the title compound.

Example 71: Synthesis of 4-[5-[(3S)-3-aminopyrrolidine-1-carbonyl]-2-[2-fluoro-4-(2-methoxyethyl)phenyl]phenyl]benzonitrile The procedure of steps 1 to 5 in Example 9 was repeated using 1-bromo-2-fluoro-4-(2-methoxyethyl)benzene instead of 1-bromo-2-chloro-4-methyl-benzene to give the title compound.

Example 72: Synthesis of 4-[5-[(3S)-3-aminopyrrolidine-1-carbonyl]-2-[4-(2-hydroxy-1,1-dimethyl-ethyl)phenyl]phenyl]benzonitrile The procedure of steps 1 to 5 in Example 9 was repeated using 2-(4-bromophenyl)-2-methyl-propan-1-ol instead of 1-bromo-2-chloro-4-methyl-benzene to give the title compound.

Example 73: Synthesis of 4-[5-[(3S)-3-aminopyrrolidine-1-carbonyl]-2-[4-(2-fluoroethyl)phenyl]phenyl]benzonitrile The procedure of steps 1 to 5 in Example 9 was repeated using 1-bromo-4-(2-fluoroethyl)benzene instead of 1-bromo-2-chloro-4-methyl-benzene to give the title compound.

Example 74: Synthesis of 4-[5-(2,7-diazaspiro[3.4]octane-7-carbonyl)-2-[2-fluoro-4-(2-methoxyethyl)phenyl]phenyl]-2-fluoro-benzonitrile The procedure of steps 1 to 4 in Example 22 was repeated using tert-butyl 2,7-diazaspiro[3.4]octane-2-carboxylic acid instead of tert-butyl N-[(3-endo)-8-azabicyclo[3.2.1]octan-3-yl]carbamate to give the title compound.

Example 75: Synthesis of 4-[5-(2,8-diazaspiro[3.5]nonane-2-carbonyl)-2-[2-fluoro-4-(2-methoxyethyl)phenyl]phenyl]-2-fluoro-benzonitrile The procedure of steps 1 to 4 in Example 22 was repeated using tert-butyl 2,8-diazaspiro[3.5]nonane-8-carboxylic acid instead of tert-butyl N-[(3-endo)-8-azabicyclo[3.2.1]octan-3-yl]carbamate to give the title compound.

Example 76: Synthesis of 4-[5-(2,7-diazaspiro[3.4]octane-7-carbonyl)-2-[2-fluoro-4-(2-hydroxy-2-methyl-propyl)phenyl]phenyl]-2-fluoro-benzonitrile The procedure of steps 1 to 5 in Example 41 was repeated using tert-butyl 2,7-diazaspiro[3.4]octane-2-carboxylic acid instead of tert-butyl N-[(3-endo)-8-azabicyclo[3.2.1]octan-3-yl]carbamate to give the title compound.

Example 77: Synthesis of 4-[5-(2,8-diazaspiro[3.5]nonane-2-carbonyl)-2-[2-fluoro-4-(2-hydroxy-2-methyl-propyl)phenyl]phenyl]-2-fluoro-benzonitrile The procedure of steps 1 to 5 in Example 41 was repeated using tert-butyl 2,8-diazaspiro[3.5]nonane-8-carboxylic acid instead of tert-butyl N-[(3-endo)-8-azabicyclo[3.2.1]octan-3-yl]carbamate to give the title compound.

Example 78: Synthesis of 4-[5-(3,8-diazaspiro[4.5]decane-8-carbonyl)-2-[2-fluoro-4-(2-methoxyethyl)phenyl]phenyl]-2-fluoro-benzonitrile hydrochloride The procedure of steps 1 to 4 in Example 22 was repeated using tert-butyl 3,8-diazaspiro[4.5]decane-3-carboxylic acid instead of tert-butyl N-[(3-endo)-8-azabicyclo[3.2.1]octan-3-yl]carbamate to give the title compound.

Example 79: Synthesis of 4-[5-(2,8-diazaspiro[3.5]nonane-8-carbonyl)-2-[2-fluoro-4-(2-methoxyethyl)phenyl]phenyl]-2-fluoro-benzonitrile The procedure of steps 1 to 4 in Example 22 was repeated using tert-butyl 2,8-diazaspiro[3.5]nonane-2-carboxylic acid instead of tert-butyl N-[(3-endo)-8-azabicyclo[3.2.1]octan-3-yl]carbamate to give the title compound.

Example 80: Synthesis of 4-[5-(1,4-diazepane-1-carbonyl)-2-[2-fluoro-4-(2-methoxyethyl)phenyl]phenyl]-2-fluoro-benzonitrile hydrochloride The procedure of steps 1 to 4 in Example 22 was repeated using tert-butyl-1,4-diazepane-1-carboxylic acid instead of tert-butyl N-[(3-endo)-8-azabicyclo[3.2.1]octan-3-yl]carbamate to give the title compound.

Example 81: Synthesis of 4-[5-(3,7-diazaspiro[3.4]octane-7-carbonyl)-2-[2-fluoro-4-(2-methoxyethyl)phenyl]phenyl]-2-fluoro-benzonitrile The procedure of steps 1 to 4 in Example 22 was repeated using tert-butyl-3,7-diazaspiro[3.4]octane-3-carboxylic acid instead of tert-butyl N-[(3-endo)-8-azabicyclo[3.2.1]octan-3-yl]carbamate to give the title compound.

Example 82: Synthesis of 4-[5-[(1S,4S)-2,5-diazabicyclo[2.2.1]heptane-2-carbonyl]-2-[2-fluoro-4-(2-methoxyethyl)phenyl]phenyl]-2-fluoro-benzonitrile The procedure of steps 1 to 4 in Example 22 was repeated using tert-butyl (1S,4S)-2,5-diazabicyclo[2.2.1]heptane-2-carboxylic acid instead of tert-butyl N-[(3-endo)-8-azabicyclo[3.2.1]octan-3-yl]carbamate to give the title compound.

Example 83: Synthesis of 4-[5-(3,7-diazaspiro[3.5]nonane-7-carbonyl)-2-[2-fluoro-4-(2-methoxyethyl)phenyl]phenyl]-2-fluoro-benzonitrile The procedure of steps 1 to 4 in Example 22 was repeated using tert-butyl 3,7-diazaspiro[3.5]nonane-3-carboxylic acid instead of tert-butyl N-[(3-endo)-8-azabicyclo[3.2.1]octan-3-yl]carbamate to give the title compound.

Example 84: Synthesis of 4-[5-(2,7-diazaspiro[3.5]nonane-2-carbonyl)-2-[2-fluoro-4-(2-methoxyethyl)phenyl]phenyl]-2-fluoro-benzonitrile The procedure of steps 1 to 4 in Example 22 was repeated using tert-butyl 2,7-diazaspiro[3.5]nonane-7-carboxylic acid hydrochloride instead of tert-butyl N-[(3-endo)-8-azabicyclo[3.2.1]octan-3-yl]carbamate to give the title compound.

Example 85: Synthesis of 4-[5-[(1R,4R)-2,5-diazabicyclo[2.2.1]heptane-2-carbonyl]-2-[2-fluoro-4-(2-methoxyethyl)phenyl]phenyl]-2-fluoro-benzonitrile The procedure of steps 1 to 4 in Example 22 was repeated using tert-butyl (1R,4R)-2,5-diazabicyclo[2.2.1]heptane-2-carboxylic acid instead of tert-butyl N-[(3-endo)-8-azabicyclo[3.2.1]octan-3-yl]carbamate to give the title compound.

Example 86: Synthesis of 2-fluoro-4-[2-[2-fluoro-4-(2-methoxyethyl)phenyl]-5-[(1S,4S)-5-methyl-2,5-diazabicyclo[2.2.1]heptane-2-carbonyl]phenyl]benzonitrile The procedure of steps 1 to 4 in Example 22 was repeated using (1S,4S)-2-methyl-2,5-diazabicyclo[2.2.1]heptane instead of tert-butyl N-[(3-endo)-8-azabicyclo[3.2.1]octan-3-yl]carbamate to give the title compound.

Example 87: Synthesis of 2-fluoro-4-[2-[2-fluoro-4-(2-methoxyethyl)phenyl]-5-[(1R,4R)-5-methyl-2,5-diazabicyclo[2.2.1]heptane-2-carbonyl]phenyl]benzonitrile The procedure of steps 1 to 4 in Example 22 was repeated using (1R,4R)-2-methyl-2,5-diazabicyclo[2.2.1]heptane instead of tert-butyl N-[(3-endo)-8-azabicyclo[3.2.1]octan-3-yl]carbamate to give the title compound.

Example 88: Synthesis of 4-[5-(3,8-diazabicyclo[3.2.1]octane-3-carbonyl)-2-[2-fluoro-4-(2-methoxyethyl)phenyl]phenyl]-2-fluoro-benzonitrile The procedure of steps 1 to 4 in Example 22 was repeated using tert-butyl 3,8-diazabicyclo[3.2.1]octane-8-carboxylic acid instead of tert-butyl N-[(3-endo)-8-azabicyclo[3.2.1]octan-3-yl]carbamate to give the title compound.

Example 89: Synthesis of 4-[5-[(3S)-3-aminopyrrolidine-1-carbonyl]-2-(1,3-benzothiazol-5-yl)phenyl]-2-fluoro-benzonitrile The procedure of steps 1 to 3 in Example 16 was repeated using 1,3-benzothiazol-5-yl boronic acid instead of p-tolylboronic acid to give the title compound.

Example 90: Synthesis of 4-[5-[(3S)-3-aminopyrrolidine-1-carbonyl]-2-(1-methylpyrazolo[3,4-b]pyridin-5-yl)phenyl]-2-fluoro-benzonitrile The procedure of steps 1 to 3 in Example 16 was repeated using (1-methylpyrazolo[3,4-b]pyridin-5-yl)boronic acid instead of p-tolylboronic acid to give the title compound.

Example 91: Synthesis of 4-[5-[(3S)-3-aminopyrrolidine-1-carbonyl]-2-(1-methylbenzimidazol-5-yl)phenyl]-2-fluoro-benzonitrile The procedure of steps 1 to 3 in Example 37 was repeated using 5-bromo-1-methyl-benzimidazole instead of 1-(4-bromo-3-fluoro-phenyl)-2-methyl-propan-2-ol to give the title compound.

Example 92: Synthesis of 4-[5-[(3S)-3-aminopyrrolidine-1-carbonyl]-2-(1-methylindazol-5-yl)phenyl]-2-fluoro-benzonitrile The procedure of steps 1 to 3 in Example 16 was repeated using (1-methylindazol-5-yl)boronic acid instead of p-tolylboronic acid to give the title compound.

Example 93: Synthesis of 4-[5-[(3S)-3-aminopyrrolidine-1-carbonyl]-2-(2-methylindazol-5-yl)phenyl]-2-fluoro-benzonitrile The procedure of steps 1 to 3 in Example 16 was repeated using 2-methyl-5-(4,4,5,5-tetramethyl-1,3,2-dioxaborolan-2-yl)indazole instead of p-tolylboronic acid to give the title compound.

Example 94: Synthesis of 4-[5-[(3S)-3-aminopyrrolidine-1-carbothioyl]-2-[2-fluoro-4-(2-methoxyethyl)phenyl]phenyl]-2-fluoro-benzonitrile The procedure of Example 2 was repeated using the 4-[5-[(3S)-3-aminopyrrolidine-1-carbonyl]-2-[2-fluoro-4-(2-methoxyethyl)phenyl]phenyl]-2-fluoro-benzonitrile obtained in Example 20 (step 3) instead of 4-[5-[(3S)-3-aminopyrrolidine-1-carbonyl]-2-(p-tolyl)phenyl]benzonitrile to give the title compound.

Example 95: Synthesis of 4-[5-[(3S)-3-aminopyrrolidine-1-carbonyl]-2-(6-fluoro-1-methyl-benzimidazol-5-yl)phenyl]-2-fluoro-benzonitrile The procedure of steps 1 to 3 in Example 37 was repeated using 5-bromo-6-fluoro-1-methyl-benzimidazole instead of 1-(4-bromo-3-fluoro-phenyl)-2-methyl-propan-2-ol to give the title compound.

Example 96: Synthesis of 4-[5-[(3S)-3-aminopyrrolidine-1-carbonyl]-2-(6-fluoro-1-methyl-benzotriazol-5-yl)phenyl]-2-fluoro-benzonitrile Step 1

The tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate (15 mg) obtained in Example 37 (step 1) was dissolved in 1,4-dioxane (0.5 mL). At room temperature, 5-bromo-6-fluoro-1-methyl-benzotriazole (9.7 mg), PdCl$_2$(dppf) (1.0 mg), and tripotassium phosphate (18 mg) were added thereto, and the mixture was stirred in a microwave reactor at 125° C. for 30 minutes. Ethyl acetate was added thereto, and the mixture was put on NH-silica gel and washed with ethyl acetate/methanol. The solvent was distilled off to give tert-butyl N-[(3S)-1-[3-(4-cyano-3-fluoro-phenyl)-4-(6-fluoro-1-methyl-benzotriazol-5-yl)benzoyl]pyrrolidin-3-yl]carbamate.

Step 2

The tert-butyl N-[(3S)-1-[3-(4-cyano-3-fluoro-phenyl)-4-(6-fluoro-1-methyl-benzotriazol-5-yl)benzoyl]pyrrolidin-3-yl]carbamate (15 mg) obtained in step 1 above was dissolved in TFA (0.3 mL), and the progress of the reaction was confirmed with LCMS, followed by vacuum concentration. The residue was purified by reversed-phase HPLC (mobile phase: water/acetonitrile) to give the title compound.

Example 97: Synthesis of 4-[5-[(3-exo)-3-amino-8-azabicyclo[3.2.1]octane-8-carbonyl]-2-(4-fluorophenyl)phenyl]benzonitrile The procedure of steps 1 to 3 in Example 23 was repeated using 1-bromo-4-fluorobenzene instead of 5-bromo-6-fluoro-1-methyl-indole to give the title compound.

Example 98: Synthesis of 4-[5-[(3-exo)-3-amino-8-azabicyclo[3.2.1]octane-8-carbonyl]-2-(4-chlorophenyl)phenyl]benzonitrile The procedure of steps 1 to 3 in Example 23 was repeated using 1-bromo-4-chloro-benzene instead of 5-bromo-6-fluoro-1-methyl-indole to give the title compound.

Example 99: Synthesis of [(3S)-3-aminopyrrolidin-1-yl]-[3-(4-nitrophenyl)-4-(p-tolyl)phenyl]methanone The procedure of steps 1 to 5 in Example 19 was repeated using 1-bromo-4-nitro-benzene instead of 4-bromo-2,6-difluoro-benzonitrile to give the title compound.

Example 100: Synthesis of 4-[5-[(3S)-3-aminopyrrolidine-1-carbonyl]-2-[6-(dimethylamino)-3-pyridyl]phenyl]-2-fluoro-benzonitrile The procedure of steps 1 to 3 in Example 37 was repeated using 5-bromo-N,N-dimethylpyridin-2-amine instead of 1-(4-bromo-3-fluoro-phenyl)-2-methyl-propan-2-ol to give the title compound.

Example 101: Synthesis of 4-[5-[(3S)-3-aminopyrrolidine-1-carbonyl]-2-(1-methylbenzotriazol-5-yl)phenyl]-2-fluoro-benzonitrile The procedure of steps 1 to 3 in Example 37 was repeated using 5-bromo-1-methyl-benzotriazole instead of 1-(4-bromo-3-fluoro-phenyl)-2-methyl-propan-2-ol to give the title compound.

Example 102: Synthesis of 4-[5-[(3S)-3-aminopyrrolidine-1-carbonyl]-2-(6,7-difluoro-1-methyl-benzimidazol-5-yl)phenyl]-2-fluoro-benzonitrile The procedure of steps 1 to 3 in Example 37 was repeated using 5-bromo-6,7-difluoro-1-methyl-benzimidazole instead of 1-(4-bromo-3-fluoro-phenyl)-2-methyl-propan-2-ol to give the title compound.

Example 103: Synthesis of 4-[5-[(3S)-3-aminopyrrolidine-1-carbonyl]-2-(1,2-dimethylbenzimidazol-5-yl)phenyl]-2-fluoro-benzonitrile The procedure of steps 1 to 3 in Example 37 was repeated using 5-bromo-1,2-dimethyl-benzimidazole instead of 1-(4-bromo-3-fluoro-phenyl)-2-methyl-propan-2-ol to give the title compound.

Example 104: Synthesis of 4-[5-[(3-exo)-3-amino-8-azabicyclo[3.2.1]octane-8-carbonyl]-2-(2-naphthyl)phenyl]-2-fluoro-benzonitrile The procedure of steps 1 to 3 in Example 23 was repeated using 2-bromonaphthalene instead of 5-bromo-6-fluoro-1-methyl-indole to give the title compound.

Example 105: Synthesis of 4-[5-[(3-exo)-3-amino-8-azabicyclo[3.2.1]octane-8-carbonyl]-2-(8-fluoro-7-quinolyl)phenyl]-2-fluoro-benzonitrile The procedure of steps 1 to 3 in Example 23 was repeated using 7-bromo-8-fluoroquinoline instead of 5-bromo-6-fluoro-1-methyl-indole to give the title compound.

Example 106: Synthesis of 4-[5-[(3-exo)-3-amino-8-azabicyclo[3.2.1]octane-8-carbonyl]-2-(4-methyl-2,3-dihydro-1,4-benzoxazin-7-yl)phenyl]-2-fluoro-benzonitrile The procedure of steps 1 to 3 in Example 23 was repeated using 7-bromo-4-methyl-3,4-dihydro-2H-benzo[b][1,4]oxazine instead of 5-bromo-6-fluoro-1-methyl-indole to give the title compound.

Example 107: Synthesis of 4-[5-[(3-exo)-3-amino-8-azabicyclo[3.2.1]octane-8-carbonyl]-2-(7-quinonyl)phenyl]-2-fluoro-benzonitrile The procedure of steps 1 to 3 in Example 23 was repeated using 7-bromoquinoline instead of 5-bromo-6-fluoro-1-methyl-indole to give the title compound.

Example 108: Synthesis of 4-[5-[(3-exo)-3-amino-8-azabicyclo[3.2.1]octane-8-carbonyl]-2-(6-fluoro-1-methyl-benzimidazol-5-yl)phenyl]-2-fluoro-benzonitrile The procedure of steps 1 to 3 in Example 23 was repeated using 5-bromo-6-fluoro-1-methyl-benzimidazole instead of 5-bromo-6-fluoro-1-methyl-indole to give the title compound.

Example 109: Synthesis of 4-[5-[(3-exo)-3-amino-8-azabicyclo[3.2.1]octane-8-carbonyl]-2-(6-fluoro-1-methyl-benzotriazol-5-yl)phenyl]-2-fluoro-benzonitrile The procedure of steps 1 to 3 in Example 23 was repeated using 5-bromo-6-fluoro-1-methyl-benzotriazole instead of 5-bromo-6-fluoro-1-methyl-indole to give the title compound.

Example 110: Synthesis of 4-[5-[(3-exo)-3-amino-8-azabicyclo[3.2.1]octane-8-carbonyl]-2-(4-fluoro-1-methyl-indazol-5-yl)phenyl]-2-fluoro-benzonitrile The procedure of steps 1 to 3 in Example 23 was repeated using 5-bromo-4-fluoro-1-methyl-indazole instead of 5-bromo-6-fluoro-1-methyl-indole to give the title compound.

Example 111: Synthesis of 4-[5-[(3-exo)-3-amino-8-azabicyclo[3.2.1]octane-8-carbonyl]-2-(2-methyl-indazol-5-yl)phenyl]benzonitrile The procedure of steps 1 to 3 in Example 23 was repeated using 5-bromo-2-methyl-2H-indazole instead of 5-bromo-6-fluoro-1-methyl-indole to give the title compound.

Example 112: Synthesis of 2-fluoro-4-[2-[2-fluoro-4-(2-methoxyethyl)phenyl]-5-[(3-exo)-3-(isopropylamino)-8-azabicyclo[3.2.1]octane-8-carbonyl]phenyl]benzonitrile Acetone (0.002 mL) was added at 25° C. to a solution of the 4-[5-[(3-exo)-3-amino-8-azabicyclo[3.2.1]octane-8-carbonyl]-2-[2-fluoro-4-(2-methoxyethyl)phenyl]phenyl]-2-fluoro-benzonitrile obtained in Example 26 (step 2) in dichloromethane (0.05 mL). Subsequently, NaBH(OAc)3 (8.45 mg) was added thereto, followed by stirring at room temperature for 1 hour. MeOH was added thereto, and the solvent was distilled off. Then, the residue was purified by reversed-phase HPLC (mobile phase: water/acetonitrile) to give the title compound.

Example 113: Synthesis of 2-fluoro-4-[2-[2-fluoro-4-(2-hydroxy-2-methyl-propyl)phenyl]-5-[(3-exo)-3-(isopropylamino)-8-azabicyclo[3.2.1]octane-8-carbonyl]phenyl]benzonitrile The procedure of Example 112 was repeated using the 4-[5-[(3-exo)-3-amino-8-azabicyclo[3.2.1]octane-8-carbonyl]-2-[2-fluoro-4-(2-hydroxy-2-methyl-propyl)phenyl]phenyl]-2-fluoro-benzonitrile obtained in Example 28 (step 3) instead of 4-[5-[(3-exo)-3-amino-8-azabicyclo[3.2.1]octane-8-carbonyl]-2-[2-fluoro-4-(2-methoxyethyl)phenyl]phenyl]-2-fluoro-benzonitrile to give the title compound.

Example 114: Synthesis of 4-[5-[(3S)-3-(ethylamino)pyrrolidine-1-carbonyl]-2-(6-fluoro-1-methyl-benzotriazol-5-yl)phenyl]-2-fluoro-benzonitrile Step 1

The tert-butyl N-[(3S)-1-[3-(4-cyano-3-fluoro-phenyl)-4-(6-fluoro-1-methyl-benzotriazol-5-yl)benzoyl]pyrrolidin-3-yl]carbamate (10 mg) obtained in Example 96 (step 1) was dissolved in THF (0.5 mL). At room temperature, sodium hydride (0.85 mg), and then iodoethane (5.58 mg) were added thereto, the mixture was stirred at 50° C. overnight, and the solvent was distilled off to give (S)-tert-butyl (1-(4'-cyano-3'-fluoro-6-(6-fluoro-1-methyl-1H-benzo[d][1,2,3]triazol-5-yl)-[1,1'-biphenyl]-3-carbonyl)pyrrolidin-3-yl)(ethyl)carbamate. The thus obtained product was used in the next step without purification.

Step 2

The procedure of step 2 in Example 26 was repeated using the (S)-tert-butyl (1-(4'-cyano-3'-fluoro-6-(6-fluoro-1-methyl-1H-benzo[d][1,2,3]triazol-5-yl)-[1,1'-biphenyl]-3-carbonyl)pyrrolidin-3-yl)(ethyl)carbamate obtained in step 1 above instead of [(3-exo)-8-[3-(4-cyano-3-fluoro-phenyl)-4-[2-fluoro-4-(2-methoxyethyl)phenyl]benzoyl]-8-azabicyclo[3.2.1]octan-3-yl]carbamate to give the title compound.

Example 115: Synthesis of 2-fluoro-4-[2-(6-fluoro-1-methyl-benzotriazol-5-yl)-5-[(3S)-3-(isopropylamino)pyrrolidine-1-carbonyl]phenyl]benzonitrile The procedure of Example 112 was repeated using the 4-[5-[(3S)-3-aminopyrrolidine-1-carbonyl]-2-(6-fluoro-1-methyl-benzotriazol-5-yl)phenyl]-2-fluoro-benzonitrile obtained in Example 96 (step 2) instead of 4-[5-[(3-exo)-3-amino-8-azabicyclo[3.2.1]octane-8-carbonyl]-2-[2-fluoro-4-(2-methoxyethyl)phenyl]phenyl]-2-fluoro-benzonitrile to give the title compound.

Example 116: Synthesis of 4-[5-[(3S)-3-(cyclobutylamino)pyrrolidine-1-carbonyl]-2-(6-fluoro-1-methyl-benzotriazol-5-yl)phenyl]-2-fluoro-benzonitrile The procedure of Example 112 was repeated using the 4-[5-[(3S)-3-aminopyrrolidine-1-carbonyl]-2-(6-fluoro-1-methyl-benzotriazol-5-yl)phenyl]-2-fluoro-benzonitrile obtained in Example 96 (step 2) instead of 4-[5-[(3-exo)-3-amino-8-azabicyclo[3.2.1]octane-8-carbonyl]-2-[2-fluoro-4-(2-methoxyethyl)phenyl]phenyl]-2-fluoro-benzonitrile, and using cyclobutanone instead of acetone to give the title compound.

Example 117: Synthesis of 4-[5-[(3S)-3-aminopyrrolidine-1-carbonyl]-2-(1-methylindolin-5-yl)phenyl]-2-fluoro-benzonitrile The procedure of steps 1 to 3 in Example 37 was repeated using 5-bromo-1-methyl-indoline instead of 1-(4-bromo-3-fluoro-phenyl)-2-methyl-propan-2-ol to give the title compound.

Example 118: Synthesis of 4-[5-[(3S)-3-aminopyrrolidine-1-carbonyl]-2-(4-methyl-2,3-dihydro-1,4-benzoxazin-7-yl)phenyl]-2-fluoro-benzonitrile The procedure of steps 1 to 3 in Example 37 was repeated using 7-bromo-4-methyl-3,4-dihydro-2H-benzo[b][1,4]oxazine instead of 1-(4-bromo-3-fluoro-phenyl)-2-methyl-propan-2-ol to give the title compound.

Example 119: Synthesis of 4-[5-[(3S)-3-aminopyrrolidine-1-carbonyl]-2-(3-methyl-2-oxo-1,3-benzooxazol-6-yl)phenyl]-2-fluoro-benzonitrile The procedure of steps 1 to 3 in Example 37 was repeated using 6-bromo-3-methyl-1,3-benzooxazol-2-one instead of 1-(4-bromo-3-fluoro-phenyl)-2-methyl-propan-2-ol to give the title compound.

Example 120: Synthesis of 4-[5-[(3S)-3-aminopyrrolidine-1-carbonyl]-2-(3-methyl-2-oxo-1,3-benzothiazol-6-yl)phenyl]-2-fluoro-benzonitrile The procedure of steps 1 to 3 in Example 37 was repeated using 6-bromo-3-methyl-1,3-benzothiazol-2-one instead of 1-(4-bromo-3-fluoro-phenyl)-2-methyl-propan-2-ol to give the title compound.

Example 121: Synthesis of 4-[5-[(3S)-3-aminopyrrolidine-1-carbonyl]-2-(2,3-dihydro-1,4-benzodioxin-6-yl)phenyl]-2-fluoro-benzonitrile The procedure of steps 1 to 3 in Example 16 was repeated using 2,3-dihydro-1,4-benzodioxan-6-yl boronic acid instead of p-tolylboronic acid to give the title compound.

Example 122: Synthesis of 4-[5-[(3S)-3-aminopyrrolidine-1-carbonyl]-2-(1,3-benzodioxol-5-yl)phenyl]-2-fluoro-benzonitrile The procedure of steps 1 to 3 in Example 16 was repeated using 1,3-benzodioxol-5-yl boronic acid instead of p-tolylboronic acid to give the title compound.

Example 123: Synthesis of 4-[5-[(3-endo)-3-amino-8-azabicyclo[3.2.1]octane-8-carbonyl]-2-(6-fluoro-1-methyl-indol-5-yl)phenyl]-2-fluoro-benzonitrile The procedure of steps 1 to 5 in Example 41 was repeated using 5-bromo-6-fluoro-1-methyl-indole instead of 1-(4-bromo-3-fluoro-phenyl)-2-methyl-propan-2-ol to give the title compound.

Example 124: Synthesis of 4-[5-[(3-endo)-3-amino-8-azabicyclo[3.2.1]octane-8-carbonyl]-2-(6-fluoro-1-methyl-indazol-5-yl)phenyl]-2-fluoro-benzonitrile The procedure of steps 1 to 5 in Example 41 was repeated using 5-bromo-6-fluoro-1-methyl-indazole instead of 1-(4-bromo-3-fluoro-phenyl)-2-methyl-propan-2-ol to give the title compound.

Example 125: Synthesis of 4-[5-[(3-endo)-3-amino-8-azabicyclo[3.2.1]octane-8-carbonyl]-2-(6-fluoro-1-methyl-benzotriazol-5-yl)phenyl]-2-fluoro-benzonitrile The procedure of steps 1 to 5 in Example 41 was repeated using 5-bromo-6-fluoro-1-methyl-benzotriazole instead of 1-(4-bromo-3-fluoro-phenyl)-2-methyl-propan-2-ol to give the title compound.

Example 126: Synthesis of 4-[5-[(3-endo)-3-amino-8-azabicyclo[3.2.1]octane-8-carbonyl]-2-(6,7-difluoro-1-methyl-benzimidazol-5-yl)phenyl]-2-fluoro-benzonitrile The procedure of steps 1 to 5 in Example 41 was repeated using 5-bromo-6,7-difluoro-1-methyl-benzimidazole instead of 1-(4-bromo-3-fluoro-phenyl)-2-methyl-propan-2-ol to give the title compound.

Example 127: Synthesis of 4-[5-[(3-exo)-3-amino-9-azabicyclo[3.3.1]nonane-9-carbonyl]-2-[2-fluoro-4-(2-methoxyethyl)phenyl]phenyl]-2-fluoro-benzonitrile The procedure of steps 1 to 4 in Example 22 was repeated using tert-butyl N-[(3-exo)-9-azabicyclo[3.3.1]nonan-3-yl]

carbamate instead of tert-butyl N-[(3-endo-azabicyclo [3.2.1]octan-3-yl]carbamate to give the title compound.

Example 128: Synthesis of 4-[5-[(3-endo)-3-amino-8-azabicyclo[3.2.1]octane-8-carbonyl]-2-(4-methyl-2,3-dihydro-1,4-benzoxazin-7-yl)phenyl]-2-fluoro-benzonitrile The procedure of steps 1 to 5 in Example 41 was repeated using 7-bromo-4-methyl-3,4-dihydro-2H-benzo[b][1,4]oxazine instead of 1-(4-bromo-3-fluoro-phenyl)-2-methyl-propan-2-ol to give the title compound.

Example 129: Synthesis of 4-[5-[(3-endo)-3-amino-9-azabicyclo[3.3.1]nonane-9-carbonyl]-2-[2-fluoro-4-(2-methoxyethyl)phenyl]phenyl]-2-fluoro-benzonitrile The procedure of steps 1 to 4 in Example 22 was repeated using tert-butyl N-[(3-endo)-9-azabicyclo[3.3.1]nonan-3-yl] carbamate instead of tert-butyl N-[(3-endo)-8-azabicyclo [3.2.1]octan-3-yl]carbamate to give the title compound.

Example 130: Synthesis of 4-[5-[(3-endo)-3-amino-8-azabicyclo[3.2.1]octane-8-carbonyl]-2-(6-fluoro-1-methyl-benzimidazol-5-yl)phenyl]-2-fluoro-benzonitrile The procedure of steps 1 to 5 in Example 41 was repeated using 5-bromo-6-fluoro-1-methyl-benzimidazole instead of 1-(4-bromo-3-fluoro-phenyl)-2-methyl-propan-2-ol to give the title compound.

Example 131: Synthesis of 4-[5-[(3-endo)-3-amino-8-azabicyclo[3.2.1]octane-8-carbonyl]-2-[6-(dimethylamino)-3-pyridyl]phenyl]-2-fluoro-benzonitrile The procedure of steps 1 to 5 in Example 41 was repeated using 5-bromo-N,N-dimethylpyridin-2-amine instead of 1-(4-bromo-3-fluoro-phenyl)-2-methyl-propan-2-ol to give the title compound.

Example 132: Synthesis of 4-[5-[(3-endo)-3-amino-8-azabicyclo[3.2.1]octane-8-carbonyl]-2-(1,3,3-trimethyl-2-oxo-indolin-5-yl)phenyl]-2-fluoro-benzonitrile The procedure of steps 1 to 5 in Example 41 was repeated using 5-bromo-1,3,3-trimethyl-indolin-2-one instead of 1-(4-bromo-3-fluoro-phenyl)-2-methyl-propan-2-ol to give the title compound.

Example 133: Synthesis of 4-[5-[(3-endo)-3-amino-8-azabicyclo[3.2.1]octane-8-carbonyl]-2-(3-methyl-2-oxo-1,3-benzothiazol-6-yl)phenyl]-2-fluoro-benzonitrile The procedure of steps 1 to 5 in Example 41 was repeated using 6-bromo-3-methyl-1,3-benzothiazol-2-one instead of 1-(4-bromo-3-fluoro-phenyl)-2-methyl-propan-2-ol to give the title compound.

Example 134: Synthesis of (S)-5'-(3-aminopyrrolidine-1-carbonyl)-3-fluoro-2'-(6-fluoro-1-methyl-1H-indol-5-yl)-[1,1'-biphenyl]-4-carbonitrile The procedure of steps 1 to 3 in Example 37 was repeated using 5-bromo-6-fluoro-1-methyl-1H-indole instead of 1-(4-bromo-3-fluoro-phenyl)-2-methyl-propan-2-ol to give the title compound.

Example 135: Synthesis of (S)-5'-(3-amino pyrrolidine-1-carbonyl)-3-fluoro-2'-(6-fluoro-1-methyl-1H-indazol-5-yl)-[1,1'-biphenyl]-4-carbonitrile The procedure of steps 1 to 3 in Example 37 was repeated using 5-bromo-6-fluoro-1-methyl-1H-indazole instead of 1-(4-bromo-3-fluoro-phenyl)-2-methyl-propan-2-ol to give the title compound.

Example 136: Synthesis of 5'-((3-endo)-3-amino-8-azabicyclo[3.2.1]octane-8-carbonyl)-3-fluoro-2'-(6-fluoro-1-(2-hydroxy-2-methylpropyl)-1H-indol-5-yl)-[1,1'-biphenyl]-4-carbonitrile Step 1
5-Bromo-6-fluoro-1H-indole (50 mg) was dissolved in DMF (0.78 mL). At room temperature, $Cs_2CO_3$ (151 mg) and 2,2-dimethyloxirane (42 μL) were added thereto, followed by stirring at 90° C. for 16 hours. The reaction was quenched with a saturated $NH_4Cl$ aqueous solution, ethyl acetate was added thereto, and the mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(5-bromo-6-fluoro-indol-1-yl)-2-methyl-propan-2-ol.

Step 2
The procedure of steps 1 to 5 in Example 41 was repeated using the 1-(5-bromo-6-fluoro-indol-1-yl)-2-methyl-propan-2-ol obtained in step 1 above instead of 1-(4-bromo-3-fluoro-phenyl)-2-methyl-propan-2-ol to give the title compound.

Example 137: Synthesis of 5'-((3-endo)-3-amino-8-azabicyclo[3.2.1]octane-8-carbonyl)-2'-(1,3-dihydroisobenzofuran-5-yl)-3-fluoro-[1,1'-biphenyl]-4-carbonitrile The procedure of steps 1 to 5 in Example 41 was repeated using 5-bromo-1,3-dihydroisobenzofuran instead of 1-(4-bromo-3-fluoro-phenyl)-2-methyl-propan-2-ol to give the title compound.

Example 138: Synthesis of 5'-((3-endo)-3-amino-8-azabicyclo[3.2.1]octane-8-carbonyl)-3-fluoro-2'-(3-isopropyl-2-oxo-2,3-dihydrobenzo[d]thiazol-6-yl)-[1,1'-biphenyl]-4-carbonitrile Step 1
6-Bromo-3H-1,3-benzothiazol-2-one (100 mg) was dissolved in DMF (0.87 mL). At room temperature, potassium carbonate (90 mg) was added thereto, followed by stirring at 0° C. for 15 minutes. At room temperature, 2-bromopropane (0.082 mL) was added thereto, followed by stirring at 100° C. for 3 hours. The reaction was quenched with a saturated $NH_4Cl$ aqueous solution, ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 6-bromo-3-isopropyl-1,3-benzothiazol-2-one.

Step 2
The procedure of steps 1 to 5 in Example 41 was repeated using the 6-bromo-3-isopropyl-1,3-benzothiazol-2-one obtained in step 1 above instead of 1-(4-bromo-3-fluoro-phenyl)-2-methyl-propan-2-ol to give the title compound.

Example 139: Synthesis of 5'-((3-endo)-3-amino-8-azabicyclo[3.2.1]octane-8-carbonyl)-2'-(1-(tert-butyl)-6-fluoro-1H-benzo[d][1,2,3]triazol-5-yl)-3-fluoro-[1,1'-biphenyl]-4-carbonitrile The procedure of steps 1 to 5 in Example 41 was repeated using 5-bromo-1-(tert-butyl)-6-fluoro-1H-benzo[d][1,2,3]triazole instead of 1-(4-bromo-3-fluoro-phenyl)-2-methyl-propan-2-ol to give the title compound.

Example 140: Synthesis of (S)-5'-(3-aminopyrrolidine-1-carbonyl)-2'-(1,3-dihydroisobenzofuran-5-yl)-3-fluoro-[1,1'-biphenyl]-4-carbonitrile The procedure of steps 1 to 3 in Example 37 was repeated using 5-bromo-1,3-dihydroisobenzofuran instead of 1-(4-bromo-3-fluoro-phenyl)-2-methyl-propan-2-ol to give the title compound.

Example 141: Synthesis of (S)-5'-(3-aminopyrrolidine-1-carbonyl)-3-fluoro-2'-(5-fluoro-3-methyl-2-oxo-2,3-dihydrobenzo[d]thiazol-6-yl)-[1,1'-biphenyl]-4-carbonitrile Step 1
5-Fluoro-3H-1,3-benzothiazol-2-one (200 mg) was suspended in MeCN (1 mL). At room temperature, N-bromo-succinimide (231 mg) was added thereto, followed by stirring at room temperature for 1 hour. The solvent was vacuum-concentrated, and the residue was purified by silica gel column chromatography (mobile phase: hexane/ethyl acetate) to give 6-bromo-5-fluoro-3H-1,3-benzothiazol-2-one.
Step 2
The 6-bromo-5-fluoro-3H-1,3-benzothiazol-2-one (100 mg) obtained in step 1 above was dissolved in DMF (1.3 mL). At room temperature, potassium carbonate (84 mg) was added thereto, followed by stirring at 0° C. for 15 minutes. At room temperature, iodomethane (0.050 mL) was added thereto, followed by stirring at room temperature for 0.5 hours. The reaction was quenched with a saturated NH₄Cl aqueous solution, ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 6-bromo-5-fluoro-3-methyl-1,3-benzothiazol-2-one.
Step 3
The procedure of steps 1 to 3 in Example 37 was repeated using the 6-bromo-5-fluoro-3-methyl-1,3-benzothiazol-2-one obtained in step 2 above instead of 1-(4-bromo-3-fluoro-phenyl)-2-methyl-propan-2-ol to give the title compound.

Example 142: Synthesis of 5'-((3-endo)-3-amino-8-azabicyclo[3.2.1]octane-8-carbonyl)-3-fluoro-2'-(6-fluoro-1-(2-hydroxy-2-methylpropyl)-1H-indazol-5-yl)-[1,1'-biphenyl]-4-carbonitrile Step 1
5-Bromo-6-fluoro-1H-indazole (94 mg) was dissolved in DMF (1.5 mL). At room temperature, cesium carbonate (285 mg) and 2,2-dimethyloxirane (0.078 mL) were added thereto, followed by stirring at 90° C. for 16 hours. The reaction was quenched with a saturated NH₄Cl aqueous solution, ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(5-bromo-6-fluoro-indazol-1-yl)-2-methyl-propan-2-ol.
Step 2
The procedure of steps 1 to 5 in Example 41 was repeated using the 1-(5-bromo-6-fluoro-indazol-1-yl)-2-methyl-propan-2-ol obtained in step 1 above instead of 1-(4-bromo-3-fluoro-phenyl)-2-methyl-propan-2-ol to give the title compound.

Example 143: Synthesis of 4-[5-[(1S,3R,4R)-rel-3-amino-7-azabicyclo[2.2.1]heptane-7-carbonyl]-2-[2-fluoro-4-(2-methoxyethyl)phenyl]phenyl]-2-fluoro-benzonitrile Step 1
tert-Butyl (1S,3R,4R)-rel-3-amino-7-azabicyclo[2.2.1]heptane-7-carboxylate (50 mg) was dissolved in THF (1.2 mL). At 0° C., TEA (0.066 mL) and 2-nitrobenzene sulfonyl chloride (57 mg) were added thereto, followed by stirring at room temperature for 1 hour. Ethyl acetate was added thereto, and the mixture was washed sequentially with water and saturated brine. After the organic layer was dried over anhydrous sodium sulfate, the solvent was distilled off. The residue was purified by silica gel column chromatography (mobile phase: hexane/ethyl acetate), and the solvent was distilled off. The residue was dissolved in a 4 N hydrochloric acid-ethyl acetate solution (2 mL), followed by stirring at room temperature for 30 minutes. The reaction solution was vacuum-concentrated to give N-[(1S,3R,4R)-rel-7-azabicyclo[2.2.1]heptan-3-yl]-2-nitrobenzenesulfonamide hydrochloride.
Step 2
The procedure of step 3 in Example 22 was repeated using the N-[(1S,3R,4R)-rel-7-azabicyclo[2.2.1]heptan-3-yl]-2-nitrobenzenesulfonamide hydrochloride obtained in step 1 above instead of tert-butyl N-[(3-endo)-8-azabicyclo[3.2.1]octan-3-yl]carbamate to give N-[(1S,3R,4R)-rel-7-[3-(4-cyano-3-fluoro-phenyl)-4-[2-fluoro-4-(2-methoxyethyl)phenyl]benzoyl]-7-azabicyclo[2.2.1]heptan-3-yl]-2-nitrobenzenesulfonamide.
Step 3
The N-[(1S,3R,4R)-rel-7-[3-(4-cyano-3-fluoro-phenyl)-4-[2-fluoro-4-(2-methoxyethyl)phenyl]benzoyl]-7-azabicyclo[2.2.1]heptan-3-yl]-2-nitrobenzenesulfonamide (20 mg) obtained in step 2 above was dissolved in DMF (0.5 mL). At room temperature, K₂CO₃ (21 mg) and 4-mercaptobenzoic acid (12 mg) were added thereto, followed by stirring at 40° C. for 12 hours. Ethyl acetate was added thereto, and the mixture was washed sequentially with water and saturated brine. After the organic layer was dried over anhydrous sodium sulfate, the solvent was distilled off. The residue was purified by reversed-phase HPLC (mobile phase: water/acetonitrile) to give the title compound.

Example 144: Synthesis of 5'-((3-endo)-3-amino-8-azabicyclo[3.2.1]octane-8-carbonyl)-2",3,3"-trifluoro-4"-methyl-[1,1':2',1"-terphenyl]-4-carbonitrile The procedure of steps 1 to 5 in Example 41 was repeated using 1-bromo-2,3-difluoro-4-methyl-benzene instead of 1-(4-bromo-3-fluoro-phenyl)-2-methyl-propan-2-ol to give the title compound.

Example 145: Synthesis of 5'-((3-endo)-3-amino-8-azabicyclo[3.2.1]octane-8-carbonyl)-2'-(6,7-difluoro-1-methyl-1H-benzo[d][1,2,3]triazol-5-yl)-3-fluoro-[1,1'-biphenyl]-4-carbonitrile Step 1

The tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate (200 mg) obtained in step 3 in Example 41 and 5-bromo-6,7-difluoro-1-methyl-benzotriazole (129 mg) were dissolved in 1,4-dioxane (1.74 mL). At room temperature, Pd(dba)$_2$ (16.0 mg), X-phos (26.5 mg), and tripotassium phosphate (221 mg) were added thereto, and the mixture was stirred in a microwave reactor at 125° C. for 1 hour. The reaction solution was filtrated, and the solvent was distilled off. The residue was purified by silica gel column chromatography (mobile phase: ethyl acetate/hexane) to give tert-butyl N-[(3-endo)-8-[3-(4-cyano-3-fluoro-phenyl)-4-(6,7-difluoro-1-methyl-benzotriazol-5-yl)benzoyl]-8-azabicyclo[3.2.1]octan-3-yl]carbamate.

Step 2

The tert-butyl N-[(3-endo)-8-[3-(4-cyano-3-fluoro-phenyl)-4-(6,7-difluoro-1-methyl-benzotriazol-5-yl)benzoyl]-8-azabicyclo[3.2.1]octan-3-yl]carbamate (210 mg) obtained in step 1 above was dissolved in MeOH (1.60 mL). At room temperature, a 4 N hydrochloric acid-ethyl acetate solution (2.40 mL) was added thereto, followed by stirring at room temperature for 1 hour. The reaction solution was vacuum-concentrated, and the solvent was distilled off. The residue was purified by reversed-phase HPLC (mobile phase: water/acetonitrile) to give the title compound.

Example 146: Synthesis of (S)-5'-(3-aminopyrrolidine-1-carbonyl)-3-fluoro-2'-(6-fluoro-1-(2-hydroxy-2-methylpropyl)-1H-indol-5-yl)-[1,1'-biphenyl]-4-carbonitrile Step 1

The tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate (60 mg) obtained in step 1 of Example 37 and the 1-(5-bromo-6-fluoro-indol-1-yl)-2-methyl-propan-2-ol (48.1 mg) obtained in step 1 of Example 136 were dissolved in 1,4-dioxane (0.50 mL). At room temperature, Pd(dba)$_2$ (3.22 mg), X-phos (5.34 mg), and tripotassium phosphate (71.4 mg) were added thereto, and the mixture was stirred in a microwave reactor at 125° C. for 1 hour. The reaction solution was filtrated, and the solvent was distilled off. The residue was purified by silica gel column chromatography (mobile phase: chloroform/methanol) to give tert-butyl N-[(3S)-1-[3-(4-cyano-3-fluoro-phenyl)-4-[6-fluoro-1-(2-hydroxy-2-methyl-propyl)indol-5-yl]benzoyl]pyrrolidin-3-yl]carbamate.

Step 2

The tert-butyl N-[(3S)-1-[3-(4-cyano-3-fluoro-phenyl)-4-[6-fluoro-1-(2-hydroxy-2-methyl-propyl)indol-5-yl]benzoyl]pyrrolidin-3-yl]carbamate (68.0 mg) obtained in step 1 above was dissolved in MeOH (1.0 mL). At room temperature, 12 N hydrochloric acid (1.0 mL) was added thereto, followed by stirring at room temperature for 1 hour. A 2 N aqueous sodium hydroxide solution (6.00 mL) and chloroform were added thereto, the mixture was washed sequentially with water and saturated brine, and dried over anhydrous sodium sulfate, and the solvent was distilled off. The residue was purified by reversed-phase HPLC (mobile phase: water/acetonitrile) to give the title compound.

Example 147: Synthesis of (S)-5'-(3-aminopyrrolidine-1-carbonyl)-3-fluoro-2'-(6-fluoro-1-(2-hydroxy-2-methylpropyl)-1H-indazol-5-yl)-[1,1'-biphenyl]-4-carbonitrile Step 1

The tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate (70 mg) obtained in step 1 of Example 37 and the 1-(5-bromo-6-fluoro-indazol-1-yl)-2-methyl-propan-2-ol (56.3 mg) obtained in step 1 of Example 142 were dissolved in 1,4-dioxane (0.50 mL). At room temperature, Pd(dba)$_2$ (3.76 mg), X-phos (6.23 mg), and tripotassium phosphate (83.3 mg) were added thereto, and the mixture was stirred in a microwave reactor at 125° C. for 1 hour. The reaction solution was filtrated, and the solvent was distilled off. The residue was purified by silica gel column chromatography (mobile phase: chloroform/methanol) to give tert-butyl N-[(3S)-1-[3-(4-cyano-3-fluoro-phenyl)-4-[6-fluoro-1-(2-hydroxy-2-methyl-propyl)indazol-5-yl]benzoyl]pyrrolidin-3-yl]carbamate.

Step 2

The tert-butyl N-[(3S)-1-[3-(4-cyano-3-fluoro-phenyl)-4-[6-fluoro-1-(2-hydroxy-2-methyl-propyl)indazol-5-yl]benzoyl]pyrrolidin-3-yl]carbamate (70.0 mg) obtained in step 1 above was dissolved in MeOH (1.0 mL). At room temperature, 12 N hydrochloric acid (1.0 mL) was added thereto, followed by stirring at room temperature for 1 hour. A 2 N aqueous sodium hydroxide solution (6.00 mL) and chloroform were added thereto, the mixture was washed sequentially with water and saturated brine, and dried over anhydrous sodium sulfate, and the solvent was distilled off. The residue was purified by reversed-phase HPLC (mobile phase: water/acetonitrile) to give the title compound.

Example 148: Synthesis of 5'-((3-endo)-3-amino-8-azabicyclo[3.2.1]octane-8-carbonyl)-3-fluoro-2'-(quinoxalin-6-yl)-[1,1'-biphenyl]-4-carbonitrile The procedure of steps 1 to 5 in Example 41 was repeated using 6-bromoquinoxaline instead of 1-(4-bromo-3-fluoro-phenyl)-2-methyl-propan-2-ol to give the title compound.

Example 149: Synthesis of 5'-((3-endo)-3-amino-8-azabicyclo[3.2.1]octane-8-carbonyl)-3-fluoro-2'-(isoquinolin-6-yl)-[1,1'-biphenyl]-4-carbonitrile The procedure of steps 1 to 5 in Example 41 was repeated using 6-bromoisoquinoline instead of 1-(4-bromo-3-fluoro-phenyl)-2-methyl-propan-2-ol to give the title compound.

Example 150: Synthesis of 5'-((3-endo)-3-amino-8-azabicyclo[3.2.1]octane-8-carbonyl)-3-fluoro-2'-(isoquinolin-7-yl)-[1,1'-biphenyl]-4-carbonitrile The procedure of steps 1 to 5 in Example 41 was repeated using 7-bromoisoquinoline instead of 1-(4-bromo-3-fluoro-phenyl)-2-methyl-propan-2-ol to give the title compound.

Example 151: Synthesis of 5'-((3-endo)-3-amino-8-azabicyclo[3.2.1]octane-8-carbonyl)-3-fluoro-2'-(quinolin-6-yl)-[1,1'-biphenyl]-4-carbonitrile The procedure of steps 1 to 5 in Example 41 was repeated using 6-bromoquinoline instead of 1-(4-bromo-3-fluoro-phenyl)-2-methyl-propan-2-ol to give the title compound.

Example 152: Synthesis of 5'-((3-endo)-3-amino-8-azabicyclo[3.2.1]octane-8-carbonyl)-3-fluoro-2'-(quinazolin-7-yl)-[1,1'-biphenyl]-4-carbonitrile The procedure of steps 1 to 5 in Example 41 was repeated using 7-bromoquinazolin instead of 1-(4-bromo-3-fluorophenyl)-2-methyl-propan-2-ol to give the title compound.

Example 153: Synthesis of 5'-((3-endo)-3-amino-8-azabicyclo[3.2.1]octane-8-carbonyl)-3-fluoro-2'-(quinazolin-6-yl)-[1,1'-biphenyl]-4-carbonitrile The procedure of steps 1 to 5 in Example 41 was repeated using 6-bromoquinazolin instead of 1-(4-bromo-3-fluorophenyl)-2-methyl-propan-2-ol to give the title compound.

Example 154: Synthesis of 5'-((3-endo)-3-amino-8-azabicyclo[3.2.1]octane-8-carbonyl)-3-fluoro-2'-(phthalazin-6-yl)-[1,1'-biphenyl]-4-carbonitrile The procedure of steps 1 to 5 in Example 41 was repeated using 6-bromophthalazine instead of 1-(4-bromo-3-fluorophenyl)-2-methyl-propan-2-ol to give the title compound.

Example 155: Synthesis of 5'-((1R,2R,4S)-rel-2-amino-7-azabicyclo[2.2.1]heptane-7-carbonyl)-2'',3-difluoro-4''-(2-methoxyethyl)-[1,1':2',1''-terphenyl]-4-carbonitrile-isomer-B Step 1
tert-Butyl (1S,3R,4R)-rel-3-amino-7-azabicyclo[2.2.1]heptane-7-carboxylate (550 mg) was dissolved in THF (13.0 mL). At 0° C., TEA (0.720 mL) and 2,4-dinitrobenzene sulfonyl chloride (829 mg) were added thereto, followed by stirring at room temperature for 1 hour. Ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give tert-butyl (1S,3R,4R)-rel-3-[(2,4-dinitrophenyl)sulfonylamino]-7-azabicyclo[2.2.1]heptane-7-carboxylate.

Step 2
The tert-butyl (1S,3R,4R)-rel-3-[(2,4-dinitrophenyl)sulfonylamino]-7-azabicyclo[2.2.1]heptane-7-carboxylate (440 mg) obtained in step 1 above was subjected to chiral separation using SFC (device: Thar SFC prep 80 system, column: Chiralpak IE 20×250 mm, flow rate: 50 g/min, mobile phase: CO2/MeOH=90/10) to give (1S,3R,4R)-rel-3-[(2,4-dinitrophenyl)sulfonylamino]-7-azabicyclo[2.2.1]heptane-7-carboxylate-isomer-A (faster isomer) and (1S,3R,4R)-rel-3-[(2,4-dinitrophenyl)sulfonylamino]-7-azabicyclo[2.2.1]heptane-7-carboxylate-isomer-B (slower isomer).

Each isomer was analyzed under the following HPLC conditions.
Column: CHIRALPAK IE 4.6×150 mm
Mobile phase: hexane (0.1% triethylamine)/ethanol=85/15
Flow rate: 1.0 mL/min
Retention time of each isomer:
(1S,3R,4R)-rel-3-[(2,4-dinitrophenyl)sulfonylamino]-7-azabicyclo[2.2.1]heptane-7-carboxylate-isomer-A: 10.903 min (faster isomer)
(1S,3R,4R)-rel-3-[(2,4-dinitrophenyl)sulfonylamino]-7-azabicyclo[2.2.1]heptane-7-carboxylate-isomer-B: 14.028 min (slower isomer)

Step 3
The (1S,3R,4R)-rel-3-[(2,4-dinitrophenyl)sulfonylamino]-7-azabicyclo[2.2.1]heptane-7-carboxylate-isomer-B (200 mg) obtained in step 2 above was dissolved in ethyl acetate (1.00 mL). At room temperature, a 4 N hydrochloric acid-ethyl acetate solution (2.00 mL) was added thereto, followed by stirring at room temperature for 2 hours. The reaction solution was vacuum-concentrated to give N-((1R,2R,4S)-rel-7-azabicyclo[2.2.1]heptan-2-yl)-2,4-dinitrobenzenesulfonamide-isomer-B hydrochloride.

Step 4
The 3-(4-cyano-3-fluoro-phenyl)-4-[2-fluoro-4-(2-methoxyethyl)phenyl]benzoic acid (8 mg) obtained in step 2 of Example 22 and the N-((1R,2R,4S)-rel-7-azabicyclo[2.2.1]heptan-2-yl)-2,4-dinitrobenzenesulfonamide-isomer-B hydrochloride (8.47 mg) obtained in step 3 above were dissolved in THF (0.30 mL). At room temperature, TEA (8.49 µL) and HATU (15.5 mg) were added thereto, followed by stirring at 50° C. for 1 hour. The solvent was distilled off under reduced pressure. The residue was purified by silica gel column chromatography (mobile phase: hexane/ethyl acetate) to give N-[(1S,3R,4R)-rel-7-[3-(4-cyano-3-fluoro-phenyl)-4-[2-fluoro-4-(2-methoxyethyl)phenyl]benzoyl]-7-azabicyclo[2.2.1]heptan-3-yl]-2,4-dinitrobenzenesulfonamide-isomer-B.

Step 5
The N-[(1S,3R,4R)-rel-7-[3-(4-cyano-3-fluoro-phenyl)-4-[2-fluoro-4-(2-methoxyethyl)phenyl]benzoyl]-7-azabicyclo[2.2.1]heptan-3-yl]-2,4-dinitrobenzenesulfonamide-isomer-B (14.5 mg) obtained in step 4 above was dissolved in DCM (1 mL). At 0° C., mercaptoacetic acid (2.83 µL) and TEA (7.49 µL) were added thereto, followed by stirring at room temperature for 2 hours. Chloroform was added thereto, the mixture was washed with a 4 N aqueous sodium hydroxide solution, and dried over anhydrous sodium sulfate, and the solvent was distilled off. The residue was purified by reversed-phase HPLC (mobile phase: water/acetonitrile) to give the title compound.

Example 156: Synthesis of 5'-((1R,2R,4S)-rel-2-amino-7-azabicyclo[2.2.1]heptane-7-carbonyl)-2'',3-difluoro-4''-(2-methoxyethyl)-[1,1':2',1''-terphenyl]-4-carbonitrile-isomer-A Step 1
The (1S,3R,4R)-rel-3-[(2,4-dinitrophenyl)sulfonylamino]-7-azabicyclo[2.2.1]heptane-7-carboxylate-isomer-A (200 mg) obtained in step 2 of Example 155 was dissolved in ethyl acetate (1.00 mL). At room temperature, a 4 N hydrochloric acid-ethyl acetate solution (2.00 mL) was added thereto, followed by stirring at room temperature for 2 hours. The reaction solution was vacuum-concentrated to give N-((1R,2R,4S)-rel-7-azabicyclo[2.2.1]heptan-2-yl)-2,4-dinitrobenzenesulfonamide-isomer-A hydrochloride.

Step 2
The 3-(4-cyano-3-fluoro-phenyl)-4-[2-fluoro-4-(2-methoxyethyl)phenyl]benzoic acid (8 mg) obtained in step 2 of Example 22 and the N-((1r,2r,4s)-rel-7-azabicyclo[2.2.1]heptan-2-yl)-2,4-dinitrobenzenesulfonamide-isomer-A hydrochloride (8.47 mg) obtained in step 1 above were dissolved in THF (0.30 mL). At room temperature, TEA (8.49 µL) and HATU (15.5 mg) were added thereto, followed by stirring at 50° C. for 1 hour. The solvent was distilled off under reduced pressure. The residue was purified by silica gel column chromatography (mobile phase: hexane/ethyl acetate) to give N-[(1S,3R,4R)-rel-7-[3-(4-cyano-3-fluoro-phenyl)-4-[2-fluoro-4-(2-methoxyethyl)

phenyl]benzoyl]-7-azabicyclo[2.2.1]heptan-3-yl]-2,4-dinitrobenzenesulfonamide-isomer-A.

Step 3

The N-[(1S,3R,4R)-rel-7-[3-(4-cyano-3-fluoro-phenyl)-4-[2-fluoro-4-(2-methoxyethyl)phenyl]benzoyl]-7-azabicyclo[2.2.1]heptan-3-yl]-2,4-dinitrobenzenesulfonamide-isomer-A (14.5 mg) obtained in step 2 above was dissolved in DCM (1 mL). At 0° C., mercaptoacetic acid (2.83 μL) and TEA (7.49 μL) were added thereto, followed by stirring at room temperature for 2 hours. Chloroform was added thereto, the mixture was washed with a 4 N aqueous sodium hydroxide solution, and dried over anhydrous sodium sulfate, and the solvent was distilled off. The residue was purified by reversed-phase HPLC (mobile phase: water/acetonitrile) to give the title compound.

Example 157: Synthesis of 5'-((3-endo)-3-amino-8-azabicyclo[3.2.1]octane-8-carbonyl)-3-fluoro-2'-(3-methylimidazo[1,5-a]pyridin-7-yl)-[1,1'-biphenyl]-4-carbonitrile The procedure of steps 1 to 5 in Example 41 was repeated using 7-bromo-3-methyl-imidazo[1,5-a]pyridine instead of 1-(4-bromo-3-fluoro-phenyl)-2-methyl-propan-2-ol to give the title compound.

Example 158: Synthesis of 5'-((3-endo)-3-amino-8-azabicyclo[3.2.1]octane-8-carbonyl)-3-fluoro-2'-(3-methylpyrazolo[1,5-a]pyrimidin-6-yl)-[1,1'-biphenyl]-4-carbonitrile The procedure of steps 1 to 5 in Example 41 was repeated using 6-bromo-3-methyl-pyrazolo[1,5-a]pyrimidine instead of 1-(4-bromo-3-fluoro-phenyl)-2-methyl-propan-2-ol to give the title compound.

Example 159: Synthesis of 5'-((3-endo)-3-amino-8-azabicyclo[3.2.1]octane-8-carbonyl)-3-fluoro-2'-(6-fluoro-2-(2-hydroxy-2-methylpropyl)-2H-indazol-5-yl)-[1,1'-biphenyl]-4-carbonitrile Step 1

5-Bromo-6-fluoro-1H-indazole (94 mg) was dissolved in DMF (1.5 mL). At room temperature, cesium carbonate (285 mg) and 2,2-dimethyloxirane (0.078 mL) were added thereto, followed by stirring at 90° C. for 16 hours. The reaction was quenched with a saturated NH$_4$Cl aqueous solution, ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(5-bromo-6-fluoro-indazol-2-yl)-2-methyl-propan-2-ol.

Step 2

The procedure of steps 1 to 5 in Example 41 was repeated using the 1-(5-bromo-6-fluoro-indazol-2-yl)-2-methyl-propan-2-ol obtained in step 1 above instead of 1-(4-bromo-3-fluoro-phenyl)-2-methyl-propan-2-ol to give the title compound.

Example 160: Synthesis of 5'-((3-endo)-3-amino-8-azabicyclo[3.2.1]octane-8-carbonyl)-2'-(1-ethyl-6-fluoro-1H-benzo[d][1,2,3]triazol-5-yl)-3-fluoro-[1,1'-biphenyl]-4-carbonitrile The procedure of steps 1 to 5 in Example 41 was repeated using 5-bromo-1-ethyl-6-fluoro-benzotriazole instead of 1-(4-bromo-3-fluoro-phenyl)-2-methyl-propan-2-ol to give the title compound.

Example 161: Synthesis of 5'-((3-endo)-3-amino-8-azabicyclo[3.2.1]octane-8-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile Step 1

1-(2,3-Difluoro-6-nitro-anilino)-2-methyl-propan-2-ol (6.20 g) was dissolved in DMF (84.0 mL). At room temperature, N-bromosuccinimide (5.80 g) was added thereto, followed by stirring at 90° C. for 1 hour. Ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give 1-(4-bromo-2,3-difluoro-6-nitro-anilino)-2-methyl-propan-2-ol.

Step 2

The 1-(4-bromo-2,3-difluoro-6-nitro-anilino)-2-methyl-propan-2-ol (5.67 g) obtained in step 1 above was dissolved in ethanol (87.2 mL). At room temperature, ammonium chloride (5.67 g), iron (5.67 g), and water (87.2 mL) were added thereto, followed by stirring at 60° C. overnight. The reaction solution was passed through Celite and washed with ethyl acetate. The filtrate was vacuum-concentrated, ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give 1-(6-amino-4-bromo-2,3-difluoro-anilino)-2-methyl-propan-2-ol.

Step 3

The 1-(6-amino-4-bromo-2,3-difluoro-anilino)-2-methyl-propan-2-ol (4.36 g) obtained in step 2 above was dissolved in water (28.4 mL) and THF (28.4 mL). At 0° C., 12 N hydrochloric acid (28.4 mL) and sodium nitrite (1.80 g) were added thereto, followed by stirring at room temperature for 1 hour. Ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give 1-(5-bromo-6,7-difluoro-benzotriazol-1-yl)-2-methyl-propan-2-ol.

Step 4

The tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate (50 mg) obtained in step 3 of Example 41 and the 1-(5-bromo-6,7-difluoro-benzotriazol-1-yl)-2-methyl-propan-2-ol (39.9 mg) obtained in step 3 above were dissolved in 1,4-dioxane (0.50 mL). At room temperature, Pd(dba)$_2$ (2.50 mg), X-phos (4.14 mg), and tripotassium phosphate (55.3 mg) were added thereto, and the mixture was stirred in a microwave reactor at 125° C. for 1 hour. The reaction solution was filtrated, and the solvent was distilled off. The residue was purified by silica gel column chromatography (mobile phase: chloroform/methanol) to give tert-butyl N-[(3-endo)-8-[3-(4-cyano-3-fluoro-phenyl)-4-[6,7-difluoro-1-(2-hydroxy-2-methyl-propyl)benzotriazol-5-yl]benzoyl]-8-azabicyclo[3.2.1]octan-3-yl]carbamate.

Step 5

The tert-butyl N-[(3-endo)-8-[3-(4-cyano-3-fluoro-phenyl)-4-[6,7-difluoro-1-(2-hydroxy-2-methyl-propyl)benzotriazol-5-yl]benzoyl]-8-azabicyclo[3.2.1]octan-3-yl]carbamate (55.0 mg) obtained in step 4 above was dissolved in MeOH (1.0 mL). At room temperature, 12 N hydrochloric acid (1.0 mL) was added thereto, followed by stirring at room temperature for 1 hour. A 2 N aqueous sodium hydroxide solution (6.00 mL) and chloroform were added thereto, the mixture was washed sequentially with water and saturated brine, and dried over anhydrous sodium sulfate, and the solvent was distilled off. The residue was purified by reversed-phase HPLC (mobile phase: water/acetonitrile) to give the title compound.

Example 162: Synthesis of (S)-5'-(3-aminopyrrolidine-1-carbonyl)-2'-(6,7-difluoro-1-(2-hydroxy-2-methylpropyl)-1H-benzo[d][1,2,3]triazol-5-yl-3-fluoro-[1,1'-biphenyl]-4-carbonitrile Step 1

The tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate (100 mg) obtained in step 1 of Example 37 and the 1-(5-bromo-6,7-difluoro-benzotriazol-1-yl)-2-methyl-propan-2-ol (85.8 mg) obtained in step 3 of Example 161 were dissolved in 1,4-dioxane (0.934 mL). At room temperature, Pd(dba)$_2$ (5.37 mg), X-phos (8.90 mg), and tripotassium phosphate (119 mg) were added thereto, and the mixture was stirred in a microwave reactor at 125° C. for 1 hour. The reaction solution was filtrated, and the solvent was distilled off. The residue was purified by silica gel column chromatography (mobile phase: chloroform/methanol) to give tert-butyl N-[(3S)-1-[3-(4-cyano-3-fluoro-phenyl)-4-[6,7-difluoro-1-(2-hydroxy-2-methyl-propyl)benzotriazol-5-yl]benzoyl]pyrrolidin-3-yl]carbamate.

Step 2

The tert-butyl N-[(3S)-1-[3-(4-cyano-3-fluoro-phenyl)-4-[6,7-difluoro-1-(2-hydroxy-2-methyl-propyl)benzotriazol-5-yl]benzoyl]pyrrolidin-3-yl]carbamate (99.8 mg) obtained in step 1 above was dissolved in MeOH (1.0 mL). At room temperature, 12 N hydrochloric acid (1.0 mL) was added thereto, followed by stirring at room temperature for 1 hour. Then, a 2 N aqueous sodium hydroxide solution (6.00 mL) and chloroform were added thereto, the mixture was washed sequentially with water and saturated brine, and dried over anhydrous sodium sulfate, and the solvent was distilled off. The residue was purified by reversed-phase HPLC (mobile phase: water/acetonitrile) to give the title compound.

Example 163: Synthesis of 2",3-difluoro-4"-(2-methoxyethyl)-5'-(piperazine-1-carbonyl)-[1,1':2',1"-terphenyl]-4-carbonitrile The procedure of steps 1 to 4 in Example 22 was repeated using tert-butyl piperazine-1-carboxylate instead of tert-butyl N-[(3-endo)-8-azabicyclo[3.2.1]octan-3-yl]carbamate to give the title compound.

Example 164: Synthesis of (R)-5'-(3-aminopiperidine-1-carbonyl)-2",3-difluoro-4"-(2-methoxyethyl)-[1,1':2',1"-terphenyl]-4-carbonitrile The procedure of steps 1 to 4 in Example 22 was repeated using tert-butyl N-[(3R)-3-piperidyl]carbamate instead of tert-butyl N-[(3-endo)-8-azabicyclo[3.2.1]octan-3-yl]carbamate to give the title compound.

Example 165: Synthesis of 5'-(4-aminoazepan-1-carbonyl)-2",3-difluoro-4"-(2-methoxyethyl)-[1,1':2',1"-terphenyl]-4-carbonitrile The procedure of steps 1 to 4 in Example 22 was repeated using tert-butyl N-(azepan-4-yl)carbamate instead of tert-butyl N-[(3-endo)-8-azabicyclo[3.2.1]octan-3-yl]carbamate to give the title compound.

Example 166: Synthesis of 5'-((1S,2S,4R)-rel-2-amino-7-azabicyclo[2.2.1]heptane-7-carbonyl)-2",3-difluoro-4"-(2-hydroxy-2-methylpropyl)-[1,1':2',1"-terphenyl]-4-carbonitrile-isomer-B Step 1

The tert-butyl 3-(4-cyano-3-fluoro-phenyl)-4-(4,4,5,5-tetramethyl-1,3,2-dioxaborolan-2-yl)benzoate (500 mg) obtained in step 1 of Example 41 and the 1-(4-bromo-3-fluoro-phenyl)-2-methyl-propan-2-ol (379 mg) obtained in step 1 of Example 28 were dissolved in 1,4-dioxane (5.9 mL). At room temperature, Pd(dba)$_2$ (68 mg), X-phos (113 mg), and tripotassium phosphate (752 mg) were added thereto, followed by stirring at 100° C. overnight. The solvent was distilled off, and the residue was purified by silica gel column chromatography (mobile phase: hexane/ethyl acetate) to give tert-butyl 3-(4-cyano-3-fluoro-phenyl)-4-[2-fluoro-4-(2-hydroxy-2-methyl-propyl)phenyl]benzoate.

Step 2

The tert-butyl 3-(4-cyano-3-fluoro-phenyl)-4-[2-fluoro-4-(2-hydroxy-2-methyl-propyl)phenyl]benzoate (300 mg) obtained in step 1 above was dissolved in THF (0.9 mL). At 0° C., 12 N hydrochloric acid (0.9 mL) was added thereto, followed by stirring at room temperature for 2 hours. Then, MTBE was added thereto, the mixture was washed with water and dried over anhydrous sodium sulfate, and the solvent was distilled off to give 3-(4-cyano-3-fluoro-phenyl)-4-[2-fluoro-4-(2-hydroxy-2-methyl-propyl)phenyl]benzoic acid.

Step 3

The 3-(4-cyano-3-fluoro-phenyl)-4-[2-fluoro-4-(2-hydroxy-2-methyl-propyl)phenyl]benzoic acid (10 mg) obtained in step 2 above and the N-((1R,2R,4S)-rel-7-azabicyclo[2.2.1]heptan-2-yl)-2,4-dinitrobenzenesulfonamide-isomer-B hydrochloride (10.2 mg) obtained in step 3 of Example 155 were dissolved in THF (0.12 mL). At room temperature, TEA (0.014 mL) and HATU (18.7 mg) were added thereto, followed by stirring at 50° C. for 1 hour. The reaction solution was vacuum-concentrated, and the residue was purified by silica gel column chromatography (mobile phase: hexane/ethyl acetate) to give N-[(1S,3R,4R)-rel-7-[3-(4-cyano-3-fluoro-phenyl)-4-[2-fluoro-4-(2-hydroxy-2-methyl-propyl)phenyl]benzoyl]-7-azabicyclo[2.2.1]heptan-3-yl]-2,4-dinitrobenzenesulfonamide-isomer-B.

Step 4

The N-[(1S,3R,4R)-rel-7-[3-(4-cyano-3-fluoro-phenyl)-4-[2-fluoro-4-(2-hydroxy-2-methyl-propyl)phenyl]benzoyl]-7-azabicyclo[2.2.1]heptan-3-yl]-2,4-dinitrobenzenesulfonamide-isomer-B (15 mg) obtained in step 3 above was dissolved in DCM (0.2 mL). At 0° C., mercaptoacetic acid (2 µL) and TEA (8.6 µL) were added thereto, followed by stirring at room temperature for 2 hours. Ethyl acetate was added thereto, and the mixture was washed sequentially with water and saturated brine. After the organic layer was dried over anhydrous sodium sulfate, the solvent was distilled off. The residue was purified by reversed-phase HPLC (mobile phase: water/acetonitrile) to give the title compound.

Example 167: Synthesis of (S)-5'-(3-aminopyrrolidine-1-carbonyl)-2'-(6,7-difluoro-1-methyl-1H-benzo[d][1,2,3]triazol-5-yl)-3-fluoro-[1,1'-biphenyl]-4-carbonitrile Step 1

The tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate (60 mg) obtained in step 1 of Example 37 and 5-bromo-6,7-difluoro-1-methyl-benzotriazole (41.7 mg) were dissolved in 1,4-dioxane (0.56 mL). At room temperature, Pd(dba)$_2$ (3.22 mg), X-phos (5.34 mg), and tripotassium phosphate (71.4 mg) were added thereto, and the mixture was stirred in a microwave reactor at 125° C. for 1 hour. The reaction solution was filtrated, and the solvent was distilled off. The residue was purified by silica gel column chromatography (mobile phase: chloroform/methanol) to give tert-butyl N-[(3S)-1-[3-(4-cyano-3-fluoro-phenyl)-4-(6,7-difluoro-1-methyl-benzotriazol-5-yl)benzoyl]pyrrolidin-3-yl]carbamate.

Step 2

The tert-butyl N-[(3S)-1-[3-(4-cyano-3-fluoro-phenyl)-4-(6,7-difluoro-1-methyl-benzotriazol-5-yl)benzoyl]pyrrolidin-3-yl]carbamate (20 mg) obtained in step 1 above was dissolved in TFA (0.40 mL), followed by stirring at room temperature for 5 minutes. After the completion of the reaction was confirmed by LCMS, DMSO (1.60 mL) was added thereto, and purification was performed by reversed-phase HPLC (mobile phase: water/acetonitrile) to give the title compound.

Example 168: Synthesis of 5'-((3-endo)-3-amino-8-azabicyclo[3.2.1]octane-8-carbonyl)-3-fluoro-2'-(6-fluoro-1-propyl-1H-benzo[d][1,2,3]triazol-5-yl)-[1,1'-biphenyl]-4-carbonitrile The procedure of steps 1 to 5 in Example 41 was repeated using 5-bromo-6-fluoro-1-propyl-benzotriazole instead of 1-(4-bromo-3-fluoro-phenyl)-2-methyl-propan-2-ol to give the title compound.

Example 169: Synthesis of (S)-5'-(3-aminopyrrolidine-1-carbonyl)-2'-(6,7-difluoro-1-(2-methoxyethyl)-1H-benzo[d][1,2,3]triazol-5-yl)-3-fluoro-[1,1'-biphenyl]-4-carbonitrile Step 1

The procedure of steps 1 to 3 in Example 161 was repeated using 2,3-difluoro-N-(2-methoxyethyl)-6-nitro-aniline instead of 1-(2,3-difluoro-6-nitro-anilino)-2-methyl-propan-2-ol to give 5-bromo-6,7-difluoro-1-(2-methoxyethyl)benzotriazole.

Step 2

The procedure of steps 1 to 3 in Example 37 was repeated using the 5-bromo-6,7-difluoro-1-(2-methoxyethyl)benzotriazole obtained in step 1 above instead of 1-(4-bromo-3-fluoro-phenyl)-2-methyl-propan-2-ol to give the title compound.

Example 170: Synthesis of (S)-5'-(3-aminopyrrolidine-1-carbonyl)-3-fluoro-2'-(6-fluoro-1-(2-hydroxyethyl)-1H-indol-5-yl)-[1,1'-biphenyl]-4-carbonitrile The procedure of steps 1 to 3 in Example 37 was repeated using 2-(5-bromo-6-fluoro-indol-1-yl)ethanol instead of 1-(4-bromo-3-fluoro-phenyl)-2-methyl-propan-2-ol to give the title compound.

Example 171: Synthesis of 5'-((1R,2R,4S)-rel-2-amino-7-azabicyclo[2.2.1]heptane-7-carbonyl)-3-fluoro-2'-(6-fluoro-1-(2-hydroxy-2-methylpropyl)-1H-indol-5-yl)-[1,1'-biphenyl]-4-carbonitrile-isomer-B Step 1

The tert-butyl 3-(4-cyano-3-fluoro-phenyl)-4-(4,4,5,5-tetramethyl-1,3,2-dioxaborolan-2-yl)benzoate (2.3 g) obtained in step 1 of Example 41 and the 1-(5-bromo-6-fluoro-indol-1-yl)-2-methyl-propan-2-ol (2.02 g) obtained in step 1 of Example 136 were dissolved in 1,4-dioxane (18.1 mL). At room temperature, Pd(dba)$_2$ (250 mg), X-phos (414 mg), and tripotassium phosphate (3.46 g) were added thereto, followed by stirring at 100° C. overnight. The solvent was distilled off, the residue was purified by silica gel column chromatography (mobile phase: hexane/ethyl acetate), and the solvent was distilled off. The residue was dissolved in THF (40.0 mL). At 0° C., 12 N hydrochloric acid (30.0 mL) was added thereto, followed by stirring at room temperature for 2 hours. Then, MTBE was added thereto, the mixture was washed with water and dried over anhydrous sodium sulfate, and the solvent was distilled off to give 3-(4-cyano-3-fluoro-phenyl)-4-[6-fluoro-1-(2-hydroxy-2-methyl-propyl)indol-5-yl]benzoic acid.

Step 2

The 3-(4-cyano-3-fluoro-phenyl)-4-[6-fluoro-1-(2-hydroxy-2-methyl-propyl)indol-5-yl]benzoic acid (8 mg) obtained in step 1 above and the N-((1R,2R,4S)-rel-7-azabicyclo[2.2.1]heptan-2-yl)-2,4-dinitrobenzenesulfonamide-isomer-B hydrochloride (7.47 mg) obtained in step 3 of Example 155 were dissolved in THF (0.30 mL). At room temperature, TEA (0.00748 mL) and HATU (13.6 mg) were added thereto, followed by stirring at 50° C. for 1 hour. The reaction solution was vacuum-concentrated, and the residue was purified by silica gel column chromatography (mobile phase: hexane/ethyl acetate) to give N-[(1S,3R,4R)-rel-7-[3-(4-cyano-3-fluoro-phenyl)-4-[6-fluoro-1-(2-hydroxy-2-methyl-propyl)indol-5-yl]benzoyl]-7-azabicyclo[2.2.1]heptan-3-yl]-2,4-dinitrobenzenesulfonamide-isomer-B.

Step 3

The N-[(1S,3R,4R)-rel-7-[3-(4-cyano-3-fluoro-phenyl)-4-[6-fluoro-1-(2-hydroxy-2-methyl-propyl)indol-5-yl]benzoyl]-7-azabicyclo[2.2.1]heptan-3-yl]-2,4-dinitrobenzenesulfonamide-isomer-B (13.8 mg) obtained in step 2 above was dissolved in DCM (1.0 mL). At 0° C., mercaptoacetic acid (2.49 µL) and TEA (7.48 µL) were added thereto, followed by stirring at room temperature for 1 hour. Chloroform and 4 N sodium hydroxide were added thereto, and the mixture was washed sequentially with water and saturated brine. After the organic layer was dried over anhydrous sodium sulfate, the solvent was distilled off. The residue was purified by reversed-phase HPLC (mobile phase: water/acetonitrile) to give the title compound.

Example 172: Synthesis of (S)-5'-(3-aminopyrrolidine-1-carbonyl)-2'-(6,7-difluoro-1-(2-hydroxy-2-methylpropyl)-1H-indol-5-yl)-3-fluoro-[1,1'-biphenyl]-4-carbonitrile Step 1

5-Bromo-6,7-difluoro-1H-indole (300 mg) was dissolved in DMF (4.31 mL). At room temperature, $Cs_2CO_3$ (843 mg) and 2,2-dimethyloxirane (0.230 mL) were added thereto, followed by stirring at 80° C. for 3 hours. The reaction solution was filtrated, and the solvent was distilled off. Ethyl acetate was added thereto, the mixture was washed sequentially with a saturated aqueous ammonium chloride solution, water, and saturated brine, and dried over anhydrous sodium sulfate, and the solvent was distilled off. The residue was purified by silica gel column chromatography (mobile phase: hexane/ethyl acetate) to give 1-(5-bromo-6,7-difluoro-indol-1-yl)-2-methyl-propan-2-ol.

Step 2

The tert-butyl 3-(4-cyano-3-fluoro-phenyl)-4-(4,4,5,5-tetramethyl-1,3,2-dioxaborolan-2-yl)benzoate (210 mg) obtained in step 1 of Example 41 and the 1-(5-bromo-6,7-difluoro-indol-1-yl)-2-methyl-propan-2-ol (196 mg) obtained in step 1 above were dissolved in 1,4-dioxane (1.65 mL). At room temperature, $Pd(dba)_2$ (22.8 mg), X-phos (37.8 mg), and tripotassium phosphate (316 mg) were added thereto, followed by stirring at 100° C. overnight. The solvent was distilled off, the residue was purified by silica gel column chromatography (mobile phase: hexane/ethyl acetate), and the solvent was distilled off. The residue was dissolved in THF (2.63 mL). At 0° C., 12 N hydrochloric acid (2.1 mL) was added thereto, followed by stirring at room temperature for 2 hours. MTBE was added thereto, the mixture was washed with water and dried over anhydrous sodium sulfate, and the solvent was distilled off to give 3-(4-cyano-3-fluoro-phenyl)-4-[6,7-difluoro-1-(2-hydroxy-2-methyl-propyl)indol-5-yl]benzoic acid.

Step 3

The 3-(4-cyano-3-fluoro-phenyl)-4-[6,7-difluoro-1-(2-hydroxy-2-methyl-propyl)indol-5-yl]benzoic acid (30 mg) obtained in step 2 above and tert-butyl N-[(3S)-pyrrolidin-3-yl]carbamate (13.2 mg) were dissolved in THF (0.323 mL). At room temperature, TEA (0.027 mL) and HATU (49.1 mg) were added thereto, followed by stirring at 50° C. for 1 hour. The solvent was distilled off under reduced pressure. The residue was purified by silica gel column chromatography (mobile phase: hexane/ethyl acetate) to give tert-butyl N-[(3S)-1-[3-(4-cyano-3-fluoro-phenyl)-4-[6,7-difluoro-1-(2-hydroxy-2-methyl-propyl)indol-5-yl]benzoyl]pyrrolidin-3-yl]carbamate.

Step 4

The tert-butyl N-[(3S)-1-[3-(4-cyano-3-fluoro-phenyl)-4-[6,7-difluoro-1-(2-hydroxy-2-methyl-propyl)indol-5-yl]benzoyl]pyrrolidin-3-yl]carbamate (40 mg) obtained in step 3 above was dissolved in MeOH (0.80 mL). At room temperature, a 4 N hydrochloric acid-1,4-dioxane solution (0.80 mL) was added thereto, followed by stirring at room temperature for 1 hour. Chloroform and a 2 N aqueous sodium hydroxide solution (1.6 mL) were added thereto, the mixture was washed with water and dried over anhydrous sodium sulfate, and the solvent was distilled off. The residue was purified by reversed-phase HPLC (mobile phase: water/acetonitrile) to give the title compound.

Example 173: Synthesis of 5'-(7-amino-2-azabicyclo[2.2.1]heptane-2-carbonyl)-3-fluoro-2'-(6-fluoro-1-(2-hydroxy-2-methylpropyl)-1H-indol-5-yl)-[1,1'-biphenyl]-4-carbonitrile The 3-(4-cyano-3-fluoro-phenyl)-4-[6-fluoro-1-(2-hydroxy-2-methyl-propyl)indol-5-yl]benzoic acid (8 mg) obtained in step 1 of Example 171 was dissolved in THF (0.3 mL). At room temperature, tert-butyl N-(3-azabicyclo[2.2.1]heptan-7-yl)carbamate (3.80 mg), TEA (0.0075 mL), and HATU (13.6 mg) were added thereto, followed by stirring at 50° C. for 3 hours. After the completion of the reaction was confirmed by LCMS, the reaction solution was concentrated. TFA (0.20 mL) was added to the residue, followed by stirring at room temperature for 5 minutes. After the completion of the reaction was confirmed by LCMS, DMSO (0.8 mL) was added to the reaction solution, and purification was performed by reversed-phase HPLC (mobile phase: water/acetonitrile) to give the title compound.

Example 174: Synthesis of 5'-(7-amino-2-azabicyclo[2.2.1]heptane-2-carbonyl)-2'',3-difluoro-4''-(2-hydroxy-2-methylpropyl)-[1,1':2',1''-terphenyl]-4-carbonitrile Step 1

The 3-(4-cyano-3-fluoro-phenyl)-4-[2-fluoro-4-(2-hydroxy-2-methyl-propyl)phenyl]benzoic acid (100 mg) obtained in step 2 of Example 166 was dissolved in THF (0.982 mL). At room temperature, tert-butyl N-(3-azabicyclo[2.2.1]heptan-7-yl)carbamate (52.1 mg), TEA (0.103 mL), and HATU (187 mg) were added thereto, followed by stirring at 50° C. for 3 hours. The residue was purified by silica gel column chromatography (mobile phase: hexane/ethyl acetate) to give tert-butyl N-[3-[3-(4-cyano-3-fluoro-phenyl)-4-[2-fluoro-4-(2-hydroxy-2-methyl-propyl)phenyl]benzoyl]-3-azabicyclo[2.2.1]heptan-7-yl]carbamate.

Step 2

The tert-butyl N-[3-[3-(4-cyano-3-fluoro-phenyl)-4-[2-fluoro-4-(2-hydroxy-2-methyl-propyl)phenyl]benzoyl]-3-azabicyclo[2.2.1]heptan-7-yl]carbamate (30 mg) obtained in step 1 above was dissolved in MeOH (0.5 mL). At room temperature, 12 N hydrochloric acid (0.5 mL) was added thereto. After the mixture was stirred at room temperature for 0.5 hour, water and a 2 N aqueous sodium hydroxide solution (3.0 mL) were added thereto. The mixture was extracted with chloroform, and the solvent was distilled off. The residue was purified by reversed-phase HPLC (mobile phase: water/acetonitrile) to give the title compound.

Example 175: Synthesis of 5'-((1S,2S,4R)-rel-2-amino-7-azabicyclo[2.2.1]heptane-7-carbonyl)-2'-(6,7-difluoro-1-methyl-1H-benzo[d][1,2,3]triazol-5-yl)-3-fluoro-[1,1'-biphenyl]-4-carbonitrile-isomer-B Step 1

The tert-butyl 3-(4-cyano-3-fluoro-phenyl)-4-(4,4,5,5-tetramethyl-1,3,2-dioxaborolan-2-yl)benzoate (90 mg) obtained in step 1 of Example 41 and 5-bromo-6,7-difluoro-1-methyl-benzotriazole (68.6 mg) were dissolved in 1,4-dioxane (0.71 mL). At room temperature, $Pd(dba)_2$ (9.8 mg), X-phos (16 mg), and tripotassium phosphate (135 mg) were added thereto, followed by stirring at 100° C. overnight. The solvent was distilled off, the residue was purified by silica gel column chromatography (mobile phase: hexane/ethyl acetate), and the solvent was distilled off. The residue was dissolved in TFA (1.0 mL), followed by stirring at room temperature for 2 hours. MTBE was added thereto, the mixture was washed with water and dried over anhydrous sodium sulfate, and the solvent was distilled off to give 3-(4-cyano-3-fluoro-phenyl)-4-(6,7-difluoro-1-methyl-benzotriazol-5-yl)benzoic acid.

Step 2

The 3-(4-cyano-3-fluoro-phenyl)-4-(6,7-difluoro-1-methyl-benzotriazol-5-yl)benzoic acid (30 mg) obtained in step 1 above and the N-((1R,2R,4S)-rel-7-azabicyclo[2.2.1]heptan-2-yl)-2,4-dinitrobenzenesulfonamide-isomer-B hydrochloride (30.6 mg) obtained in step 3 of Example 155 were dissolved in THF (0.367 mL). At room temperature, TEA (0.042 mL) and HATU (55.9 mg) were added thereto, followed by stirring at 50° C. for 1 hour. The reaction solution was vacuum-concentrated, and the residue was purified by silica gel column chromatography (mobile phase: hexane/ethyl acetate) to give N-[(1R,3S,4S)-rel-7-[3-(4-cyano-3-fluoro-phenyl)-4-(6,7-difluoro-1-methyl-benzotriazol-5-yl)benzoyl]-7-azabicyclo[2.2.1]heptan-3-yl]-2,4-dinitrobenzenesulfonamide-isomer-B.

Step 3

The N-[(1R,3S,4S)-rel-7-[3-(4-cyano-3-fluoro-phenyl)-4-(6,7-difluoro-1-methyl-benzotriazol-5-yl)benzoyl]-7-azabicyclo[2.2.1]heptan-3-yl]-2,4-dinitrobenzenesulfonamide-isomer-B (51 mg) obtained in step 2 above was dissolved in DCM (0.70 mL). At 0° C., mercaptoacetic acid (5.8 µL) and TEA (29.1 µL) were added thereto, followed by stirring at room temperature for 2 hours. Ethyl acetate was added thereto, and the mixture was washed sequentially with water and saturated brine. After the organic layer was dried over anhydrous sodium sulfate, the solvent was distilled off. The residue was purified by reversed-phase HPLC (mobile phase: water/acetonitrile) to give the title compound.

Example 176: Synthesis of 5'-((1S,2S,4R)-rel-2-amino-7-azabicyclo[2.2.1]heptane-7-carbonyl)-3-fluoro-2'-(6-fluoro-1-(2-hydroxy-2-methylpropyl)-1H-indazol-5-yl)-[1,1'-biphenyl]-4-carbonitrile-isomer-B Step 1

The tert-butyl 3-(4-cyano-3-fluoro-phenyl)-4-(4,4,5,5-tetramethyl-1,3,2-dioxaborolan-2-yl)benzoate (2.3 g) obtained in step 1 of Example 41 and the 1-(5-bromo-6-fluoro-1H-indazol-1-yl)-2-methylpropan-2-ol (2.03 g) obtained in step 1 of Example 142 were dissolved in 1,4-dioxane (18.7 mL). At room temperature, Pd(dba)$_2$ (250 mg), X-phos (414 mg), and tripotassium phosphate (3.46 g) were added thereto, followed by stirring at 100° C. overnight. The solvent was distilled off, the residue was purified by silica gel column chromatography (mobile phase: hexane/ethyl acetate), and the solvent was distilled off. The residue was dissolved in THF (10.0 mL). At 0° C., 12 N hydrochloric acid (10.0 mL) was added thereto, followed by stirring at room temperature for 2 hours. MTBE was added thereto, the mixture was washed with water and dried over anhydrous sodium sulfate, and the solvent was distilled off to give 3-(4-cyano-3-fluoro-phenyl)-4-[6-fluoro-1-(2-hydroxy-2-methyl-propyl)indazol-5-yl]benzoic acid.

Step 2

The 3-(4-cyano-3-fluoro-phenyl)-4-[6-fluoro-1-(2-hydroxy-2-methyl-propyl)indazol-5-yl]benzoic acid (30 mg) obtained in step 1 above and the N-((1R,2R,4S)-rel-7-azabicyclo[2.2.1]heptan-2-yl)-2,4-dinitrobenzenesulfonamide-isomer-B hydrochloride (27.9 mg) obtained in step 3 of Example 155 were dissolved in THF (0.34 mL). At room temperature, TEA (0.038 mL) and HATU (51.0 mg) were added thereto, followed by stirring at 50° C. for 1 hour. The reaction solution was vacuum-concentrated, and the residue was purified by silica gel column chromatography (mobile phase: hexane/ethyl acetate) to give N-[(1S,3R,4R)-rel-7-[3-(4-cyano-3-fluoro-phenyl)-4-[6-fluoro-1-(2-hydroxy-2-methyl-propyl)indazol-5-yl]benzoyl]-7-azabicyclo[2.2.1]heptan-3-yl]-2,4-dinitrobenzenesulfonamide-isomer-B.

Step 3

The N-[(1S,3R,4R)-rel-7-[3-(4-cyano-3-fluoro-phenyl)-4-[6-fluoro-1-(2-hydroxy-2-methyl-propyl)indazol-5-yl]benzoyl]-7-azabicyclo[2.2.1]heptan-3-yl]-2,4-dinitrobenzenesulfonamide-isomer-B (45 mg) obtained in step 2 above was dissolved in DCM (0.58 mL). At 0° C., mercaptoacetic acid (4.9 µL) and TEA (24 µL) were added thereto, followed by stirring at room temperature for 2 hours. Ethyl acetate was added thereto, and the mixture was washed sequentially with water and saturated brine. After the organic layer was dried over anhydrous sodium sulfate, the solvent was distilled off. The residue was purified by reversed-phase HPLC (mobile phase: water/acetonitrile) to give the title compound.

Example 177: Synthesis of 5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-B Step 1

The tert-butyl 3-(4-cyano-3-fluoro-phenyl)-4-(4,4,5,5-tetramethyl-1,3,2-dioxaborolan-2-yl)benzoate (3.2 g) obtained in step 1 of Example 41 and the 1-(5-bromo-6,7-difluoro-benzotriazol-1-yl)-2-methyl-propan-2-ol (3.01 g) obtained in step 3 of Example 161 were dissolved in 1,4-dioxane (25.2 mL). At room temperature, Pd(dba)$_2$ (348 mg), X-phos (577 mg), and tripotassium phosphate (4.81 g) were added thereto, followed by stirring at 100° C. overnight. The solvent was distilled off, the residue was purified by silica gel column chromatography (mobile phase: hexane/ethyl acetate), and the solvent was distilled off. The residue was dissolved in THF (15.0 mL). At 0° C., 12 N hydrochloric acid (15.0 mL) was added thereto, followed by stirring at room temperature for 2 hours. MTBE was added thereto, the mixture was washed with water and dried over anhydrous sodium sulfate, and the solvent was distilled off to give 3-(4-cyano-3-fluoro-phenyl)-4-[6,7-difluoro-1-(2-hydroxy-2-methyl-propyl)benzotriazol-5-yl]benzoic acid.

Step 2

The 3-(4-cyano-3-fluoro-phenyl)-4-[6,7-difluoro-1-(2-hydroxy-2-methyl-propyl)benzotriazol-5-yl]benzoic acid (30 mg) obtained in step 1 above and the N-((1S,2S,4R)-rel-7-azabicyclo[2.2.1]heptan-2-yl)-2,4-dinitrobenzenesulfonamide-isomer-B hydrochloride (26.8 mg) obtained in step 3 of Example 155 were dissolved in THF (0.33 mL). At room temperature, TEA (0.037 mL) and HATU (48.9 mg) were added thereto, followed by stirring at 50° C. for 1 hour. The reaction solution was vacuum-concentrated, and the residue was purified by silica gel column chromatography (mobile phase: hexane/ethyl acetate) to give N-[(1S,2S,4R)-rel-7-[3-(4-cyano-3-fluoro-phenyl)-4-[6,7-difluoro-1-(2-hydroxy-2-methyl-propyl)benzotriazol-5-yl]benzoyl]-7-azabicyclo[2.2.1]heptan-3-yl]-2,4-dinitrobenzenesulfonamide-isomer-B.

Step 3

The N-[(1S,2S,4R)-rel-7-[3-(4-cyano-3-fluoro-phenyl)-4-[6,7-difluoro-1-(2-hydroxy-2-methyl-propyl)benzotriazol-5-yl]benzoyl]-7-azabicyclo[2.2.1]heptan-3-yl]-2,4-dinitrobenzenesulfonamide-isomer-B (43 mg) obtained in step 2 above was dissolved in DCM (0.54 mL). At 0° C., mercaptoacetic acid (4.5 µL) and TEA (22.7 µL) were added thereto, followed by stirring at room temperature for 2 hours. Ethyl acetate was added thereto, and the mixture was washed sequentially with water and saturated brine. After the organic layer was dried over anhydrous sodium sulfate, the solvent was distilled off. The residue was purified by reversed-phase HPLC (mobile phase: water/acetonitrile) to give the title compound.

Example 178: Synthesis of 5'-((3-endo)-3-amino-8-azabicyclo[3.2.1]octane-8-carbonyl)-2'-(3-bromo-6-fluoro-1-(2-hydroxy-2-methylpropyl)-1H-indazol-5-yl)-3-fluoro-[1,1'-biphenyl]-4-carbonitrile Step 1

The procedure of steps 1 to 4 in Example 41 was repeated using the 1-(5-bromo-6-fluoro-indazol-1-yl)-2-methyl-propan-2-ol obtained in step 1 of Example 142 instead of 1-(4-bromo-3-fluoro-phenyl)-2-methyl-propan-2-ol to give tert-butyl N-((3-endo)-8-(4'-cyano-3'-fluoro-6-(6-fluoro-1-(2-hydroxy-2-methylpropyl)-1H-indazol-5-yl-[1,1'-biphenyl]-3-carbonyl)-8-azabicyclo[3.2.1]octan-3-yl)carbamate.
Step 2

The tert-butyl N-((3-endo)-8-(4'-cyano-3'-fluoro-6-(6-fluoro-1-(2-hydroxy-2-methylpropyl)-1H-indazol-5-yl-[1,1'-biphenyl]-3-carbonyl)-8-azabicyclo[3.2.1]octan-3-yl)carbamate (10 mg) obtained in step 1 above was dissolved in DMF (0.076 mL). NBS (3.5 mg) was added thereto, followed by stirring at 80° C. overnight. The reaction solution was diluted with DMSO to 1 mL, and purification was performed by reversed-phase HPLC (mobile phase: water/acetonitrile) to give the title compound.

Example 179: Synthesis of 5'-((3-endo)-3-amino-8-azabicyclo[3.2.1]octane-8-carbonyl)-3-fluoro-2'-(5-fluoro-3-methylbenzo[d]isoxazol-6-yl)-[1,1'-biphenyl]-4-carbonitrile Step 1

3-Bromo-4-fluorophenol (5 g) was dissolved in dichloromethane (114 mL). At 0° C., TEA (5.5 mL) was added thereto, and acetyl chloride (2.8 mL) was added thereto dropwise. The reaction solution was stirred at 20° C. for 30 minutes and diluted with dichloromethane (100 mL). The resulting product was washed with 0.5 N hydrochloric acid, a saturated aqueous sodium hydrogen carbonate solution, and saturated brine, and the solvent was distilled off to give 3-bromo-4-fluorophenyl acetate.
Step 2

A boron trifluoride-acetic acid complex (53 mL) was added to the 3-bromo-4-fluorophenyl acetate (6.2 g) obtained in step 1 above, followed by stirring at 155° C. for 14 hours. The reaction solution was cooled to 0° C., and ice was added thereto. The precipitate was collected by filtration, washed with water at 0° C., and dried. The obtained solid was purified by silica gel column chromatography (mobile phase: hexane/ethyl acetate) to give 1-(4-bromo-5-fluoro-2-hydroxyphenyl)ethanone.
Step 3

MeOH (30 mL) was added to the 1-(4-bromo-5-fluoro-2-hydroxyphenyl)ethanone (2.16 g) obtained in step 2 above, hydroxylamine hydrochloride (1.29 g), and sodium acetate (1.14 g), followed by stirring at 60° C. for 1 hour. Ice water was added to the reaction solution, and the precipitate was collected by filtration, washed with water, and dried. The obtained solid was dissolved in THF (31 mL), and TEA (1.68 mL) and N,N'-carbonyldiimidazole (1.65 g) were added thereto, followed by stirring at 70° C. for 1 hour. The solvent was distilled off, and the residue was purified by silica gel column chromatography (mobile phase: chloroform/ethyl acetate) to give 6-bromo-5-fluoro-3-methylbenzo[d]isoxazol.
Step 4

The procedure of steps 1 to 5 in Example 41 was repeated using the 6-bromo-5-fluoro-3-methylbenzo[d]isoxazol obtained in step 3 above instead of 1-(4-bromo-3-fluoro-phenyl)-2-methyl-propan-2-ol to give the title compound.

Example 180: Synthesis of (S)-5'-(3-aminopyrrolidine-1-carbonyl)-3-fluoro-2'-(5-fluoro-3-methylbenzo[d]isoxazol-6-yl)-[1,1'-biphenyl]-4-carbonitrile The procedure of steps 1 to 3 in Example 37 was repeated using the 6-bromo-5-fluoro-3-methylbenzo[d]isoxazol obtained in step 3 of Example 179 instead of 1-(4-bromo-3-fluoro-phenyl)-2-methyl-propan-2-ol to give the title compound.

Example 181: Synthesis of 5'-((3-endo)-3-amino-8-azabicyclo[3.2.1]octane-8-carbonyl)-3-fluoro-2'-(6-fluoro-1-(2-hydroxy-2-methylpropyl)-3-methyl-1H-indazol-5-yl)-[1,1'-biphenyl]-4-carbonitrile Step 1

The tert-butyl N-((3-endo)-8-(4'-cyano-3'-fluoro-6-(6-fluoro-1-(2-hydroxy-2-methylpropyl)-1H-indazol-5-yl-[1,1'-biphenyl]-3-carbonyl)-8-azabicyclo[3.2.1]octan-3-yl)carbamate (69 mg) obtained in step 1 of Example 178 was dissolved in DMF (0.53 mL), and NBS (38 mg) was added thereto, followed by stirring at 80° C. overnight. The mixture was cooled to room temperature, and Boc$_2$O (200 mg) and DMAP (1 mg) were added thereto, followed by stirring at room temperature for 2 hours. Ethyl acetate was added thereto, and the resulting mixture was washed sequentially with water and saturated brine. After the organic layer was dried over anhydrous sodium sulfate, the solvent was distilled off. The solvent was distilled off, and the residue was purified by silica gel column chromatography (mobile phase: hexane/ethyl acetate) to give tert-butyl ((3-endo)-8-(4'-cyano-3'-fluoro-6-(6-fluoro-1-(2-hydroxy-2-methylpropyl)-1H-indazol-5-yl)-[1,1'-biphenyl]-3-carbonyl)-8-azabicyclo[3.2.1]octan-3-yl)carbamate.
Step 2

The tert-butyl ((3-endo)-8-(4'-cyano-3'-fluoro-6-(6-fluoro-1-(2-hydroxy-2-methylpropyl)-1H-indazol-5-yl)-[1,1'-biphenyl]-3-carbonyl)-8-azabicyclo[3.2.1]octan-3-yl)carbamate (15 mg) obtained in step 1 above, trimethylboroxine (7.7 mg), PdCl$_2$(dppf)CH$_2$Cl$_2$ (1 mg), and cesium carbonate (20 mg) were suspended in 1,4-dioxane, followed by stirring at 125° C. for 30 minutes under microwave irradiation. The solvent was distilled off, and trifluoroacetic acid (0.2 mL) was added to the residue, followed by stirring at room temperature for 10 minutes. The reaction solution was diluted with DMSO to 1 mL, and purification was performed by reversed-phase HPLC (mobile phase: water/acetonitrile) to give the title compound.

Example 182: Synthesis of 5'-((1R,2S,4S)-rel-2-amino-7-azabicyclo[2.2.1]heptane-7-carbonyl)-2",3-difluoro-4"-(2-hydroxy-2-methylpropyl)-[1,1':2',1"-terphenyl]-4-carbonitrile Step 1 tert-Butyl (1S,3S,4R)-rel-3-amino-7-azabicyclo[2.2.1]heptane-7-carboxylate (919 mg) was dissolved in THF (14.4 mL). At 0° C., TEA (1.81 mL) and 2,4-dinitrobenzenesulfonyl chloride (1.73 g) were added thereto, followed by stirring at room temperature overnight. Ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give tert-butyl (1S,3S,4R)-rel-3-[(2,4-dinitrophenyl)sulfonylamino]-7-azabicyclo [2.2.1]heptane-7-carboxylate.

Step 2

The tert-butyl (1S,3S,4R)-rel-3-[(2,4-dinitrophenyl)sulfonylamino]-7-azabicyclo[2.2.1]heptane-7-carboxylate (100 mg) obtained in step 1 above was dissolved in ethyl acetate (1.00 mL). At room temperature, a 4 N hydrochloric acid-ethyl acetate solution (2.00 mL) was added thereto, followed by stirring at room temperature for 1 hour. The reaction solution was vacuum-concentrated to give N-[(1S,3S,4R)-rel-7-azabicyclo[2.2.1]heptan-3-yl]-2,4-dinitrobenzenesulfonamide hydrochloride.

Step 3

The 3-(4-cyano-3-fluoro-phenyl)-4-[2-fluoro-4-(2-hydroxy-2-methyl-propyl)phenyl]benzoic acid (30 mg) obtained in step 2 of Example 166 and the N-[(1S,3S,4R)-rel-7-azabicyclo[2.2.1]heptan-3-yl]-2,4-dinitrobenzenesulfonamide hydrochloride (30.7 mg) obtained in step 2 above were dissolved in THF (0.40 mL). At room temperature, TEA (0.0420 mL) and HATU (56.0 mg) were added thereto, followed by stirring at 50° C. for 1 hour. The reaction solution was vacuum-concentrated, and the residue was purified by silica gel column chromatography (mobile phase: hexane/ethyl acetate) to give N-[(1S,3S,4R)-rel-7-[3-(4-cyano-3-fluoro-phenyl)-4-[2-fluoro-4-(2-hydroxy-2-methyl-propyl)phenyl]benzoyl]-7-azabicyclo[2.2.1]heptan-3-yl]-2,4-dinitrobenzenesulfonamide.

Step 4

The N-[(1S,3S,4R)-rel-7-[3-(4-cyano-3-fluoro-phenyl)-4-[2-fluoro-4-(2-hydroxy-2-methyl-propyl)phenyl]benzoyl]-7-azabicyclo[2.2.1]heptan-3-yl]-2,4-dinitrobenzenesulfonamide (55 mg) obtained in step 3 above was dissolved in DCM (0.752 mL). At 0° C., mercaptoacetic acid (6.27 μL) and TEA (31.4 μL) were added thereto, followed by stirring at room temperature for 2 hours. Chloroform was added thereto, the mixture was washed with a 4 N aqueous sodium hydroxide solution, and dried over anhydrous sodium sulfate, and the solvent was distilled off. The residue was purified by reversed-phase HPLC (mobile phase: water/acetonitrile) to give the title compound.

Example 183: Synthesis of 5'-((3-endo)-3-amino-8-azabicyclo[3.2.1]octane-8-carbonyl)-2'-(6,7-difluoro-1-(2-hydroxy-2-methylpropyl)-1H-indol-5-yl)-3-fluoro-[1,1'-biphenyl]-4-carbonitrile Step 1

The 3-(4-cyano-3-fluoro-phenyl)-4-[6,7-difluoro-1-(2-hydroxy-2-methyl-propyl)indol-5-yl]benzoic acid (30 mg) obtained in step 2 of Example 172 and tert-butyl N-[(3-endo)-8-azabicyclo[3.2.1]octan-3-yl]carbamate (16.1 mg) were dissolved in THF (0.323 mL). At room temperature, TEA (0.027 mL) and HATU (49.1 mg) were added thereto, followed by stirring at 50° C. for 1 hour. The solvent was distilled off under reduced pressure. The residue was purified by silica gel column chromatography (mobile phase: hexane/ethyl acetate) to give tert-butyl N-[(3-endo)-8-azabicyclo[3.2.1]octan-3-yl]carbamate.

Step 2

The tert-butyl N-[(3-endo)-8-[3-(4-cyano-3-fluoro-phenyl)-4-[6,7-difluoro-1-(2-hydroxy-2-methyl-propyl)indol-5-yl]benzoyl]-8-azabicyclo[3.2.1]octan-3-yl]carbamate (42 mg) obtained in step 1 above was dissolved in MeOH (0.84 mL). At room temperature, a 4 N hydrochloric acid-1,4-dioxane solution (0.84 mL) was added thereto, followed by stirring at room temperature for 1 hour. Chloroform and a 2 N aqueous sodium hydroxide solution (1.68 mL) were added thereto, the mixture was washed with water and dried over anhydrous sodium sulfate, and the solvent was distilled off. The residue was purified by reversed-phase HPLC (mobile phase: water/acetonitrile) to give the title compound.

Example 184: Synthesis of 5'-((1R,2S,4S)-rel-2-amino-7-azabicyclo[2.2.1]heptane-7-carbonyl)-3-fluoro-2'-(6-fluoro-1-(2-hydroxy-2-methylpropyl)-1H-indol-5-yl)-[1,1'-biphenyl]-4-carbonitrile The procedure of steps 1 to 3 in Example 171 was repeated using the N-[(1R,2S,4S)-rel-7-azabicyclo[2.2.1]heptan-3-yl]-2,4-dinitrobenzenesulfonamide hydrochloride obtained in step 2 of Example 182 instead of N-((1R,2R,4S)-rel-7-azabicyclo[2.2.1]heptan-2-yl)-2,4-dinitrobenzenesulfonamide-isomer-B hydrochloride to give the title compound.

Example 185: Synthesis of 5'-((1S,2S,4S)-rel-2-amino-7-azabicyclo[2.2.1]heptane-7-carbonyl)-2'-(6,7-difluoro-1-methyl-1H-benzo[d][1,2,3]triazol-5-yl)-3-fluoro-[1,1'-biphenyl]-4-carbonitrile The procedure of steps 3 to 4 in Example 172 was repeated using the 3-(4-cyano-3-fluoro-phenyl)-4-(6,7-difluoro-1-methyl-benzotriazol-5-yl)benzoic acid obtained in step 1 of Example 175 instead of 3-(4-cyano-3-fluoro-phenyl)-4-[6,7-difluoro-1-(2-hydroxy-2-methyl-propyl)indol-5-yl]benzoic acid, and using tert-butyl ((1S,2S,4S)-rel-7-azabicyclo[2.2.1]heptan-2-yl)carbamate hydrochloride instead of tert-butyl N-[(3S)-pyrrolidin-3-yl]carbamate to give the title compound.

Example 186: Synthesis of 5'-((3-endo)-3-amino-8-azabicyclo[3.2.1]octane-8-carbonyl)-3-fluoro-2'-(6-fluoro-1-(2-hydroxy-2-methylpropyl)-7-methoxy-1H-indazol-5-yl)-[1,1'-biphenyl]-4-carbonitrile Step 1

5-Bromo-2,3,4-trifluoro-benzaldehyde (480 mg) was dissolved in 1,2-dimethoxyethane (4.8 mL). At room temperature, hydrazine monohydrate (7.68 mL) was added thereto, followed by stirring at 80° C. for 5 hours. Ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give 5-bromo-6,7-difluoro-1H-indazole.

Step 2

The 5-bromo-6,7-difluoro-1H-indazole (97 mg) obtained in step 1 above was dissolved in DMF (1.38 mL). At room temperature, methanol (0.1 mL), cesium carbonate (271 mg), 2,2-dimethyloxirane (0.074 mL) were added thereto, followed by stirring at 80° C. for 1 hour. Ethyl acetate was added thereto, the mixture was washed sequentially with water and saturated brine, and dried over anhydrous sodium sulfate, and the solvent was distilled off. The residue was purified by silica gel column chromatography (mobile phase: hexane/ethyl acetate) to give 1-(5-bromo-6-fluoro-7-methoxy-indazol-1-yl)-2-methyl-propan-2-ol.

Step 3

The tert-butyl 3-(4-cyano-3-fluoro-phenyl)-4-(4,4,5,5-tetramethyl-1,3,2-dioxaborolan-2-yl)benzoate (45.0 mg) obtained in step 1 of Example 41 and the 1-(5-bromo-6-fluoro-7-methoxy-indazol-1-yl)-2-methyl-propan-2-ol (43.8 mg) obtained in step 2 above were dissolved in 1,4-dioxane (0.50 mL). At room temperature, Pd(dba)$_2$ (4.89 mg), X-phos (8.11 mg), and tripotassium phosphate (67.7 mg) were added thereto, followed by stirring at 100° C. overnight. The solvent was distilled off, the residue was purified by silica gel column chromatography (mobile phase: hexane/ethyl acetate), and the solvent was distilled off. The residue was dissolved in THF (0.45 mL). At 0° C., 12 N hydrochloric acid (0.56 mL) was added thereto, followed by stirring at room temperature for 2 hours. MTBE was added thereto, and the mixture was washed with water and dried over anhydrous sodium sulfate. Thereafter, the solvent was distilled off to give 3-(4-cyano-3-fluoro-phenyl)-4-[6-fluoro-1-(2-hydroxy-2-methyl-propyl)-7-methoxy-indazol-5-yl]benzoic acid.

Step 4

The procedure of steps 3 to 4 in Example 172 was repeated using the 3-(4-cyano-3-fluoro-phenyl)-4-[6-fluoro-1-(2-hydroxy-2-methyl-propyl)-7-methoxy-indazol-5-yl]benzoic acid obtained in step 3 above instead of 3-(4-cyano-3-fluoro-phenyl)-4-[6,7-difluoro-1-(2-hydroxy-2-methyl-propyl)indol-5-yl]benzoic acid, and using tert-butyl ((3-endo)-8-azabicyclo[3.2.1]octan-3-yl)carbamate instead of tert-butyl N-[(3S)-pyrrolidin-3-yl]carbamate to give the title compound.

Example 187: Synthesis of (S)-5'-(3-aminopyrrolidine-1-carbonyl)-2'-(6,7-difluoro-1-(2-hydroxy-2-methylpropyl)-1H-indazol-5-yl)-3-fluoro-[1,1'-biphenyl]-4-carbonitrile Step 1

The 5-bromo-6,7-difluoro-1H-indazole (101 mg) obtained in step 1 of Example 186 was dissolved in DMF (1.44 mL). At room temperature, cesium carbonate (283 mg) and 2,2-dimethyloxirane (0.077 mL) were added thereto, followed by stirring at 80° C. overnight. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 1-(5-bromo-6,7-difluoro-indazol-1-yl)-2-methyl-propan-2-ol.

Step 2

The procedure of steps 2 to 4 in Example 172 was repeated using the 1-(5-bromo-6,7-difluoro-indazol-1-yl)-2-methyl-propan-2-ol obtained in step 1 above instead of 1-(5-bromo-6,7-difluoro-indol-1-yl)-2-methyl-propan-2-ol to give the title compound.

Example 188: Synthesis of 5'-((3-endo)-3-amino-8-azabicyclo[3.2.1]octane-8-carbonyl)-2'-(6,7-difluoro-1-(2-hydroxy-2-methylpropyl)-1H-indazol-5-yl)-3-fluoro-[1,1'-biphenyl]-4-carbonitrile The procedure of steps 2 to 4 in Example 172 was repeated using the 1-(5-bromo-6,7-difluoro-indazol-1-yl)-2-methyl-propan-2-ol obtained in step 1 of Example 187 instead of 1-(5-bromo-6,7-difluoro-indol-1-yl)-2-methyl-propan-2-ol, and using tert-butyl ((3-endo)-8-azabicyclo[3.2.1]octan-3-yl)carbamate instead of tert-butyl N-[(3S)-pyrrolidin-3-yl]carbamate to give the title compound.

Example 189: Synthesis of 5'-((1S,2S,4R)-rel-2-amino-7-azabicyclo[2.2.1]heptane-7-carbonyl)-3-fluoro-2'-(6-fluoro-1-(2-hydroxy-2-methylpropyl)-1H-indazol-5-yl)-[1,1'-biphenyl]-4-carbonitrile The procedure of steps 2 to 4 in Example 172 was repeated using the 1-(5-bromo-6-fluoro-indazol-1-yl)-2-methyl-propan-2-ol obtained in step 1 of Example 142 instead of 1-(5-bromo-6,7-difluoro-indol-1-yl)-2-methyl-propan-2-ol, and using tert-butyl ((1S,2S,4R)-rel-7-azabicyclo[2.2.1]heptan-2-yl)carbamate hydrochloride instead of tert-butyl N-[(3S)-pyrrolidin-3-yl]carbamate to give the title compound.

Example 190: Synthesis of (S)-5'-(3-amino-3-methylpyrrolidine-1-carbonyl)-3-fluoro-2'-(6-fluoro-1-(2-hydroxy-2-methylpropyl)-1H-indol-5-yl)-[1,1'-biphenyl]-4-carbonitrile The procedure of steps 2 to 4 in Example 172 was repeated using the 1-(5-bromo-6-fluoro-indol-1-yl)-2-methyl-propan-2-ol obtained in step 1 of Example 136 instead of 1-(5-bromo-6,7-difluoro-indol-1-yl)-2-methyl-propan-2-ol, and using tert-butyl (S)-(3-methylpyrrolidin-3-yl)carbamate instead of tert-butyl N-[(3S)-pyrrolidin-3-yl]carbamate to give the title compound.

Example 191: Synthesis of (S)-5'-(3-amino-3-methylpyrrolidine-1-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile The procedure of steps 3 to 4 in Example 172 was repeated using the 3-(4-cyano-3-fluoro-phenyl)-4-[6,7-difluoro-1-(2-hydroxy-2-methyl-propyl)benzotriazol-5-yl]benzoic acid obtained in step 1 of Example 177 instead of 3-(4-cyano-3-fluoro-phenyl)-4-[6,7-difluoro-1-(2-hydroxy-2-methyl-propyl)indol-5-yl]benzoic acid, and using tert-butyl (S)-(3-methylpyrrolidin-3-yl)carbamate instead of tert-butyl N-[(3S)-pyrrolidin-3-yl]carbamate to give the title compound.

Example 192: Synthesis of 5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile The procedure of steps 3 to 4 in Example 172 was repeated using the 3-(4-cyano-3-fluoro-phenyl)-4-[6,7-difluoro-1-(2-hydroxy-2-methyl-propyl)benzotriazol-5-yl]benzoic acid obtained in step 1 of Example 177 instead of 3-(4-cyano-3-fluoro-phenyl)-4-[6,7-difluoro-1-(2-hydroxy-2-methyl-propyl)indol-5-yl]benzoic acid, and using tert-butyl ((1S,2S,4R)-rel-7-azabicyclo[2.2.1]heptan-2-yl)carbamate hydrochloride instead of tert-butyl N-[(3S)-pyrrolidin-3-yl]carbamate to give the title compound.

Example 193: Synthesis of 5'-((1S,2S,4R)-rel-2-amino-7-azabicyclo[2.2.1]heptane-7-carbonyl)-2'',3-difluoro-4''-(2-hydroxy-2-methylpropyl)-[1,1':2',1''-terphenyl]-4-carbonitrile The procedure of steps 3 to 4 in Example 172 was repeated using the 3-(4-cyano-3-fluoro-phenyl)-4-[2-fluoro- 4-(2-hydroxy-2-methyl-propyl)phenyl]benzoic acid obtained in step 2 of Example 166 instead of 3-(4-cyano-3-fluoro-phenyl)-4-[6,7-difluoro-1-(2-hydroxy-2-methyl-propyl)indol-5-yl]benzoic acid, and using tert-butyl ((1S,2S,4R)-rel-7-azabicyclo[2.2.1]heptan-2-yl)carbamate hydrochloride instead of tert-butyl N-[(3S)-pyrrolidin-3-yl]carbamate to give the title compound.

Example 194: Synthesis of 5'-((3-endo)-3-amino-8-azabicyclo[3.2.1]octane-8-carbonyl)-3-fluoro-2'-(6-fluoro-1-(3-hydroxy-3-methylbutyl)-1H-indazol-5-yl)-[1,1'-biphenyl]-4-carbonitrile Step 1
5-Bromo-6-fluoro-1H-indazole (200 mg) was dissolved in DMF (3.1 mL). At room temperature, cesium carbonate (606 mg), and 3-hydroxy-3-methyl-butyl ester of 4-methylbenzene sulfonic acid (481 mg) were added thereto, followed by stirring at 90° C. for 16 hours. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 4-(5-bromo-6-fluoro-indazol-1-yl)-2-methyl-butan-2-ol.
Step 2
The procedure of steps 2 to 4 in Example 172 was repeated using the 4-(5-bromo-6-fluoro-indazol-1-yl)-2-methyl-butan-2-ol obtained in step 1 above instead of 1-(5-bromo-6,7-difluoro-indol-1-yl)-2-methyl-propan-2-ol, and using tert-butyl ((3-endo)-8-azabicyclo[3.2.1]octan-3-yl)carbamate instead of tert-butyl N-[(3S)-pyrrolidin-3-yl]carbamate to give the title compound.

Example 195: Synthesis of 5'-((1S,2S,4R)-rel-2-amino-7-azabicyclo[2.2.1]heptane-7-carbonyl)-2'-(6,7-difluoro-1-(2-hydroxy-2-methylpropyl)-1H-indazol-5-yl)-3-fluoro-[1,1'-biphenyl]-4-carbonitrile The procedure of steps 2 to 4 in Example 172 was repeated using the 1-(5-bromo-6,7-difluoro-indazol-1-yl)-2-methyl-propan-2-ol obtained in step 1 of Example 187 instead of 1-(5-bromo-6,7-difluoro-indol-1-yl)-2-methyl-propan-2-ol, and using tert-butyl ((1S,2S,4R)-rel-7-azabicyclo[2.2.1]heptan-2-yl)carbamate hydrochloride instead of tert-butyl N-[(3S)-pyrrolidin-3-yl]carbamate to give the title compound.

Example 196: Synthesis of 5'-((1S,2S,4R)-rel-2-amino-7-azabicyclo[2.2.1]heptane-7-carbonyl)-2'-(6,7-difluoro-1-(2-hydroxy-2-methylpropyl)-1H-indol-5-yl)-3-fluoro-[1,1'-biphenyl]-4-carbonitrile The procedure of steps 1 to 4 in Example 172 was repeated using tert-butyl ((1S,2S,4R)-rel-7-azabicyclo[2.2.1]heptan-2-yl)carbamate hydrochloride instead of tert-butyl N-[(3S)-pyrrolidin-3-yl]carbamate to give the title compound.

Example 197: Synthesis of (S)-5'-(3-amino-3-methylpyrrolidine-1-carbonyl)-2'-(6,7-difluoro-1-(2-hydroxy-2-methylpropyl)-1H-indol-5-yl)-3-fluoro-[1,1'-biphenyl]-4-carbonitrile The procedure of steps 2 to 4 in Example 172 was repeated using the 1-(5-bromo-6,7-difluoro-indazol-1-yl)-2-methyl-propan-2-ol obtained in step 1 of Example 187 instead of 1-(5-bromo-6,7-difluoro-indol-1-yl)-2-methyl-propan-2-ol, and using tert-butyl (S)-(3-methylpyrrolidin-3-yl)carbamate instead of tert-butyl N-[(3S)-pyrrolidin-3-yl]carbamate to give the title compound.

Example 198: Synthesis of (S)-5'-(3-amino-3-methylpyrrolidine-1-carbonyl)-2'-(6,7-difluoro-1-(2-hydroxy-2-methylpropyl)-1H-indol-5-yl)-3-fluoro-[1,1'-biphenyl]-4-carbonitrile The procedure of steps 1 to 4 in Example 172 was repeated using tert-butyl (S)-(3-methylpyrrolidin-3-yl)carbamate instead of tert-butyl N-[(3S)-pyrrolidin-3-yl]carbamate to give the title compound.

Example 199: Synthesis of 3-fluoro-2'-(6-fluoro-1-(2-hydroxy-2-methylpropyl)-1H-indazol-5-yl)-5'-(2,7-diazaspiro[3.4]octane-6-carbonyl)-[1,1'-biphenyl]-4-carbonitrile The procedure of steps 2 to 4 in Example 172 was repeated using the 1-(5-bromo-6-fluoro-indazol-1-yl)-2-methyl-propan-2-ol obtained in step 1 of Example 142 instead of 1-(5-bromo-6,7-difluoro-indol-1-yl)-2-methyl-propan-2-ol, and using tert-butyl 2,7-diazaspiro[3.4]octane-2-carboxylate instead of tert-butyl N-[(3S)-pyrrolidin-3-yl]carbamate to give the title compound.

Example 200: Synthesis of 2'-(6,7-difluoro-1-(2-hydroxy-2-methylpropyl)-1H-indol-5-yl)-3-fluoro-5'-(2,7-diazaspiro[3.4]octane-6-carbonyl)-[1,1'-biphenyl]-4-carbonitrile The procedure of steps 1 to 4 in Example 172 was repeated using tert-butyl 2,7-diazaspiro[3.4]octane-2-carboxylate instead of tert-butyl N-[(3S)-pyrrolidin-3-yl]carbamate to give the title compound.

Example 201: Synthesis of 2'-(6,7-difluoro-1-(2-hydroxy-2-methylpropyl)-1H-indol-5-yl)-3-fluoro-5'-(2,8-diazaspiro[3.5]nonane-2-carbonyl)-[1,1'-biphenyl]-4-carbonitrile The procedure of steps 1 to 4 in Example 172 was repeated using tert-butyl 2,8-diazaspiro[3.5]nonane-6-carboxylate instead of tert-butyl N-[(3S)-pyrrolidin-3-yl]carbamate to give the title compound.

Example 202: Synthesis of 5'-((1S,2S,4R)-rel-2-amino-7-azabicyclo[2.2.1]heptane-7-carbonyl)-3-fluoro-2'-(5-fluoro-3-methylbenzo[d]isoxazol-6-yl)-[1,1'-biphenyl]-4-carbonitrile-isomer-X Step 1
tert-Butyl ((1S,2S,4R)-rel-7-azabicyclo[2.2.1]heptan-2-yl)carbamate hydrochloride (36 mg) was dissolved in DCM (2.89 mL). At room temperature, TEA (40 μL) and benzyl chloroformate (25 μL) were added thereto, followed by stirring at the room temperature for 1 hour. The solvent was distilled off, and chloroform and water were added thereto. The mixture was extracted twice with chloroform and washed with water and saturated brine. The solvent was distilled off, and the residue was purified by silica gel column chromatography (mobile phase: hexane/ethyl acetate) to give benzyl (1S,2S,4R)-rel-2-((tert-butoxycarbonyl)amino)-7-azabicyclo[2.2.1]heptane-7-carboxylate.

The benzyl (1S,2S,4R)-rel-2-((tert-butoxycarbonyl)amino)-7-azabicyclo[2.2.1]heptane-7-carboxylate was obtained as a 10 mg/mL ethanol solution, and separation was performed under the following conditions.

The isomer having a shorter retention time was defined as "isomer-X," and the isomer having a longer retention time was defined as "isomer-Y."
Column: Daicel CHIRALPAK IC 2.0×25 cm
Mobile phase: hexane/2-propanol=85/15
Flow rate: 12.5 mL/min
Retention time of each isomer:
benzyl (1S,2S,4R)-rel-2-((tert-butoxycarbonyl)amino)-7-azabicyclo[2.2.1]heptane-7-carboxylate-isomer-X: 16.93 minutes benzyl (1S,2S,4R)-rel-2-((tert-butoxycarbonyl)amino)-7-azabicyclo[2.2.1]heptane-7-carboxylate-isomer-Y: 23.82 minutes.
Chiral analysis conditions:
Column: CHIRALPAK IC 4.6×150 mm
Mobile phase: hexane/2-propanol=85/15
Flow rate: 1.0 mL/min
Retention time of each isomer:
benzyl (1S,2S,4R)-rel-2-((tert-butoxycarbonyl)amino)-7-azabicyclo[2.2.1]heptane-7-carboxylate-isomer-X: 6.972 minutes
benzyl (1S,2S,4R)-rel-2-((tert-butoxycarbonyl)amino)-7-azabicyclo[2.2.1]heptane-7-carboxylate-isomer-Y: 9.895 minutes.
Step 2
The benzyl (1S,2S,4R)-rel-2-((tert-butoxycarbonyl)amino)-7-azabicyclo[2.2.1]heptane-7-carboxylate-isomer-X (93 g) obtained in step 1 above and 10% Pd/C (10 g) were suspended in methanol (1.0 L). The mixture was stirred at room temperature for 5 hours under a hydrogen atmosphere (50 psi). The reaction solution was filtrated, and the filtrate was concentrated to give tert-butyl ((1S,2S,4R)-rel-7-azabicyclo[2.2.1]heptan-2-yl)carbamate-isomer-X.
Step 3
The procedure of steps 2 to 4 in Example 172 was repeated using the 6-bromo-5-fluoro-3-methylbenzo[d]isoxazol obtained in step 3 of Example 179 instead of 1-(5-bromo-6,7-difluoro-indol-1-yl)-2-methyl-propan-2-ol, and using the tert-butyl ((1S,2S,4R)-rel-7-azabicyclo[2.2.1]heptan-2-yl)carbamate-isomer-X obtained in step 2 above instead of tert-butyl N-[(3S)-pyrrolidin-3-yl]carbamate to give the title compound.

Example 203: Synthesis of 2'-(6,7-difluoro-1-(2-hydroxy-2-methylpropyl)-1H-indol-5-yl)-3-fluoro-5'-(octahydropyrrolo[3,4-c]pyrrole-2-carbonyl)-[1,1'-biphenyl]-4-carbonitrile The procedure of steps 1 to 4 in Example 172 was repeated using tert-butyl hexahydropyrrolo[3,4-c]pyrrole-2(1H)-carboxylate instead of tert-butyl N-[(3S)-pyrrolidin-3-yl]carbamate to give the title compound.

Example 204: Synthesis of (S)-5'-(3-aminopyrrolidine-1-carbonyl)-2'-(1-(2-ethyl-2-hydroxybutyl)-6-fluoro-1H-indazol-5-yl)-3-fluoro-[1,1'-biphenyl]-4-carbonitrile Step 1
5-Bromo-6-fluoro-1H-indazole (300 mg) was dissolved in DMF (4.65 mL). At room temperature, cesium carbonate (90.9 mg) and 2,2-diethyloxirane (0.20 mL) were added thereto, followed by stirring at 90° C. for 16 hours. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 3-[(5-bromo-6-fluoro-indazol-1-yl)methyl]pentan-3-ol.
Step 2
The procedure of steps 2 to 4 in Example 172 was repeated using the 3-[(5-bromo-6-fluoro-indazol-1-yl)methyl]pentan-3-ol obtained in step 1 above instead of 1-(5-bromo-6,7-difluoro-indol-1-yl)-2-methyl-propan-2-ol to give the title compound.

Example 205: Synthesis of 5'-((3-endo)-3-amino-8-azabicyclo[3.2.1]octane-8-carbonyl)-2'-(1-(2-ethyl-2-hydroxybutyl)-6-fluoro-1H-indazol-5-yl)-3-fluoro-[1,1'-biphenyl]-4-carbonitrile The procedure of steps 2 to 4 in Example 172 was repeated using the 3-[(5-bromo-6-fluoro-indazol-1-yl)methyl]pentan-3-ol obtained in step 1 of Example 204 instead of 1-(5-bromo-6,7-difluoro-indol-1-yl)-2-methyl-propan-2-ol, and using tert-butyl ((3-endo)-8-azabicyclo[3.2.1]octan-3-yl)carbamate instead of tert-butyl N-[(3S)-pyrrolidin-3-yl]carbamate to give the title compound.

Example 206: Synthesis of 5'-((1S,2S,4R)-rel-2-amino-7-azabicyclo[2.2.1]heptane-7-carbonyl)-2'-(1-(2-ethyl-2-hydroxybutyl)-6-fluoro-1H-indazol-5-yl)-3-fluoro-[1,1'-biphenyl]-4-carbonitrile-isomer-X The procedure of steps 2 to 4 in Example 172 was repeated using the 3-[(5-bromo-6-fluoro-indazol-1-yl)methyl]pentan-3-ol obtained in step 1 of Example 204 instead of 1-(5-bromo-6,7-difluoro-indol-1-yl)-2-methyl-propan-2-ol, and using the tert-butyl ((1S,2S,4R)-rel-7-azabicyclo[2.2.1]heptan-2-yl)carbamate-isomer-X obtained in step 2 of Example 202 instead of tert-butyl N-[(3S)-pyrrolidin-3-yl]carbamate to give the title compound.

Example 207: Synthesis of 2-(5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1H-indol-1-yl)acetic acid-isomer-X Step 1
5-Bromo-6-fluoro-1H-indole (500 mg) was dissolved in DMF (7.79 mL). At room temperature, cesium carbonate (1.67 g) and ethyl 2-chloro acetate (573 mg) were added thereto, followed by stirring at 90° C. for 16 hours. The reaction was terminated with a saturated aqueous ammonium chloride solution. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give ethyl 2-(5-bromo-6-fluoro-indol-1-yl)acetate.
Step 2
The 3-(4-cyano-3-fluoro-phenyl)-4-(4,4,5,5-tetramethyl-1,3,2-dioxaborolan-2-yl)benzoic acid (2 g) obtained in step 2 of Example 41, and the tert-butyl ((1S,2S,4R)-rel-7-azabicyclo[2.2.1]heptan-2-yl)carbamate-isomer-X (1.24 g) obtained in step 2 of Example 202 were dissolved in THF (21.8 mL). At room temperature, TEA (1.52 mL) and HATU (2.28 g) were added thereto, followed by stirring at 50° C. for 1 hour. The reaction solution was vacuum-concentrated, and the residue was purified by silica gel column chromatography (mobile phase: hexane/ethyl acetate) to give tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X.

Step 3

The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X (100 mg) obtained in step 2 above, and the ethyl 2-(5-bromo-6-fluoro-indol-1-yl)acetate (69.5 mg) obtained in step 1 above were suspended in 1,4-dioxane (0.59 mL). At room temperature, Pd(dba)$_2$ (8.2 mg), X-phos (13.6 mg) and tripotassium phosphate (113 mg) were added thereto, followed by degassing and nitrogen substitution. Under a nitrogen atmosphere, stirring was performed at an external temperature of 100° C. overnight. The solvent was distilled off, and the residue was purified by silica gel column chromatography (mobile phase: chloroform/methanol). The residue was dissolved in MeOH (1.0 mL), and a 5 N aqueous sodium hydroxide solution (1.0 mL) was added thereto, followed by stirring for 1 hour. MTBE was added thereto, and the aqueous layer was extracted. The aqueous layer was acidified with hydrochloric acid, MTBE was added thereto, and the resulting mixture was washed sequentially with water and saturated brine. After the organic layer was dried over anhydrous sodium sulfate, the solvent was distilled off to give 2-(5-(5-(((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl-6-fluoro-1H-indole-1-yl)acetic acid-isomer-X.

Step 4

Acetonitrile (1.0 mL) and a 4 N hydrochloric acid-1,4-dioxane solution (1.0 mL) were added to the 2-(5-(5-(((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl-6-fluoro-1H-indole-1-yl)acetic acid-isomer-X (10 mg) obtained in step 3 above, followed by stirring for 30 minutes. The solvent was distilled off, and the residue was purified by reversed-phase HPLC (mobile phase: water/acetonitrile) to give the title compound.

Example 208: Synthesis of 2-(4'-((1S,2S,4R)-rel-2-amino-7-azabicyclo[2.2.1]heptane-7-carbonyl)-4''-cyano-2,3''-difluoro-[1,1':2',1''-terphenyl]-4-yl)acetic acid-isomer-X The procedure of steps 3 to 4 in Example 207 was repeated using methyl 2-(4-bromo-3-fluorophenyl)acetate instead of ethyl 2-(5-bromo-6-fluoro-indol-1-yl)acetate to give the title compound.

Example 209: Synthesis of 5'-((1S,2S,4R)-rel-2-amino-7-azabicyclo[2.2.1]heptane-7-carbonyl)-2'-(7-chloro-6-fluoro-1-(2-hydroxy-2-methylpropyl)-1H-benzo[d][1,2,3]triazol-5-yl)-3-fluoro-[1,1'-biphenyl]-4-carbonitrile-isomer-X Step 1

2-Chloro-1,3-difluoro-4-nitro-benzene (1 g) was dissolved in THF (12.9 mL). TEA (1.08 mL) and 1-amino-2-methyl-propan-2-ol (0.59 mL) were added thereto, followed by stirring at room temperature for 1 hour. Ethyl acetate was added thereto, and the mixture was washed sequentially with water and saturated brine. The organic layer was dried over anhydrous sodium sulfate, and the solvent was distilled off to give 1-(2-chloro-3-fluoro-6-nitro-anilino)-2-methyl-propan-2-ol.

Step 2

The 1-(2-chloro-3-fluoro-6-nitro-anilino)-2-methyl-propan-2-ol (1.3 g) obtained in step 1 above was dissolved in DMF (9.9 mL). At room temperature, N-bromosuccinimide (1.1 g) was added thereto, followed by stirring at 90° C. for 1 hour. Ethyl acetate was added thereto, and the mixture was washed sequentially with water and saturated brine, and dried over anhydrous sodium sulfate. Thereafter, the solvent was distilled off. The residue was crystallized from IPE:hexane=1:1, and washed twice with hexane to give 1-(4-bromo-2-chloro-3-fluoro-6-nitro-anilino)-2-methyl-propan-2-ol.

Step 3

The 1-(4-bromo-2-chloro-3-fluoro-6-nitro-anilino)-2-methyl-propan-2-ol (1.6 g) obtained in step 2 above, NH$_4$Cl (1.6 g), and iron (0.8 g) were suspended in EtOH (7.81 mL) and water (7.81 mL), followed by stirring at 60° C. overnight. MTBE was added thereto, and the mixture was passed through Celite. MTBE was added thereto, and the mixture was washed sequentially with water and saturated brine, and dried over anhydrous sodium sulfate. The solvent was then distilled off to give 1-(6-amino-4-bromo-2-chloro-3-fluoro-anilino)-2-methyl-propan-2-ol.

Step 4

The 1-(6-amino-4-bromo-2-chloro-3-fluoro-anilino)-2-methyl-propan-2-ol (352 mg) obtained in step 3 above was dissolved in water (0.70 mL) and THF (1.76 mL). At 0° C., 12 N hydrochloric acid (1.06 mL) and sodium nitrite (an aqueous solution (0.3 mL) in which 101 mg of sodium nitrite was dissolved) were added thereto dropwise, followed by stirring at room temperature for 1 hour. MTBE was added thereto, and the mixture was washed sequentially with water and saturated brine, and dried over anhydrous sodium sulfate. The solvent was then distilled off. IPE:hexane=1:1 (68 mL) was added to the residue, and the target compound was collected by filtration and washed with IPE:hexane=1:1 to give 1-(5-bromo-7-chloro-6-fluoro-benzotriazol-1-yl)-2-methyl-propan-2-ol.

Step 5

The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X (50 mg) obtained in step 2 of Example 207, and the 1-(5-bromo-7-chloro-6-fluoro-benzotriazol-1-yl)-2-methyl-propan-2-ol (37.4 mg) obtained in step 4 above were suspended in 1,4-dioxane (0.3 mL). At room temperature, Pd(dba)$_2$ (4.1 mg), X-phos (6.8 mg), and tripotassium phosphate (56.7 mg) were added thereto. After nitrogen substitution, the mixture was stirred at 100° C. for 2 hours. Ethyl acetate was added thereto, and the mixture was put on NH-silica gel, and washed with ethyl acetate: methanol=10:1. The solvent was distilled off, and acetonitrile (1.0 mL) and a 4 N hydrochloric acid-1,4-dioxane solution (1.0 mL) were added to the residue, followed by stirring for 10 minutes. The solvent was distilled off, the residue was dissolved in DMSO, and purification was performed by reversed-phase HPLC (mobile phase: water/acetonitrile) to give the title compound.

Example 210: Synthesis of (S)-5'-(3-aminopyrrolidine-1-carbonyl)-2'-(7-chloro-6-fluoro-1-(2-hydroxy-2-methylpropyl)-1H-benzo[d][1,2,3]triazol-5-yl-3-fluoro-[1,1'-biphenyl]-4-carbonitrile The procedure of steps 1 to 5 in Example 209 was repeated using the tert-butyl N-[(3S)-1-[3-(4-cyano-3- fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 211: Synthesis of 5'-((3-endo)-3-amino-8-azabicyclo[3.2.1]octane-8-carbonyl)-2'-(7-chloro-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 209 was repeated using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 212: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-(2-hydroxy-2-methylpropyl)-1H-indazole-3-carboxylic acid-isomer-X Step 1
The 3-(4-cyano-3-fluoro-phenyl)-4-[6-fluoro-1-(2-hydroxy-2-methyl-propyl)indazol-5-yl]benzoic acid (250 mg) obtained in step 1 of Example 176 was dissolved in THF (2.24 mL). At room temperature, HATU (234 mg), the tert-butyl ((1S,2S,4R)-rel-7-azabicyclo[2.2.1]heptan-2-yl)carbamate-isomer-X (125 mg) obtained in step 2 of Example 202, and TEA (0.156 mL) were added thereto, followed by stirring at 50° C. for 1 hour. The solvent was distilled off under reduced pressure. The residue was purified by silica gel column chromatography (mobile phase: chloroform/methanol) to give tert-butyl ((1S,2S,4R)-rel-7-(4'-cyano-3'-fluoro-6-(6-fluoro-1-(2-hydroxy-2-methylpropyl)-1H-indazol-5-yl)-[1,1'-biphenyl]-3-carbonyl)-7-azabicyclo[2.2.1]heptan-2-yl)carbamate-isomer-X.
Step 2
The tert-butyl ((1S,2S,4R)-rel-7-(4'-cyano-3'-fluoro-6-(6-fluoro-1-(2-hydroxy-2-methylpropyl)-1H-indazol-5-yl)-[1,1'-biphenyl]-3-carbonyl)-7-azabicyclo[2.2.1]heptan-2-yl)carbamate-isomer-X (289 mg) obtained in step 1 above was dissolved in DMF (4.50 mL). At room temperature, NBS (120 mg) was added thereto, followed by stirring at room temperature for 1 hour. Ethyl acetate was added thereto, and the mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl ((1S,2S,4R)-rel-7-(6-(3-bromo-6-fluoro-1-(2-hydroxy-2-methylpropyl)-1H-indazol-5-yl)-4'-cyano-3'-fluoro-[1,1'-biphenyl]-3-carbonyl)-7-azabicyclo[2.2.1]heptan-2-yl)carbamate-isomer-X.
Step 3
The tert-butyl ((1S,2S,4R)-rel-7-(6-(3-bromo-6-fluoro-1-(2-hydroxy-2-methylpropyl)-1H-indazol-5-yl)-4'-cyano-3'-fluoro-[1,1'-biphenyl]-3-carbonyl)-7-azabicyclo[2.2.1]heptan-2-yl)carbamate-isomer-X (50 mg) obtained in step 2 above and PdCl$_2$(PPh$_3$)$_2$ (2.4 mg) were suspended in 1-methyl-2-pyrrolidinone (0.5 mL). At room temperature, N,N-diethylethanolamine (0.046 mL) was added thereto, and after CO substitution, the mixture was stirred at 125° C. for 1 hour. tert-Butyl alcohol (0.5 mL) and a 2 N aqueous sodium hydroxide solution (0.25 mL) were added to the reaction solution, followed by stirring at the room temperature for 1 hour. MTBE was added thereto, and the aqueous layer was separated. The aqueous layer was acidified with hydrochloric acid, and extraction was performed with MTBE. After the organic layer was dried over anhydrous sodium sulfate, the solvent was distilled off. Acetonitrile (0.5 mL) and a 4 N hydrochloric acid-1,4-dioxane solution (0.5 mL) were added to the residue, followed by stirring for 10 minutes. The reaction solution was concentrated, and the residue was purified by reversed-phase HPLC (mobile phase: water/acetonitrile) to give the title compound.

Example 213: Synthesis of 5'-((1S,2S,4R)-rel-2-amino-7-azabicyclo[2.2.1]heptane-7-carbonyl)-2'-(7-chloro-6-fluoro-1-(2-hydroxy-2-methylpropyl)-1H-benzo[d][1,2,3]triazol-5-yl-3-fluoro-[1,1'-biphenyl]-4-carbonitrile Step 1
The 3-(4-cyano-3-fluoro-phenyl)-4-(4,4,5,5-tetramethyl-1,3,2-dioxaborolan-2-yl)benzoic acid (500 mg) obtained in step 2 of Example 41 and tert-butyl ((1S,2S,4R)-rel-7-azabicyclo[2.2.1]heptan-2-yl)carbamate hydrochloride (303.5 mg) were dissolved in THF (5.45 mL). At room temperature, TEA (0.379 mL) and HATU (569.5 mg) were added thereto, followed by stirring at 50° C. for 1 hour. The reaction solution was vacuum-concentrated, and the residue was purified by silica gel column chromatography (mobile phase: hexane/ethyl acetate) to give tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate.
Step 2
The procedure of steps 1 to 5 in Example 209 was repeated using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 above instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 214: Synthesis of 5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile-isomer-X The procedure of steps 1 to 5 in Example 161 was repeated using 3-[(2,3-difluoro-6-nitro-anilino)methyl]pentan-3-ol instead of 1-(2,3-difluoro-6-nitro-anilino)-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X obtained in step 2 of Example 207 instead of tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate to give the title compound.

Example 215: Synthesis of (S)-5'-(3-aminopyrrolidine-1-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile The procedure of steps 1 to 5 in Example 161 was repeated using 3-[(2,3-difluoro-6-nitro-anilino)methyl]pentan-3-ol instead of 1-(2,3-difluoro-6-nitro-anilino)-2-methyl-propan-2-ol, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate to give the title compound.

Example 216: Synthesis of 5'-((3-endo)-3-amino-8-azabicyclo[3.2.1]octane-8-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile The procedure of steps 1 to 5 in Example 161 was repeated using 3-[(2,3-difluoro-6-nitro-anilino)methyl]pentan-3-ol instead of 1-(2,3-difluoro-6-nitro-anilino)-2-methyl-propan-2-ol to give the title compound.

Example 217: Synthesis of 5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1,1'-biphenyl]-4-carbonitrile The procedure of steps 1 to 5 in Example 161 was repeated using 3-[(2,3-difluoro-6-nitro-anilino)methyl]pentan-3-ol instead of 1-(2,3-difluoro-6-nitro-anilino)-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate to give the title compound.

Example 218: Synthesis of 5'-((1S,2S,4R)-rel-2-amino-7-azabicyclo[2.2.1]heptane-7-carbonyl)-2'-(7-chloro-1-(2-ethyl-2-hydroxybutyl)-6-fluoro-1H-benzo[d][1,2,3]triazol-5-yl)-3-fluoro-[1,1'-biphenyl]-4-carbonitrile-isomer-X The procedure of steps 1 to 5 in Example 209 was repeated using 3-(aminomethyl)pentan-3-ol instead of 1-amino-2-methyl-propan-2-ol to give the title compound.

Example 219: Synthesis of (S)-5'-(3-aminopyrrolidine-1-carbonyl)-2'-(7-chloro-1-(2-ethyl-2-hydroxybutyl)-6-fluoro-1H-benzo[d][1,2,3]triazol-5-yl)-3-fluoro-[1,1'-biphenyl]-4-carbonitrile The procedure of steps 1 to 5 in Example 209 was repeated using 3-(aminomethyl)pentan-3-ol instead of 1-amino-2-methyl-propan-2-ol, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 220: Synthesis of 5'-((3-endo)-3-amino-8-azabicyclo[3.2.1]octane-8-carbonyl)-2'-(7-chloro-1-(2-ethyl-2-hydroxybutyl)-6-fluoro-1H-benzo[d][1,2,3]triazol-5-yl)-3-fluoro-[1,1'-biphenyl]-4-carbonitrile The procedure of steps 1 to 5 in Example 209 was repeated using 3-(aminomethyl)pentan-3-ol instead of 1-amino-2-methyl-propan-2-ol, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 221: Synthesis of 5'-((1S,2S,4R)-rel-2-amino-7-azabicyclo[2.2.1]heptane-7-carbonyl)-2'-(7-chloro-1-(2-ethyl-2-hydroxybutyl)-6-fluoro-1H-benzo[d][1,2,3]triazol-5-yl)-3-fluoro-[1,1'-biphenyl]-4-carbonitrile The procedure of steps 1 to 5 in Example 209 was repeated using 3-(aminomethyl)pentan-3-ol instead of 1-amino-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 222: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-(2-hydroxy-2-methylpropyl)-1H-indole-3-carboxylic acid-isomer-X Step 1

The 3-(4-cyano-3-fluoro-phenyl)-4-[6-fluoro-1-(2-hydroxy-2-methyl-propyl)indol-5-yl]benzoic acid (250 mg) obtained in step 1 of Example 171 was dissolved in THF (2.24 mL). At room temperature, HATU (234 mg), the tert-butyl ((1S,2S,4R)-rel-7-azabicyclo[2.2.1]heptan-2-yl)carbamate-isomer-X (125 mg) obtained in step 2 of Example 202, and TEA (0.156 mL) were added thereto, followed by stirring at 50° C. for 1 hour. The solvent was distilled off under reduced pressure. The residue was purified by silica gel column chromatography (mobile phase: chloroform/methanol) to give tert-butyl ((1S,2S,4R)-rel-7-(4'-cyano-3'-fluoro-6-(6-fluoro-1-(2-hydroxy-2-methylpropyl)-1H-indol-5-yl)-[1,1'-biphenyl]-3-carbonyl)-7-azabicyclo[2.2.1]heptan-2-yl)carbamate-isomer-X.

Step 2

The tert-butyl ((1S,2S,4R)-rel-7-(4'-cyano-3'-fluoro-6-(6-fluoro-1-(2-hydroxy-2-methylpropyl)-1H-indol-5-yl)-[1,1'-biphenyl]-3-carbonyl)-7-azabicyclo[2.2.1]heptan-2-yl)carbamate-isomer-X (289 mg) obtained in step 1 above was dissolved in DMF (4.50 mL). At room temperature, N-iodosuccinimide (120 mg) was added thereto, followed by stirring at room temperature for 1 hour. Ethyl acetate was added thereto, and the mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl ((1S,2S,4R)-rel-7-(4'-cyano-3'-fluoro-6-(6-fluoro-1-(2-hydroxy-2-methylpropyl)-3-iodo-1H-indol-5-yl)-[1,1'-biphenyl]-3-carbonyl)-7-azabicyclo[2.2.1]heptan-2-yl)carbamate-isomer-X.

Step 3

The tert-butyl ((1S,2S,4R)-rel-7-(4'-cyano-3'-fluoro-6-(6-fluoro-1-(2-hydroxy-2-methylpropyl)-3-iodo-1H-indol-5-yl)-[1,1'-biphenyl]-3-carbonyl)-7-azabicyclo[2.2.1]heptan-2-yl)carbamate-isomer-X (20 mg) obtained in step 2 above and Pd(PPh$_3$)$_4$ (0.92 mg) were suspended in 1-methyl-2-pyrrolidinone (0.2 mL). At room temperature, N,N-diethylethanolamine (0.0173 mL) was added thereto, and after CO substitution, the mixture was stirred at 100° C. for 1 hour. tert-Butyl alcohol (0.2 mL) and a 2 N aqueous sodium hydroxide solution (0.2 mL) were added to the reaction solution, followed by stirring at room temperature overnight. MTBE was added thereto, and the aqueous layer was separated. The aqueous layer was acidified with hydrochloric acid, and extraction was performed with MTBE. After the organic layer was dried over anhydrous sodium sulfate, the solvent was distilled off. Acetonitrile (0.5 mL) and a 4 N hydrochloric acid-1,4-dioxane solution (0.5 mL) were added to the residue, followed by stirring for 10 minutes. The reaction solution was concentrated, and the residue was purified by reversed-phase HPLC (mobile phase: water/acetonitrile) to give the title compound.

Example 223: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-methyl-1H-indazole-3-carboxylic acid-isomer-X Step 1

The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X (350 mg) obtained in step 2 of Example 207, and 5-bromo-6-fluoro-1-methyl-indazole (186 mg) were suspended in 1,4-dioxane (2.08 mL).

At room temperature, Pd(dba)$_2$ (28.7 mg), X-phos (47.6 mg), and tripotassium phosphate (397 mg) were added thereto, followed by degassing and nitrogen substitution. Under a nitrogen atmosphere, stirring was performed at an external temperature of 100° C. overnight. The solvent was distilled off, and the residue was purified by silica gel column chromatography (mobile phase: chloroform/methanol) to give tert-butyl ((1S,2S,4R)-rel-7-(4'-cyano-3'-fluoro-6-(6-fluoro-1-methyl-1H-indazol-5-yl)-[1,1'-biphenyl]-3-carbonyl)-7-azabicyclo[2.2.1]heptan-2-yl)carbamate-isomer-X.

Step 2

The procedure of steps 2 to 3 in Example 212 was repeated using the tert-butyl ((1S,2S,4R)-rel-7-(4'-cyano-3'-fluoro-6-(6-fluoro-1-methyl-1H-indazol-5-yl)-[1,1'-biphenyl]-3-carbonyl)-7-azabicyclo[2.2.1]heptan-2-yl)carbamate-isomer-X obtained in step 1 above instead of tert-butyl ((1S,2S,4R)-rel-7-(4'-cyano-3'-fluoro-6-(6-fluoro-1-(2-hydroxy-2-methylpropyl)-1H-indazol-5-yl)-[1,1'-biphenyl]-3-carbonyl)-7-azabicyclo[2.2.1]heptan-2-yl)carbamate-isomer-X to give the title compound.

Example 224: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X Step 1

The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X (350 mg) obtained in step 2 of Example 207, and 5-bromo-6-fluoro-1-methyl-indole (185 mg) were suspended in 1,4-dioxane (2.08 mL). At room temperature, Pd(dba)$_2$ (28.7 mg), X-phos (47.6 mg), and tripotassium phosphate (397 mg) were added thereto, followed by degassing and nitrogen substitution. Under a nitrogen atmosphere, stirring was performed at an external temperature of 100° C. overnight. The solvent was distilled off, and the residue was purified by silica gel column chromatography (mobile phase: chloroform/methanol) to give tert-butyl ((1S,2S,4R)-rel-7-(4'-cyano-3'-fluoro-6-(6-fluoro-1-methyl-1H-indol-5-yl)-[1,1'-biphenyl]-3-carbonyl)-7-azabicyclo[2.2.1]heptan-2-yl carbamate-isomer-X.

Step 2

The tert-butyl ((1S,2S,4R)-rel-7-(4'-cyano-3'-fluoro-6-(6-fluoro-1-methyl-1H-indol-5-yl)-[1,1'-biphenyl]-3-carbonyl)-7-azabicyclo[2.2.1]heptan-2-yl carbamate-isomer-X (209 mg) obtained in step 1 above was dissolved in DMF (3.6 mL). At room temperature, N-iodosuccinimide (121 mg) was added thereto, followed by stirring at room temperature for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl ((1S,2S,4R)-rel-7-(4'-cyano-3'-fluoro-6-(6-fluoro-3-iodo-1-methyl-1H-indol-5-yl)-[1,1'-biphenyl]-3-carbonyl)-7-azabicyclo[2.2.1]heptan-2-yl)carbamate-isomer-X.

Step 3

The tert-butyl ((1S,2S,4R)-rel-7-(4'-cyano-3'-fluoro-6-(6-fluoro-3-iodo-1-methyl-1H-indol-5-yl)-[1,1'-biphenyl]-3-carbonyl)-7-azabicyclo[2.2.1]heptan-2-yl)carbamate-isomer-X (211 mg) obtained in step 2 above and PdCl$_2$(PPh$_3$)$_2$ (10.5 mg) were suspended in 1-methyl-2-pyrrolidinone (2.11 mL). At room temperature, N,N-diethylethanolamine (0.197 mL) was added thereto, and after CO substitution, the mixture was stirred at 100° C. for 1 hour. tert-Butyl alcohol (0.2 mL) and a 2 N aqueous sodium hydroxide solution (0.2 mL) were added to the reaction solution, and the resulting mixture was stirred at room temperature overnight. MTBE was added thereto, and the aqueous layer was separated. The aqueous layer was acidified with hydrochloric acid, and extraction was performed with MTBE. The organic layer was dried over anhydrous sodium sulfate, and the solvent was distilled off to give 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X.

Step 4

Acetonitrile (0.5 mL) and a 4 N hydrochloric acid-1,4-dioxane solution (0.5 mL) were added to the 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X (10 mg) obtained in step 3 above, followed by stirring for 10 minutes. The reaction solution was concentrated, and the residue was purified by reversed-phase HPLC (mobile phase: water/acetonitrile) to give the title compound.

Example 225: Synthesis of 5'-((1S,2S,4R)-rel-2-amino-7-azabicyclo[2.2.1]heptane-7-carbonyl)-2'-(1-(2-ethyl-2-hydroxybutyl)-6-fluoro-1H-indazol-5-yl)-3-fluoro-[1,1'-biphenyl]-4-carbonitrile The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate (40 mg) obtained in step 1 of Example 213 and the 3-[(5-bromo-6-fluoro-indazol-1-yl)methyl]pentan-3-ol (29.2 mg) obtained in step 1 of Example 204 were suspended in 1,4-dioxane (0.5 mL). At room temperature, Pd(dba)$_2$ (3.3 mg), X-phos (5.5 mg), and tripotassium phosphate (45.4 mg) were added thereto, followed by stirring at 100° C. for 1 hour. The reaction solution was filtered, and the solvent was distilled off. The residue was dissolved in acetonitrile (0.5 mL). At room temperature, a 4 N hydrochloric acid-1,4-dioxane solution (0.5 mL) was added thereto, followed by stirring at room temperature for 5 minutes. The reaction solution was concentrated, and the residue was purified by reversed-phase HPLC (mobile phase: water/acetonitrile) to give the title compound.

Example 226: Synthesis of 5'-((1S,2S,4R)-rel-2-amino-7-azabicyclo[2.2.1]heptane-7-carbonyl)-3-fluoro-2'-(6-fluoro-1-(2-hydroxy-2-methylpropyl)-1,3-dihydroisobenzofuran-5-yl)-[1,1'-biphenyl]-4-carbonitrile-isomer-X Step 1
Methyl 5-bromo-4-fluoro-2-iodo-benzoate (2 g) was dissolved in diethyl ether (55.7 mL). At 0° C., a solution of 2.0 M LiBH$_4$ in THF (6.13 mL) and MeOH (0.56 mL) were added thereto, followed by stirring at 0° C. for 1 hour. MTBE was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give (5-bromo-4-fluoro-2-iodo-phenyl) methanol.
Step 2
The (5-bromo-4-fluoro-2-iodo-phenyl)methanol (1.39 g) obtained in step 1 above and 3,4-dihydro-2H-pyran (0.419 mL) were dissolved in CH$_2$Cl$_2$ (8.4 mL). At room temperature, pyridinium p-toluenesulfonic acid (106 mg) was added thereto, followed by stirring at room temperature overnight. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 2-[(5-bromo-4-fluoro-2-iodo-phenyl)methoxy]tetrahydropyran.
Step 3
The 2-[(5-bromo-4-fluoro-2-iodo-phenyl)methoxy]tetrahydropyran (1.5 g) obtained in step 2 above, PdCl$_2$(PPh$_3$)$_2$ (130 mg), and CuI (34 mg) were suspended in THF (18 mL). At room temperature, TEA (18 mL) and 2-methyl-3-BUTYN-2-ol (0.42 mL) were added thereto, followed by stirring at room temperature for 4 hours. The reaction solution was filtered, and the solvent was distilled off. The residue was purified by silica gel column chromatography (mobile phase: hexane/ethyl acetate) to give 4-[4-bromo-5-fluoro-2-(tetrahydropyran-2-yloxymethyl)phenyl]-2-methyl-3-butyn-2-ol.
Step 4
The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X (150 mg) obtained in step 2 of Example 207, and the 4-[4-bromo-5-fluoro-2-(tetrahydropyran-2-yloxymethyl)phenyl]-2-methyl-3-butyn-2-ol (129 mg) obtained in step 3 above were suspended in 1,4-dioxane (0.89 mL). At room temperature, Pd(dba)$_2$ (12.3 mg), X-phos (20.4 mg) were added thereto, followed by stirring at 100° C. for 1 hour. The reaction solution was filtered, and the solvent was distilled off. The residue was purified by silica gel column chromatography (mobile phase: hexane/ethyl acetate). The residue was dissolved in THF (0.92 mL) and water (0.46 mL). At room temperature, p-toluenesulfonic acid monohydrate (6.9 mg) was added thereto, followed by stirring at 70° C. for 1 hour. Ethyl acetate was added thereto, and the mixture was washed sequentially with water and saturated brine, and dried over anhydrous sodium sulfate. Then, the solvent was distilled off. The residue was purified by silica gel column chromatography (mobile phase: hexane/ethyl acetate) to give tert-butyl ((1S,2S,4R)-rel-7-(4"-cyano-2,3"-difluoro-4-(3-hydroxy-3-methyl-1-butyn-1-yl)-5-(hydroxymethyl)-[1,1':2',1"-terphenyl]-4'-carbonyl-7-azabicyclo[2.2.1]heptan-2-yl) carbamate-isomer-X.
Step 5
The tert-butyl ((1S,2S,4R)-rel-7-(4"-cyano-2,3"-difluoro-4-(3-hydroxy-3-methyl-1-butyn-1-yl)-5-(hydroxymethyl)-[1,1':2',1"-terphenyl]-4'-carbonyl-7-azabicyclo[2.2.1]heptan-2-yl)carbamate-isomer-X (30 mg) obtained in step 4 above was dissolved in 1,4-dioxane (0.24 mL). At room temperature, a solution of 1.0 M TBAF in THF (0.14 mL) was added thereto, followed by stirring at 100° C. for 1 hour. EtOH (0.12 mL) and 10% Pd/C (30 mg) were added to the reaction solution, and after, hydrogen substitution, the mixture was stirred at 70° C. for 30 minutes. The reaction solution was filtrated, and the filtrate was concentrated. The residue was dissolved in THF. At room temperature, TEA (0.013 mL), DMAP (1.1 mg), and Boc$_2$O (20.4 mg) were added thereto, followed by stirring at 70° C. for 1 hour. Ethyl acetate was added thereto, the mixture was washed 5 times with phosphoric acid at a concentration of about 0.5 mol/L, washed with saturated brine, and dried over anhydrous sodium sulfate. Thereafter, the solvent was distilled off. The residue was dissolved in acetonitrile (0.5 mL). At room temperature, a 4 N hydrochloric acid-1,4-dioxane solution (0.5 mL) was added thereto, followed by stirring at room temperature for 5 minutes. After the completion of the reaction was confirmed by LCMS, the solvent was distilled off. The residue was purified by reversed-phase HPLC (mobile phase: water/acetonitrile) to give the title compound.

Example 227: Synthesis of 5'-((S)-3-aminopyrrolidine-1-carbonyl)-3-fluoro-2'-(6-fluoro-1-(2-hydroxy-2-methylpropyl)-1,3-dihydroisobenzofuran-5-yl)-[1,1'-biphenyl]-4-carbonitrile Step 1
The tert-butyl 3-(4-cyano-3-fluoro-phenyl)-4-(4,4,5,5-tetramethyl-1,3,2-dioxaborolan-2-yl)benzoate (400 mg) obtained in step 1 of Example 41, and the 4-[4-bromo-5-fluoro-2-(tetrahydropyran-2-yloxymethyl)phenyl]-2-methyl-3-butyn-2-ol (456 mg) obtained in step 3 of Example 226 were suspended in 1,4-dioxane (3.15 mL). At room temperature, Pd(dba)$_2$ (43.5 mg), X-phos (144 mg), and tripotassium phosphate (601 mg) were added thereto, followed by stirring at 100° C. for 1 hour. The reaction solution was filtrated, and the solvent was distilled off. The residue was purified by silica gel column chromatography (mobile phase: chloroform/methanol). The residue was dissolved in THF (1.62 mL). At room temperature, water (0.81 mL), p-toluenesulfonic acid monohydrate (12.3 mg) were added thereto, followed by stirring at 70° C. for 1 hour. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give tert-butyl 3-(4-cyano-3-fluoro-phenyl)-4-[2-fluoro-5-(hydroxymethyl)-4-(3-hydroxy-3-methyl-1-butenyl)phenyl]benzoate.

Step 2

The tert-butyl 3-(4-cyano-3-fluoro-phenyl)-4-[2-fluoro-5-(hydroxymethyl)-4-(3-hydroxy-3-methyl-1-butenyl)phenyl]benzoate (90 mg) obtained in step 1 above was dissolved in 1,4-dioxane (0.9 mL). At room temperature, a solution of 1.0 M TBAF in THF (0.54 mL) was added thereto, followed by stirring at 100° C. for 2 hours. EtOH (0.30 mL) and 10% Pd/C (90 mg) were added to the reaction solution, and after hydrogen substitution, stirring was performed at 70° C. overnight. The reaction solution was filtrated, and the solvent was distilled off. The residue was purified by silica gel column chromatography (mobile phase: hexane/ethyl acetate). The residue was dissolved in THF (1.0 mL). At room temperature, 12 N hydrochloric acid (0.5 mL) was added thereto, followed by stirring at room temperature for 1.5 hours. MTBE was added thereto, and extraction was performed twice with a 2 N aqueous sodium hydroxide solution. The aqueous layer was acidified with 2 N hydrochloric acid, and extraction was performed twice with MTBE. The organic layer was sequentially washed with saturated brine, and dried over anhydrous sodium sulfate, and the solvent was distilled off to give 3-(4-cyano-3-fluoro-phenyl)-4-[6-fluoro-1-(2-hydroxy-2-methyl-propyl)-1,3-dihydroisobenzofuran-5-yl]benzoic acid.

Step 3

The 3-(4-cyano-3-fluoro-phenyl)-4-[6-fluoro-1-(2-hydroxy-2-methyl-propyl)-1,3-dihydroisobenzofuran-5-yl]benzoic acid (10 mg) obtained in step 2 above was dissolved in THF (0.5 mL). At room temperature, HATU (9.31 mg), tert-butyl N-[(3S)-pyrrolidin-3-yl]carbamate (43.5 mg), and TEA (6.2 µL) were added thereto, followed by stirring at 50° C. for 1 hour. The solvent was distilled off, and MeOH (0.5 mL) and a 4 N hydrochloric acid-1,4-dioxane solution (0.5 mL) were added thereto, followed by stirring at room temperature for 30 minutes. The solvent was distilled off, and the residue was purified by reversed-phase HPLC (mobile phase: water/acetonitrile) to give the title compound.

Example 228: Synthesis of 5'-((1S,2S,4R)-rel-2-amino-7-azabicyclo[2.2.1]heptane-7-carbonyl)-3-fluoro-2'-(6-fluoro-1-(2-hydroxy-2-methylpropyl)-7-methyl-1H-benzo[d][1,2,3]triazol-5-yl)-[1,1'-biphenyl]-4-carbonitrile-isomer-X The procedure of steps 1 to 5 in Example 209 was repeated using 1,3-difluoro-2-methyl-4-nitro-benzene instead of 2-chloro-1,3-difluoro-4-nitro-benzene to give the title compound.

Example 229: Synthesis of (S)-5'-(3-aminopyrrolidine-1-carbonyl)-3-fluoro-2'-(5-fluoro-3-(2-hydroxy-2-methylpropyl)benzo[d]isoxazol-6-yl)-[1,1'-biphenyl]-4-carbonitrile Step 1

The 1-(4-bromo-5-fluoro-2-hydroxyphenyl)ethanone (150 mg) obtained in step 2 of Example 179 was dissolved in THF (3.2 mL). At −25° C., lithium diisopropylamide (1.0 M, a THF solution) (3.2 mL) was added thereto, followed by stirring at −25° C. for 1 hour. The mixture was cooled to −40° C., and acetone (0.118 mL) was added thereto, followed by stirring at −40° C. for 1 hour. After a phosphoric acid aqueous solution was added thereto, ethyl acetate was added thereto, and the mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(4-bromo-5-fluoro-2-hydroxy-phenyl)-3-hydroxy-3-methyl-butan-1-one.

Step 2

The 1-(4-bromo-5-fluoro-2-hydroxy-phenyl)-3-hydroxy-3-methyl-butan-1-one (60 mg) obtained in step 1 above, hydroxylamine hydrochloride (28.6 mg), and sodium acetate (25.4 mg) were dissolved in methanol (0.69 mL), followed by stirring at 60° C. overnight. MTBE was added thereto, and the mixture was washed sequentially with water and saturated brine. After the organic layer was dried over anhydrous sodium sulfate, the solvent was distilled off. The residue was dissolved in THF (0.69 mL), and N,N'-carbonyldiimidazole (36.8 mg), TEA (0.037 mL) were added thereto, followed by stirring at 70° C. for 1 hour. The solvent was distilled off, and the residue was purified by silica gel column chromatography (mobile phase: hexane/ethyl acetate) to give 1-(6-bromo-5-fluoro-1,2-benzooxazol-3-yl)-2-methyl-propan-2-ol.

Step 3

The procedure of steps 1 to 3 in Example 37 was repeated using the 1-(6-bromo-5-fluoro-1,2-benzooxazol-3-yl)-2-methyl-propan-2-ol obtained in step 2 above instead of 1-(4-bromo-3-fluoro-phenyl)-2-methyl-propan-2-ol to give the title compound.

Example 230: Synthesis of 2-(5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1H-indol-1-yl)acetamide Step 1

The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate (100 mg) obtained in step 1 of Example 213, and the ethyl 2-(5-bromo-6-fluoro-indol-1-yl)acetate (69.5 mg) obtained in step 1 of Example 207 were suspended in 1,4-dioxane (0.59 mL). At room temperature, Pd(dba)$_2$ (8.2 mg), X-phos (13.6 mg), and tripotassium phosphate (113 mg) were added thereto, followed by degassing and nitrogen substitution. Under a nitrogen atmosphere, stirring was performed at an external temperature of 100° C. overnight. The solvent was distilled off, and the residue was purified by silica gel column chromatography (mobile phase: chloroform/methanol). The residue was dissolved in MeOH (1.0 mL), and a 5 N aqueous sodium hydroxide solution (1.0 mL) was added thereto, followed by stirring for 1 hour. MTBE was added thereto, and the aqueous layer was extracted. The aqueous layer was acidified with hydrochloric acid, MTBE was added thereto, and the mixture was washed sequentially with water and saturated brine. The organic layer was dried over anhydrous sodium sulfate, and the solvent was distilled off to give 2-(5-(5-(((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1H-indol-1-yl)acetic acid.

Step 2

The 2-(5-(5-(((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1H-indol-1-yl)acetic acid (10 mg) obtained in step 1 above was dissolved in THF (0.32 mL). Then, N,N'-carbonyldiimidazole (5.2 mg) was added thereto, and the mixture was stirred at room temperature for 20 minutes. Twenty-eight percent aqueous ammonia (0.06 mL) was added thereto, and the mixture was stirred at room temperature for 20 minutes. The solvent was distilled off, and acetonitrile (0.2 mL) and a 4 N hydrochloric acid-1,4-dioxane solution (0.2 mL) were added to the residue, followed by stirring for 30 minutes. The solvent was distilled off, and the residue was purified by reversed-phase HPLC (mobile phase: water/acetonitrile) to give the title compound.

Example 231: Synthesis of 2-(5-(5-(((1S,2S,4R)-rel-2-amino-7-azabicyclo[2.2.1]heptane-7-carbonyl)-4'-cyano-3'-fluoro-[1,1'-biphenyl]-2-yl)-6-fluoro-1H-indol-1-yl)-N-methylacetamide The 2-(5-(5-(((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1H-indol-1-yl)acetic acid (10 mg) obtained in step 1 of Example 230 was dissolved in THF (0.064 mL). At room temperature, HATU (6.7 mg), methylamine hydrochloride (2.2 mg), and TEA (6.7 µL) were added thereto, followed by stirring at 50° C. for 1 hour. The solvent was distilled off, and acetonitrile (1.0 mL) and a 4 N hydrochloric acid-1,4-dioxane solution (1.0 mL) were added to the residue, followed by stirring for 10 minutes. The solvent was distilled off, the residue was dissolved in DMSO, and purification was performed by reversed-phase HPLC (mobile phase: water/acetonitrile) to give the title compound.

Example 232: Synthesis of 2-(5-(5-(((1S,2S,4R)-rel-2-amino-7-azabicyclo[2.2.1]heptane-7-carbonyl)-4'-cyano-3'-fluoro-[1,1'-biphenyl]-2-yl)-6-fluoro-1H-indol-1-yl)-N,N-dimethylacetamide The procedure of Example 231 was repeated using dimethylamine hydrochloride instead of methylamine hydrochloride to give the title compound.

Example 233: Synthesis of 2-(4'-(((1S,2S,4R)-rel-2-amino-7-azabicyclo[2.2.1]heptane-7-carbonyl)-4"-cyano-2,3"-difluoro-[1,1':2',1"-terphenyl]-4-yl)acetamide Step 1

2-(4-Bromo-3-fluoro-phenyl)acetic acid (600 mg) was dissolved in THF (10.3 mL). At room temperature, HATU (1.08 g), NH$_4$Cl (275.4 mg), and TEA (1.08 mL) were added thereto, followed by stirring at 50° C. for 1 hour. The solvent was distilled off, and the residue was purified by silica gel column chromatography (mobile phase: chloroform/methanol) to give 2-(4-bromo-3-fluoro-phenyl)acetamide.

Step 2

The procedure of Example 225 was repeated using the 2-(4-bromo-3-fluoro-phenyl)acetamide obtained in step 1 above instead of 3-[(5-bromo-6-fluoro-indazol-1-yl)methyl]pentan-3-ol to give the title compound.

Example 234: Synthesis of 2-(4'-(((1S,2S,4R)-rel-2-amino-7-azabicyclo[2.2.1]heptane-7-carbonyl)-4"-cyano-2,3"-difluoro-[1,1':2',1"-terphenyl]-4-yl)-N-methylacetamide Step 1

2-(4-Bromo-3-fluoro-phenyl)acetic acid (600 mg) was dissolved in THF (10.3 mL). At room temperature, HATU (1.08 g), methylamine (ca. 9.8 mol/L in MeOH) (0.525 mL), and TEA (1.08 mL) were added thereto, followed by stirring at 50° C. for 1 hour. The solvent was distilled off, and the residue was purified by silica gel column chromatography (mobile phase: chloroform/methanol) to give 2-(4-bromo-3-fluoro-phenyl)-N-methyl-acetamide.

Step 2

The procedure of Example 225 was repeated using the 2-(4-bromo-3-fluoro-phenyl)-N-methyl-acetamide obtained in step 1 above instead of 3-[(5-bromo-6-fluoro-indazol-1-yl)methyl]pentan-3-ol to give the title compound.

Example 235: Synthesis of 2-(4'-(((1S,2S,4R)-rel-2-amino-7-azabicyclo[2.2.1]heptane-7-carbonyl)-4"-cyano-2,3"-difluoro-[1,1':2',1"-terphenyl]-4-yl)-N,N-dimethylacetamide Step 1

2-(4-Bromo-3-fluoro-phenyl)acetic acid (600 mg) was dissolved in THF (10.3 mL). At room temperature, HATU (1.08 g), dimethylamine hydrochloride (419.9 mg), and TEA (1.08 mL) were added thereto, followed by stirring at 50° C. for 1 hour. The solvent was distilled off, and the residue was purified by silica gel column chromatography (mobile phase: chloroform/methanol) to give 2-(4-bromo-3-fluoro-phenyl)-N,N-dimethyl-acetamide.

Step 2

The procedure of Example 225 was repeated using the 2-(4-bromo-3-fluoro-phenyl)-N,N-dimethyl-acetamide obtained in step 1 above instead of 3-[(5-bromo-6-fluoro-indazol-1-yl)methyl]pentan-3-ol to give the title compound.

Example 236: Synthesis of 5-(5-(((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-methyl-1H-indole-3-carboxyamide-isomer-X The 5-(5-(((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X (10 mg) obtained in step 3 of Example 224 was dissolved in THF (0.32 mL). Then, N,N'-carbonyldiimidazole (5.2 mg) was added thereto, and the mixture was stirred at room temperature for 20 minutes. Twenty-eight percent aqueous ammonia (0.1 mL) was added thereto, and the mixture was stirred at room temperature for 20 minutes. The solvent was distilled off, and acetonitrile (0.2 mL) and a 4 N hydrochloric acid-1,4-dioxane solution (0.2 mL) were added to the residue, followed by stirring for 30 minutes. The solvent was distilled off, and the residue was purified by reversed-phase HPLC (mobile phase: water/acetonitrile) to give the title compound.

Example 237: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-N,1-dimethyl-1H-indole-3-carboxyamide-isomer-X The 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X (10 mg) obtained in step 3 of Example 224 was dissolved in THF (0.064 mL). At room temperature, HATU (6.7 mg), methylamine hydrochloride (2.2 mg), and TEA (6.7 µL) were added thereto, followed by stirring at 50° C. for 1 hour. The solvent was distilled off, and acetonitrile (0.5 mL) and a 4 N hydrochloric acid-1,4-dioxane solution (0.5 mL) were added to the residue, followed by stirring for 10 minutes. The solvent was distilled off, the residue was dissolved in DMSO, and purification was performed by reversed-phase HPLC (mobile phase: water/acetonitrile) to give the title compound.

Example 238: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-N,N,1-trimethyl-1H-indole-3-carboxyamide-isomer-X The procedure of Example 237 was repeated using dimethylamine hydrochloride instead of methylamine hydrochloride to give the title compound.

Example 239: Synthesis of (S)-5'-(3-aminopyrrolidine-1-carbonyl)-3-fluoro-2'-(6-fluoro-1-(2-hydroxy-2-methylpropyl)-7-methyl-1H-benzo[d][1,2,3]triazol-5-yl)-[1,1'-biphenyl]-4-carbonitrile The procedure of steps 1 to 5 of Example 209 was repeated using 1,3-difluoro-2-methyl-4-nitro-benzene instead of 2-chloro-1,3-difluoro-4-nitro-benzene, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 240: Synthesis of 5'-((3-endo)-3-amino-8-azabicyclo[3.2.1]octane-8-carbonyl)-3-fluoro-2'-(6-fluoro-1-(2-hydroxy-2-methylpropyl)-7-methyl-1H-benzo[d][1,2,3]triazol-5-yl)-[1,1'-biphenyl]-4-carbonitrile The procedure of steps 1 to 5 in Example 209 was repeated using 1,3-difluoro-2-methyl-4-nitro-benzene instead of 2-chloro-1,3-difluoro-4-nitro-benzene, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 241: Synthesis of 5'-((1S,2S,4R)-rel-2-amino-7-azabicyclo[2.2.1]heptane-7-carbonyl)-3-fluoro-2'-(6-fluoro-1-(2-hydroxy-2-methylpropyl)-7-methyl-1H-benzo[d][1,2,3]triazol-5-yl)-[1,1'-biphenyl]-4-carbonitrile The procedure of steps 1 to 5 in Example 209 was repeated using 1,3-difluoro-2-methyl-4-nitro-benzene instead of 2-chloro-1,3-difluoro-4-nitro-benzene, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 242: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid Step 1

The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate (200 mg) obtained in step 1 of Example 213 and 5-bromo-6-fluoro-1-methyl-indole (105.6 mg) were suspended in 1,4-dioxane (1.19 mL). At room temperature, Pd(dba)$_2$ (16.4 mg), X-phos (27.2 mg), and tripotassium phosphate (226.9 mg) were added thereto, followed by degassing and nitrogen substitution. Under a nitrogen atmosphere, stirring was performed at an external temperature of 100° C. overnight. The solvent was distilled off, and the residue was purified by silica gel column chromatography (mobile phase: chloroform/methanol) to give tert-butyl ((1S,2S,4R)-rel-7-(4'-cyano-3'-fluoro-6-(6-fluoro-1-methyl-1H-indol-5-yl)-[1,1'-biphenyl]-3-carbonyl)-7-azabicyclo[2.2.1]heptan-2-yl)carbamate.

Step 2

The tert-butyl ((1S,2S,4R)-rel-7-(4'-cyano-3'-fluoro-6-(6-fluoro-1-methyl-1H-indol-5-yl)-[1,1'-biphenyl]-3-carbonyl)-7-azabicyclo[2.2.1]heptan-2-yl)carbamate (209 mg) obtained in step 1 above was dissolved in DMF (3.6 mL). At room temperature, N-iodosuccinimide (121 mg) was added thereto, followed by stirring at room temperature for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give tert-butyl ((1S,2S,4R)-rel-7-(4'-cyano-3'-fluoro-6-(6-fluoro-3-iodo-1-methyl-1H-indol-5-yl)-[1,1'-biphenyl]-3-carbonyl)-7-azabicyclo[2.2.1]heptan-2-yl)carbamate.

Step 3

The tert-butyl ((1S,2S,4R)-rel-7-(4'-cyano-3'-fluoro-6-(6-fluoro-3-iodo-1-methyl-1H-indol-5-yl)-[1,1'-biphenyl]-3-carbonyl)-7-azabicyclo[2.2.1]heptan-2-yl)carbamate (211 mg) obtained in step 2 above and PdCl$_2$(PPh$_3$)$_2$ (10.5 mg) were suspended in 1-methyl-2-pyrrolidinone (2.11 mL). At room temperature, N,N-diethylethanolamine (0.197 mL) was added thereto, and after CO substitution, the mixture was stirred at 100° C. for 1 hour. tert-Butyl alcohol (0.2 mL) and a 2 N aqueous sodium hydroxide solution (0.2 mL) were added to the reaction solution, and the resulting mixture was stirred at room temperature overnight. MTBE was added thereto, and the aqueous layer was separated. The aqueous layer was acidified with hydrochloric acid, and extraction was performed with MTBE. The organic layer was dried over anhydrous sodium sulfate, and the solvent was distilled off to give 5-(5-((1S,2S,4R)-rel-2-((tert-butoxycarbonyl)

amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid.

Step 4

Acetonitrile (0.5 mL) and a 4 N hydrochloric acid-1,4-dioxane solution (0.5 mL) were added to the 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid (10 mg) obtained in step 3 above, followed by stirring for 10 minutes. The reaction solution was concentrated, and the residue was purified by reversed-phase HPLC (mobile phase: water/acetonitrile) to give the title compound.

Example 243: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-N,1-dimethyl-1H-indole-3-carboxyamide The procedure of Example 237 was repeated using the 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid obtained in step 3 of Example 242 instead of 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X to give the title compound.

Example 244: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-N,N,1-trimethyl-1H-indole-3-carboxyamide The procedure of Example 237 was repeated using the 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid obtained in step 3 of Example 242 instead of 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X, and using dimethylamine hydrochloride instead of methylamine hydrochloride to give the title compound.

Example 245: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-methyl-1H-indole-3-carboxyamide The procedure of Example 236 was repeated using the 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid obtained in step 3 of Example 242 instead of 5-(5-((1S,2S,4R)-rel-2-((tert-butoxycarbonyl)amino)-7-azabicyclo[2.2.1]heptane-7-carbonyl)-4'-cyano-3'-fluoro-[1,1'-biphenyl]-2-yl)-6-fluoro-1-methyl-1H-indole-3-carboxylic acid-isomer-X to give the title compound.

Example 246: Synthesis of 5'-((1S,2S,4R)-rel-2-amino-7-azabicyclo[2.2.1]heptane-7-carbonyl)-2'-(7-(difluoromethyl)-6-fluoro-1-(2-hydroxy-2-methylpropyl)-1H-benzo[d][1,2,3]triazol-5-yl)-3-fluoro-[1,1'-biphenyl]-4-carbonitrile-isomer-X The procedure of steps 1 to 5 in Example 209 was repeated using 2-(difluoromethyl)-1,3-difluoro-4-nitro-benzene instead of 2-chloro-1,3-difluoro-4-nitro-benzene to give the title compound.

Example 247: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-(2-hydroxy-2-methylpropyl)-1H-benzo[d][1,2,3]triazole-7-carbonitrile-isomer-X The procedure of steps 1 to 5 in Example 209 was repeated using 2,6-difluoro-3-nitro-benzonitrile instead of 2-chloro-1,3-difluoro-4-nitro-benzene, and using THF instead of EtOH to give the title compound.

Example 248: Synthesis of (S)-5'-(3-aminopyrrolidine-1-carbonyl)-2'-(7-(difluoromethyl)-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 209 was repeated using 2-(difluoromethyl)-1,3-difluoro-4-nitro-benzene instead of 2-chloro-1,3-difluoro-4-nitro-benzene, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 249: Synthesis of (S)-5-(5-(3-aminopyrrolidine-1-carbonyl)-4'-cyano-3'-fluoro-[1,1'-biphenyl]-2-yl)-6-fluoro-1-(2-hydroxy-2-methylpropyl)-1H-benzo[d][1,2,3]triazole-7-carbonitrile The procedure of steps 1 to 5 in Example 209 was repeated using 2,6-difluoro-3-nitro-benzonitrile instead of 2-chloro-1,3-difluoro-4-nitro-benzene, using THF instead of EtOH, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 250: Synthesis of 5'-((3-endo)-3-amino-8-azabicyclo[3.2.1]octane-8-carbonyl)-2'-(7-(difluoromethyl)-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 209 was repeated using 2-(difluoromethyl)-1,3-difluoro-4-nitro-benzene instead of 2-chloro-1,3-difluoro-4-nitro-benzene, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)- rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 251: Synthesis of 5-(5-((3-endo)-3-amino-8-azabicyclo[3.2.1]octane-8-carbonyl)-4'-cyano-3'-fluoro-[1,1'-biphenyl]-2-yl)-6-fluoro-1-(2-hydroxy-2-methylpropyl)-1H-benzo[d][1,2,3]triazole-7-carbonitrile The procedure of steps 1 to 5 in Example 209 was repeated using 2,6-difluoro-3-nitro-benzonitrile instead of 2-chloro-1,3-difluoro-4-nitro-benzene, using THF instead of EtOH, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 252: Synthesis of 5'-((1S,2S,4R)-rel-2-amino-7-azabicyclo[2.2.1]heptane-7-carbonyl)-2'-(7-(difluoromethyl)-6-fluoro-1-(2-hydroxy-2-methylpropyl)-1H-benzo[d][1,2,3]triazol-5-yl-3-fluoro-[1,1'-biphenyl]-4-carbonitrile The procedure of steps 1 to 5 in Example 209 was repeated using 2-(difluoromethyl)-1,3-difluoro-4-nitro-benzene instead of 2-chloro-1,3-difluoro-4-nitro-benzene, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 253: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-(2-hydroxy-2-methylpropyl)-1H-benzo[d][1,2,3]triazole-7-carbonitrile The procedure of steps 1 to 5 in Example 209 was repeated using 2,6-difluoro-3-nitro-benzonitrile instead of 2-chloro-1,3-difluoro-4-nitro-benzene, using THF instead of EtOH, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 254: Synthesis of 5'-((1S,2S,4R)-rel-2-amino-7-azabicyclo[2.2.1]heptane-7-carbonyl)-2'-(6,7-difluoro-1-((1-hydroxycyclobutyl)methyl)-1H-benzo[d][1,2,3]triazol-5-yl)-3-fluoro-[1,1'-biphenyl]-4-carbonitrile-isomer-X The procedure of steps 1 to 5 in Example 209 was repeated using 1,2,3-trifluoro-4-nitro-benzene instead of 2-chloro-1,3-difluoro-4-nitro-benzene, and using 1-(aminomethyl)cyclobutanol instead of 1-amino-2-methyl-propan-2-ol to give the title compound.

Example 255: Synthesis of (S)-5'-(3-aminopyrrolidine-1-carbonyl)-2'-(6,7-difluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was repeated using 1,2,3-trifluoro-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 256: Synthesis of 5'-((3-endo)-3-amino-8-azabicyclo[3.2.1]octane-8-carbonyl)-2'-(6,7-difluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was repeated using 1,2,3-trifluoro-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 257: Synthesis of 5'-((1S,2S,4R)-rel-2-amino-7-azabicyclo[2.2.1]heptane-7-carbonyl)-2'-(7-chloro-6-fluoro-1-((1-hydroxycyclobutyl)methyl)-1H-benzo[d][1,2,3]triazol-5-yl)-3-fluoro-[1,1'-biphenyl]-4-carbonitrile-isomer-X The procedure of steps 1 to 5 in Example 209 was repeated using 1-(aminomethyl)cyclobutanol instead of 1-amino-2-methyl-propan-2-ol to give the title compound.

Example 258: Synthesis of (S)-5'-(3-aminopyrrolidine-1-carbonyl)-2'-(7-chloro-6-fluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was repeated using 1-(aminomethyl)cyclobutanol instead of 1-amino-2-methyl-propan-2-ol, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 259: Synthesis of 5'-((3-endo)-3-amino-8-azabicyclo[3.2.1]octane-8-carbonyl)-2'-(7-chloro-6-fluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was repeated using 1-(aminomethyl)cyclobutanol instead of 1-amino-2-methyl-propan-2-ol, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 260: Synthesis of 5'-((1S,2S,4R)-rel-2-amino-7-azabicyclo[2.2.1]heptane-7-carbonyl)-2'-(7-(difluoromethyl)-6-fluoro-1-((1-hydroxycyclobutyl)methyl)-1H-benzo[d][1,2,3]triazol-5-yl)-3-fluoro-[1,1'-biphenyl]-4-carbonitrile-isomer-X The procedure of steps 1 to 5 in Example 209 was repeated using 2-(difluoromethyl)-1,3-difluoro-4-nitro-benzene instead of 2-chloro-1,3-difluoro-4-nitro-benzene, and using 1-(aminomethyl)cyclobutanol instead of 1-amino-2-methyl-propan-2-ol to give the title compound.

Example 261: Synthesis of (S)-5'-(3-aminopyrrolidine-1-carbonyl)-2'-(7-(difluoromethyl)-6-fluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was repeated using 2-(difluoromethyl)-1,3-difluoro-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 262: Synthesis of 5'-((3-endo)-3-amino-8-azabicyclo[3.2.1]octane-8-carbonyl)-2'-(7-(difluoromethyl)-6-fluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was repeated using 2-(difluoromethyl)-1,3-difluoro-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 263: Synthesis of 5'-((1S,2S,4R)-rel-2-amino-7-azabicyclo[2.2.1]heptane-7-carbonyl)-2'-(7-(difluoromethyl)-6-fluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was repeated using 2-(difluoromethyl)-1,3-difluoro-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 264: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-((1-hydroxycyclobutyl)methyl)-1H-benzo[d][1,2,3]triazole-7-carbonitrile-isomer-X The procedure of steps 1 to 5 in Example 209 was repeated using 2,6-difluoro-3-nitro-benzonitrile instead of 2-chloro-1,3-difluoro-4-nitro-benzene, and using 1-(aminomethyl)cyclobutanol instead of 1-amino-2-methyl-propan-2-ol to give the title compound.

Example 265: Synthesis of (S)-5-(5-(3-aminopyrrolidine-1-carbonyl)-4'-cyano-3'-fluoro-[1,1'-biphenyl]-2-yl)-6-fluoro-1-((1-hydroxycyclobutyl)methyl)-1H-benzo[d][1,2,3]triazole-7-carbonitrile The procedure of steps 1 to 5 in Example 209 was repeated using 2,6-difluoro-3-nitro-benzonitrile instead of 2-chloro-1,3-difluoro-4-nitro-benzene, using 1-(aminomethyl)cyclobutanol instead of 1-amino-2-methyl-propan-2-ol, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 266: Synthesis of 5-(5-((3-endo)-3-amino-8-azabicyclo[3.2.1]octane-8-carbonyl)-4'-cyano-3'-fluoro-[1,1'-biphenyl]-2-yl)-6-fluoro-1-((1-hydroxycyclobutyl)methyl)-1H-benzo[d][1,2,3]triazole-7-carbonitrile The procedure of steps 1 to 5 in Example 209 was repeated using 2,6-difluoro-3-nitro-benzonitrile instead of 2-chloro-1,3-difluoro-4-nitro-benzene, using 1-(aminomethyl)cyclobutanol instead of 1-amino-2-methyl-propan-2-ol, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 267: Synthesis of 5-(5-((1S,2S,4R)-rel-2-amino-7-azabicyclo[2.2.1]heptane-7-carbonyl)-4'-cyano-3'-fluoro-[1,1'-biphenyl]-2-yl)-6-fluoro-1-((1-hydroxycyclobutyl)methyl)-1H-benzo[d][1,2,3]triazole-7-carbonitrile The procedure of steps 1 to 5 in Example 209 was repeated using 2,6-difluoro-3-nitro-benzonitrile instead of 2-chloro-1,3-difluoro-4-nitro-benzene, using 1-(aminomethyl)cyclobutanol instead of 1-amino-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 268: Synthesis of 5'-((1S,2S,4R)-rel-2-amino-7-azabicyclo[2.2.1]heptane-7-carbonyl)-2'-(6,7-difluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was repeated using 1,2,3-trifluoro-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 269: Synthesis of 5'-((1S,2S,4R)-rel-2-amino-7-azabicyclo[2.2.1]heptane-7-carbonyl)-2'-(7-chloro-6-fluoro-1-((1-hydroxycyclobutyl)methyl)-1H-benzo[d][1,2,3]triazol-5-yl)-3-fluoro-[1,1'-biphenyl]-4-carbonitrile The procedure of steps 1 to 5 in Example 209 was repeated using 1-(aminomethyl)cyclobutanol instead of 1-amino-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 270: Synthesis of 5'-((1S,2S,4R)-rel-2-amino-7-azabicyclo[2.2.1]heptane-7-carbonyl)-3-fluoro-2'-(6-fluoro-1-((1-hydroxycyclobutyl)methyl)-7-methyl-1H-benzo[d][1,2,3]triazol-5-yl)-[1,1'-biphenyl]-4-carbonitrile-isomer-X The procedure of steps 1 to 5 in Example 209 was repeated using 1,3-difluoro-2-methyl-4-nitro-benzene instead of 2-chloro-1,3-difluoro-4-nitro-benzene, and using 1-(aminomethyl)cyclobutanol instead of 1-amino-2-methyl-propan-2-ol to give the title compound.

Example 271: Synthesis of (S)-5'-(3-aminopyrrolidine-1-carbonyl)-3-fluoro-2'-(6-fluoro-1-((1-hydroxycyclobutyl)methyl)-7-methyl-1H-benzo[d][1,2,3]triazol-5-yl)-[1,1'-biphenyl]-4-carbonitrile The procedure of steps 1 to 5 in Example 209 was repeated using 1,3-difluoro-2-methyl-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 272: Synthesis of 5'-((3-endo)-3-amino-8-azabicyclo[3.2.1]octane-8-carbonyl)-3-fluoro-2'-(6-fluoro-1-((1-hydroxycyclobutyl)methyl)-7-methyl-1H-benzo[d][1,2,3]triazol-5-yl)-[1,1'-biphenyl]-4-carbonitrile The procedure of steps 1 to 5 in Example 209 was repeated using 1,3-difluoro-2-methyl-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 273: Synthesis of 5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile-isomer-X Step 1

2-Bromo-1,3-difluoro-4-nitro-benzene (3 g) was dissolved in THF (31.5 mL). TEA (2.6 mL) and 1-amino-2-methyl-propan-2-ol (1.4 mL) were added thereto, followed by stirring at room temperature for 1 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: hexane/ethyl acetate) to give 1-(2-bromo-3-fluoro-6-nitro-anilino)-2-methyl-propan-2-ol.

Step 2

The 1-(2-bromo-3-fluoro-6-nitro-anilino)-2-methyl-propan-2-ol (1.03 g) obtained in step 1 above was dissolved in acetic acid (6.7 mL). At room temperature, N-iodosuccinimide (981 mg) was added thereto, followed by stirring at 50° C. for 3 hours. MTBE and water were added thereto, and extraction was performed twice with MTBE. The combined organic layers were dried over anhydrous sodium sulfate, and the solvent was distilled off. The residue was purified by silica gel column chromatography (mobile phase: hexane/ethyl acetate) to give 1-(2-bromo-3-fluoro-4-iodo-6-nitro-anilino)-2-methyl-propan-2-ol.

Step 3

The 1-(2-bromo-3-fluoro-4-iodo-6-nitro-anilino)-2-methyl-propan-2-ol (1.33 g) obtained in step 2 above and iron (1.33 g) were dissolved in THF (10.2 mL) and a 2 N hydrochloric acid (10.2 mL), followed by stirring at 60° C. for 1 hour. MTBE was added thereto, and the mixture was passed through Celite. MTBE was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 1-(6-amino-2-bromo-3-fluoro-4-iodo-anilino)-2-methyl-propan-2-ol.

Step 4

The 1-(6-amino-2-bromo-3-fluoro-4-iodo-anilino)-2-methyl-propan-2-ol (940 mg) obtained in step 3 above was dissolved in water (1.88 mL) and THF (4.7 mL). At 0° C., 12 N hydrochloric acid (2.82 mL) and an aqueous sodium nitrite solution (an aqueous solution obtained by dissolving 209 mg of sodium nitrite in 0.63 mL of water) were added thereto dropwise, followed by stirring at room temperature for 1 hour. MTBE was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 1-(7-bromo-6-fluoro-5-iodo-benzotriazol-1-yl)-2-methyl-propan-2-ol.

Step 5

The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X (50 mg) obtained in step 2 of Example 207 and the 1-(7-bromo-6-fluoro-5-iodo-benzotriazol-1-yl)-2-methyl-propan-2-ol (47.9 mg) obtained in step 4 above were dissolved in 1,4-dioxane (0.3 mL). At room temperature, Pd(dba)$_2$ (4.1 mg), X-phos (6.8 mg), and tripotassium phosphate (56.7 mg) were added thereto. After nitrogen substitution, the mixture was stirred at 90° C. overnight. Ethyl acetate was added thereto, and the mixture was put on NH-silica gel, and washed with ethyl acetate:methanol=10:1. The solvent was distilled off, and acetonitrile (1.0 mL) and a 4 N hydrochloric acid-1,4-dioxane solution (1.0 mL) were added to the residue, followed by stirring for 10 minutes. The solvent was distilled off, the residue was dissolved in DMSO, and purification was performed by reversed-phase HPLC (mobile phase: water/acetonitrile) to give the title compound.

Example 274: Synthesis of (S)-5'-(3-aminopyrrolidine-1-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 273 was repeated using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 275: Synthesis of 5'-((3-endo)-3-amino-8-azabicyclo[3.2.1]octane-8-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 273 was repeated using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 276: Synthesis of 5'-((1S,2S,4R)-rel-2-amino-7-azabicyclo[2.2.1]heptane-7-carbonyl)-3-fluoro-2'-(6-fluoro-1-((1-hydroxycyclobutyl)methyl)-7-methyl-1H-benzo[d][1,2,3]triazol-5-yl)-[1,1'-biphenyl]-4-carbonitrile The procedure of steps 1 to 5 in Example 209 was repeated using 1,3-difluoro-2-methyl-4-nitro-benzene instead of 2-chloro-1,3-difluoro-4-nitro-benzene, using 1-(aminomethyl)cyclobutanol instead of 1-amino-2-methyl-propan-2-ol, and using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 277: Synthesis of 5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 273 was repeated using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate obtained in step 1 of Example 213 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X to give the title compound.

Example 278: Synthesis of 5'-((1R,2R,4S)-rel-2-amino-7-azabicyclo[2.2.1]heptane-7-carbonyl)-2'-(7-cyclopropyl-6-fluoro-1-(2-hydroxy-2-methylpropyl)-1H-benzo[d][1,2,3]triazol-5-yl)-3-fluoro-[1,1'-biphenyl]-4-carbonitrile Step 1

The 1-(2-bromo-3-fluoro-6-nitro-anilino)-2-methyl-propan-2-ol (975 mg) obtained in step 1 of Example 273 was dissolved in 1,4-dioxane (10.6 mL). At room temperature, dichlorobis(tricyclohexylphosphine)palladium(II) (234 mg), cyclopropyl boronic acid (464 mg), and tripotassium phosphate (2.02 g) were added thereto, followed by stirring at 10° C. overnight. The solvent was distilled off, and the residue was purified by silica gel column chromatography (mobile phase: hexane/ethyl acetate) to give 1-((2-cyclopropyl-3-fluoro-6-nitrophenyl)amino)-2-methylpropan-2-ol.

Step 2

The 1-((2-cyclopropyl-3-fluoro-6-nitrophenyl)amino)-2-methylpropan-2-ol (204 mg) obtained in step 1 above was dissolved in acetonitrile (1.5 mL). At room temperature, N-bromosuccinimide (196 mg) was added thereto, followed by stirring at 50° C. for 1 hour. The solvent was distilled off, and the residue was purified by silica gel column chromatography (mobile phase: hexane/ethyl acetate) to give 1-((4-bromo-2-cyclopropyl-3-fluoro-6-nitrophenyl)amino)-2-methylpropan-2-ol.

Step 3

The 1-((4-bromo-2-cyclopropyl-3-fluoro-6-nitrophenyl)amino)-2-methylpropan-2-ol (250 mg) obtained in step 2 above and iron (250 mg) were dissolved in THF (2.4 mL) and a 2 N hydrochloric acid (2.4 mL), followed by stirring at 60° C. for 1 hour. Ethyl acetate was added thereto, and the mixture was passed through Celite. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 1-((6-amino-4-bromo-2-cyclopropyl-3-fluorophenyl)amino)-2-methylpropan-2-ol.

Step 4

The 1-((6-amino-4-bromo-2-cyclopropyl-3-fluorophenyl)amino)-2-methylpropan-2-ol (192 mg) obtained in step 3 above was dissolved in THF (2.0 mL) and a 2 N hydrochloric acid (2.0 mL). An aqueous sodium nitrite solution (an aqueous solution obtained by dissolving 54 mg of sodium nitrite in 0.16 mL of water) was added thereto dropwise, followed by stirring at room temperature for 1 hour. Ethyl acetate was added thereto, and the mixture was washed sequentially with water and saturated brine, and dried over anhydrous sodium sulfate. Thereafter, the solvent was distilled off. The residue was purified by silica gel column chromatography (mobile phase: hexane/ethyl acetate) to give 1-(5-bromo-7-cyclopropyl-6-fluoro-1H-benzo[d][1,2,3]triazol-1-yl)-2-methylpropan-2-ol.

Step 5

The tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate (15 mg) obtained in step 1 of Example 213, and the 1-(5-bromo-7-cyclopropyl-6-fluoro-1H-benzo[d][1,2,3]triazol-1-yl)-2-methylpropan-2-ol (10.5 mg) obtained in step 4 above were dissolved in 1,4-dioxane (0.2 mL). Pd(dba)$_2$ (1.2 mg), X-phos (2.0 mg), and tripotassium phosphate (17 mg) were added thereto. After nitrogen substitution, the mixture was stirred at 100° C. overnight. Ethyl acetate was added thereto, and the mixture was put on NH-silica gel, and washed with ethyl acetate:methanol=10:1. The solvent was distilled off, and acetonitrile (1.0 mL) and a 4 N hydrochloric acid-1,4-dioxane solution (1.0 mL) were added to the residue, followed by stirring for 10 minutes. The solvent was distilled off, the residue was dissolved in DMSO, and purification was performed by reversed-phase HPLC (mobile phase: water/acetonitrile) to give the title compound.

Example 279: Synthesis of 5'-((1R,2R,4S)-rel-2-amino-7-azabicyclo[2.2.1]heptane-7-carbonyl)-2'-(7-cyclopropyl-6-fluoro-1-(2-hydroxy-2-methylpropyl)-1H-benzo[d][1,2,3]triazol-5-yl)-3-fluoro-[1,1'-biphenyl]-4-carbonitrile-isomer-X The procedure of steps 1 to 5 in Example 278 was repeated using the tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate-isomer-X obtained in step 2 of Example 207 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate.

Example 280: Synthesis of (S)-5'-(3-aminopyrrolidine-1-carbonyl)-2'-(7-cyclopropyl-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 278 was repeated using the tert-butyl N-[(3S)-1-[3-(4-cyano-3-fluoro-phenyl)-4-(4,4,5,5-tetramethyl-1,3,2-dioxaborolan-2-yl)benzoyl]pyrrolidin-3-yl]carbamate obtained in step 1 of Example 37 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate to give the title compound.

Example 281: Synthesis of 5'-((3-endo)-3-amino-8-azabicyclo[3.2.1]octane-8-carbonyl)-2'-(7-cyclopropyl-6-fluoro-1-(2-hydroxy-2-methylpropyl)-1H-benzo[d][1,2,3]triazol-5-yl)-3-fluoro-[1,1'-biphenyl]-4-carbonitrile The procedure of steps 1 to 5 in Example 278 was repeated using the tert-butyl N-[(3-endo)-8-[3-(4-cyano-3-fluoro-phenyl)-4-(4,4,5,5-tetramethyl-1,3,2-dioxaborolan-2-yl)benzoyl]-8-azabicyclo[3.2.1]octan-3-yl]carbamate obtained in step 3 of Example 41 instead of tert-butyl ((1S,2S,4R)-rel-7-(4'-cyano-3'-fluoro-6-(4,4,5,5-tetramethyl-1,3,2-dioxaborolan-2-yl)-[1,1'-biphenyl]-3-carbonyl)-7-azabicyclo[2.2.1]heptan-2-yl)carbamate to give the title compound.

Comparative Example 1: Synthesis of 4-(2-((3-exo)-3-amino-8-azabicyclo[3.2.1]octan-8-yl)-5-(2-methyl-2H-indazol-5-yl)pyrimidin-4-yl)benzonitrile The procedure of Example 59 disclosed in Patent Literature (PTL) 1 was repeated using (4-cyanophenyl)boronic acid instead of (4-cyano-3-fluorophenyl)boronic acid, and using tert-butyl N-[(3-exo)-8-azabicyclo[3.2.1]octan-3-yl]carbamate instead of 4-Boc-aminopiperidine to give the title compound.

Comparative Example 2: Synthesis of (S)-4-(3-(3-aminopyrrolidine-1-carbonyl)-5-(4-fluorophenyl)-1H-pyrazol-1-yl)benzonitrile Step 1

The procedure of the synthetic method of Scheme C disclosed in PTL 3 was repeated using 1-(4-fluorophenyl)ethanone as C-1, using 4-hydrazinobenzonitrile instead of (4-(trifluoromethyl)phenyl)hydrazine, and using (S)-tert-butyl pyrrolidin-3-yl carbamate instead of 1-(4-fluorophenyl)-1,3,8-triazaspiro[4.5]decan-4-one to give (S)-tert-butyl (1-(1-(4-cyanophenyl)-5-(4-fluorophenyl)-1H-pyrazole-3-carbonyl)pyrrolidin-3-yl)carbamate.

Step 2

The procedure of step 5 in Example 1 was repeated using the (S)-tert-butyl (1-(1-(4-cyanophenyl)-5-(4-fluorophenyl)-1H-pyrazole-3-carbonyl)pyrrolidin-3-yl)carbamate obtained in step 1 above instead of tert-butyl N-[(3S)-1-[3-(4-cyanophenyl)-4-(p-tolyl)benzoyl]pyrrolidin-3-yl]carbamate to give the title compound.

Comparative Example 3: Synthesis of 4-(5-(4-fluorophenyl)-3-(2,6-diazaspiro[3.5]nonane-6-carbonyl)-1H-pyrazol-1-yl)benzonitrile Step 1

The procedure of the synthetic method of Scheme C disclosed in PTL 3 was repeated using 1-(4-fluorophenyl)ethanone as C-1, using 4-hydrazinobenzonitrile instead of (4-(trifluoromethyl)phenyl)hydrazine, and using tert-butyl 2,6-diazaspiro[3.5]nonane-2-carboxylate instead of 1-(4-fluorophenyl)-1,3,8-triazaspiro[4.5]decan-4-one to give tert-butyl 6-(1-(4-cyanophenyl)-5-(4-fluorophenyl)-1H-pyrazole-3-carbonyl)-2,6-diazaspiro[3.5]nonane-2-carboxylate.

Step 2

The procedure of step 5 of Example 1 was repeated using the tert-butyl 6-(1-(4-cyanophenyl)-5-(4-fluorophenyl)-1H-pyrazole-3-carbonyl)-2,6-diazaspiro[3.5]nonane-2-carboxylate obtained in step 1 above instead of tert-butyl N-[(3S)-1-[3-(4-cyanophenyl)-4-(p-tolyl)benzoyl]pyrrolidin-3-yl]carbamate to give the title compound.

Comparative Example 4: Synthesis of 4-[5-[(3R)-3-aminopiperidine-1-carbonyl]-2-(3-pyridylmethoxy)phenyl]benzonitrile Step 1

The procedure of steps 1 to 2 in Example 9 was repeated using 3-bromo-4-methoxybenzoic acid instead of 3-bromo-4-chloro-benzoic acid, and using (R)-tert-butyl piperidine-3-yl carbamate instead of tert-butyl N-[(3S)-pyrrolidin-3-yl] carbamic acid to give (R)-tert-butyl (1-(4'-cyano-6-methoxy-[1,1'-biphenyl]-3-carbonyl)piperidin-3-yl) carbamate.

Step 2

The (R)-tert-butyl (1-(4'-cyano-6-methoxy-[1,1'-biphenyl]-3-carbonyl)piperidin-3-yl)carbamate (430 mg) obtained in step 1 above was dissolved in methylene chloride (10 mL). At 0° C., a solution of 1 M $BBr_3$ in methylene chloride (2.17 mL) was added thereto dropwise, followed by stirring at room temperature for 30 minutes. A saturated aqueous sodium hydrogen carbonate solution (17 mL), water (4 mL), and $CH_2Cl_2$ (8 mL) were added thereto, followed by stirring for 10 minutes. $Boc_2O$ (0.2370 g) was added thereto, followed by stirring at room temperature for 1 hour. After the organic layer was dried over anhydrous sodium sulfate, the solvent was distilled off. The residue was purified by silica gel column chromatography (mobile phase: hexane/ethyl acetate) to give tert-butyl N-[(3R)-1-[3-(4-cyanophenyl)-4-hydroxy-benzoyl]-3-piperidyl]carbamate.

Step 3

The tert-butyl N-[(3R)-1-[3-(4-cyanophenyl)-4-hydroxy-benzoyl]-3-piperidyl]carbamate (10 mg) obtained in step 2 above was dissolved in THF (0.500 mL). At 25° C., 3-pyridyl methanol (7 mg), polymer-supported $PPh_3$ (30 mg), and DMEAD (27.8 mg) were added thereto, followed by stirring at 50° C. for 3 hour. Ethyl acetate was added thereto, and the resulting mixture was washed sequentially with water and saturated brine. After the organic layer was dried over anhydrous sodium sulfate, the solvent was distilled off. The residue was purified by silica gel column chromatography (mobile phase: chloroform/methanol) to give (S)-tert-butyl (1-(4'-cyano-6-(pyridin-3-ylmethoxy)-[1,1'-biphenyl]-3-carbonyl)piperidin-3-yl)carbamate.

Step 4

The procedure of step 5 in Example 1 was repeated using the (S)-tert-butyl (1-(4'-cyano-6-(pyridin-3-ylmethoxy)-[1, 1'-biphenyl]-3-carbonyl)piperidin-3-yl)carbamate obtained in step 3 above instead of tert-butyl N-[(3S)-1-[3-(4-cyanophenyl)-4-(p-tolyl)benzoyl]pyrrolidin-3-yl]carbamate to give the title compound.

Comparative Example 5: Synthesis of (S)-(3-aminopyrrolidin-1-yl)(4-methyl-4"-(trifluoromethyl)-[1,1':2',1"-terphenyl]-4'-yl)methanone The procedure of steps 1 to 5 in Example 19 was repeated using 1-bromo-4-(trifluoromethyl)benzene instead of 4-bromo-2,6-difluoro-benzonitrile to give the title compound.

Comparative Example 6: Synthesis of 4"-methyl-5'-(3-(pyridin-3-yl)pyrrolidine-1-carbonyl)-[1,1':2',1"-terphenyl]-4-carbonitrile The procedure of steps 1 to 5 in Example 1 was repeated using 3-(pyrrolidin-3-yl)pyridine instead of tert-butyl N-[(3S)-pyrrolidin-3-yl]carbamate to give 4"-methyl-5'-(3-(pyridin-3-yl)pyrrolidine-1-carbonyl)-[1,1':2',1"-terphenyl]-4-carbonitrile.

Comparative Example 7: Synthesis of 4-(3-(4-aminopiperidine-1-carbonyl)-5-(p-tolyl)-1H-pyrazol-1-yl)benzonitrile Step 1

The procedure of the synthetic method of Scheme C disclosed in WO2015/103060 was repeated using 1-(4-methylphenyl)ethanone as C-1, using 4-hydrazinobenzonitrile instead of (4-(trifluoromethyl)phenyl)hydrazine, and using tert-butyl piperidin-4-yl carbamate instead of 1-(4-fluorophenyl)-1,3,8-triazaspiro[4.5]decan-4-one to give tert-butyl (1-(1-(4-cyanophenyl)-5-(p-tolyl)-1H-pyrazole-3-carbonyl)piperidin-4-yl)carbamate.

Step 2

The procedure of step 5 in Example 1 was repeated using the tert-butyl (1-(1-(4-cyanophenyl)-5-(p-tolyl)-1H-pyrazole-3-carbonyl)piperidin-4-yl)carbamate obtained in step 1 above instead of N-[(3S)-1-[3-(4-cyanophenyl)-4-(p-tolyl)benzoyl]pyrrolidin-3-yl]carbamate to give the title compound.

The following are lists of the compounds of Examples 1 to 281 and Comparative Examples 1 to 7.

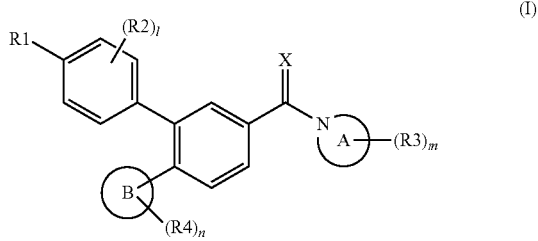

In the following tables, if the structure:

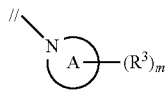

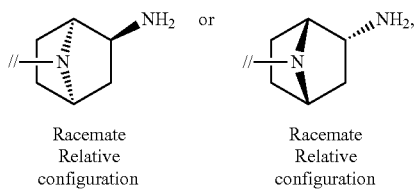

TABLE 1-continued

| Ex. No. | X | R¹ (R²)ₗ | A (R³)ₘ | B (R⁴)ₙ | MS m/z (M + 1) | NMR |
|---|---|---|---|---|---|---|
| 3 | O | 4-CN-phenyl | 4-aminopiperidinyl | 4-methylphenyl | 396.4 | 1H-NMR (DMSO-D6) δ: 7.74 (2H, d, J = 8.1 Hz), 7.49 (2H, s), 7.38 (1H, s), 7.33 (2H, d, J = 8.1 Hz), 7.09 (2H, d, J = 8.1 Hz), 7.01 (2H, d, J = 8.1 Hz), 4.38-4.23 (1H, m), 3.73-3.61 (1H, m), 3.18-3.05 (1H, m), 3.01-2.89 (1H, m), 2.87-2.79 (1H, m), 2.27 (3H, s), 1.87-1.64 (4H, m). |
| 4 | O | 4-CN-phenyl | 2,6-diazaspiro[3.5]nonane | 4-methylphenyl | 422.5 | 1H-NMR (DMSO-D6) δ: 7.76 (3H, d, J = 8.2 Hz), 7.63 (1H, s), 7.53 (1H, d, J = 7.6 Hz), 7.32 (2H, d, J = 8.2 Hz), 7.10 (2H, d, J = 7.6 Hz), 7.00 (2H, d, J = 7.6 Hz), 4.24 (1H, d, J = 8.9 Hz), 4.12 (1H, d, J = 8.9 Hz), 3.95 (1H, d, J = 9.5 Hz), 3.78 (1H, d, J = 10.2 Hz), 3.51 (2H, s), 2.96 (2H, s), 2.27 (3H, s), 1.86-1.80 (2H, m), 1.71-1.60 (2H, m). |
| 5 | O | 4-CN-phenyl | 2,6-diazaspiro[3.4]octane | 4-methylphenyl | 408.5 | 1H-NMR (DMSO-D6) δ: 7.76 (2H, d, J = 8.2 Hz), 7.67-7.61 (1H, m), 7.58-7.47 (2H, m), 7.35-7.29 (2H, m), 7.14-7.07 (2H, m), 7.00 (2H, d, J = 8.2 Hz), 4.12-4.03 (1H, m), 3.96-3.84 (2H, m), 3.76-3.71 (2H, m), 3.59-3.47 (3H, m), 2.28 (3H, s), 2.19-2.11 (2H, m). |
| 6 | O | 4-CN-phenyl | 2,7-diazaspiro[4.4]nonane | 4-methylphenyl | 422.2 | 1H-NMR (DMSO-D6) δ: 7.76 (2H, t, J = 4.3 Hz), 7.65 (1H, dd, J = 7.9, 1.8 Hz), 7.56 (1H, dd, J = 18.9, 1.5 Hz), 7.50 (1H, d, J = 7.9 Hz), 7.34 (2H, d, J = 8.2 Hz), 7.11 (2H, d, J = 7.6 Hz), 7.01 (2H, dd, J = 8.2, 2.4 Hz), 3.61-3.47 (4H, m), 2.95 (4H, t, J = 1.7 Hz), 2.28 (3H, s), 1.92-1.72 (4H, m). |
| 7 | O | 4-CN-phenyl | tropane-NH₂ | 4-methylphenyl | 422.3 | 1H-NMR (DMSO-D6) δ: 7.73 (2H, d, J = 8.4 Hz), 7.56 (1H, d, J = 7.7 Hz), 7.50 (1H, d, J = 7.7 Hz), 7.44 (1H, s), 7.32 (2H, d, J = 8.4 Hz), 7.08 (2H, d, J = 8.1 Hz), 6.99 (2H, d, J = 7.7 Hz), 4.65-4.57 (1H, m), 4.19-4.11 (1H, m), 3.47-3.35 (2H, m), 2.26 (2H, s), 2.04-1.44 (8H, m). |
| 8 | O | 4-CN-phenyl | 3-amino-3-methylpyrrolidinyl | 4-methylphenyl | 396.1 | 1H-NMR (DMSO-D6) δ: 7.76 (2H, d, J = 8.2 Hz), 7.63-7.61 (1H, m), 7.51 (2H, d, J = 7.9 Hz) 7.33-7.32 (2H, m), 7.10 (2H, d, J = 7.9 Hz), 7.01 (2H, d, J = 7.0 Hz), 3.81-3.40 (4H, m), 2.27 (3H, s), 2.03-1.90 (2H, m), 1.44-1.22 (3H, m). |
| 9 | O | 4-CN-phenyl | (3R)-3-aminopyrrolidinyl | 4-methyl-3-chlorophenyl | 416.0 / 418.0 | 1H-NMR (DMSO-D6) δ: 7.74 (2H, d, J = 8.2 Hz), 7.67-7.59 (2H, m), 7.44 (1H, d, J = 7.9 Hz), 7.34-7.23 (3H, m), 7.16-7.10 (2H, m), 3.95-3.45 (5H, m), 2.29 (3H, s), 2.28-2.19 (1H, m), 2.06-1.96 (1H, m). |
| 10 | O | 4-CN-phenyl | (3S)-3-aminopyrrolidinyl | 4-methyl-3-chlorophenyl | 416.2 / 418.1 | 1H-NMR (DMSO-D6) δ: 7.72 (2H, d, J = 8.2 Hz), 7.62-7.57 (1H, m), 7.50 (2H, d, J = 8.2 Hz), 7.28 (2H, d, J = 7.6 Hz), 7.17 (2H, d, J = 9.5 Hz), 6.85 (1H, d, J = 7.0 Hz), 3.82-3.52 (5H, m), 2.22 (3H, s), 2.19-2.12 (1H, m), 1.95-1.87 (1H, m). |

TABLE 2

| 11 | O | 4-CN-phenyl | (3R)-3-aminopyrrolidinyl | 4-CF₃-3-fluorophenyl | 454.2 | 1H-NMR (DMSO-D6) δ: 7.74 (2H, d, J = 8.2 Hz), 7.66-7.52 (4H, m), 7.35-7.26 (3H, m), 7.01 (1H, d, J = 8.2 Hz), 3.86-3.47 (5H, m), 2.23-2.10 (1H, m), 1.98-1.87 (1H, m). |

TABLE 2-continued

| | | | | | |
|---|---|---|---|---|---|
| 12 | O | 4-cyanophenyl | (3-aminopyrrolidin-1-yl) | 2-methyl-4-nitrophenyl | 427.2 1H-NMR (DMSO-D6) δ: 7.80 (2H, d, J = 8.2 Hz), 7.76 (1H, s), 7.73-7.67 (1H, m), 7.66-7.58 (7H, m), 7.43-7.35 (3H, m), 7.31 (1H, d, J = 7.6 Hz), 4.13-4.07 (1H, m), 3.92-3.67 (2H, m), 3.64-3.49 (2H, m), 3.16 (3H, s), 2.28-2.15 (1H, m), 2.02-1.91 (1H, m). |
| 13 | O | 4-cyanophenyl | (3-aminopyrrolidin-1-yl) | 4-(difluoromethyl)phenyl | 418.2 1H-NMR (DMSO-D6) δ: 7.70 (2H, d, J = 8.2 Hz), 7.65-7.59 (1H, m), 7.52 (2H, d, J = 8.2 Hz), 7.43 (2H, d, J = 8.2 Hz), 7.27 (2H, d, J = 7.0 Hz), 7.20 (2H, d, J = 8.2 Hz), 3.87-3.48 (5H, m), 3.14-3.06 (1H, m), 2.22-2.10 (1H, m), 1.99-1.86 (1H, m). |
| 14 | O | 4-cyanophenyl | (3-aminopyrrolidin-1-yl) | 4-(trifluoromethyl)phenyl | 436.2 1H-NMR (DMSO-D6) δ: 7.71 (2H, d, J = 8.2 Hz), 7.65-7.58 (3H, m), 7.54 (2H, d, J = 7.6 Hz), 7.33-7.24 (4H, m), 3.83-3.53 (5H, m), 2.23-2.11 (1H, m), 1.98-1.89 (1H, m). |
| 15 | O | 4-cyanophenyl | (3-aminopyrrolidin-1-yl) | 2-fluoro-4-methylphenyl | 400.2 1H-NMR (DMSO-D6) δ: 7.68 (2H, d, J = 8.2 Hz), 7.63-7.56 (1H, m), 7.56-7.49 (1H, m), 7.44 (1H, d, J = 8.2 Hz), 7.24 (2H, d, J = 7.6 Hz), 7.10 (1H, t, J = 7.9 Hz), 6.95 (1H d, J = 7.6 Hz), 6.85 (1H, d, J = 10.8 Hz), 3.83-3.53 (5H, m), 2.22 (3H, s), 2.19-2.10 (1H, m), 1.98-1.88 (1H, m). |
| 16 | O | 2-fluoro-4-cyanophenyl | (3-aminopyrrolidin-1-yl) | 4-methylphenyl | 400.1 1H-NMR (DMSO-D6) δ: 7.75 (1H, t, J = 7.6 Hz), 7.50 (1H, d, J = 7.6 Hz), 7.47 (1H, d, J = 7.6 Hz), 7.33-7.24 (1H, m), 7.07-6.95 (6H, m), 4.02-3.52 (5H, m), 2.22 (3H, s), 2.18-2.11 (1H, m), 1.98-1.87 (1H, m). |
| 17 | O | 2-fluoro-4-cyanophenyl | 8-azabicyclo[3.2.1]-3-amino | 4-methylphenyl | 440.2 1H-NMR (DMSO-D6) δ: 7.80 (1H, t, J = 7.5 Hz), 7.61-7.58 (1H, m), 7.52-7.49 (2H, m), 7.38 (1H, dd, J = 10.5, 1.4 Hz), 7.12 (2H, d, J = 7.9 Hz), 7.11-7.09 (1H, m), 7.04 (2H, d, J = 7.9 Hz), 4.63-4.57 (1H, m), 4.14-4.06 (1H, m), 2.28 (3H, s), 2.24-2.02 (2H, m), 2.00-1.89 (1H, m), 1.84-1.51 (3H, m), 1.34-1.14 (3H, m). |
| 18 | O | 2-fluoro-4-cyanophenyl | 8-azabicyclo[3.2.1]-3-amino | 1-methylindol-5-yl | 479.2 1H-NMR (DMSO-D6) δ: 7.76 (1H, t, J = 7.5 Hz), 7.62-7.56 (2H, m), 7.51-7.50 (1H, m), 7.44-7.42 (1H, m), 7.41-7.37 (1H, m), 7.35-7.31 (2H, m), 7.11 (1H, d, J = 8.2 Hz), 6.83 (1H, d, J = 8.2 Hz), 6.40 (1H, d, J = 3.1 Hz), 4.65-4.58 (1H, m), 4.22-4.10 (1H, m), 3.77 (3H, s), 3.74-3.72 (1H, m), 2.04-1.19 (8H, m). |
| 19 | O | 2,6-difluoro-4-cyanophenyl | (3-aminopyrrolidin-1-yl) | 4-methylphenyl | 418.1 1H-NMR (DMSO-D6) δ: 7.71-7.68 (1H, m), 7.62 (1H, s), 7.55 (1H, d, J = 7.9 Hz), 7.24-7.13 (4H, m), 7.06 (2H, d, J = 7.9 Hz), 3.90-3.53 (4H, m), 3.49-3.41 (1H, m), 2.30 (3H, s), 2.25-2.16 (1H, m), 1.99-1.93 (1H, m). |
| 20 | O | 2-fluoro-4-cyanophenyl | (3-aminopyrrolidin-1-yl) | 3-fluoro-4-(2-methoxyethyl)phenyl | 462.1 1H-NMR (DMSO-D6) δ: 7.80 (1H, t, J = 7.5 Hz), 7.70-7.66 (1H, m), 7.62 (1H, dd, J = 6.6, 1.5 Hz), 7.51 (1H, d, J = 7.7 Hz), 7.33 (1H, d, J = 10.6 Hz), 7.24 (1H, t, J = 7.9 Hz), 7.13-7.08 (2H, m), 7.00 (1H, d, J = 10.3 Hz), 3.68-3.56 (2H, m), 3.55-3.40 (4H, m), 3.23 (3H, s), 3.22-3.11 (1H, m), 2.81 (2H, t, J = 6.6 Hz), 2.03-1.88 (1H, m), 1.69-1.57 (1H, m). |

TABLE 3

| | | | | | |
|---|---|---|---|---|---|
| 21 | O | 2-fluoro-4-cyanophenyl | 8-azabicyclo[3.2.1]-3-amino | 2-fluoro-4-methyl-cyanophenyl | 458.2 1H-NMR (DMSO-D6) δ: 7.81 (1H, t, J = 7.6 Hz), 7.61 (1H, dd, J = 7.8, 1.7 Hz), 7.54 (1H, d, J = 1.5 Hz), 7.50 (1H, d, J = 7.6 Hz), 7.37 (1H, d, J = 9.2 Hz), 7.21 (1H, t, J = 7.9 Hz), 7.11 (1H, dd, J = 7.9, 1.5 Hz), 7.05 (1H, d, J = 8.2 Hz), 6.95 (1H, d, J = 11.3 Hz), 4.63-4.57 (1H, m), 4.12-4.05 (1H, m), 2.31 (3H, s), 2.25-2.02 (3H, m), 2.00-1.69 (3H, m), 1.65-1.50 (2H, m), 1.47-1.34 (1H, m). |

TABLE 3-continued

| | | | | | |
|---|---|---|---|---|---|
| 22 | O | 4-cyano-2-fluorophenyl | tropane-NH₂ | 2-(3-fluoro-4-methoxyethyl)benzonitrile | 502.2 1H-NMR (DMSO-D6) δ: 7.81 (1H, t, J = 7.5 Hz), 7.62 (1H, dd, J = 7.8, 1.7 Hz), 7.56-7.52 (2H, m), 7.35 (1H, dd, J = 10.5, 1.4 Hz), 7.24 (1H, t, J = 7.9 Hz), 7.13-7.09 (2H, m), 7.02-6.99 (1H, m), 4.62 (1H, s), 4.10 (1H, s), 3.53 (2H, t, J = 6.7 Hz), 3.40-3.34 (1H, m), 3.23 (3H, s), 2.81 (2H, t, J = 6.7 Hz), 2.33-1.90 (6H, m), 1.70-1.55 (2H, m). |
| 23 | O | 4-cyano-2-fluorophenyl | tropane-NH₂ | 5-fluoro-1-methylindole | 497.2 1H-NMR (DMSO-D6) δ: 7.76 (1H, t, J = 7.6 Hz), 7.62 (1H, dd, J = 7.8, 1.7 Hz), 7.57-7.50 (3H, m), 7.39-7.34 (2H, m), 7.22 (1H, d, J = 11.3 Hz), 7.13-7.09 (1H, m), 6.46-6.43 (1H, m), 4.63 (1H, s), 4.15 (1H, s), 3.74 (3H, s), 3.19-3.13 (1H, m), 2.05-1.78 (4H, m), 1.77-1.67 (2H, m), 1.65-1.56 (1H, m), 1.48-3.39 (1H, m). |
| 24 | O | 4-cyano-2-fluorophenyl | tropane-NH₂ | 5-fluoro-1-methylindazole | 498.2 1H-NMR (DMSO-D6) δ: 8.09 (1H, d, J = 0.9 Hz), 7.81-7.75 (2H, m), 7.65 (1H, dd, J = 7.8, 1.7 Hz), 7.60-7.55 (2H, m), 7.46 (1H, d, J = 10.7 Hz), 7.41 (1H, dd, J = 10.5, 1.4 Hz), 7.11 (1H, dd, J = 7.9, 1.5 Hz), 4.64 (1H, s), 4.14 (1H, s), 3.99 (3H, s), 3.36-3.30 (1H, m), 2.06-1.44 (8H, m). |
| 25 | O | 4-cyano-2-fluorophenyl | 3-methyl-pyrrolidin-3-amine | 3-fluoro-4-(methoxyethyl)phenyl | 476.1 1H-NMR (DMSO-D6) δ: 7.85-7.80 (1H, m), 7.74-7.59 (2H, m), 7.55 (1H, d, J = 7.9 Hz), 7.35-7.29 (1H, m), 7.26-7.21 (1H, m), 7.11 (2H, d, J = 7.9 Hz), 7.01 (1H, d, J = 11.0 Hz), 3.79-3.44 (6H, m), 3.23 (3H, s), 2.85-2.79 (2H, m), 2.10-1.98 (2H, m), 1.47-1.27 (3H, m). |
| 26 | O | 4-cyano-2-fluorophenyl | tropane-NH₂ | 3-fluoro-4-(methoxyethyl)phenyl | 502.1 1H-NMR (DMSO-D6) δ: 7.82 (1H, t, J = 7.5 Hz), 7.63 (1H, d, J = 7.9 Hz), 7.57-7.52 (2H, m), 7.34 (1H, d, J = 9.8 Hz), 7.24 (1H, t, J = 7.9 Hz), 7.15-7.09 (2H, m), 7.01 (1H, d, J = 11.3 Hz), 4.63 (1H, s), 4.13 (1H, s), 3.53 (2H, t, J = 6.6 Hz), 3.42-3.36 (1H, m), 3.23 (1H, s), 2.81 (2H, t, J = 6.6 Hz), 2.09-1.45 (8H, m). |
| 27 | O | 4-cyano-2-fluorophenyl | bicyclic diamine | 3-fluoro-4-(methoxyethyl)phenyl | 488.2 1H-NMR (DMSO-D6) δ: 7.83-7.78 (1H, m), 7.71-7.48 (3H, m), 7.39-7.31 (1H, m), 7.27-7.21 (1H, m), 7.15-7.08 (2H, m), 7.03-6.98 (1H, m), 4.77-4.47 (1H, m), 4.29-3.95 (1H, m), 3.66-3.38 (4H, m), 3.23 (3H, d, J = 0.9 Hz), 2.99-2.88 (1H, m), 2.81 (2H, t, J = 6.5 Hz), 2.72-2.55 (1H, m), 2.01-1.43 (4H, m). |
| 28 | O | 4-cyano-2-fluorophenyl | tropane-NH₂ | 3-fluoro-4-(2-hydroxy-2-methylpropyl)phenyl | 516.3 1H-NMR (DMSO-D6) δ: 7.80 (1H, t, J = 7.5 Hz), 7.64-7.61 (1H, m), 7.57-7.52 (2H, m), 7.29-7.26 (1H, m), 7.21 (1H, t, J = 7.9 Hz), 7.15 (1H, dd, J = 8.2, 1.2 Hz), 7.07 (1H, dd, J = 7.9, 0.9 Hz), 6.95 (1H, d, J = 11.3 Hz), 4.61 (1H, s), 4.40 (1H, s), 4.09 (1H, s), 3.19-3.11 (1H, m), 2.65 (2H, s), 2.11-1.59 (6H, m), 1.58-1.48 (1H, m), 1.41-1.33 (1H, m), 1.04 (6H, s). |

TABLE 4

| | | | | | |
|---|---|---|---|---|---|
| 29 | O | 4-cyanophenyl | (3S)-pyrrolidin-3-amine | 4-(hydroxymethyl)phenyl | 398.6 1H-NMR (DMSO-D6) δ: 7.74 (2H, d, J = 8.5 Hz), 7.67-7.63 (1H, m), 7.54 (1H, dd, J = 10.5, 1.7 Hz), 7.50 (1H, d, J = 7.9 Hz), 7.34 (2H, d, J = 8.2 Hz), 7.22 (2H, d, J = 8.2 Hz), 7.08 (2H, d, J = 8.2 Hz), 5.19 (1H, t, J = 5.6 Hz), 4.47 (2H, d, J = 5.8 Hz), 3.71-3.50 (2H, m), 3.27-3.13 (2H, m), 2.55-2.53 (1H, m), 2.04-1.90 (1H, m), 1.70-1.61 (1H, m). |
| 30 | O | 4-cyanophenyl | (3S)-pyrrolidin-3-amine | 4-(2-methoxyethyl)phenyl | 426.2 1H-NMR (DMSO-D6) δ: 7.73 (2H, d, J = 8.5 Hz), 7.66-7.62 (1H, m), 7.55-7.49 (2H, m), 7.32 (2H, d, J = 7.3 Hz), 7.15 (2H, d, J = 8.2 Hz), 7.03 (2H, d, J = 8.2 Hz), 3.68-3.46 (6H, m), 3.22 (3H, s), 3.20-3.12 (1H, m), 2.77 (2H, t, J = 6.9 Hz), 2.02-1.87 (1H, m), 1.69-1.57 (1H, m). |

TABLE 4-continued

| | | | | | |
|---|---|---|---|---|---|
| 31 | O | | | | 412.1 1H-NMR (DMSO-D6) δ: 7.74 (2H, d, J = 8.5 Hz), 7.66-7.62 (1H, m), 7.55-7.49 (2H, m), 7.35-7.32 (2H, m), 7.13 (2H, d, J = 7.9 Hz), 7.03 (2H, d, J = 8.2 Hz), 4.63 (1H, t, J = 5.2 Hz), 3.62-3.56 (2H, m), 3.30-3.14 (4H, m), 2.73-2.66 (2H, m), 2.55-2.53 (1H, m), 2.03-1.90 (1H, m), 1.67-1.59 (1H, m). |
| 32 | O | | | | 426.2 1H-NMR (DMSO-D6) δ: 7.49-7.38 (2H, m), 7.39-7.30 (1H, m), 7.27-7.14 (2H, m), 7.10-6.98 (2H, m), 6.90-6.67 (4H, m), 4.26-4.08 (1H, m), 3.47-3.11 (5H, m), 2.93-2.75 (2H, m), 2.38-2.14 (2H, m), 1.78-1.44 (2H, m), 1.42-1.27 (2H, m). |
| 33 | O | | | | 438.2 1H-NMR (DMSO-D6) δ: 7.68 (2H, d, J = 8.2 Hz), 7.63-7.53 (1H, m), 7.46 (2H, t, J = 8.2 Hz), 7.26 (2H, d, J = 7.0 Hz), 7.12 (2H, d, J = 7.6 Hz), 6.95 (2H, d, J = 8.2 Hz), 4.65 (1H, s), 3.92-3.60 (5H, m), 3.09 (2H, s), 2.24-2.08 (1H, m), 2.01-1.86 (1H, m), 0.77 (2H, s), 0.65 (2H, s). |
| 34 | O | | | | 440.2 1H-NMR (DMSO-D6) δ: 7.63 (2H, d, J = 7.0 Hz), 7.56 (1H, d, J = 5.7 Hz), 7.46 (2H, t, J = 10.2 Hz), 7.24 (2H, d, J = 7.6 Hz), 7.04 (2H, d, J = 7.6 Hz), 6.93 (2H, d, J = 7.0 Hz), 4.28 (1H, s), 3.64-3.48 (5H, m), 2.55 (2H, s), 1.98-1.87 (1H, m), 1.65-1.54 (1H, m), 0.96 (6H, s). |
| 35 | O | | | | 442.2 1H-NMR (DMSO-D6) δ: 7.78 (2H, d, J = 8.5 Hz), 7.67-7.61 (1H, m), 7.57-7.51 (2H, m), 7.36-7.30 (2H, m), 7.03 (2H, d, J = 8.5 Hz), 6.85 (2H, d, J = 8.5 Hz), 3.96-3.87 (1H, m), 3.85-3.68 (4H, m), 3.66-3.46 (2H, m), 3.27-3.21 (1H, m), 2.59-2.51 (1H, m), 2.29-2.17 (1H, m), 2.04-1.94 (1H, m), 1.13 (3H, d, J = 6.4 Hz). |
| 36 | O | | | | 418.1 1H-NMR (DMSO-D6) δ: 7.85-7.81 (1H, m), 7.71-7.67 (1H, m), 7.63 (1H, s), 7.54 (1H, d, J = 7.6 Hz), 7.38-7.32 (1H, m), 7.24-7.18 (1H, m), 7.10 (1H, d, J = 7.6 Hz), 7.06 (1H, d, J = 8.2 Hz), 6.96 (1H, d, J = 11.4 Hz), 4.12-4.07 (1H, m), 3.92-3.53 (4H, m), 2.31 (3H, s), 2.26-2.17 (1H, m), 2.02-1.91 (1H, m). |
| 37 | O | | | | 476.1 1H-NMR (DMSO-D6) δ: 7.79 (1H, t, J = 7.5 Hz), 7.70-7.67 (1H, m), 7.63 (1H, dd, J = 6.6, 1.5 Hz), 7.52 (1H, d, J = 8.1 Hz), 7.27 (1H, d, J = 10.3 Hz), 7.21 (1H, t, J = 7.9 Hz), 7.14 (1H, dd, J = 8.1, 1.5 Hz), 7.06 (1H, d, J = 7.7 Hz), 6.95 (1H, d, J = 11.4 Hz), 4.39 (1H, s), 3.68-3.55 (2H, m), 3.54-3.41 (2H, m), 3.21-3.12 (1H, m), 2.65 (2H, s), 2.03-1.88 (1H, m), 1.70-1.59 (1H, m), 1.04 (6H, s). |

TABLE 5

| | | | | | |
|---|---|---|---|---|---|
| 38 | O | | | | 504.2 1H-NMR (CDCl3) δ: 7.76-7.69 (2H, m), 7.49-7.43 (2H, m), 7.09-6.96 (4H, m), 6.83 (1H, dd, J = 10.8, 0.9 Hz), 4.23 (2H, dd, J = 23.5, 9.2 Hz), 4.10 (2H, s), 3.75-3.64 (2H, m), 3.60 (2H, t, J = 6.6 Hz), 3.35 (3H, s), 3.00 (2H, s), 2.90-2.80 (4H, m). |
| 39 | O | | | | 488.1 1H-NMR (DMSO-D6) δ: 7.80 (1H, t, J = 7.6 Hz), 7.65 (1H, d, J = 7.0 Hz), 7.57 (1H, d, J = 10.8 Hz), 7.51 (1H, d, J = 7.6 Hz), 7.33 (1H, d, J = 10.2 Hz), 7.23 (1H, t, J = 7.9 Hz), 7.14-7.06 (2H, m), 7.00 (1H, t, J = 11.4 Hz), 3.86-3.64 (2H, m), 3.58-3.47 (4H, m), 3.23 (3H, s), 3.03-2.86 (2H, m), 2.81 (2H, t, J = 6.7 Hz), 2.77-2.55 (4H, m). |
| 40 | O | | | | 458.3 1H-NMR (DMSO-D6) δ: 7.82-7.77 (1H, m), 7.69-7.64 (1H, m), 7.60 (1H, d, J = 8.9 Hz), 7.54 (1H, J = 7.6 Hz), 7.27 (1H, d, J = 10.8 Hz), 7.15 (3H, d, J = 7.0 Hz), 7.03 (2H, d, J = 7.0 Hz), 3.74-3.53 (4H, m), 3.52-3.49 (1H, m), 3.22-3.13 (1H, m), 2.63 (2H, s), 2.07-1.97 (1H, m), 1.76-1.67 (1H, m), |

TABLE 5-continued

| | | | | | |
|---|---|---|---|---|---|
| | | | | | 1.03 (6H, s). |
| 41 | O | 4-cyano-2-fluorophenyl | 8-azabicyclo[3.2.1] with NH₂ | 3-fluoro-4-(2-hydroxypropan-2-yl)phenyl | 516.2 1H-NMR (DMSO-D6) δ: 7.80 (1H, t, J = 7.6 Hz), 7.61 (1H, dd, J = 7.8, 1.7 Hz), 7.53 (2H, dd, J = 10.8, 4.7 Hz), 7.29 (1H, dd, J = 10.7, 1.2 Hz), 7.22 (1H, t, J = 7.9 Hz), 7.15 (1H, dd, J = 7.5, 1.5 Hz), 7.07 (1H, dd, J = 7.9, 1.2 Hz), 6.96 (1H, d, J = 11.3 Hz), 4.57 (1H, br s), 4.40 (1H, s), 4.05 (1H, br s), 2.65 (2H, s), 2.35-2.21 (2H, m), 2.12-2.03 (1H, m), 1.99-1.81 (3H, m), 1.61-1.47 (3H, m), 1.06 (6H, d, J = 14.6 Hz). |
| 42 | O | 4-cyanophenyl | (3S)-3-(methylamino)pyrrolidin-1-yl | 4-methylphenyl | 396.3 1H-NMR (DMSO-D6) δ: 7.71 (2H, d, J = 7.7 Hz), 7.61 (1H, dd, J = 7.7, 1.5 Hz), 7.50 (1H, s), 7.46 (1H, dd, J = 8.1, 2.6 Hz), 7.30 (2H, d, J = 8.4 Hz), 7.07 (2H, d, J = 8.1 Hz), 6.98 (2H, d, J = 7.7 Hz), 3.63-3.44 (3H, m), 3.26-3.07 (2H, m), 2.27-2.16 (6H, m), 1.94-1.85 (1H, m), 1.75-1.68 (1H, m). |
| 43 | O | 4-cyanophenyl | (3S)-3-aminopyrrolidin-1-yl | 4-(benzyloxy)phenyl | 474.5 1H-NMR (DMSO-D6) δ: 7.76 (2H, d, J = 7.6 Hz), 7.67-7.61 (1H, m), 7.56-7.50 (2H, m), 7.45-7.30 (7H, m), 7.04 (2H, d, J = 7.6 Hz), 6.93 (2H, d, J = 7.6 Hz), 5.07 (2H, s), 4.17-4.07 (1H, m), 3.91-3.52 (4H, m), 2.26-2.15 (1H, m), 2.00-1.90 (1H, m). |
| 44 | O | 4-cyanophenyl | (3S)-3-aminopyrrolidin-1-yl | 1-(4-phenyl)-N-phenylcyclopropanecarboxamide | 527.2 1H-NMR (DMSO-D6) δ: 8.96 (1H, s), 7.74 (2H, dd, J = 6.7, 1.8 Hz), 7.67-7.64 (1H, m), 7.54 (4H, tt, J = 12.7, 4.8 Hz), 7.37 (2H, dd, J = 8.2, 1.5 Hz), 7.32-7.28 (4H, m), 7.13 (2H, d, J = 8.2 Hz), 7.07-7.04 (1H, m), 3.68-3.43 (5H, m), 1.99 (1H, d, J = 6.1 Hz), 1.66 (1H, dt, J = 7.0, 2.2 Hz), 1.44 (2H, dd, J = 6.7, 4.3 Hz), 1.12 (2H, dd, J = 6.9, 4.4 Hz). |
| 45 | O | 4-cyanophenyl | (3R)-3-aminopyrrolidin-1-yl | 4-(2-acetoxyethyl)phenyl | 454.5 1H-NMR (DMSO-D6) δ: 7.73 (2H, d, J = 8.2 Hz), 7.67-7.62 (1H, m), 7.56-7.50 (2H, m), 7.32 (2H, d, J = 6.7 Hz), 7.16 (2H, d, J = 8.2 Hz), 7.05 (2H, d, J = 8.2 Hz), 4.19 (2H, t, J = 6.9 Hz), 3.72-3.43 (4H, m), 3.22-3.13 (1H, m), 2.86 (2H, d, J = 6.9 Hz), 2.06-1.88 (4H, m), 1.69-1.58 (1H, m). |
| 46 | O | 4-cyanophenyl | (3S)-3-(methylamino)pyrrolidin-1-yl | 4-(2-hydroxyethyl)phenyl | 426.5 1H-NMR (DMSO-D6) δ: 7.74 (2H, d, J = 8.2 Hz), 7.64 (1H, d, J = 8.2 Hz), 7.53 (1H, s), 7.49 (1H, d, J = 8.2 Hz), 7.33 (2H, d, J = 8.2 Hz), 7.13 (2H, d, J = 8.2 Hz), 7.03 (2H, d, J = 7.6 Hz), 3.71-3.45 (7H, m), 3.26-3.12 (1H, m), 2.69 (2H, d, J = 6.7 Hz), 2.34-2.19 (3H, m), 2.06-1.90 (1H, m), 1.83-1.72 (1H, m). |

TABLE 6

| | | | | | |
|---|---|---|---|---|---|
| 47 | O | 4-cyanophenyl | (3S)-3-(methylamino)pyrrolidin-1-yl | 4-(2-methoxyethyl)phenyl | 440.5 1H-NMR (DMSO-D6) δ: 7.73 (2H, d, J = 8.2 Hz), 7.64 (1H, d, J = 8.9 Hz), 7.56-7.47 (2H, m), 7.33 (2H, d, J = 8.2 Hz), 7.15 (2H, d, J = 7.6 Hz), 7.03 (2H, d, J = 7.6 Hz), 3.69-3.38 (6H, m), 3.26-3.08 (4H, m), 2.78 (2H, t, J = 6.7 Hz), 2.32-2.19 (3H, m), 2.04-1.87 (1H, m), 1.81-1.69 (1H, m). |
| 48 | O | 4-cyanophenyl | (3S)-3-(dimethylamino)pyrrolidin-1-yl | 1-(4-phenyl)cyclopropylmethanol | 466.2 1H-NMR (DMSO-D6) δ: 7.67 (2H, d, J = 7.6 Hz), 7.57 (1H, t, J = 8.6 Hz), 7.43 (2H, dd, J = 19.4, 4.8 Hz), 7.27 (2H, d, J = 8.2 Hz), 7.11 (2H, d, J = 8.2 Hz), 6.95 (2H, d, J = 5.7 Hz), 4.65-4.53 (1H, m), 3.68-3.38 (5H, m), 3.17-3.08 (1H, m), 2.71-2.58 (1H, m), 2.11 (3H, s), 2.04 (3H, s), 1.99-1.91 (1H, m), 1.74-1.58 (1H, m), 0.76 (2H, s), 0.65 (2H, s). |
| 49 | O | 4-cyanophenyl | (3R)-3-aminopyrrolidin-1-yl | 3-fluoro-4-methylphenyl | 400.2 1H-NMR (DMSO-D6) δ: 7.71 (2H, d, J = 8.2 Hz), 7.62-7.56 (1H, m), 7.49 (2H, d, J = 8.2 Hz), 7.28 (2H, d, J = 7.0 Hz), 7.11 (1H, t, J = 7.9 Hz), 6.87 (1H, d, J = 10.8 Hz), 6.73 (1H, d, J = 7.6 Hz), 3.86-3.47 (5H, m), 2.21-2.09 (4H, m), 2.00-1.86 (1H, m). |

TABLE 6-continued

| | | | | | |
|---|---|---|---|---|---|
| 50 | O | 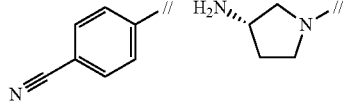 | 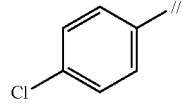 | 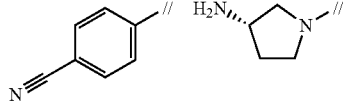 | 402.1 404.1 1H-NMR (DMSO-D6) δ: 7.71 (2H, d, J = 8.2 Hz), 7.64-7.56 (1H, m), 7.54-7.46 (2H, m), 7.33-7.22 (4H, m), 7.07 (2H, d, J = 8.2 Hz), 4.04-3.50 (5H, m), 2.20-2.04 (1H, m), 1.96-1.82 (1H, m). |
| 51 | O | 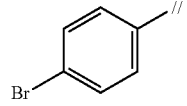 | 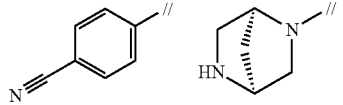 | 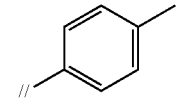 | 446.0 448.0 1H-NMR (DMSO-D6) δ: 7.71 (2H, d, J = 7.6 Hz), 7.65-7.57 (1H, m), 7.55-7.46 (2H, m), 7.43 (2H, d, J = 8.2 Hz), 7.27 (2H, d, J = 7.0 Hz), 7.01 (2H, d, J = 8.2 Hz), 3.78-3.50 (5H, m), 2.17-2.06 (1H, m), 1.92-1.82 (1H, m). |
| 52 | O | 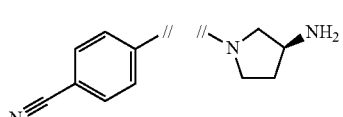 | 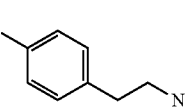 | 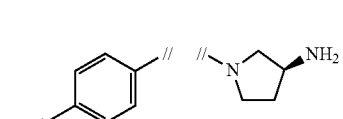 | 394.5 1H-NMR (DMSO-D6) δ: 7.75 (2H, d, J = 8.2 Hz), 7.67-7.50 (3H, m), 7.33 (2H, t, J = 8.6 Hz), 7.10 (2H, d, J = 7.6 Hz), 7.01 (2H, d, J = 7.6 Hz), 4.79-4.75 (1H, m), 4.51-4.47 (1H, m), 4.06 (1H, d, J = 18.4 Hz), 3.73-3.52 (2H, m), 3.15-3.02 (1H, m), 2.27 (3H, s), 2.04-1.91 (1H, m), 1.82-1.66 (1H, m). |
| 53 | O | 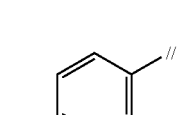 | 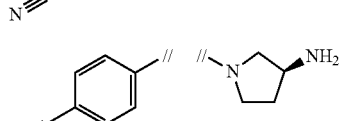 | 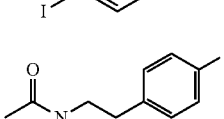 | 411.1 1H-NMR (DMSO-D6) δ: 7.74 (2H, dd, J = 6.6, 2.0 Hz), 7.65 (1H, s), 7.54-7.50 (2H, m), 7.34-7.33 (2H, m), 7.14 (2H, d, J = 8.2 Hz), 7.06 (2H, d, J = 8.2 Hz), 3.59 (5H, ddd, J = 14.0, 4.3, 2.5 Hz), 2.85 (2H, s), 2.69-2.67 (2H, m), 1.70-1.60 (1H, m), 1.24 (1H, s). |
| 54 | O | 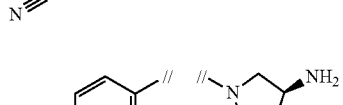 | | 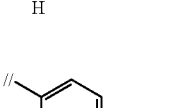 | 494 1H-NMR (DMSO-D6) δ: 7.71 (2H, d, J = 8.2 Hz), 7.63-7.56 (3H, m), 7.53-7.45 (2H, m), 7.26 (2H, d, J = 7.6 Hz), 6.86 (2H, d, J = 8.2 Hz), 3.87-3.47 (5H, m), 2.23-2.08 (1H, m), 1.98-1.86 (1H, m). |
| 55 | O | 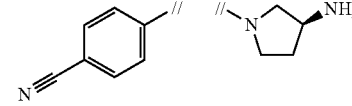 | | 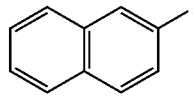 | 453.2 1H-NMR (DMSO-D6) δ: 7.85-7.79 (1H, m), 7.68 (2H, d, J = 8.2 Hz), 7.61-7.55 (1H, m), 7.52-7.44 (2H, m), 7.27-7.22 (2H, m), 7.06 (2H, d, J = 7.6 Hz), 6.97 (2H d, J = 7.6 Hz), 3.83-3.52 (5H, m), 3.17-3.12 (2H, m), 2.60 (2H, t, J = 7.3 Hz), 2.22-2.10 (1H, m), 1.98-1.86 (1H, m), 1.69 (3H, s). |
| 56 | O | 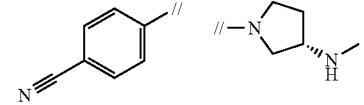 | | 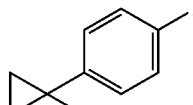 | 410.2 1H-NMR (DMSO-D6) δ: 7.67 (2H, d, J = 8.2 Hz), 7.63-7.55 (1H, m), 7.54-7.45 (2H, m), 7.25 (2H, d, J = 8.2 Hz), 7.04 (2H d, J = 8.2 Hz), 6.95 (2H, d, J = 7.6 Hz), 3.88-3.48 (5H, m), 2.48-2.44 (2H, m), 2.22-2.08 (1H, m), 1.97-1.86 (1H, m), 1.49 (2H, dd, J = 14.9, 7.3 Hz), 0.80 (3H, t, J = 7.3 Hz). |

TABLE 7

| | | | | | |
|---|---|---|---|---|---|
| 57 | O | 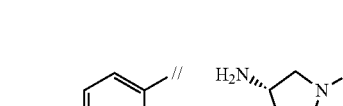 | | 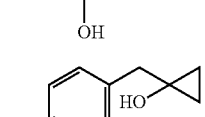 | 418.2 1H-NMR (DMSO-D6) δ: 7.83-7.76 (3H, m), 7.73-7.61 (5H, m), 7.59-7.53 (1H, m), 7.49-7.41 (2H, m), 7.29 (2H, d, J = 7.6 Hz), 7.03 (1H, d, J = 8.9 Hz), 4.03-3.55 (5H, m), 2.24-2.12 (1H, m), 1.98-1.88 (1H, m). |
| 58 | O | | 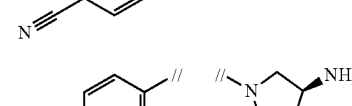 | | 452.1 1H-NMR (DMSO-D6) δ: 7.74 (2H, d, J = 8.2 Hz), 7.63 (1H, d, J = 8.2 Hz), 7.53-7.51 (1H, m), 7.49 (1H, d, J = 7.9 Hz), 7.34 (2H, d, J = 8.5 Hz), 7.19 (2H, d, J = 8.2 Hz), 7.03 (2H, d, J = 8.2 Hz), 4.67 (1H, t, J = 5.5 Hz), 3.71-3.47 (6H, m), 3.27-2.16 (1H, m), 2.35-2.21 (3H, m), 2.03-1.94 (1H, m), 1.81-1.72 (1H, m), 0.85-0.82 (2H, m), 0.74-0.70 (2H, m). |
| 59 | O | | 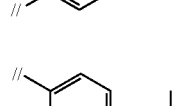 | | 438.1 1H-NMR (DMSO-D6) δ: 7.76-7.62 (3H, m), 7.58-7.50 (2H, m), 7.36-7.26 (2H, m), 7.14-7.02 (4H, m), 5.34-5.31 (1H, m), 3.89-3.58 (6H, m), 3.23-3.13 (1H, m), 2.05-1.95 (1H, m), 1.74-1.66 (1H, m), 0.94-0.84 (4H, m). |
| 60 | O | | | | 422.1 1H-NMR (DMSO-D6) δ: 7.67 (2H, d, J = 7.6 Hz), 7.62-7.55 (1H, m), 7.51-7.43 (2H, m), 7.26 (2H, d, J = 7.6 Hz), 7.03 (4H, dd, J = 28.6, 7.6 Hz), 6.15 (1H, s), 3.68-3.48 (5H, m), 2.01-1.89 (1H, m), 1.79 (3H, s), 1.74 (3H, s), 1.67-1.59 (1H, m). |

TABLE 7-continued

| | | | | | |
|---|---|---|---|---|---|
| 61 | O | 4-cyanophenyl | (3S)-3-aminopyrrolidine | 4-(2-hydroxy-2-methylpropyl)phenyl | 454.3 1H-NMR (DMSO-D6) δ: 7.74 (2H, d, J = 7.0 Hz), 7.67-7.61 (1H, m), 7.57-7.49 (2H, m), 7.33 (2H, d, J = 7.6 Hz), 7.11 (2H, d, J = 7.6 Hz), 7.02 (2H, d, J = 7.0 Hz), 3.82-3.56 (4H, m), 3.53-3.47 (1H, m), 3.21-3.13 (1H, m), 2.62-2.55 (2H, m), 2.13-2.03 (1H, m), 1.86-1.75 (1H, m), 1.64-1.57 (2H, m), 1.12 (6H, s). |
| 62 | O | 4-cyanophenyl | (3S)-3-aminopyrrolidine | 1-(4-phenylmethyl)cyclopropanol | 452.2 1H-NMR (DMSO-D6) δ: 7.74 (2H, d, J = 8.2 Hz), 7.68-7.62 (1H, m), 7.58-7.51 (2H, m), 7.32 (2H, d, J = 7.0 Hz), 7.12 (2H, d, J = 7.6 Hz), 7.02 (2H, d, J = 7.0 Hz), 4.15-4.08 (1H, m), 3.94-3.55 (4H, m), 3.53-3.48 (2H, m), 3.19-3.14 (1H, m), 2.77-2.69 (2H, m), 2.41-2.39 (2H, m), 2.31-2.17 (2H, m), 2.02-1.94 (1H, m), 0.91-0.89 (2H, m). |
| 63 | O | 2-fluoro-4-cyanophenyl | (3R)-3-aminopyrrolidine | 4-(2-hydroxyethyl)phenyl | 430.3 1H-NMR (DMSO-D6) δ: 8.30 (1H, s), 7.80 (1H, t, J = 7.0 Hz), 7.69-7.64 (1H, m), 7.58 (1H, d, J = 7.6 Hz), 7.51 (1H, d, J = 8.2 Hz), 7.35 (1H, d, J = 11.4 Hz), 7.16 (2H, d, J = 7.6 Hz), 7.11 (1H, d, J = 8.2 Hz), 7.05 (2H, d, J = 7.0 Hz), 3.69-3.52 (6H, m), 3.24-3.17 (1H, m), 2.71 (2H, t, J = 6.3 Hz), 2.04-1.93 (1H, m), 1.73-1.63 (1H, m). |
| 64 | O | 4-cyanophenyl | (3S)-3-aminopyrrolidine | 3-fluoro-4-(2-hydroxy-2-methylpropyl)phenyl | 458.2 1H-NMR (DMSO-D6) δ: 7.73-7.63 (3H, m), 7.59 (1H, d, J = 10.8 Hz), 7.51 (1H, d, J = 8.2 Hz), 7.31 (2H, d, J = 7.6 Hz), 7.20-7.14 (1H, m), 7.03 (1H, d, J = 7.6 Hz), 6.92 (1H, d, J = 11.4 Hz), 3.70-3.54 (4H, m), 3.52-3.49 (1H, m), 3.24-3.20 (1H, m), 2.64 (2H, s), 2.08-1.96 (1H, m), 1.76-1.66 (1H, m), 1.04 (6H, s). |
| 65 | O | 2-fluoro-4-cyanophenyl | (3R)-3-aminopyrrolidine | 4-(2-hydroxy-2-methylpropyl)phenyl | 472.2 1H-NMR (DMSO-D6) δ: 7.80 (1H, t, J = 7.3 Hz), 7.69-7.64 (1H, m), 7.59 (1H, d, J = 8.2 Hz), 7.52 (1H, d, J = 8.2 Hz), 7.33 (1H, d, J = 10.8 Hz), 7.15-7.09 (3H, m), 7.04 (2H, d, J = 7.6 Hz), 3.70-3.57 (4H, m), 3.54-3.49 (1H, m), 3.24-3.17 (1H, m), 2.63-2.57 (2H, m), 2.07-1.93 (1H, m), 1.77-1.64 (1H, m), 1.64-1.58 (2H, m), 1.12 (6H, s). |

TABLE 8

| | | | | | |
|---|---|---|---|---|---|
| 66 | O | 4-cyanophenyl | (3R)-3-aminopyrrolidine | 1-(4-(methoxymethyl)cyclopropyl)phenyl | 452.2 1H-NMR (DMSO-D6) δ: 7.74 (2H, d, J = 7.6 Hz), 7.67-7.61 (1H, m), 7.56-7.49 (2H, m), 7.33 (2H, d, J = 8.2 Hz), 7.17 (2H, d, J = 7.0 Hz), 7.03 (2H, d, J = 7.0 Hz), 3.82-3.52 (5H, m), 3.51 (2H, s), 3.21 (3H, s), 2.15-2.01 (1H, m), 1.89-1.75 (1H, m), 0.89-0.78 (4H, m). |
| 67 | O | 4-cyanophenyl | (3S)-3-aminopyrrolidine | 1-((3-fluoro-4-phenyl)methyl)cyclopropanol | 456.2 1H-NMR (DMSO-D6) δ: 7.73 (2H, d, J = 6.3 Hz), 7.67-7.61 (1H, m), 7.57-7.48 (2H, m), 7.39-7.24 (4H, m), 7.02 (1H, d, J = 7.6 Hz), 3.73-3.53 (4H, m), 3.51 (1H, s), 3.19-3.10 (1H, m), 2.54 (2H, s), 1.72-1.58 (1H, m), 1.48-1.35 (1H, m), 0.83-0.42 (4H, m). |
| 68 | O | 4-cyanophenyl | (3S)-3-aminopyrrolidine | spiro[2.2]pentanol-phenyl | 464.2 1H-NMR (DMSO-D6) δ: 7.74 (2H, d, J = 8.5 Hz), 7.67-7.61 (1H, m), 7.57-7.48 (2H, m), 7.39-7.33 (3H, m), 7.28 (2H, d, J = 8.2 Hz), 7.02 (1H, d, J = 8.2 Hz), 5.16 (1H, s), 3.78-3.54 (4H, m), 3.21-3.13 (1H, m), 2.04-1.95 (1H, m), 1.67-1.58 (1H, m), 0.82-0.70 (4H, m), 0.57-0.42 (4H, m). |
| 69 | O | 2-fluoro-4-cyanophenyl | (3S)-3-aminopyrrolidine | 4-(2-methoxyethyl)phenyl | 444.1 1H-NMR (DMSO-D6) δ: 7.81 (1H, s), 7.72-7.47 (3H, m), 7.37-7.31 (1H, m), 7.18 (2H, d, J = 7.6 Hz), 7.13-7.01 (3H, m), 4.29-4.11 (1H, m), 3.88-3.56 (4H, m), 3.52 (2H, t, J = 6.7 Hz), 3.22 (3H, s), 2.79 (2H, t, J = 6.4 Hz), 2.23-2.03 (1H, m), 1.54-1.34 (1H, m). |

TABLE 8-continued

| | | | | | |
|---|---|---|---|---|---|
| 70 | O | | | | 430 | 1H-NMR (DMSO-D6) δ: 7.74 (2H, d, J = 8.2 Hz), 7.69-7.63 (1H, m), 7.58 (1H, d, J = 12.5 Hz), 7.49 (1H, d, J = 7.9 Hz), 7.32 (2H, d, J = 7.6 Hz), 7.19 (1H, t, J = 7.9 Hz), 7.06 (1H, d, J = 7.6 Hz), 6.96 (1H, d, J = 11.0 Hz), 4.70-4.64 (1H, m), 3.72-3.46 (6H, m), 3.26-3.18 (1H, m), 2.74-2.68 (2H, m), 2.08-1.98 (1H, m), 1.78-1.68 (1H, m). |
| 71 | O | | | | 444.1 | 1H-NMR (DMSO-D6) δ: 7.73 (2H, d, J = 6.7 Hz), 7.67-7.64 (1H, m), 7.57 (1H, dd, J = 10.8, 1.4 Hz), 7.50 (1H, d, J = 7.9 Hz), 7.31 (2H, d, J = 7.6 Hz), 7.20 (1H, t, J = 7.8 Hz), 7.07 (1H, dd, J = 7.9, 1.2 Hz), 6.97 (1H, d, J = 11.3 Hz), 3.68-3.45 (6H, m), 3.23 (3H, s), 3.21-3.15 (1H, m), 2.80 (2H, t, J = 6.6 Hz), 2.04-1.93 (1H, m), 1.72-1.62 (1H, m). |
| 72 | O | | | | 440.1 | 1H-NMR (DMSO-D6) δ: 7.74 (2H, d, J = 8.2 Hz), 7.64 (1H, t, J = 7.3 Hz), 7.55-7.49 (2H, m), 7.34 (2H, d, J = 7.0 Hz), 7.28 (2H, d, J = 8.2 Hz), 7.05 (2H, d, J = 8.2 Hz), 4.69-4.65 (1H, m), 3.70-3.37 (6H, m), 3.25-3.18 (1H, m), 2.08-1.95 (1H, m), 1.76-1.68 (1H, m), 1.19 (6H, s). |
| 73 | O | | | | 414.1 | 1H-NMR (DMSO-D6) δ: 7.75 (2H, d, J = 7.9 Hz), 7.65 (1H, t, J = 7.6 Hz), 7.58-7.49 (2H, m), 7.33 (2H, d, J = 7.3 Hz), 7.19 (2H, d, J = 7.9 Hz), 7.07 (2H, d, J = 7.6 Hz), 4.63 (2H, dt, J = 47.2, 6.2 Hz), 3.72-3.47 (4H, m), 3.27-3.21 (1H, m), 2.95 (2H, dt, J = 25.2, 6.2 Hz), 2.10-1.99 (1H, m), 1.81-1.71 (1H, m). |
| 74 | O | | | | 488.1 | 1H-NMR (DMSO-D6) δ: 7.84-7.78 (2H, m), 7.71-7.62 (2H, m), 7.56-7.51 (1H, m), 7.36-7.30 (1H, m), 7.25-7.21 (1H, m), 7.13-7.09 (2H, m), 7.03-6.98 (1H, m), 4.09-3.49 (10H, m), 3.22 (3H, s), 2.84-2.78 (2H, m), 2.19-2.10 (2H, m). |

TABLE 9

| | | | | | |
|---|---|---|---|---|---|
| 75 | O | | | | 502.1 | 1H-NMR (DMSO-D6) δ: 7.84-7.79 (2H, m), 7.73-7.70 (1H, m), 7.57-7.52 (1H, m), 7.32 (1H, d, J = 10.4 Hz), 7.25-7.20 (1H, m), 7.11 (1H, d, J = 7.3 Hz), 7.00 (1H, d, J = 11.0 Hz), 4.19 (1H, d, J = 8.2 Hz), 4.10 (1H, d, J = 8.2 Hz), 3.90 (1H, d, J = 9.8 Hz), 3.75 (1H, d, J = 10.1 Hz), 3.55-3.50 (2H, m), 3.25-3.07 (7H, m), 2.88-2.78 (2H, m), 1.86-1.73 (2H, m), 1.67-1.52 (2H, m). |
| 76 | O | | | | 502.1 | 1H-NMR (DMSO-D6) δ: 7.82-7.77 (1H, m), 7.72-7.62 (2H, m), 7.57-7.51 (1H, m), 7.29-7.25 (1H, m), 7.22-7.18 (1H, m), 7.16-7.11 (1H, m), 7.09-7.05 (1H, m), 6.98-6.92 (1H, m), 4.40 (1H, s), 3.90-3.44 (6H, m), 2.67-2.64 (2H, m), 2.18-2.06 (2H, m), 2.04-1.90 (2H, m), 1.04 (6H, s). |
| 77 | O | | | | 516.1 | 1H-NMR (DMSO-D6) δ: 7.84-7.71 (3H, m), 7.57-7.54 (1H, m), 7.29-7.24 (1H, m), 7.21-7.17 (1H, m), 7.15-7.11 (1H, m), 7.08-7.05 (1H, m), 6.97-6.93 (1H, m), 4.39 (1H, s), 4.14-4.02 (2H, m), 3.85-3.68 (2H, m), 2.95-2.84 (2H, m), 2.71-2.62 (4H, m), 1.78-1.68 (2H, m), 1.52-1.42 (2H, m), 1.04 (6H, s). |
| 78 | O | | | | 516.2 | 1H-NMR (CD3OD) δ: 7.64-7.55 (4H, m), 7.22-7.08 (4H, m), 6.92 (1H, d, J = 11.0 Hz), 4.01-3.88 (1H, m), 3.77-3.71 (2H, m), 3.67 (3H, s), 3.63-3.58 (3H, m), 3.47-3.40 (2H, m), 3.23-3.15 (2H, m), 2.87 (2H, t, J = 6.6 Hz), 2.09-2.01 (2H, m), 1.83-1.65 (4H, m). |
| 79 | O | | | | 502.1 | 1H-NMR (DMSO-D6) δ: 7.83-7.00 (9H, m), 3.82 (12H, tt, J = 147.2, 54.5 Hz), 3.24 (3H, d, J = 5.5 Hz), 2.82 (2H, t, J = 6.4 Hz), 1.76 (1H, s), 1.48 (1H, s). |

TABLE 9-continued

| 80 | O | 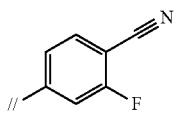 | 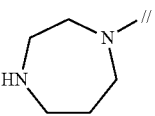 | 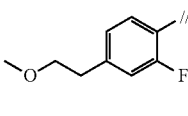 | 476.2 | 1H-NMR (CD3OD) δ: 7.65-7.54 (4H, m), 7.13 (4H, ddd, J = 29.3, 15.0, 6.6 Hz), 6.90 (1H, d, J = 11.4 Hz), 4.02-3.97 (1H, m), 3.90-3.82 (1H, m), 3.74-3.67 (2H, m), 3.59 (2H, t, J = 6.4 Hz), 3.49-3.43 (2H, m), 3.39-3.35 (2H, m), 3.31 (3H, s), 2.85 (2H, t, J = 6.6 Hz), 2.24-2.05 (2H, m). |
| --- | --- | --- | --- | --- | --- | --- |
| 81 | O | 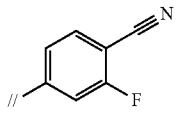 | 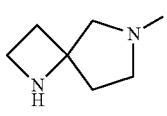 | 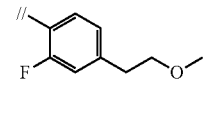 | 488.2 | 1H-NMR (DMSO-D6) δ: 7.83-7.79 (1H, m), 7.72-7.60 (2H, m), 7.55-7.51 (1H, m), 7.36-7.30 (1H, m), 7.27-7.21 (1H, m), 7.15-7.08 (2H, m), 7.03-6.98 (1H, m), 3.86-3.38 (10H, m), 3.23 (3H, s), 2.85-2.79 (2H, m), 2.38-2.02 (2H, m). |
| 82 | O | 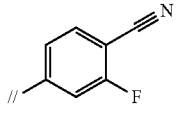 | 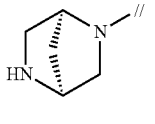 | 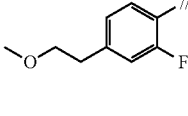 | 474.1 | 1H-NMR (DMSO-D6) δ: 7.82 (1H, t, J = 7.3 Hz), 7.74-7.60 (2H, m), 7.56 (1H, d, J = 7.9 Hz), 7.39-7.30 (1H, m), 7.24 (1H, t, J = 7.6 Hz), 7.14-7.09 (2H, m), 7.01 (1H, d, J = 11.0 Hz), 4.57 (1H, s), 4.27 (1H, s), 3.79-3.72 (1H, m), 3.66-3.61 (1H, m), 3.57-3.51 (2H, m), 3.46-3.40 (1H, m), 3.22 (3H, s), 3.21-3.17 (1H, m), 2.84-2.79 (2H, m), 2.14-2.05 (1H, m), 1.50-1.73 (1H, m). |
| 83 | O | 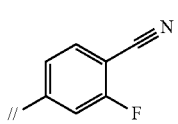 | 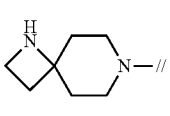 | 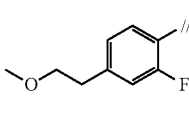 | 502.1 | 1H-NMR (DMSO-D6) δ: 7.81 (1H, t, J = 7.6 Hz), 7.59-7.51 (3H, m), 7.33 (1H, dd, J = 10.7, 1.2 Hz), 7.24 (1H, t, J = 7.9 Hz), 7.11 (2H, d, J = 8.2 Hz), 7.00 (1H, d, J = 10.4 Hz), 3.79-3.57 (6H, m), 3.53 (2H, t, J = 6.7 Hz), 3.23 (3H, s), 2.81 (2H, t, J = 6.7 Hz), 2.25-2.17 (2H, m), 2.01-1.81 (4H, m). |
| 84 | O | 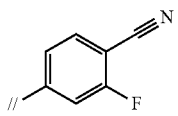 | 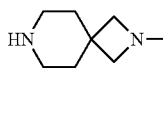 | 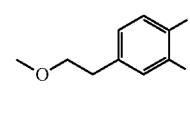 | 502.2 | 1H-NMR (DMSO-D6) δ: 7.84-7.79 (2H, m), 7.72 (1H, s), 7.54 (1H, d, J = 7.9 Hz), 7.33 (1H, d, J = 10.4 Hz), 7.22 (1H, t, J = 7.9 Hz), 7.14-7.09 (2H, m), 7.00 (1H, d, J = 11.3 Hz), 4.15 (2H, s), 3.83 (2H, s), 3.53 (2H, t, J = 6.6 Hz), 3.22 (3H, s), 2.97-2.85 (4H, m), 2.81 (2H, t, J = 6.6 Hz), 1.89-1.63 (4H, m). |

TABLE 10

| 85 | O | 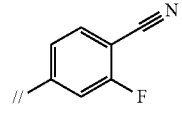 | 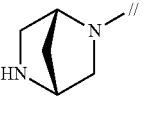 | 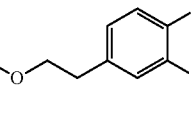 | 474.2 | 1H-NMR (DMSO-D6) δ: 7.81 (1H, t, J = 7.6 Hz), 7.71-7.62 (2H, m), 7.59-7.51 (1H, m), 7.38-7.30 (1H, m), 7.27-7.22 (1H, m), 7.15-7.08 (2H, m), 7.03-6.98 (1H, m), 4.72 (1H, s), 4.39 (1H, s), 3.86-3.61 (2H, m), 3.56-3.49 (2H, m), 3.22 (3H, s), 3.10-2.93 (2H, m), 2.84-2.79 (2H, m), 1.91-1.60 (2H, m). |
| --- | --- | --- | --- | --- | --- | --- |
| 86 | O | 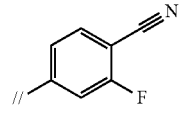 | 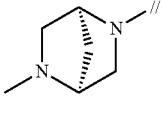 | 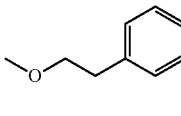 | 488.2 | 1H-NMR (DMSO-D6) δ: 7.81 (1H, t, J = 7.5 Hz), 7.74-7.53 (3H, m), 7.38-7.31 (1H, m), 7.24 (1H, t, J = 7.9 Hz), 7.14-7.09 (2H, m), 7.01 (1H, d, J = 11.0 Hz), 4.76 (1H, s), 4.44 (1H, s), 4.02-3.85 (1H, m), 3.72-3.57 (1H, m), 3.53 (2H, t, J = 6.7 Hz), 3.22 (3H, s), 3.12-2.97 (2H, m), 2.81 (2H, t, J = 6.7 Hz), 2.63 (3H, s), 2.18-1.91 (2H, m). |
| 87 | O | 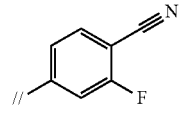 | 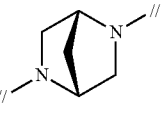 | 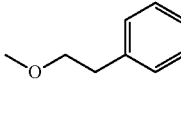 | 488.1 | 1H-NMR (DMSO-D6) δ: 7.81 (1H, t, J = 7.5 Hz), 7.75-751 (3H, m), 7.34 (1H, t, J = 10.5 Hz), 7.24 (1H, t, J = 7.9 Hz), 7.14-7.08 (2H, m), 7.01 (1H, d, J = 11.3 Hz), 4.72 (1H, s), 4.39 (1H, s), 3.89-3.59 (2H, m), 3.53 (2H, t, J = 6.6 Hz), 3.22 (3H, s), 3.08-2.90 (2H, m), 2.81 (2H, t, J = 6.7 Hz), 2.54 (3H, s), 2.16-1.84 (2H, m). |
| 88 | O | 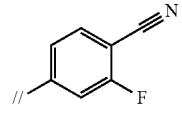 | 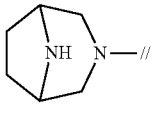 | 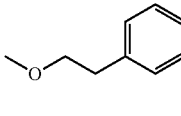 | 488.1 | 1H-NMR (DMSO-D6) δ: 7.80-7.75 (1H, m), 7.55-7.49 (2H, m), 7.47 (1H, d, J = 1.5 Hz), 7.28 (1H, dd, J = 10.5, 1.4 Hz), 7.22 (1H, t, J = 7.9 Hz), 7.10 (2H, dt, J = 10.5, 3.8 Hz), 6.97 (1H, d, J = 11.3 Hz), 4.31-4.21 (1H, m), 3.54-3.29 (6H, m), 3.21 (3H, s), 3.00-2.93 (1H, m), 2.79 (2H, t, J = 6.6 Hz), 1.76-1.48 (4H, m). |

TABLE 10-continued

| | | | | | |
|---|---|---|---|---|---|
| 89 | O | 4-cyano-2-fluorophenyl | (3R)-3-aminopyrrolidin-1-yl | benzothiazol-6-yl | 443.1 1H-NMR (DMSO-D6) δ: 9.34 (1H, s), 7.89 (1H, s), 7.73-7.58 (5H, m), 7.42-7.33 (1H, m), 7.11 (1H, d, J = 8.2 Hz), 7.07-7.01 (1H, m), 3.85-3.50 (5H, m), 2.20-2.07 (1H, m), 1.97-1.82 (1H, m). |
| 90 | O | 4-cyano-2-fluorophenyl | (3R)-3-aminopyrrolidin-1-yl | 1-methylpyrazolo[3,4-b]pyridin-5-yl | 441.2 1H-NMR (DMSO-D6) δ: 8.19 (1H, d, J = 1.9 Hz), 8.08 (1H, s), 8.04 (1H, d, J = 1.9 Hz), 7.72 (1H, t, J = 7.6 Hz), 7.68-7.65 (1H, m), 7.61 (2H, d, J = 8.2 Hz), 7.44-7.37 (1H, m), 7.07-6.99 (1H, m), 3.97 (3H, s), 3.86-3.42 (5H, m), 2.23-2.39 (1H, m), 1.99-1.86 (1H, m). |
| 91 | O | 4-cyano-2-fluorophenyl | (3R)-3-aminopyrrolidin-1-yl | 1-methylbenzimidazol-6-yl | 440.2 1H-NMR (DMSO-D6) δ: 8.23 (1H, s), 7.69 (1H, t, J = 7.6 Hz), 7.66-7.60 (1H, m), 7.54 (2H, d, J = 7.6 Hz), 7.43 (2H, d, J = 6.3 Hz), 7.35-7.28 (1H, m 7.06-7.00 (1H, m), 6.98-6.91 (1H, m), 3.86-3.53 (8H, m), 2.22-2.10 (1H, m), 1.99-1.89 (1H, m). |
| 92 | O | 4-cyano-2-fluorophenyl | (3R)-3-aminopyrrolidin-1-yl | 1-methylindazol-5-yl | 440.2 1H-NMR (DMSO-D6) δ: 7.75-7.71 (1H, m), 7.70-7.66 (1H, m), 7.64 (1H, s), 7.62-7.58 (2H, m), 7.50 (1H, d, J = 8.9 Hz), 7.37-7.32 (2H, m), 7.08 (1H, d, J = 7.9 Hz), 7.04 (1H, d, J = 8.5 Hz), 4.41-4.12 (4H, m), 3.32-3.24 (1H, m), 3.16 (3H, s), 2.21-2.10 (1H, m), 1.82-1.59 (1H, m). |
| 93 | O | 4-cyano-2-fluorophenyl | (3S)-3-aminopyrrolidin-1-yl | 2-methylindazol-5-yl | 440.2 1H-NMR (DMSO-D6) δ: 8.30 (1H, s), 7.75 (1H, t, J = 7.5 Hz), 7.69-7.64 (1H, m), 7.62-7.58 (2H, m), 7.55 (1H, s), 7.44 (1H, d, J = 9.2 Hz), 7.40-7.33 (1H, m), 7.08 (1H, d, J = 8.4 Hz), 6.86 (1H, d, J = 9.2 Hz), 4.13 (3H, s), 3.91-3.40 (4H, m), 3.19-3.09 (1H, m), 2.27-2.17 (1H, m), 2.06-1.93 (1H, m). |
| 94 | S | 4-cyano-2-fluorophenyl | (3R)-3-aminopyrrolidin-1-yl | 3-fluoro-4-(2-methoxyethyl)phenyl | 478.2 1H-NMR (DMSO-D6) δ: 7.80 (1H, t, J = 7.5 Hz), 7.57-7.54 (1H, m), 7.51-7.49 (1H, m), 7.47 (1H, d, J = 7.9 Hz), 7.31 (1H, ddd, J = 10.6, 5.3, 1.4 Hz), 7.24 (1H, td, J = 7.9, 2.4 Hz), 7.10 (2H, d, J = 7.6 Hz), 7.00 (1H, d, J = 11.3 Hz), 4.00-3.56 (4H, m), 3.53 (2H, t, J = 6.7 Hz), 3.32-3.27 (1H, m), 3.23 (3H, s), 2.81 (2H, t, J = 6.6 Hz), 2.18-2.04 (1H, m), 1.85-1.74 (1H, m). |

TABLE 11

| | | | | | |
|---|---|---|---|---|---|
| 95 | O | 4-cyano-2-fluorophenyl | (3R)-3-aminopyrrolidin-1-yl | 5-fluoro-1-methylbenzimidazol-6-yl | 458.2 1H-NMR (DMSO-D6) δ: 8.34 (1H, s), 7.78 (1H, t, J = 7.5 Hz), 7.71 (1H, t, J = 6.4 Hz), 7.67-7.63 (2H, m), 7.60 (1H, d, J = 7.9 Hz), 7.47-7.35 (2H, m), 7.11 (1H, d, J = 7.9 Hz), 3.81 (3H, s), 3.78-3.60 (5H, m), 2.31-2.19 (1H, m), 2.07-1.96 (1H, m). |
| 96 | O | 4-cyano-2-fluorophenyl | (3S)-3-aminopyrrolidin-1-yl | 5-fluoro-1-methylbenzotriazol-6-yl | 459.2 1H-NMR (DMSO-D6) δ: 7.95-8.15 (2H, m), 7.60-7.79 (4H, m), 7.37-7.46 (1H, m), 7.07-7.13 (1H, m), 4.24 (3H, s), 4.09-3.49 (5H, m), 1.95-2.20 (2H, m). |
| 97 | O | 4-cyanophenyl | 3-amino-8-azabicyclo[3.2.1]octan-8-yl | 4-fluorophenyl | 426.3 1H-NMR (DMSO-D6) δ: 8.30 (1H, d, J = 9.9 Hz), 7.75 (2H, d, J = 8.4 Hz), 7.57 (1H, d, J = 8.1 Hz), 7.52 (1H, d, J = 7.7 Hz), 7.46 (1H, s), 7.32 (2H, d, J = 8.1 Hz), 7.16-7.09 (3H, m), 4.64-4.52 (1H, m), 4.19-4.07 (1H, m), 3.45-3.37 (1H, m), 2.11-1.40 (8H, m). |
| 98 | O | 4-cyanophenyl | 3-amino-8-azabicyclo[3.2.1]octan-8-yl | 4-chlorophenyl | 442.2 444.2 1H-NMR (DMSO-D6) δ: 8.30 (1H, d, J = 8.4 Hz), 7.76 (2H, d, J = 8.4 Hz), 7.58 (1H, d, J = 7.7 Hz), 7.53 (1H, d, J = 8.1 Hz), 7.46 (1H, s), 7.35-7.32 (3H, m), 7.13 (2H, d, J = 8.4 Hz), 4.65-4.58 (1H, m), 4.16-4.08 (1H, m), 3.44-3.38 (1H, m), 2.04-1.47 (8H, m). |

TABLE 11-continued

| # | | | | | |
|---|---|---|---|---|---|
| 99 | O | nitro-phenyl | (3-amino)pyrrolidine | methylphenyl | 402.2 1H-NMR (DMSO-D6) δ: 8.36 (2H, d, J = 6.7 Hz), 7.90 (1H, t, J = 7.8 Hz), 7.81 (1H, d, J = 13.1 Hz), 7.75 (1H, dd, J = 7.9, 1.8 Hz), 7.64 (2H, d, J = 7.6 Hz), 7.33 (2H, d, J = 6.7 Hz), 7.26 (2H, d, J = 6.4 Hz), 3.95-3.72 (4H, m), 3.51-3.45 (1H, m), 2.50 (3H, s), 2.31-2.21 (1H, m), 2.02-1.93 (1H, m). |
| 100 | O | 4-fluoro-2-cyanophenyl | (3-amino)pyrrolidine | N,N-dimethylaminopyridine | 430.3 1H-NMR (DMSO-D6) δ: 7.94-7.86 (3H, m), 7.73-7.65 (1H, m), 7.62-7.54 (2H, m), 7.50-7.43 (1H, m), 7.29-7.22 (1H, m), 7.19-7.14 (1H, m), 3.93-3.57 (5H, m), 3.03 (6H, s), 2.30-2.18 (1H, m), 2.06-1.94 (1H, m). |
| 101 | O | 4-fluoro-2-cyanophenyl | (3-amino)pyrrolidine | 1-methyl-benzotriazole | 441.2 1H-NMR (DMSO-D6) δ: 7.93-7.88 (2H, m), 7.76-7.62 (4H, m), 7.42 (1H, t, J = 9.5 Hz), 7.19 (1H, d, J = 8.8 Hz), 7.10-7.05 (1H, m), 4.28 (3H, s), 3.72-3.41 (5H, m), 2.27-2.18 (1H, m), 2.05-1.95 (1H, m). |
| 102 | O | 4-fluoro-2-cyanophenyl | (3-amino)pyrrolidine | fluoro-1-methyl-benzimidazole | 476.2 1H-NMR (DMSO-D6) δ: 8.27 (1H, s), 7.80 (1H, t, J = 7.6 Hz), 7.73 (1H, t, J = 5.5 Hz), 7.67 (1H, s), 7.63 (1H, d, J = 7.9 Hz), 7.48-7.40 (2H, m), 7.16-7.10 (1H, m), 3.98 (3H, s), 3.92-3.44 (5H, m), 2.31-2.20 (1H, m), 2.07-1.96 (1H, m). |
| 103 | O | 4-fluoro-2-cyanophenyl | (3-amino)pyrrolidine | 1,2-dimethyl-benzimidazole | 454.2 1H-NMR (DMSO-D6) δ: 7.79-7.73 (1H, m), 7.70-7.65 (1H, m), 7.63-7.55 (2H, m), 7.39 (2H, d, J = 8.2 Hz), 7.32 (1H, d, J = 1.2 Hz), 7.12-7.07 (1H, m), 6.96-6.91 (1H, m), 3.72 (3H, t, J = 6.7 Hz), 3.67-3.48 (5H, m), 2.54 (3H, s), 1.99 (1H, dd, J = 9.0, 3.8 Hz), 1.67-1.62 (1H, m). |
| 104 | O | 4-fluoro-2-cyanophenyl | tropane-NH2 | naphthyl | 476.2 1H-NMR (DMSO-D6) δ: 7.91-7.86 (3H, m), 7.81-7.65 (4H, m), 7.57 (1H, d, J = 1.5 Hz), 7.53 (2H, td, J = 6.6, 3.4 Hz), 7.46 (1H, dd, J = 10.4, 1.2 Hz), 7.16-7.12 (2H, m), 4.65 (1H, s), 4.19 (1H, s), 3.51-3.43 (1H, m), 2.11-1.49 (8H, m). |
| 105 | O | 4-fluoro-2-cyanophenyl | tropane-NH2 | fluoroquinoline | 495.2 1H-NMR (DMSO-D6) δ: 8.93 (1H, d, J = 2.1 Hz), 8.44 (1H, d, J = 8.9 Hz), 7.81 (1H, d, J = 8.5 Hz), 7.78-7.51 (5H, m), 7.50-7.43 (2H, m), 7.13 (1H, d, J = 6.7 Hz), 4.65 (1H, s), 4.18 (1H, s), 3.49-3.40 (1H, m), 2.09-1.17 (8H, m). |

TABLE 12

| # | | | | | |
|---|---|---|---|---|---|
| 106 | O | 4-fluoro-2-cyanophenyl | tropane-NH2 | N-methyl-dihydrobenzoxazine | 497.3 1H-NMR (DMSO-D6) δ: 7.85 (1H, t, J = 7.6 Hz), 7.59-7.38 (4H, m), 7.16 (1H, dd, J = 7.9, 0.9 Hz), 6.58 (1H, d, J = 8.2 Hz), 6.52 (1H, d, J = 1.8 Hz), 6.48 (1H, dd, J = 8.2, 1.8 Hz), 4.61 (1H, s), 4.22-4.13 (3H, m), 3.45-3.40 (1H, m), 3.26-3.22 (2H, m), 2.31 (3H, s), 2.06-1.15 (8H, m). |
| 107 | O | 4-fluoro-2-cyanophenyl | tropane-NH2 | quinoline | 477.3 1H-NMR (DMSO-D6) δ: 8.92 (1H, dd, J = 4.3, 1.8 Hz), 8.39-8.35 (1H, m), 7.95-7.88 (2H, m), 7.80-7.73 (2H, m), 7.69 (1H, dd, J = 7.8, 1.7 Hz), 7.59-7.55 (2H, m), 7.50 (1H, dd, J = 10.4, 1.5 Hz), 7.30 (1H, dd, J = 8.4, 1.7 Hz), 7.15 (1H, dd, J = 8.2, 1.5 Hz), 4.68 (1H, s), 4.25 (1H, s), 3.69-3.57 (1H, m), 2.54-1.56 (8H, m). |
| 108 | O | 4-fluoro-2-cyanophenyl | tropane-NH2 | fluoro-1-methyl-benzimidazole | 498.2 1H-NMR (DMSO-D6) δ: 8.23 (1H, s), 7.77 (1H, t, J = 7.5 Hz), 7.65-7.62 (2H, m), 7.59 (1H, d, J = 7.9 Hz), 7.55 (1H, d, J = 1.5 Hz), 7.43-7.38 (2H, m), 7.12 (1H, dd, J = 7.9, 1.5 Hz), 4.65 (1H, s), 4.18 (1H, s), 3.80 (3H, s), 3.39-3.35 (1H, m), 2.11-1.66 (7H, m), 1.58-1.44 (1H, m). |

TABLE 12-continued

| | | | | | |
|---|---|---|---|---|---|
| 109 | O | 4-cyano-2-fluorophenyl | 8-azabicyclo[3.2.1]octan-3-amine | 1-methyl-5,6-difluoro-1H-benzotriazole | 499.3 1H-NMR (DMSO-D6) δ: 8.14 (1H, d, J = 6.4 Hz), 7.77 (1H, t, J = 7.5 Hz), 7.72-7.63 (3H, m), 7.53 (1H, d, J = 1.5 Hz), 7.46 (1H, d, J = 10.4 Hz), 7.14 (1H, dd, J = 8.1, 1.4 Hz), 4.65 (1H, s), 4.26 (3H, s), 4.16 (1H, s), 3.37-3.33 (1H, m), 2.12-1.46 (8H, m). |
| 110 | O | 4-cyano-2-fluorophenyl | 8-azabicyclo[3.2.1]octan-3-amine | 1-methyl-4-fluoro-1H-indazole | 498.2 1H-NMR (DMSO-D6) δ: 8.11 (1H, s), 7.76 (1H, t, J = 7.5 Hz), 7.65 (1H, dd, J = 7.9, 1.8 Hz), 7.61 (1H, d, J = 7.9 Hz), 7.58 (1H, d, J = 1.5 Hz), 7.50 (1H, d, J = 8.5 Hz), 7.42 (1H, dd, J = 10.5, 1.4 Hz), 7.25 (1H, dd, J = 8.5, 7.0 Hz), 7.10 (1H, dd, J = 7.9, 1.5 Hz), 4.64 (1H, s), 4.16 (1H, s), 4.06 (3H, s), 3.42-3.36 (1H, m), 2.08-1.44 (8H, m). |
| 111 | O | 4-cyanophenyl | 8-azabicyclo[3.2.1]octan-3-amine | 2-methyl-2H-indazole | 462.2 1H-NMR (DMSO-D6) δ: 8.32 (1H, s), 7.74 (2H, d, J = 8.5 Hz), 7.63 (2H, t, J = 5.5 Hz), 7.56 (1H, s), 7.50 (1H, s), 7.45 (1H, d, J = 8.9 Hz), 7.37 (2H, d, J = 8.5 Hz), 6.88 (1H, dd, J = 8.9, 1.8 Hz), 4.72-4.65 (1H, m), 4.32-4.22 (1H, m), 4.15 (3H, s), 2.12-1.54 (9H, m). |
| 112 | O | 4-cyano-2-fluorophenyl | N-isopropyl-8-azabicyclo[3.2.1]octan-3-amine | 4-(2-methoxyethyl)-2-fluorophenyl | 544.2 1H-NMR (DMSO-D6) δ: 7.82 (1H, t, J = 7.5 Hz), 7.64 (1H, dd, J = 7.8, 1.7 Hz), 7.56-7.53 (2H, m), 7.35 (1H, d, J = 10.7 Hz), 7.25 (1H, t, J = 7.9 Hz), 7.15-7.10 (2H, m), 7.01 (1H, d, J = 11.9 Hz), 4.67-4.61 (1H, m), 4.17-4.10 (1H, m), 3.54 (2H, t, J = 6.7 Hz), 3.47-3.45 (1H, m), 3.23 (3H, s), 3.02-2.94 (1H, m), 2.82 (2H, t, J = 6.7 Hz), 2.04-1.31 (8H, m), 1.01 (6H, d, J = 6.1 Hz). |
| 113 | O | 4-cyano-2-fluorophenyl | N-isopropyl-8-azabicyclo[3.2.1]octan-3-amine | 4-(2-hydroxy-2-methylpropyl)-2-fluorophenyl | 558.2 1H-NMR (DMSO-D6) δ: 7.81 (1H, t, J = 7.5 Hz), 7.64 (1H, dd, J = 7.8, 1.7 Hz), 7.58-7.54 (2H, m), 7.29 (1H, d, J = 9.2 Hz), 7.22 (1H, t, J = 7.8 Hz), 7.16 (1H, dd, J = 8.1, 1.4 Hz), 7.07 (1H, d, J = 7.9 Hz), 6.96 (1H, d, J = 11.3 Hz), 4.66-4.61 (1H, m), 4.42-4.38 (1H, m), 4.16-4.10 (1H, m), 3.48-3.43 (1H, m), 3.02-2.93 (1H, m), 2.68-2.65 (2H, m), 2.06-1.32 (8H, m), 1.04 (6H, s), 1.00 (6H, m), J = 5.8 Hz). |
| 114 | O | 4-cyano-2-fluorophenyl | (3S)-N-ethylpyrrolidin-3-amine | 1-methyl-5,6-difluoro-1H-benzotriazole | 487.2 1H-NMR (DMSO-D6) δ: 7.82-7.63 (6H, m), 7.49-7.40 (1H, m), 7.13 (1H, d, J = 7.6 Hz), 4.27 (3H, s), 3.77-3.57 (5H, m), 2.50-2.49 (2H, m), 1.15 (2H, s), 1.06 (3H, t, J = 6.9 Hz). |
| 115 | O | 4-cyano-2-fluorophenyl | (3S)-N-isopropylpyrrolidin-3-amine | 1-methyl-5,6-difluoro-1H-benzotriazole | 501.3 1H-NMR (DMSO-D6) δ: 8.16-8.14 (1H, m), 7.79-7.72 (2H, m), 7.70 (1H, d, J = 9.2 Hz), 7.66 (1H, s), 7.62 (1H, d, J = 7.6 Hz), 7.47-7.43 (1H, m), 7.14-7.12 (1H, m), 4.28 (3H, s), 3.74-3.52 (6H, m), 2.13-2.03 (1H, m), 1.81-1.72 (1H, m), 1.07-0.96 (6H, m). |

TABLE 13

| | | | | | |
|---|---|---|---|---|---|
| 116 | O | 4-cyano-2-fluorophenyl | (3S)-N-cyclobutylpyrrolidin-3-amine | 1-methyl-5,6-difluoro-1H-benzotriazole | 513.2 1H-NMR (DMSO-D6) δ: 8.14-8.13 (1H, m), 7.78-7.61 (5H, m), 7.45 (1H, dd, J = 9.9, 4.7 Hz), 7.13 (1H, dd, J = 7.9, 1.5 Hz), 4.27 (3H, s), 3.68-3.48 (6H, m), 2.18-1.95 (4H, m), 1.79-1.58 (4H, m). |
| 117 | O | 4-cyano-2-fluorophenyl | (3S)-pyrrolidin-3-amine | 1-methyl-2,3-dihydro-1H-indole | 441.2 1H-NMR (DMSO-D6) δ: 7.84 (1H, t, J = 7.5 Hz), 7.65-7.60 (1H, m), 7.55 (1H, s), 7.50 (1H, d, J = 8.2 Hz), 7.39-7.34 (1H, m), 7.12 (1H, d, J = 7.3 Hz), 6.88 (1H, s), 6.69 (1H, d, J = 8.2 Hz), 6.38 (1H, d, J = 7.9 Hz), 3.93-3.54 (6H, m), 3.20-3.15 (1H, m), 2.82 (2H, t, J = 8.1 Hz), 2.69 (3H, s), 2.30-2.18 (1H, m), 2.06-1.92 (1H, m). |

TABLE 13-continued

| | | | | | |
|---|---|---|---|---|---|
| 118 | O | 4-cyano-2-fluorophenyl | (3-aminopyrrolidin-1-yl) | 4-methyl-3,4-dihydro-2H-benzo[b][1,4]oxazin-6-yl | 457.2 1H-NMR (DMSO-D6) δ: 7.86 (1H, t, J = 7.6 Hz), 7.64-7.60 (1H, m), 7.54 (1H, s), 7.50 (1H, d, J = 7.9 Hz), 7.42-7.36 (1H, m), 7.17-7.11 (1H, m), 6.58 (1H, d, J = 8.5 Hz), 6.52 (1H, d, J = 2.1 Hz), 6.47 (1H, d, J = 9.8 Hz), 4.22-4.17 (2H, m), 3.94-3.53 (4H, m), 3.30-3.21 (3H, m), 2.81 (3H, s), 2.29-2.15 (1H, m), 2.02-1.89 (1H, m). |
| 119 | O | 4-cyano-2-fluorophenyl | (3-aminopyrrolidin-1-yl) | 3-methyl-2-oxo-2,3-dihydrobenzo[d]oxazol-6-yl | 457.2 1H-NMR (DMSO-D6) δ: 7.82 (1H, t, J = 7.5 Hz), 7.71-7.67 (1H, m), 7.62-7.57 (2H, m), 7.41 (1H, t, J = 10.7 Hz), 7.22 (1H, s), 7.18 (1H, d, J = 8.2 Hz), 7.13-7.08 (1H, m), 6.94 (1H, d, J = 9.5 Hz), 3.96-3.56 (4H, m), 3.30-3.26 (3H, m), 3.24-3.17 (1H, m), 2.31-2.18 (1H, m), 2.07-1.95 (1H, m). |
| 120 | O | 4-cyano-2-fluorophenyl | (3-aminopyrrolidin-1-yl) | 3-methyl-2-oxo-2,3-dihydrobenzo[d]thiazol-6-yl | 473.2 1H-NMR (DMSO-D6) δ: 7.82 (1H, t, J = 7.5 Hz), 7.69 (1H, t, J = 6.1 Hz), 7.63-7.56 (3H, m), 7.44 (1H, t, J = 9.2 Hz), 7.22 (1H, d, J = 8.2 Hz), 7.11-7.07 (1H, m), 7.07-7.04 (1H, m), 3.84-3.52 (4H, m), 3.31-3.28 (3H, m), 3.28-3.23 (1H, m), 2.21-2.12 (1H, m), 1.94-1.85 (1H, m). |
| 121 | O | 4-cyano-2-fluorophenyl | (3-aminopyrrolidin-1-yl) | 2,3-dihydrobenzo[b][1,4]dioxin-6-yl | 444.1 1H-NMR (DMSO-D6) δ: 7.85 (1H, t, J = 7.5 Hz), 7.67-7.63 (1H, m), 7.57 (1H, s), 7.53 (1H, d, J = 7.6 Hz), 7.42-7.35 (1H, m), 7.14-7.11 (1H, m), 6.76 (1H, d, J = 8.5 Hz), 6.72 (1H, d, J = 2.1 Hz), 6.50 (1H, d, J = 7.3 Hz), 4.25-4.20 (4H, m), 3.98-3.56 (4H, m), 3.30-3.25 (1H, m), 2.33-2.15 (1H, m), 2.07-1.95 (1H, m). |
| 122 | O | 4-cyano-2-fluorophenyl | (3-aminopyrrolidin-1-yl) | benzo[d][1,3]dioxol-5-yl | 430.2 1H-NMR (DMSO-D6) δ: 7.83 (1H, t, J = 7.5 Hz), 7.68-7.62 (1H, m), 7.59-7.55 (1H, m), 7.53 (1H, d, J = 7.9 Hz), 7.40-7.34 (1H, m), 7.14-7.10 (1H, m), 6.84 (1H, d, J = 7.9 Hz), 6.74 (1H, d, J = 1.5 Hz), 6.56 (1H, d, J = 7.9 Hz), 6.01 (2H, s), 4.23-3.74 (4H, m), 3.36-3.28 (3H, m), 2.30-2.14 (1H, m), 2.11-1.95 (1H, m). |
| 123 | O | 4-cyano-2-fluorophenyl | (3-amino-8-azabicyclo[3.2.1]octan-8-yl) | 5-fluoro-1-methyl-1H-indol-6-yl | 497.2 1H-NMR (DMSO-D6) δ: 7.74 (1H, t, J = 7.5 Hz), 7.60 (1H, dd, J = 7.9, 1.8 Hz), 7.55-7.49 (3H, m), 7.37-7.33 (2H, m), 7.21 (1H, d, J = 11.0 Hz), 7.10 (1H, dd, J = 8.2, 1.5 Hz), 6.45 (1H, d, J = 3.1 Hz), 4.59 (1H, s), 4.09 (1H, s), 3.75-3.69 (3H, m), 2.22-1.50 (9H, m). |
| 124 | O | 4-cyano-2-fluorophenyl | (3-amino-8-azabicyclo[3.2.1]octan-8-yl) | 5-fluoro-1-methyl-1H-indazol-6-yl | 498.2 1H-NMR (DMSO-D6) δ: 8.09 (1H, d, J = 0.9 Hz), 7.79 (1H, d, J = 7.3 Hz), 7.75 (1H, t, J = 7.5 Hz), 7.63 (1H, dd, J = 7.9, 1.8 Hz), 7.58-7.54 (2H, m), 7.44 (1H, d, J = 10.7 Hz), 7.39 (1H, dd, J = 10.5, 1.4 Hz), 7.10 (1H, dd, J = 7.9, 1.5 Hz), 4.61 (1H, s), 4.10 (1H, s), 3.98 (3H, s), 2.61-2.57 (2H, m), 2.47-2.42 (1H, m), 2.27-1.52 (6H, m). |
| 125 | O | 4-cyano-2-fluorophenyl | (3-amino-8-azabicyclo[3.2.1]octan-8-yl) | 5-fluoro-1-methyl-1H-benzo[d][1,2,3]triazol-6-yl | 499.2 1H-NMR (DMSO-D6) δ: 8.12 (1H, d, J = 6.4 Hz), 7.74 (1H, t, J = 7.5 Hz), 7.69-7.65 (1H, m), 7.62 (1H, d, J = 7.9 Hz), 7.58 (1H, d, J = 1.5 Hz), 7.44 (2H, dd, J = 10.5, 1.4 Hz), 7.13 (1H, dd, J = 7.9, 1.5 Hz), 4.64 (1H, s), 4.25 (3H, s), 4.11 (1H, s), 2.34-2.10 (3H, m), 2.07-1.94 (3H, m), 1.93-1.52 (3H, m). |

TABLE 14

| | | | | | |
|---|---|---|---|---|---|
| 126 | O | 4-cyano-2-fluorophenyl | (3-amino-8-azabicyclo[3.2.1]octan-8-yl) | 4,5-difluoro-1-methyl-1H-benzo[d]imidazol-6-yl | 516.2 1H-NMR (DMSO-D6) δ: 8.25 (1H, s), 7.76 (1H, t, J = 7.5 Hz), 7.66-7.63 (1H, m), 7.60-7.56 (2H, m), 7.45-7.41 (2H, m), 7.12 (1H, dd, J = 7.9, 1.5 Hz), 4.61 (1H, s), 4.10 (1H, s), 3.96 (3H, s), 2.30-2.17 (2H, m), 2.14-2.04 (1H, m), 2.01-1.51 (6H, m). |

TABLE 14-continued

| | | | | | |
|---|---|---|---|---|---|
| 127 | O | 2-fluoro-4-cyanophenyl | 3-amino-azabicyclic | methoxyethyl-fluorophenyl | 516.2 1H-NMR (DMSO-D6) δ: 7.83 (1H, t, J = 7.5 Hz), 7.56 (2H, d, J = 0.9 Hz), 7.48 (1H, d, J = 0.9 Hz), 7.34 (1H, dd, J = 10.5, 1.4 Hz), 7.25 (1H, t, J = 7.9 Hz), 7.13-7.10 (2H, m), 7.04-6.99 (1H, m), 4.78-4.72 (1H, m), 3.97-3.92 (1H, m), 3.54 (2H, t, J = 8.5 Hz), 3.29-3.28 (1H, m), 3.23 (3H, s), 2.82 (2H, t, J = 6.7 Hz), 2.07-1.56 (10H, m). |
| 128 | O | 2-fluoro-4-cyanophenyl | 3-amino-azabicyclic | N-methylbenzoxazine | 497.2 1H-NMR (DMSO-D6) δ: 7.84 (1H, t, J = 7.5 Hz), 7.54 (1H, dd, J = 7.9, 1.5 Hz), 7.44 (3H, dt, J = 17.3, 7.9 Hz), 7.16 (1H, dd, J = 8.1, 1.4 Hz), 6.59 (1H, d, J = 8.2 Hz), 6.53 (1H, d, J = 2.1 Hz), 6.48 (1H, dd, J = 8.2, 2.1 Hz), 4.58 (1H, s), 4.20 (2H, t, J = 4.4 Hz), 4.10 (1H, s), 3.24 (2H, t, J = 4.4 Hz), 2.82 (3H, s), 2.40-1.90 (7H, m), 1.60-1.52 (2H, m). |
| 129 | O | 2-fluoro-4-cyanophenyl | 3-amino-azabicyclic | methoxyethyl-fluorophenyl | 516.2 1H-NMR (DMSO-D6) δ: 7.82 (1H, t, J = 7.5 Hz), 7.54 (2H, s), 7.48 (1H, s), 7.34 (1H, d, J = 10.7 Hz), 7.25 (1H, t, J = 7.9 Hz), 7.16-7.08 (2H, m), 7.01 (1H, d, J = 11.0 Hz), 4.91-4.84 (1H, m), 4.07-4.01 (1H, m), 3.54 (2H, t, J = 6.6 Hz), 3.24 (3H, s), 2.93-2.86 (1H, m), 2.82 (2H, t, J = 6.6 Hz), 2.31-1.96 (3H, m), 1.67-1.50 (4H, m), 1.43-1.24 (3H, m). |
| 130 | O | 2-fluoro-4-cyanophenyl | 3-amino-azabicyclic | fluoro-N-methylbenzimidazole | 498.1 1H-NMR (DMSO-D6) δ: 8.28 (1H, s), 7.77-7.73 (1H, m), 7.64 (2H, dd, J = 9.8, 7.9 Hz), 7.58 (2H, d, J = 7.9 Hz), 7.42 (2H, d, J = 9.8 Hz), 7.11 (1H, d, J = 7.9 Hz), 4.69 (1H, s), 4.18 (1H, s), 3.80 (3H, s), 2.45-2.28 (3H, m), 2.13-2.02 (2H, m), 1.88-1.80 (2H, m), 1.73-1.59 (2H, m). |
| 131 | O | 2-fluoro-4-cyanophenyl | 3-amino-azabicyclic | N,N-dimethylaminopyridine | 470.2 1H-NMR (DMSO-D6) δ: 7.91 (1H, d, J = 2.4 Hz), 7.87 (1H, t, J = 7.5 Hz), 7.79-7.74 (1H, m), 7.60 (1H, d, J = 7.9 Hz), 7.55-7.46 (2H, m), 7.22 (1H, d, J = 7.9 Hz), 7.17 (1H, d, J = 7.9 Hz), 6.60-6.56 (1H, m), 4.66 (1H, s), 4.17 (1H, s), 3.02 (6H, s), 2.40-2.25 (3H, m, 2.10-2.01 (2H, m), 1.84-1.78 (2H, m), 1.70-1.59 (2H, m). |
| 132 | O | 2-fluoro-4-cyanophenyl | 3-amino-azabicyclic | 1,3,3-trimethyloxindole | 523.2 1H-NMR (DMSO-D6) δ: 7.80 (1H, t, J = 7.5 Hz), 7.62-7.55 (2H, m), 7.51 (1H, d, J = 1.5 Hz), 7.36 (1H, d, J = 10.4 Hz), 7.22 (1H, dd, J = 7.9, 1.8 Hz), 7.09 (1H, dd, J = 8.1, 1.4 Hz), 7.02 (1H, d, J = 8.2 Hz), 6.90 (1H, d, J = 1.8 Hz), 4.58 (1H, s), 4.07 (1H, s), 3.13 (3H, s), 2.25-1.84 (7H, m), 1.63-1.48 (2H, m), 1.07 (6H, s). |
| 133 | O | 2-fluoro-4-cyanophenyl | 3-amino-azabicyclic | N-methylbenzothiazolone | 513.1 1H-NMR (DMSO-D6) δ: 7.81 (1H, t, J = 7.6 Hz), 7.62-7.58 (2H, m), 7.55 (1H, d, J = 7.9 Hz), 7.51 (1H, d, J = 1.8 Hz), 7.46 (1H, dd, J = 10.5, 1.4 Hz), 7.22 (1H, d, J = 8.2 Hz), 7.10 (1H, dd, J = 8.2, 1.5 Hz), 7.06 (1H, dd, J = 8.2, 1.8 Hz), 4.58 (1H, s), 4.07 (1H, s), 3.27-3.24 (3H, m), 2.27-1.84 (7H, m), 1.63-1.48 (2H, m). |
| 134 | O | 2-fluoro-4-cyanophenyl | 3-amino-pyrrolidine | fluoro-N-methylindole | 457.1 1H-NMR (DMSO-D6) δ: 7.79-7.73 (1H, m), 7.72-7.66 (1H, m), 7.65-7.59 (1H, m), 7.58-7.49 (2H, m), 7.39-7.32 (2H, m), 7.22 (1H, d, J = 11.0 Hz), 7.14-7.09 (1H, m), 6.45 (1H, d, J = 3.1 Hz), 3.74 (3H, s), 3.69-3.60 (5H, m), 2.04-1.94 (1H, m), 1.71-1.65 (1H, m). |

TABLE 15

| | | | | | |
|---|---|---|---|---|---|
| 135 | O | 2-fluoro-4-cyanophenyl | 3-amino-pyrrolidine | fluoro-N-methylindazole | 458.1 1H-NMR (DMSO-D6) δ: 8.10 (1H, s), 7.81-7.75 (2H, m), 7.71 (1H, t, J = 7.0 Hz), 7.66 (1H, d, J = 5.2 Hz), 7.59 (1H, d, J = 7.9 Hz), 7.46 (1H, d, J = 10.4 Hz), 7.42-7.38 (1H, m), 7.10 (1H, d, J = 8.2 Hz), 4.00 (3H, s), 3.79-3.66 (5H, m), 2.16-2.09 (1H, m), 1.88-1.80 (1H, m). |

TABLE 15-continued

| 136 | O | 4-cyano-2-fluorophenyl | 8-azabicyclo-3-amine | 6-fluoro-1-(2-hydroxy-2-methylpropyl)indole | 555.1 | 1H-NMR (DMSO-D6) δ: 7.74 (1H, t, J = 7.6 Hz), 7.61 (1H, dd, J = 7.9, 1.8 Hz), 7.58-7.53 (2H, m), 7.48 (1H, d, J = 7.6 Hz), 7.33 (3H, dd, J = 21.4, 7.0 Hz), 7.13 (1H, dd, J = 7.9, 1.5 Hz), 6.45 (1H, d, J = 3.1 Hz), 4.64 (1H, s), 4.62-4.57 (1H, m), 4.13-4.08 (1H, m), 4.02 (2H, s), 2.25-2.14 (2H, m), 2.03-1.86 (3H, m), 1.80-1.68 (1H, m), 1.63-1.51 (2H, m), 1.46-1.33 (1H, m), 1.06 (6H, s). |
| --- | --- | --- | --- | --- | --- | --- |
| 137 | O | 4-cyano-2-fluorophenyl | 8-azabicyclo-3-amine | 5-isobenzofuran | 468.1 | 1H-NMR (DMSO-D6) δ: 7.81 (1H, t, J = 7.5 Hz), 7.61 (1H, d, J = 9.8 Hz), 7.56-7.50 (2H, m), 7.42 (1H, d, J = 10.7 Hz), 7.22 (1H, d, J = 7.9 Hz), 7.18 (1H, s), 7.11 (1H, d, J = 8.2 Hz), 6.98 (1H, d, J = 7.9 Hz), 4.99 (2H, s), 4.95 (2H, s), 4.62-4.56 (1H, m), 4.12-4.07 (1H, m), 2.23-2.10 (2H, m), 2.05-1.86 (3H, m), 1.82-1.69 (1H, m), 1.63-1.50 (2H, m), 1.45-1.34 (1H, m). |
| 138 | O | 4-cyano-2-fluorophenyl | 8-azabicyclo-3-amine | 3-isopropylbenzothiazol-2-one | 541.1 | 1H-NMR (DMSO-D6) δ: 7.82 (1H, t, J = 7.6 Hz), 7.62 (1H, d, J = 7.9 Hz), 7.58-7.54 (2H, m), 7.52 (1H, s), 7.48 (1H, d, J = 10.7 Hz), 7.40 (1H, d, J = 8.5 Hz), 7.12 (1H, d, J = 7.9 Hz), 7.04 (1H, d, J = 8.5 Hz), 4.78-4.71 (1H, m), 4.65-4.58 (1H, m), 4.14-4.08 (1H, m), 2.28-2.19 (1H, m), 2.15-1.90 (3H, m), 1.87-1.70 (2H, m), 1.65-1.52 (3H, m), 1.47 (6H, d, J = 7.0 Hz). |
| 139 | O | 4-cyano-2-fluorophenyl | 8-azabicyclo-3-amine | 1-tert-butyl-6-fluorobenzotriazole | 541.2 | 1H-NMR (DMSO-D6) δ: 8.13 (1H, d, J = 7.0 Hz), 7.93 (1H, d, J = 10.4 Hz), 7.77 (1H, t, J = 7.6 Hz), 7.67-7.62 (2H, m), 7.59 (1H, s), 7.48 (1H, d, J = 10.7 Hz), 7.15 (1H, dd, J = 8.1, 1.4 Hz), 4.66-4.59 (1H, m), 4.14-4.08 (1H, m), 2.24-2.05 (4H, m), 2.01-1.86 (3H, m), 1.77 (1H, s), 1.66-1.53 (2H, m). |
| 140 | O | 4-cyano-2-fluorophenyl | (S)-3-aminopyrrolidine | 5-isobenzofuran | 428.1 | 1H-NMR (DMSO-D6) δ: 7.82 (1H, t, J = 7.6 Hz), 7.69 (1H, t, J = 7.6 Hz), 7.61 (1H, d, J = 6.4 Hz), 7.55 (1H, d, J = 7.9 Hz), 7.45-7.38 (1H, m), 7.23 (1H, d, J = 7.9 Hz), 7.18 (1H, s), 7.10 (1H, d, J = 6.4 Hz), 6.98 (1H, d, J = 7.6 Hz), 4.99 (2H, s), 4.95 (2H, s), 3.82-3.67 (5H, m), 2.13-2.06 (1H, m), 1.85-1.78 (1H, m). |
| 141 | O | 4-cyano-2-fluorophenyl | (S)-3-aminopyrrolidine | 5-fluoro-3-methylbenzothiazol-2-one | 491 | 1H-NMR (DMSO-D6) δ: 7.82 (1H, t, J = 7.3 Hz), 7.75 (1H, d, J = 7.0 Hz), 7.72-7.69 (1H, m), 7.64 (1H, t, J = 4.7 Hz), 7.54 (1H, d, J = 7.9 Hz), 7.45 (1H, d, J = 10.4 Hz), 7.24 (1H, d, J = 10.7 Hz), 7.12 (1H, dd, J = 8.2, 1.5 Hz), 3.67-3.45 (5H, m), 3.37 (3H, s), 2.02-1.91 (1H, m), 1.69-1.61 (1H, m). |
| 142 | O | 4-cyano-2-fluorophenyl | 8-azabicyclo-3-amine | 6-fluoro-1-(2-hydroxy-2-methylpropyl)indazole | 556.1 | 1H-NMR (DMSO-D6) δ: 8.10 (1H, d, J = 0.9 Hz), 7.79-7.74 (2H, m), 7.63 (1H, dd, J = 7.8, 1.7 Hz), 7.59-7.55 (2H, m), 7.45 (1H, d, J = 11.0 Hz), 7.39 (1H, dd, J = 10.7, 1.5 Hz), 7.13 (1H, dd, J = 8.2, 1.5 Hz), 4.62 (1H, s), 4.60-4.56 (1H, m), 4.26 (2H, s), 4.08-4.05 (1H, m), 2.35-2.21 (2H, m), 2.12-2.06 (1H, m), 1.99-1.83 (1H, m), 1.64-1.48 (3H, m), 1.11 (6H, s). |

TABLE 16

| 143 | O | 4-cyano-2-fluorophenyl | azabicyclo-amine Racemate Relative configuration | 4-(2-methoxyethyl)-2-fluorophenyl | 448.1 | 1H-NMR (DMSO-D6) δ: 7.82 (1H, t, J = 7.5 Hz), 7.73-7.58 (2H, m), 7.53 (1H, d, J = 7.9 Hz), 7.39-7.33 (1H, m), 7.25 (1H, t, J = 7.9 Hz), 7.16-7.10 (2H, m), 7.01 (1H, d, J = 11.3 Hz), 4.49-3.86 (3H, m), 3.54 (2H, t, J = 6.6 Hz), 3.23 (3H, s), 2.82 (2H, t, J = 6.6 Hz), 2.22-2.10 (2H, m), 1.89-1.70 (1H, m), 1.64-1.48 (2H, m), 0.91 (1H, dd, J = 12.2, 4.3 Hz). |
| --- | --- | --- | --- | --- | --- | --- |

TABLE 16-continued

| | | | | | |
|---|---|---|---|---|---|
| 144 | O | 4-cyano-2-fluorophenyl | tropane-NH₂ | 2,3-difluoro-methylphenyl | 476.0 1H-NMR (DMSO-D6) δ: 7.83 (1H, dd, J = 7.9, 7.0 Hz), 7.63 (1H, dd, J = 7.8, 1.7 Hz), 7.57-7.53 (2H, m), 7.43 (1H, dd, J = 10.5, 1.4 Hz), 7.13-7.10 (2H, m), 7.03-6.99 (1H, m), 4.59 (1H, s), 4.05 (1H, s), 2.27 (3H, d, J = 1.2 Hz), 2.23-2.09 (3H, m), 2.04-1.85 (3H, m), 1.63-1.49 (3H, m). |
| 145 | O | 4-cyano-2-fluorophenyl | tropane-NH₂ | difluoro-methyl-benzotriazole | 517.0 1H-NMR (DMSO-D6) δ: 7.97 (1H, d, J = 4.6 Hz), 7.78 (1H, dd, J = 7.9, 7.0 Hz), 7.67 (1H, dd, J = 7.9, 1.8 Hz), 7.63 (1H, dd, J = 7.6 Hz), 7.59 (1H, d, J = 1.5 Hz), 7.50 (1H, dd, J = 10.5, 1.4 Hz), 7.16 (1H, dd, J = 7.9, 1.5 Hz), 4.61 (1H, s), 4.40 (3H, s), 4.06 (1H, s), 2.24-1.86 (6H, m), 1.66-1.51 (3H, m). |
| 146 | O | 4-cyano-2-fluorophenyl | pyrrolidine-NH₂ | fluoro-indole-hydroxyisobutyl | 515.0 1H-NMR (DMSO-D6) δ: 7.74 (1H, t, J = 7.5 Hz), 7.68 (1H, t, J = 7.2 Hz), 7.62 (1H, d, J = 8.5 Hz), 7.55 (1H, d, J = 7.9 Hz), 7.47 (1H, d, J = 7.6 Hz), 7.35 (1H, d, J = 3.1 Hz), 7.30 (2H, d, J = 11.9 Hz), 7.11 (1H, t, J = 4.7 Hz), 6.44 (1H, d, J = 3.1 Hz), 4.62 (1H, s), 4.01 (2H, s), 3.78-3.58 (4H, m), 3.13-2.96 (1H, m), 2.03-1.93 (1H, m), 1.72-1.61 (1H, m), 1.05 (6H, s). |
| 147 | O | 4-cyano-2-fluorophenyl | pyrrolidine-NH₂ | fluoro-indole-hydroxyisobutyl | 516.0 1H-NMR (DMSO-D6) δ: 8.10 (1H, d, J = 0.9 Hz), 7.77-7.74 (2H, m), 7.71-7.69 (1H, m), 7.64 (1H, dd, J = 7.8, 1.7 Hz), 7.57-7.57 (1H, m), 7.44 (1H, d, J = 11.0 Hz), 7.37 (1H, d, J = 10.7 Hz), 7.11 (1H, dd, J = 8.1, 1.7 Hz), 4.61 (1H, s), 4.25 (2H, s), 3.69-3.57 (2H, m), 3.56-3.43 (2H, m), 3.24-3.14 (1H, m), 2.02-1.90 (1H, m), 1.68-1.61 (1H, m), 1.10 (6H, s). |
| 148 | O | 4-cyano-2-fluorophenyl | tropane-NH₂ | quinoxaline | 478.1 1H-NMR (DMSO-D6) δ: 8.97 (2H, s), 8.03-7.98 (2H, m), 7.30-7.74 (2H, m), 7.70 (1H, dd, J = 7.9, 1.5 Hz), 7.62 (1H, d, J = 1.5 Hz), 7.57-7.52 (2H, m), 7.15 (1H, dd, J = 8.1, 1.7 Hz), 4.69-4.62 (1H, m), 4.20-4.13 (1H, m), 2.33-1.91 (7H, m), 1.74-1.53 (2H, m). |
| 149 | O | 4-cyano-2-fluorophenyl | tropane-NH₂ | isoquinoline | 477.0 1H-NMR (DMSO-D6) δ: 9.40-9.31 (1H, m), 8.60-8.53 (1H, m), 8.07-7.95 (2H, m), 7.78-7.63 (4H, m), 7.62 (1H, s), 7.51 (1H, d, J = 9.8 Hz), 7.39-7.30 (1H, m), 7.09 (1H, d, J = 7.6 Hz), 4.76-4.63 (1H, m), 4.24-4.15 (1H, m), 2.36-1.81 (7H, m), 1.78-1.58 (2H, m). |
| 150 | O | 4-cyano-2-fluorophenyl | tropane-NH₂ | isoquinoline | 477.0 1H-NMR (DMSO-D6) δ: 9.37-9.31 (1H, m), 8.56-8.52 (1H, m), 8.13-8.08 (1H, m), 7.92-7.85 (2H, m), 7.76-7.70 (3H, m), 7.62 (1H, s), 7.50 (1H, d, J = 10.4 Hz), 7.46-7.40 (1H, m), 7.10 (1H, d, J = 7.9 Hz), 4.73-4.66 (1H, m), 4.24-4.17 (1H, m), 2.34-2.00 (5H, m), 1.92-1.57 (4H, m). |
| 151 | O | 4-cyano-2-fluorophenyl | tropane-NH₂ | quinoline | 477.0 1H-NMR (DMSO-D6) δ: 8.93 (1H, d, J = 4.3 Hz), 8.36 (1H, d, J = 8.5 Hz), 7.94 (1H, s), 7.90 (1H, d, J = 8.5 Hz), 7.76-7.69 (3H, m), 7.61 (1H, d, J = 1.5 Hz), 7.60-7.55 (1H, m), 7.51 (1H, d, J = 10.4 Hz), 7.40 (1H, d, J = 9.2 Hz), 7.10 (1H, dd, J = 7.9, 1.5 Hz), 4.74-4.65 (1H, m), 4.25-4.16 (1H, m), 2.31-1.53 (9H, m). |

TABLE 17

| | | | | | |
|---|---|---|---|---|---|
| 152 | O | 4-cyano-2-fluorophenyl | tropane-NH₂ | quinazoline | 478.0 1H-NMR (DMSO-D6) δ: 9.60 (1H, s), 8.06 (1H, d, J = 8.5 Hz), 7.93 (1H, s), 7.75-7.74 (1H, m), 7.73-7.69 (1H, m), 7.63 (1H, s), 7.53-7.52 (2H, m), 7.45-7.41 (1H, m), 7.15-7.12 (2H, m), 4.72-4.63 (1H, m), 4.22-4.15 (1H, m), 2.13-2.04 (2H, m), 1.83-1.60 (7H, m). |

TABLE 17-continued

| | | | | | |
|---|---|---|---|---|---|
| 153 | O | 2-fluoro-4-cyanophenyl | 8-azabicyclo[3.2.1] with NH₂ | 6-quinazolinyl | 478.0 1H-NMR (DMSO-D6) δ: 9.32 (1H, s), 8.12 (1H, d, J = 2.7 Hz), 7.90 (1H, d, J = 8.5 Hz), 7.75-7.71 (3H, m), 7.69-7.62 (3H, m), 7.53 (1H, d, J = 10.1 Hz), 7.11-7.09 (1H, m), 4.73-4.65 (1H, m), 4.24-4.15 (1H, m), 2.14-2.01 (3H, m), 1.87-1.65 (6H, m). |
| 154 | O | 2-fluoro-4-cyanophenyl | 8-azabicyclo[3.2.1] with NH₂ | 6-phthalazinyl | 478.0 1H-NMR (DMSO-D6) δ: 9.66 (2H, d, J = 3.4 Hz), 8.20 (1H, s), 8.12 (1H, s), 8.03 (1H, d, J = 8.5 Hz), 7.75-7.66 (4H, m), 7.62 (1H, s), 7.51 (1H, d, J = 9.2 Hz), 7.07 (1H, dd, J = 7.9, 1.5 Hz), 4.66-4.58 (1H, m), 4.15-4.07 (1H, m), 2.31-1.88 (7H, m), 1.67-1.50 (2H, m). |
| 155 | O | 2-fluoro-4-cyanophenyl | azabicyclic-NH₂ isomer-B Relative configuration | 4-fluoro-3-(2-methoxyethyl)phenyl | 488.0 1H-NMR (DMSO-D6) δ: 7.81 (1H, t, J = 7.5 Hz), 7.73-7.56 (2H, m), 7.52 (1H, d, J = 7.9 Hz), 7.35 (1H, d, J = 10.4 Hz), 7.24 (1H, t, J = 7.9 Hz), 7.14-7.09 (2H, m), 7.01 (1H, d, J = 11.3 Hz), 4.42-3.89 (3H, m), 3.53 (2H, t, J = 6.6 Hz), 3.23 (3H, s), 2.81 (2H, t, J = 6.6 Hz), 2.25-2.08 (2H, m), 1.79-1.68 (1H, m), 1.64-1.46 (2H, m), 0.91-0.87 (1H, m). |
| 156 | O | 2-fluoro-4-cyanophenyl | azabicyclic-NH₂ isomer-A Relative configuration | 4-fluoro-3-(2-methoxyethyl)phenyl | 488.0 1H-NMR (DMSO-D6) δ: 7.81 (1H, t, J = 7.5 Hz), 7.73-7.56 (2H, m), 7.52 (1H, d, J = 7.6 Hz), 7.35 (1H, d, J = 10.7 Hz), 7.24 (1H, t, J = 7.9 Hz), 7.15-7.09 (2H, m), 7.01 (1H, d, J = 11.0 Hz), 4.46-3.85 (3H, m), 3.53 (2H, t, J = 6.7 Hz), 3.23 (3H, s), 2.81 (2H, t, J = 6.6 Hz), 2.21-2.10 (2H, m), 1.70-1.68 (1H, m), 1.64-1.46 (2H, m), 0.93-0.87 (1H, m). |
| 157 | O | 2-fluoro-4-cyanophenyl | 8-azabicyclo[3.2.1] with NH₂ | 3-methylimidazo[1,5-a]pyridin-6-yl | 480.0 1H-NMR (DMSO-D6) δ: 7.87 (1H, t, J = 7.5 Hz), 7.78 (3H, s), 7.65 (2H, s), 7.59-7.51 (3H, m), 7.24 (1H, d, J = 7.0 Hz), 4.67 (1H, s), 4.16 (1H, s), 2.52 (3H, s), 2.34-2.22 (2H, m), 2.14-2.02 (1H, m), 1.89-1.80 (3H, m), 1.76-1.57 (3H, m). |
| 158 | O | 2-fluoro-4-cyanophenyl | 8-azabicyclo[3.2.1] with NH₂ | 3-methylpyrazolo[1,5-a]pyrimidin-6-yl | 481.1 1H-NMR (DMSO-D6) δ: 9.04 (1H, d, J = 2.1 Hz), 8.11 (1H, d, J = 0.6 Hz), 8.02 (1H, d, J = 2.1 Hz), 7.86 (1H, t, J = 7.5 Hz), 7.75 (1H, d, J = 7.9 Hz), 7.67 (1H, dd, J = 7.8, 1.7 Hz), 7.62 (1H, dd, J = 10.4, 1.2 Hz), 7.59 (1H, d, J = 1.5 Hz), 7.28 (1H, dd, J = 7.9, 1.5 Hz), 4.52 (1H, s), 4.08 (1H, s), 2.26 (3H, s), 2.15-1.91 (6H, m), 1.68-1.51 (3H, m). |
| 159 | O | 2-fluoro-4-cyanophenyl | 8-azabicyclo[3.2.1] with NH₂ | 5,6-difluoro-2-(2-hydroxy-2-methylpropyl)-2H-indazol-? | 556.0 1H-NMR (DMSO-D6) δ: 8.37 (1H, d, J = 0.9 Hz), 7.81-7.75 (2H, m), 7.62 (1H, dd, J = 7.9, 1.8 Hz), 7.58-7.54 (2H, m), 7.41 (1H, dd, J = 10.7, 1.5 Hz), 7.26 (1H, d, J = 11.6 Hz), 7.14 (1H, dd, J = 8.2, 1.5 Hz), 4.87 (1H, s), 4.59 (1H, s), 4.32 (2H, s), 4.08 (1H, s), 2.28-2.10 (3H, m), 2.02-1.83 (3H, m), 1.63-1.49 (3H, m), 1.11 (6H, s). |
| 160 | O | 2-fluoro-4-cyanophenyl | 8-azabicyclo[3.2.1] with NH₂ | 1-ethyl-5,6-difluoro-1H-benzotriazolyl | 513.0 1H-NMR (DMSO-D6) δ: 8.14 (1H, d, J = 6.4 Hz), 7.77-7.74 (2H, m), 7.62 (3H, ddd, J = 29.6, 12.8, 3.2 Hz), 7.46 (1H, dd, J = 10.5 1.4 Hz), 7.14 (1H, dd, J = 7.9, 1.5 Hz), 4.68 (2H, q, J = 7.3 Hz), 4.61 (1H, s), 4.09 (1H, s), 2.23-1.88 (6H, m), 1.65-1.52 (3H, m), 1.49 (3H, t, J = 7.2 Hz). |
| 161 | O | 2-fluoro-4-cyanophenyl | 8-azabicyclo[3.2.1] with NH₂ | 5,6-difluoro-1-(2-hydroxy-2-methylpropyl)-1H-benzotriazolyl | 575.0 1H-NMR (DMSO-D6) δ: 7.97 (1H, d, J = 4.6 Hz), 7.76 (1H, t, J = 7.6 Hz), 7.67-7.64 (2H, m), 7.59 (1H, d, J = 0.9 Hz), 7.48 (1H, dd, J = 10.5, 1.4 Hz), 7.16 (1H, dd, J = 7.9, 1.5 Hz), 4.81 (1H, s), 4.61 (2H, s), 4.57 (1H, s), 4.05 (1H, s), 2.34-2.21 (2H, m), 2.12-2.05 (1H, m), 1.99-1.83 (3H, m), 1.62-1.46 (3H, m), 1.15 (6H, s). |

TABLE 18

| # | | | | | MS | 1H-NMR |
|---|---|---|---|---|---|---|
| 162 | O | 4-CN-2-F-phenyl | (3R)-3-aminopyrrolidin-1-yl | 1-(2-hydroxy-2-methylpropyl)-6,7-difluoro-1H-benzotriazol-5-yl | 535.0 | 1H-NMR (DMSO-D6) δ: 7.97 (1H, d, J = 5.2 Hz), 7.78-7.64 (4H, m), 7.46 (1H, d, J = 10.4 Hz), 7.15 (1H, dd, J = 8.2, 1.5 Hz), 4.81 (1H, s), 4.61 (2H, s), 3.69-3.57 (2H, m), 3.55-3.46 (2H, m), 3.23-3.15 (1H, m), 2.04-1.90 (1H, m), 1.68-1.56 (1H, m), 1.15 (6H, s). |
| 163 | O | 4-CN-2-F-phenyl | piperazin-1-yl | 4-(2-methoxyethyl)-2-fluorophenyl | 462.0 | 1H-NMR (DMSO-D6) δ: 7.82 (1H, t, J = 7.5 Hz), 7.63-7.60 (1H, m), 7.57-7.53 (2H, m), 7.34 (1H, d, J = 10.4 Hz), 7.26-7.21 (1H, m), 7.13-7.09 (2H, m), 7.0.1 (1H, d, J = 11.3 Hz), 3.76-3.42 (8H, m), 3.23 (3H, s), 3.13-2.92 (2H, m), 2.81 (2H, t, J = 6.7 Hz). |
| 164 | O | 4-CN-2-F-phenyl | (3R)-3-aminopiperidin-1-yl | 4-(2-methoxyethyl)-2-fluorophenyl | 476.1 | 1H-NMR (DMSO-D6) δ: 7.82 (1H, t, J = 7.5 Hz), 7.59 (1H, dd, J = 7.8, 1.7 Hz), 7.56-7.52 (2H, m), 7.32 (1H, dd, J = 10.5, 1.4 Hz), 7.24 (1H, t, J = 7.9 Hz), 7.11 (2H, dd, J = 7.9, 1.5 Hz), 7.01 (1H, d, J = 11.3 Hz), 4.34-3.71 (2H, m), 3.53 (2H, t, J = 6.6 Hz), 3.23 (3H, s), 3.12-2.94 (2H, m), 2.82 (2H, t, J = 6.7 Hz), 1.99-1.91 (1H, m), 1.81-1.64 (1H, m), 1.56-1.41 (2H, m), 0.88-0.80 (1H, m). |
| 165 | O | 4-CN-2-F-phenyl | 4-aminoazepan-1-yl | 4-(2-methoxyethyl)-2-fluorophenyl | 490.1 | 1H-NMR (DMSO-D6) δ: 7.81 (1H, t, J = 7.5 Hz), 7.57-7.48 (3H, m), 7.35-7.31 (1H, m), 7.24 (1H, t, J = 7.9 Hz), 7.11 (2H, dd, J = 8.1, 1.4 Hz), 7.01 (1H, d, J = 11.3 Hz), 3.92-3.62 (2H, m), 3.58-3.41 (4H, m), 3.23 (3H, s), 2.81 (2H, t, J = 6.7 Hz), 2.14-2.03 (1H, m), 1.91-1.49 (5H, m), 0.88-0.80 (1H, m). |
| 166 | O | 4-CN-2-F-phenyl | 2-amino-azabicyclic (isomer-B, Relative configuration) | 4-(2-hydroxy-2-methylpropyl)-3-fluorophenyl | 502.0 | 1H-NMR (DMSO-D6) δ: 7.80 (1H, t, J = 7.6 Hz), 7.68 (1H, s), 7.60 (1H, s), 7.53 (1H, d, J = 7.9 Hz), 7.29 (1H, t, J = 5.3 Hz), 7.21 (1H, t, J = 7.9 Hz), 7.15 (1H, dd, J = 8.2, 1.5 Hz), 7.07 (1H, d, J = 7.9 Hz), 6.95 (1H, d, J = 11.6 Hz), 4.46-3.86 (3H, m), 2.65 (2H, s), 2.25-2.10 (2H, m), 1.74-1.49 (4H, m), 1.04 (6H, s), 0.87 (1H, dd, J = 12.2, 4.6 Hz). |
| 167 | O | 4-CN-2-F-phenyl | (3R)-3-aminopyrrolidin-1-yl | 1-methyl-6,7-difluoro-1H-benzotriazol-5-yl | 477.0 | 1H-NMR (DMSO-D6) δ: 7.99-7.96 (1H, m), 7.80-7.73 (2H, m), 7.69-7.67 (1H, m), 7.64 (1H, d, J = 7.9 Hz), 7.50-7.46 (1H, m), 7.18-7.14 (1H, m), 4.40 (3H, d, J = 6.7 Hz), 3.70-3.64 (2H, m), 3.58-3.48 (2H, m), 3.25-3.16 (1H, m), 2.08-2.04 (1H, m), 1.78-1.74 (1H, m). |
| 168 | O | 4-CN-2-F-phenyl | 3-amino-azabicyclic | 1-propyl-6-fluoro-1H-benzotriazol-5-yl | 527.0 | 1H-NMR (DMSO-D6) δ: 8.14 (1H, d, J = 6.7 Hz), 7.77-7.74 (2H, m), 7.68-7.59 (3H, m), 7.45 (1H, dd, J = 10.4, 1.5 Hz), 7.14 (1H, dd, J = 7.9, 1.5 Hz), 4.64-4.60 (3H, m), 4.14-4.07 (1H, m), 2.30-1.87 (9H, m), 1.66-1.55 (2H, m), 0.84 (3H, t, J = 7.3 Hz). |
| 169 | O | 4-CN-2-F-phenyl | (3R)-3-aminopyrrolidin-1-yl | 1-(2-methoxyethyl)-6,7-difluoro-1H-benzotriazol-5-yl | 521.0 | 1H-NMR (DMSO-D6) δ: 7.99 (1H, d, J = 4.9 Hz), 7.79-7.73 (2H, m), 7.70-7.64 (2H, m), 7.48-7.45 (1H, m), 7.16 (1H, dd, J = 8.2, 1.5 Hz), 4.91 (2H, t, J = 5.2 Hz), 3.81 (2H, t, J = 5.0 Hz), 3.69-3.45 (4H, m), 3.18-3.16 (4H, m), 2.01-1.94 (1H, m), 1.68-1.63 (1H, m). |
| 170 | O | 4-CN-2-F-phenyl | (3R)-3-aminopyrrolidin-1-yl | 1-(2-hydroxyethyl)-6-fluoro-1H-indol-5-yl | 487.0 | 1H-NMR (DMSO-D6) δ: 7.75 (1H, dd, J = 7.8, 7.2 Hz), 7.69-7.66 (1H, m), 7.62 (1H, dd, J = 7.9, 1.5 Hz), 7.51 (2H, dd, J = 18.9, 7.6 Hz), 7.39-7.35 (2H, m), 7.25 (1H, d, J = 11.3 Hz), 7.11 (1H, dd, J = 7.9, 1.5 Hz), 6.44 (1H, dd, J = 3.1, 0.6 Hz), 4.86 (1H, t, J = 5.2 Hz), 4.15 (2H, t, J = 5.3 Hz), 3.69-3.59 (4H, m), 3.54-3.47 (2H, m), 3.22-3.18 (1H, m), 1.99-1.94 (1H, m), 1.73-1.66 (1H, m). |

TABLE 19

| # | | | | MS | 1H-NMR |
|---|---|---|---|---|---|
| 171 | O | benzonitrile (4-CN, 2-F) | azabicyclic-NH2, isomer-B Relative configuration | 6-F-indole, N-CH2-C(CH3)2-OH | 541.0 | 1H-NMR (DMSO-D6) δ: 7.74 (1H, t, J = 7.5 Hz), 7.68 (1H, d, J = 7.9 Hz), 7.61-7.55 (2H, m), 7.47 (1H, d, J = 7.6 Hz), 7.35-7.29 (3H, m), 7.13 (1H, dd, J = 7.9, 1.5 Hz), 6.44 (1H, d, J = 3.4 Hz), 4.62 (1H, s), 4.48-3.87 (5H, m), 2.19-2.14 (2H, m), 1.78-1.73 (1H, m), 1.62-1.49 (2H, m), 1.05 (6H, s), 0.88 (1H, dd, J = 12.1, 4.7 Hz). |
| 172 | O | benzonitrile (4-CN, 2-F) | (R)-3-aminopyrrolidine | 6,7-diF-indole, N-CH2-C(CH3)2-OH | 533.0 | 1H-NMR (DMSO-D6) δ: 7.76 (1H, t, J = 7.6 Hz), 7.71-7.68 (1H, m), 7.66-7.64 (1H, m), 7.59 (1H, d, J = 7.9 Hz), 7.38 (1H, d, J = 3.4 Hz), 7.35-7.30 (2H, m), 7.12 (1H, dd, J = 7.9, 1.5 Hz), 6.51 (1H, t, J = 2.4 Hz), 4.70 (1H, s), 4.13 (2H, s), 3.70-3.55 (4H, m), 3.24-3.18 (1H, m), 2.01-1.99 (1H, m), 1.71-1.67 (1H, m), 1.05 (6H, s). |
| 173 | O | benzonitrile (4-CN, 2-F) | azabicyclic-NH2 | 6-F-indole, N-CH2-C(CH3)2-OH | 541.0 | 1H-NMR (DMSO-D6) δ: 7.76-7.53 (5H, m), 7.50-7.44 (1H, m), 7.35-7.28 (2H, m), 7.15-7.08 (1H, m), 6.44 (1H, t, J = 2.7 Hz), 4.62 (1H, s), 4.30-3.84 (3H, m), 3.78-3.59 (1H, m), 3.20-3.15 (1H, m), 3.09-3.04 (1H, m), 2.25-1.50 (5H, m), 1.05 (6H, dd, J = 12.4, 4.7 Hz). |
| 174 | O | benzonitrile (4-CN, 2-F) | azabicyclic-NH2 | 4-F-phenyl, CH2-C(CH3)2-OH | 502.1 | 1H-NMR (DMSO-D6) δ: 7.83-7.77 (1H, m), 7.67-7.49 (3H, m), 7.28-7.12 (3H, m), 7.09-7.05 (1H, m), 6.98-6.93 (1H, m), 4.40 (1H, d, J = 3.1 Hz), 4.11-3.72 (1H, m), 3.61-3.48 (1H, 3.22-3.16 (1H, m), 3.10-3.03 (1H, m), 2.66 (2H, s), 2.21-1.55 (5H, m), 1.04 (6H, s). |
| 175 | O | benzonitrile (4-CN, 2-F) | azabicyclic-NH2, isomer-B Relative configuration | 6,7-diF-benzotriazole, N-CH3 | 503.0 | 1H-NMR (DMSO-D6) δ: 7.98 (1H, d, J = 5.2 Hz), 7.78 (1H, t, J = 7.5 Hz), 7.75-7.70 (1H, m), 7.63 (2H, d, J = 7.6 Hz), 7.55-7.48 (1H, m), 7.17 (1H, dd, J = 8.2, 1.5 Hz), 4.48-3.88 (6H, m), 2.24-2.12 (2H, m), 1.75-1.51 (3H, m), 0.89 (1H, dd, J = 12.1, 4.7 Hz). |
| 176 | O | benzonitrile (4-CN, 2-F) | azabicyclic-NH2, isomer-B Relative configuration | 6-F-indazole, N-CH2-C(CH3)2-OH | 542.0 | 1H-NMR (DMSO-D6) δ: 8.10 (1H, d, J = 0.9 Hz), 7.80-7.74 (2H, m), 7.73-7.67 (1H, m), 7.64-7.56 (2H, m), 7.45 (1H, d, J = 11.0 Hz), 7.40 (1H, dd, J = 10.5, 1.4 Hz), 7.13 (1H, dd, J = 7.9, 1.5 Hz), 4.61 (1H, s), 4.49-3.89 (5H, m), 2.26-2.13 (2H, m), 1.81-1.50 (4H, m), 1.10 (6H, s). |
| 177 | O | benzonitrile (4-CN, 2-F) | azabicyclic-NH2, isomer-B Relative configuration | 6,7-diF-indazole, N-CH2-C(CH3)2-OH | 561.0 | 1H-NMR (DMSO-D6) δ: 7.97(1H, d, J = 5.2 Hz), 7.78-7.73 (2H, m), 7.66 (2H, d, J = 7.6 Hz), 7.49 (1H, dd, J = 10.4, 1.2 Hz), 7.17 (1H, dd, J = 8.2, 1.5 Hz), 4.81 (1H, s), 4.61 (2H, s), 4.49-3.87 (3H, m), 2.28-2.11 (2H, m), 1.80-1.51 (3H, m), 1.15 (6H, s), 0.89 (1H, dd, J = 11.7, 4.7 Hz). |
| 178 | O | benzonitrile (4-CN, 2-F) | azabicyclic-NH2 | 6,7-diF-3-Br-indazole, N-CH2-C(CH3)2-OH | 635.9 | 1H-NMR (DMSO-D6) δ: 7.77 (1H, t, J = 7.5 Hz), 7.64-7.56 (4H, m), 7.51 (1H, d, J = 10.7 Hz), 7.44 (1H, d, J = 11.6 Hz), 7.14 (1H, d, J = 9.2 Hz), 4.64 (1H, s), 4.58 (1H, s), 4.25 (2H, s), 4.06 (1H, s), 2.34-1.85 (6H, m), 1.64-1.44 (2H, m), 1.16-1.15 (1H, m), 1.13-1.08 (6H, m). |
| 179 | O | benzonitrile (4-CN, 2-F) | azabicyclic-NH2 | 5,6-diF-3-methyl-benzisoxazole | 499.0 | 1H-NMR (DMSO-D6) δ: 7.84 (1H, d, J = 5.2 Hz), 7.78 (1H, t, J = 7.5 Hz), 7.69-7.64 (2H, m), 7.63-7.58 (2H, m), 7.47 (1H, d, J = 10.4 Hz), 7.13 (1H, dd, J = 8.2, 1.5 Hz), 4.63-4.57 (1H, m), 4.11-4.02 (1H, m), 2.53 (3H, s), 2.24-1.90 (7H, m), 1.64-1.48 (2H, m). |

TABLE 19-continued

| 180 | O ... CN, F | H2N-pyrrolidine-N | benzisoxazole-F-methyl | 459.0 | 1H-NMR (DMSO-D6) δ: 7.83 (1H, d, J = 5.5 Hz), 7.79 (1H, t, J = 7.6 Hz), 7.74 (1H, t, J = 6.7 Hz), 7.70-7.62 (3H, m), 7.45 (1H, t, J = 9.0 Hz), 7.12 (1H, d, J = 8.9 Hz), 3.82-3.49 (5H, m), 2.53 (3H, s), 2.20-2.12 (1H, m), 1.94-1.84 (1H, m). |
|---|---|---|---|---|---|

TABLE 20

| 181 | O ... CN, F | tropane-NH2 | indazole-F-CH2C(CH3)2OH-methyl | 570.0 | 1H-NMR (DMSO-D6) δ: 7.80-7.73 (2H, m), 7.66-7.52 (3H, m), 7.39 (1H, d, J = 10.7 Hz), 7.32 (1H, d, J = 11.3 Hz), 7.12 (1H, dd, J = 8.2. 1.5 Hz), 4.62-4.55 (2H, m), 4.18-4.11 (2H, m), 4.10-4.03 (1H, m), 2.47 (3H, s), 2.35-1.84 (7H, m), 1.64-1.49 (2H, m), 1.10 (6H, s). |
|---|---|---|---|---|---|
| 182 | O ... CN, F | azabicyclic-NH2 Racemate Relative configuration | F-phenyl-CH2C(CH3)2OH | 502.0 | 1H-NMR (DMSO-D6) δ: 7.83-7.64 (3H, m), 7.51 (1H, d, J = 7.3 Hz), 7.30-7.25 (1H, m), 7.21 (1H, t, J = 7.9 Hz), 7.16 (1H, dd, J = 8.2, 1.5 Hz), 7.07 (1H, dd, J = 7.9, 1.2 Hz), 6.95 (1H, d, J = 11.6 Hz), 4.51-3.85 (3H, m), 3.08-2.95 (1H, m), 2.65 (2H, s), 1.82-1.68 (2H, m), 1.36-1.23 (4H, m), 1.04 (6H, s). |
| 183 | O ... CN, F | tropane-NH2 | indole-F-CH2C(CH3)2OH | 573.1 | 1H-NMR (DMSO-D6) δ: 7.76 (1H, t, J = 7.6 Hz), 7.62 (1H, dd, J = 7.9, 1.5 Hz), 7.59 (1H, d, J = 7.9 Hz), 7.56 (1H, d, J = 1.5 Hz), 7.38 (1H, d, J = 3.1 Hz), 7.34 (1H, dd, J = 10.5, 1.4 Hz), 7.31 (1H, d, J = 5.8 Hz), 7.13 (1H, dd, J = 7.9, 1.5 Hz), 6.51 (1H, t, J = 2.4 Hz), 4.70 (1H, s), 4.59 (1H, s), 4.13 (2H, s), 4.09 (1H, s), 2.27-2.11 (3H, m), 2.03-1.85 (4H, m), 1.64-1.48 (2H, m), 1.05 (6H, s). |
| 184 | O ... CN, F | azabicyclic-NH2 Racemate Relative configuration | indole-F-CH2C(CH3)2OH | 541.1 | 1H-NMR (DMSO-D6) δ: 7.79-7.72 (3H, m), 7.60-7.53 (1H, m), 7.47 (1H, d, J = 7.3 Hz), 7.37-7.28 (3H, m), 7.14-7.12 (1H, m), 6.45 (1H, d, J = 2.4 Hz), 4.62 (1H, s), 4.53-3.89 (4H, m), 3.10-3.04 (1H, m), 2.45-2.39 (1H, m), 1.87-1.79 (1H, m), 1.72-1.69 (2H, m), 1.41-1.17 (2H, m), 1.05 (6H, s). |
| 185 | O ... CN, F | azabicyclic-NH2 Racemate Relative configuration | benzotriazole-F-methyl | 503 | 1H-NMR (DMSO-D6) δ: 7.98 (1H, d, J = 5.2 Hz), 7.78 (1H, t, J = 7.5 Hz), 7.75-7.70 (1H, m), 7.63 (2H, d, J = 7.6 Hz), 7.55-7.48 (1H, m), 7.17 (1H, dd, J = 8.2, 1.5 Hz), 4.48-3.88 (6H, m), 2.24-2.12 (2H, m), 1.75-1.51 (3H, m), 0.89 (1H, dd, J = 12.1, 4.7 Hz). |
| 186 | O ... CN, F | tropane-NH2 | indazole-OMe-F-CH2C(CH3)2OH | 586.1 | 1H-NMR (DMSO-D6) δ: 8.12 (1H, s), 7.76 (1H, t, J = 7.6 Hz), 7.65-7.59 (2H, m), 7.57 (1H, d, J = 1.2 Hz), 7.50 (1H, d, J = 6.1 Hz), 7.36 (1H, dd, J = 10.5, 1.4 Hz), 7.12 (1H, dd, J = 8.1, 1.7 Hz), 4.62 (1H, s), 4.58 (1H, s), 4.41 (2H, s), 4.06 (1H, s), 3.72 (3H, d, J = 1.5 Hz), 2.30-2.18 (2H, m), 2.14-2.08 (1H, m), 2.00-1.84 (3H, m), 1.62-1.49 (3H, m), 1.09 (6H, s). |
| 187 | O ... CN, F | H2N-pyrrolidine-N | indazole-F-CH2C(CH3)2OH | 534.1 | 1H-NMR (DMSO-D6) δ: 8.19 (1H, d, J = 1.8 Hz), 7.78-7.75 (1H, m), 7.73-7.70 (1H, m), 7.66 (1H, dd, J = 8.5, 1.5 Hz), 7.62-7.58 (2H, m), 7.42-7.39 (1H, m), 7.12 (1H, dd, J = 7.9, 1.5 Hz), 4.68 (1H, s), 4.33 (2H, s), 3.72-3.59 (4H, m), 3.20-3.15 (1H, m), 2.01-1.94 (1H, m), 1.69-1.63 (1H, m), 1.10 (6H, s). |

TABLE 20-continued

| 188 | (structure) | (structure) | (structure) | 574.1 | 1H-NMR (DMSO-D6) δ: 8.19 (1H, d, J = 1.8 Hz), 7.76 (1H, dd, J = 8.1, 7.2 Hz), 7.64 (1H, dd, J = 7.9, 1.5 Hz), 7.61-7.57 (3H, m), 7.42 (1H, dd, J = 10.5, 1.4 Hz), 7.14-7.11 (1H, m), 4.68 (1H, s), 4.57 (1H, s), 4.33 (2H, s), 4.05 (1H, s), 2.33-2.20 (2H, m), 2.12-2.07 (1H, m), 1.97-1.83 (3H, m), 1.61-1.48 (3H, m), 1.10 (6H, s). |
|---|---|---|---|---|---|
| 189 | (structure) | (structure) Racemate Relative configuration | (structure) | 542.1 | 1H-NMR (DMSO-D6) δ: 8.10 (1H, d, J = 0.9 Hz), 7.80-7.74 (2H, m), 7.73-7.67 (1H, m), 7.64-7.56 (2H, m), 7.45 (1H, d, J = 11.0 Hz), 7.40 (1H, dd, J = 10.5, 1.4 Hz), 7.13 (1H, dd, J = 7.9, 1.5 Hz), 4.61 (1H, s), 4.49-3.89 (5H, m), 2.26-2.13 (2H, m), 1.81-1.50 (4H, m), 1.10 (6H, s). |

TABLE 21

| 190 | O | (structure) | (structure) | (structure) | 529.2 | 1H-NMR (DMSO-D6) δ: 7.76-7.73 (1H, m), 7.70-7.60 (2H, m), 7.56-7.54 (1H, m), 7.47 (1H, d, J = 7.3 Hz), 7.35 (1H, d, J = 3.1 Hz), 7.32-7.28 (2H, m), 7.11 (1H, d, J = 8.2 Hz), 6.44 (1H, d, J = 3.1 Hz), 4.62 (1H, s), 4.01 (2H, s), 3.75-3.50 (4H, m), 1.77-1.73 (2H, m), 1.25-1.16 (3H, m), 1.05 (6H, s). |
|---|---|---|---|---|---|---|
| 191 | O | (structure) | (structure) | (structure) | 549.1 | 1H-NMR (DMSO-D6) δ: 7.98-7.95 (1H, m), 7.78-7.64 (4H, m), 7.48-7.44 (1H, m), 7.17-7.14 (1H, m), 4.82-4.81 (1H, m), 4.63-4.60 (2H, m), 3.72-3.50 (4H, m), 1.80-1.73 (2H, m), 1.26-1.15 (9H, m). |
| 192 | O | (structure) | (structure) Racemate Relative configuration | (structure) | 561.1 | 1H-NMR (DMSO-D6) δ: 7.97 (1H, d, J = 5.2 Hz), 7.78-7.73 (2H, m), 7.66 (2H, d, J = 7.6 Hz), 7.49 (1H, dd, J = 10.4, 1.2 Hz), 7.17 (1H, dd, J = 8.2, 1.5 Hz), 4.81 (1H, s), 4.61 (2H, s), 4.49-3.87 (3H, m), 2.28-2.11 (2H, m), 1.80-1.51 (3H, m), 1.15 (6H, s), 0.89 (1H, dd, J = 11.7, 4.7 Hz). |
| 193 | O | (structure) | (structure) Racemate Relative configuration | (structure) | 502.2 | 1H-NMR (DMSO-D6) δ: 7.80 (1H, t, J = 7.6 Hz), 7.68 (1H, s), 7.60 (1H, s), 7.53 (1H, d, J = 7.9 Hz), 7.29 (1H, t, J = 5.3 Hz), 7.21 (1H, t, J = 7.9 Hz), 7.15 (1H, dd, J = 8.2, 1.5 Hz), 7.07 (1H, d, J = 7.9 Hz), 6.95 (1H, d, J = 11.6 Hz), 4.46-3.86 (3H, m), 2.65 (2H, s), 2.25-2.10 (2H, m), 1.74-1.49 (4H, m), 1.04 (6H, s), 0.87 (1H, dd, J = 12.2, 4.6 Hz). |
| 194 | O | (structure) | (structure) | (structure) | 570.2 | 1H-NMR (DMSO-D6) δ: 8.09 (1H, d, J = 0.6 Hz), 7.79-7.74 (2H, m), 7.63 (1H, dd, J = 7.9, 1.5 Hz), 7.57-7.55 (2H, m), 7.43 (1H, d, J = 10.7 Hz), 7.39 (1H, dd, J = 10.5, 1.4 Hz), 7.12 (1H, dd, J = 8.2, 1.5 Hz), 4.59 (1H, s), 4.48 (1H, s), 4.42-4.38 (2H, m), 4.08 (1H, s), 2.23-2.12 (3H, m), 1.98-1.87 (5H, m), 1.62-1.51 (3H, m), 1.12 (6H, s). |
| 195 | O | (structure) | (structure) Racemate Relative configuration | (structure) | 560.1 | 1H-NMR (DMSO-D6) δ: 8.19 (1H, d, J = 1.8 Hz), 7.79-7.75 (1H, m), 7.73-7.70 (1H, m), 7.64-7.57 (3H, m), 7.43 (1H, dd, J = 10.5, 1.4 Hz), 7.14 (1H, dd, J = 8.1, 1.7 Hz), 4.69 (1H, s), 4.33-3.66 (5H, m), 2.20-2.14 (2H, m), 1.78-1.72 (1H, m), 1.65-1.50 (2H, m), 1.10 (6H, s), 0.93-0.89 (1H, m). |

TABLE 21-continued

| | | | | | |
|---|---|---|---|---|---|
| 196 | O | benzonitrile with F | bicyclic amine NH2, Racemate Relative configuration | indole with F, F, OH substituents | 559.1 1H-NMR (DMSO-D6) δ: 7.76 (1H, t, J = 7.6 Hz), 7.62-7.58 (2H, m), 7.38-7.30 (4H, m), 7.14 (1H, dd, J = 8.2, 1.5 Hz), 6.52-6.50 (1H, m), 4.71 (1H, s), 4.44-3.93 (5H, m), 2.19-2.13 (2H, m), 1.78-1.72 (1H, m), 1.64-1.50 (2H, m), 1.04 (6H, s), 0.92-0.88 (1H, m). |
| 197 | O | benzonitrile with F | pyrrolidine with NH2 and methyl | indazole with F, F, OH | 548.2 1H-NMR (DMSO-D6) δ: 8.19 (1H, d, J = 1.8 Hz), 7.79-7.69 (3H, m), 7.64-7.58 (2H, m), 7.40 (1H, dd, J = 9.9, 4.1 Hz), 7.12 (1H, dd, J = 8.1, 1.7 Hz), 4.69 (1H, s), 4.33 (2H, s), 3.75-3.64 (4H, m), 1.80 (2H, t, J = 7.3 Hz), 1.30-1.18 (3H, m), 1.10 (6H, s). |
| 198 | O | benzonitrile with F | pyrrolidine with NH2 and methyl | indole with F, F, OH | 547.2 1H-NMR (DMSO-D6) δ: 7.76 (1H, t, J = 7.5 Hz), 7.71-7.58 (3H, m), 7.37 (1H, d, J = 3.1 Hz), 7.31-7.29 (1H, m), 7.12 (1H, dd, J = 8.1, 1.4 Hz), 6.56 (1H, s), 6.52-6.50 (1H, m), 4.71 (1H, s), 4.13 (2H, s), 3.74-3.63 (4H, m), 1.81-1.78 (2H, m), 1.29-1.17 (3H, m), 1.04 (6H, s). |
| 199 | O | benzonitrile with F | diazaspiro HN, N | indazole with F, F, OH | 542.1 1H-NMR (DMSO-D6) δ: 8.10 (1H, d, J = 3.7 Hz), 7.77-7.74 (2H, m), 7.72-7.69 (1H, m), 7.65 (1H, d, J = 9.2 Hz), 7.58 (1H, dd, J = 12.5, 7.9 Hz), 7.45 (1H, dd, J = 10.7, 4.6 Hz), 7.40-7.36 (1H, m), 7.13-7.99 (1H, m), 4.61 (1H, s), 4.25 (2H, s), 3.82-3.52 (8H, m), 2.13-2.07 (2H, m), 1.10 (6H, s). |

TABLE 22

| | | | | | |
|---|---|---|---|---|---|
| 200 | O | benzonitrile with F | diazaspiro HN, N | indole with F, F, OH | 559.1 1H-NMR (DMSO-D6) δ: 7.78-7.74 (1H, m), 7.72-7.68 (1H, m), 7.66-7.64 (1H, m), 7.62-7.58 (1H, m), 7.39-7.29 (3H, m), 7.14-7.10 (1H, m), 6.51 (1H, s), 4.71 (1H, s), 4.13 (2H, s), 3.76-3.50 (8H, m), 2.11-2.07 (2H, m), 1.05 (6H, s). |
| 201 | O | benzonitrile with F | azaspiro HN, N | indole with F, F, OH | 573.2 1H-NMR (DMSO-D6) δ: 7.82 (1H, dd, J = 7.9, 1.8 Hz), 7.77 (1H, t, J = 7.5 Hz), 7.74 (1H, d, J = 1.8 Hz), 7.61 (1H, d, J = 7.9 Hz), 7.38 (1H, d, J = 3.1 Hz), 7.34-7.29 (2H, m), 7.12 (1H, dd, J = 7.9, 1.5 Hz), 6.52-6.50 (1H, m), 4.71 (1H, s), 4.13-4.04 (4H, m), 3.75 (2H, dd, J = 46.2, 9.9 Hz), 3.25-3.16 (2H, m), 2.86-2.81 (2H, m), 1.73-1.68 (2H, m), 1.47-1.41 (2H, m), 1.04 (6H, s). |
| 202 | O | benzonitrile with F | bicyclic amine NH2, isomer-X Relative configuration | benzisoxazole with F, methyl | 485.2 1H-NMR (DMSO-D6) δ: 7.83 (1H, d, J = 5.5 Hz), 7.78 (1H, t, J = 7.5 Hz), 7.74-7.72 (1H, m), 7.66-7.61 (3H, m), 7.47 (1H, dd, J = 10.5, 1.4 Hz), 7.14 (1H, dd, J = 7.9, 1.5 Hz), 4.46-3.90 (2H, m), 3.22-3.16 (1H, m), 2.52 (3H, s), 2.21-2.12 (2H, m), 1.78-1.72 (1H, m), 1.64-1.50 (2H, m), 0.93-0.90 (1H, m). |
| 203 | O | benzonitrile with F | pyrrolopyrrolidine HN, N | indole with F, F, OH | 559.1 1H-NMR (DMSO-D6) δ: 7.76 (1H, t, J = 7.5 Hz), 7.67 (1H, dd, J = 7.9, 1.8 Hz), 7.62-7.58 (2H, m), 7.38 (1H, d, J = 3.1 Hz), 7.33 (1H, dd, J = 10.5, 1.4 Hz), 7.30 (1H, d, J = 5.8 Hz), 7.12 (1H, dd, J = 7.9, 1.5 Hz), 6.52-6.50 (1H, m), 4.70 (1H, s), 4.13 (2H, s), 3.85-3.70 (4H, m), 3.07-2.75 (6H, m), 1.05 (6H, s). |
| 204 | O | benzonitrile with F | pyrrolidine with NH2 | indazole with F, OH, ethyl | 544.2 1H-NMR (DMSO-D6) δ: 8.10 (1H, d, J = 0.6 Hz), 7.77-7.74 (2H, m), 7.71-7.68 (1H, m), 7.65-7.63 (1H, m), 7.57 (1H, d, J = 8.2 Hz), 7.43 (1H, d, J = 11.0 Hz), 7.37 (1H, dd, J = 10.5, 2.3 Hz), 7.12 (1H, dd, J = 3.2, 1.5 Hz), 4.33 (1H, s), 4.24 (2H, s), 3.68-3.60 (4H, m), 3.21-3.18 (1H, m), 2.04-1.99 (1H, m), 1.74-1.67 (1H, m), 1.38-1.30 (4H, m), 0.85 (6H, t, J = 7.3 Hz). |

TABLE 22-continued

| | | | | | |
|---|---|---|---|---|---|
| 205 | O | 4-cyano-2-fluorophenyl | 8-azabicyclo[3.2.1]octan-3-amine | 6-fluoro-5-fluoro-1-(2-hydroxy-2-ethylbutyl)-1H-indazole | 584.2 1H-NMR (DMSO-D6) δ: 8.10 (1H, d, J = 0.6 Hz), 7.77-7.74 (2H, m), 7.63 (1H, dd, J = 7.9, 1.8 Hz), 7.58-7.55 (2H, m), 7.44 (1H, d, J = 11.0 Hz), 7.38 (1H, dd, J = 10.7, 1.2 Hz), 7.12 (1H, dd, J = 8.1, 1.4 Hz), 4.59 (1H, s), 4.34 (1H, s), 4.24 (2H, s), 4.08 (1H, s), 2.23-2.13 (3H, m), 2.02-1.88 (3H, m), 1.80-1.50 (3H, m), 1.39-1.31 (4H, m), 0.85 (6H, t, J = 7.5 Hz). |
| 206 | O | 4-cyano-2-fluorophenyl | isomer-X Relative configuration | 6-fluoro-5-fluoro-1-(2-hydroxy-2-ethylbutyl)-1H-indazole | 570.2 1H-NMR (DMSO-D6) δ: 8.10 (1H, d, J = 0.9 Hz), 7.77-7.74 (2H, m), 7.72-7.69 (1H, m), 7.62-7.56 (2H, m), 7.44 (1H, d, J = 11.0 Hz), 7.39 (1H, dd, J = 10.5, 1.4 Hz), 7.13 (1H, dd, J = 8.2, 1.5 Hz), 4.45-3.64 (6H, m), 2.19-2.13 (2H, m), 1.79-1.73 (1H, m), 1.65-1.51 (2H, m), 1.37-1.31 (4H, m), 0.92 (1H, dd, J = 12.1, 4.1 Hz), 0.85 (6H, t, J = 7.3 Hz). |
| 207 | O | 4-cyano-2-fluorophenyl | isomer-X Relative configuration | 6-fluoro-1H-indol-1-yl acetic acid | 527.2 1H-NMR (DMSO-D6) δ: 7.75 (1H, t, J = 7.5 Hz), 7.70 (1H, d, J = 7.9 Hz), 7.61 (1H, s), 7.54 (1H, d, J = 7.9 Hz), 7.48 (1H, d, J = 7.3 Hz), 7.38 (1H, d, J = 10.1 Hz), 7.33 (1H, d, J = 3.1 Hz), 7.15 (1H, d, J = 11.0 Hz), 7.12 (1H, d, J = 8.9 Hz), 6.43 (1H, d, J = 2.7 Hz), 4.79 (2H, s), 4.46-3.48 (3H, m), 2.24-2.05 (2H, m), 1.80-1.76 (1H, m), 1.69-1.54 (1H, m), 1.57-1.53 (1H, m), 1.06-1.01 (1H, m). |

TABLE 23

| | | | | | |
|---|---|---|---|---|---|
| 208 | O | 4-cyano-2-fluorophenyl | isomer-X Relative configuration | 4-fluorophenylacetic acid | 488.2 1H-NMR (DMSO-D6) δ: 7.80 (1H, t, J = 7.5 Hz), 7.71-7.68 (1H, m), 7.61-7.58 (1H, m), 7.53 (1H, d, J = 7.9 Hz), 7.37 (1H, dd, J = 10.5, 1.4 Hz), 7.26 (1H, t, J = 7.9 Hz), 7.14-7.11 (2H, m), 7.03 (1H, d, J = 11.3 Hz), 4.43-3.57 (5H, m), 2.19-2.13 (2H, m), 1.78-1.72 (1H, m), 1.59-1.50 (2H, m), 0.90 (1H, dd, J = 11.9, 4.3 Hz). |
| 209 | O | 4-cyano-2-fluorophenyl | isomer-X Relative configuration | 7-chloro-6-fluoro-1-(2-hydroxy-2-methylpropyl)-1H-benzotriazole | 577.2 579.2 1H-NMR (DMSO-D6) δ: 8.10 (1H, d, J = 6.1 Hz), 7.74-7.69 (2H, m), 7.63-7.59 (2H, m), 7.44 (1H, d, J = 10.4 Hz), 7.11 (1H, dd, J = 7.9, 1.5 Hz), 4.78 (2H, s), 4.71 (1H, s), 4.41-3.56 (3H, m), 2.18-2.10 (2H, m), 1.75-1.68 (1H, m), 1.60-1.54 (1H, m), 1.51-1.46 (1H, m), 1.13 (6H, s), 0.86 (1H, dd, J = 12.1, 4.7 Hz). |
| 210 | O | 4-cyano-2-fluorophenyl | (S)-pyrrolidin-3-amine | 7-chloro-6-fluoro-1-(2-hydroxy-2-methylpropyl)-1H-benzotriazole | 551.2 553.2 1H-NMR (DMSO-D6) δ: 8.10 (1H, d, J = 6.1 Hz), 7.73-7.68 (2H, m), 7.65-7.61 (2H, m), 7.43-7.40 (1H, m), 7.10 (1H, dd, J = 8.1, 1.4 Hz), 4.78 (2H, s), 4.71 (1H, s), 3.65-3.46 (4H, m), 3.24-3.23 (1H, m), 1.98-1.93 (1H, m), 1.63-1.59 (1H, m), 1.13 (6H, s). |
| 211 | O | 4-cyano-2-fluorophenyl | 8-azabicyclo[3.2.1]octan-3-amine | 7-chloro-6-fluoro-1-(2-hydroxy-2-methylpropyl)-1H-benzotriazole | 591.2 593.2 1H-NMR (DMSO-D6) δ: 8.10 (1H, d, J = 6.1 Hz), 7.71 (1H, t, J = 7.5 Hz), 7.62-7.60 (2H, m), 7.55 (1H, s), 7.42 (1H, dd, J = 10.5, 1.4 Hz), 7.10 (1H, dd, J = 7.9, 1.5 Hz), 4.77 (2H, s), 4.70 (1H, s), 4.53 (1H, s), 4.01 (1H, s), 2.22-2.04 (3H, m), 1.92-1.80 (3H, m), 1.55-1.45 (3H, m), 1.12 (6H, s). |
| 212 | O | 4-cyano-2-fluorophenyl | isomer-X Relative configuration | 5-fluoro-1-(2-hydroxy-2-methylpropyl)-1H-indazole-3-carboxylic acid | 586.2 1H-NMR (DMSO-D6) δ: 8.10 (1H, d, J = 7.3 Hz), 7.76-7.70 (2H, m), 7.63-7.58 (2H, m), 7.48 (1H, d, J = 10.7 Hz), 7.41 (1H, d, J = 10.4 Hz), 7.12 (1H, dd, J = 7.9, 1.5 Hz), 4.67 (1H, s), 4.46-3.50 (5H, m), 2.21-2.12 (2H, m), 1.80-1.74 (1H, m), 1.66-1.60 (1H, m), 1.56-1.51 (1H, m), 1.11 (6H, s), 0.98-0.93 (1H, m). |

TABLE 23-continued

| 213 | O | 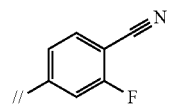 | 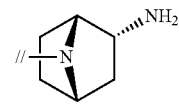 Racemate Relative configuration | 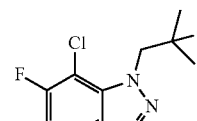 | 577.3 579.2 | 1H-NMR (DMSO-D6) δ: 8.14 (1H, d, J = 6.1 Hz), 7.78-7.73 (2H, m), 7.68-7.63 (2H, m), 7.48 (1H, d, J = 9.2 Hz), 7.15 (1H, dd, J = 8.1, 1.1 Hz), 4.81 (2H, s), 4.75 (1H, s), 4.45-3.82 (3H, m), 2.22-2.12 (2H, m), 1.79-1.73 (1H, m), 1.64-1.59 (1H, m), 1.55-1.50 (1H, m), 1.17 (6H, s), 0.91 (1H, dd, J = 11.7, 4.4 Hz). |
|---|---|---|---|---|---|---|
| 214 | O | 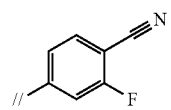 | 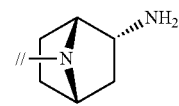 isomer-X Relative configuration | 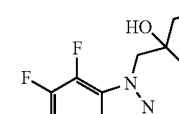 | 589.3 | 1H-NMR (DMSO-D6) δ: 7.97 (1H, d, J = 5.2 Hz), 7.79-7.72 (2H, m), 7.66-7.63 (2H, m), 7.49 (1H, dd, J = 10.4, 1.2 Hz), 7.17 (1H, dd, J = 7.9, 1.5 Hz), 4.61 (2H, s), 4.45 (1H, s), 4.33-3.50 (3H, m), 2.21-2.15 (2H, m), 1.79-1.72 (1H, m), 1.64-1.50 (2H, m), 1.44-1.35 (4H, m), 0.91-0.87 (7H, m). |
| 215 | O | 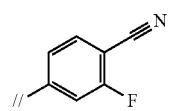 | 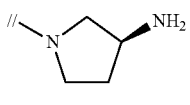 | 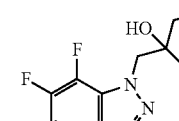 | 563.3 | 1H-NMR (DMSO-D6) δ: 7.97 (1H, d, J = 4.9 Hz), 7.78-7.72 (2H, m), 7.68 (1H, d, J = 8.2 Hz), 7.64 (1H, d, J = 7.6 Hz), 7.47 (1H, d, J = 10.4 Hz), 7.15 (1H, dd, J = 7.9, 1.5 Hz), 4.61 (2H, s), 4.46 (1H, s), 3.67-3.43 (4H, m), 3.22-3.16 (1H, m), 2.04-1.90 (1H, m), 1.70-1.62 (1H, m), 1.44-1.35 (4H, m), 0.89 (6H, t, J = 7.5 Hz). |
| 216 | O | 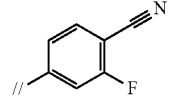 | 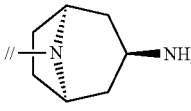 | 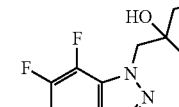 | 603.3 | 1H-NMR (DMSO-D6) δ: 7.97 (1H, d, J = 5.2 Hz), 7.77 (1H, t, J = 7.5 Hz), 7.67-7.59 (3H, m), 7.48 (1H, d, J = 11.3 Hz), 7.16 (1H, d, J = 8.9 Hz), 4.61 (2H, s), 4.58 (1H, s), 4.46 (1H, s), 4.05 (1H, s), 2.33-2.20 (2H, m), 2.12-2.07 (1H, m), 1.96-1.84 (3H, m), 1.61-1.49 (3H, m), 1.42-1.37 (4H, m), 0.83 (6H, t, J = 7.3 Hz). |

TABLE 24

| 217 | O | 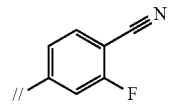 | 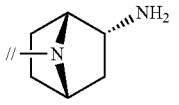 Racemate Relative configuration | 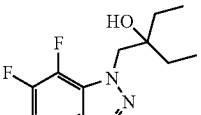 | 589.3 | 1H-NMR (DMSO-D6) δ: 7.97 (1H, d, J = 5.2 Hz), 7.79-7.72 (2H, m), 7.66-7.63 (2H, m), 7.49 (1H, dd, J = 10.4, 1.2 Hz), 7.17 (1H, dd, J = 7.9, 1.5 Hz), 4.61 (2H, s), 4.45 (1H, s), 4.33-3.50 (3H, m), 2.21-2.15 (2H, m), 1.79-3.72 (1H, m), 1.64-1.50 (2H, m), 1.44-1.35 (4H, m), 0.91-0.87 (7H, m). |
|---|---|---|---|---|---|---|
| 218 | O | 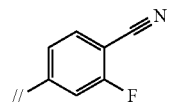 | 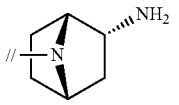 isomer-X Relative configuration | 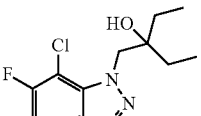 | 605.2 607.2 | 1H-NMR (DMSO-D6) δ: 8.14 (1H, d, J = 6.1 Hz), 7.79-7.72 (2H, m), 7.67-7.63 (2H, m), 7.50-7.48 (1H, m), 7.15 (1H, dd, J = 7.9, 1.5 Hz), 4.81 (2H, s), 4.45-3.92 (4H, m), 2.22-2.13 (2H, m), 1.79-1.73 (1H, m), 1.64-1.59 (1H, m), 1.55-1.37 (5H, m), 0.93-0.87 (7H, m). |
| 219 | O | 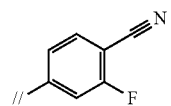 | 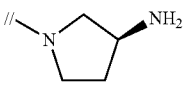 | 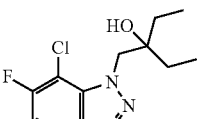 | 579.2 581.3 | 1H-NMR (DMSO-D6) δ: 8.14 (1H, d, J = 5.5 Hz), 7.78-7.72 (2H, m), 7.68 (1H, d, J = 7.9 Hz), 7.65 (1H, d, J = 7.9 Hz), 7.47 (1H, dd, J = 10.4, 3.2 Hz), 7.14 (1H, d, J = 7.9 Hz), 4.82 (2H, s), 4.37 (1H, s), 3.69-3.49 (4H, m), 3.23-3.20 (1H, m), 2.06-1.97 (1H, m), 1.75-1.67 (1H, m), 1.52-1.35 (4H, m), 0.90 (6H, t, J = 7.3 Hz). |
| 220 | O | 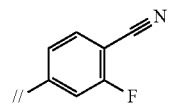 | 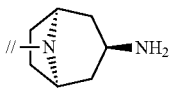 | 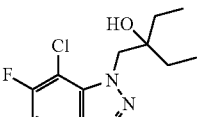 | 619.3 621.2 | 1H-NMR (DMSO-D6) δ: 8.14 (1H, d, J = 6.1 Hz), 7.78-7.74 (1H, m), 7.68-7.59 (3H, m), 7.50-7.47 (1H, m), 7.14 (1H, dd, J = 7.9, 1.5 Hz), 4.82 (2H, s), 4.50 (1H, s), 4.37 (1H, s), 4.07 (1H, s), 2.24-2.13 (3H, m), 2.02-1.88 (3H, m), 1.63-1.33 (7H, m), 0.90 (6H, t, J = 7.5 Hz). |

TABLE 24-continued

| 221 | O | 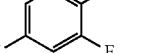 | 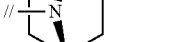Racemate Relative configuration | 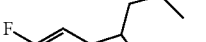 | 605.2 607.2 | 1H-NMR (DMSO-D6) δ: 8.14 (1H, d, J = 6.1 Hz), 7.79-7.72 (2H, m), 7.67-7.63 (2H, m), 7.50-7.48 (1H, m), 7.15 (1H, dd, J = 7.9, 1.5 Hz), 4.81 (2H, s), 4.45-3.92 (4H, m), 2.22-2.13 (2H, m), 1.79-1.73 (1H, m), 1.64-1.59 (1H, m), 1.55-1.37 (5H, m), 0.93-0.87 (7H, m). |
| --- | --- | --- | --- | --- | --- | --- |
| 222 | O | | isomer-X Relative configuration | | 585.3 | 1H-NMR (DMSO-D6) δ: 7.99 (1H, s), 7.94 (1H, d, J = 7.6 Hz), 7.76-7.68 (2H, m), 7.62-7.58 (2H, m), 7.46 (1H, d, J = 11.3 Hz), 7.34 (1H, d, J = 5.3 Hz), 7.11 (1H, dd, J = 7.9, 1.5 Hz), 4.73 (1H, s), 4.44-3.51 (5H, m), 2.21-2.13 (2H, m), 1.78-1.72 (1H, m), 1.60-1.50 (2H, m), 1.06 (6H, s), 0.89 (1H, dd, J = 12.1, 4.4 Hz). |
| 223 | O | | isomer-X Relative configuration | | 528.2 | 1H-NMR (DMSO-D6) δ: 8.16 (1H, d, J = 7.3 Hz), 7.77-7.70 (2H, m), 7.62-7.60 (1H, m), 7.57 (1H, d, J = 7.9 Hz), 7.43 (2H, d, J = 10.4 Hz), 7.09 (1H, dd, J = 7.9, 1.5 Hz), 4.44-3.50 (6H, m), 2.19-2.14 (2H, m), 1.79-1.74 (1H, m), 1.64-1.59 (1H, m), 1.55-1.50 (1H, m), 0.94-0.90 (1H, m). |
| 224 | O | | isomer-X Relative configuration | | 527.2 | 1H-NMR (DMSO-D6) δ: 8.07 (1H, s), 7.96 (1H, d, J = 7.3 Hz), 7.77-7.69 (2H, m), 7.62-7.55 (2H, m), 7.41 (1H, dd, J = 10.5, 1.4 Hz), 7.36 (1H, d, J = 10.7 Hz), 7.10 (1H, dd, J = 8.2, 1.5 Hz), 4.44-3.51 (6H, m), 2.20-2.13 (2H, m), 1.79-1.73 (1H, m), 1.60-1.50 (2H, m), 0.91 (1H, dd, J = 12.2, 4.6 Hz). |
| 225 | O | | Racemate Relative configuration | | 570.3 | 1H-NMR (DMSO-D6) δ: 8.10 (1H, d, J = 0.9 Hz), 7.77-7.74 (2H, m), 7.72-7.69 (1H, m), 7.62-7.56 (2H, m), 7.44 (1H, d, J = 11.0 Hz), 7.39 (1H, dd, J = 10.5, 1.4 Hz), 7.13 (1H, dd, J = 8.2, 1.5 Hz), 4.45-3.64 (6H, m), 2.19-2.13 (2H, m), 1.79-1.73 (1H, m), 1.65-1.51 (2H, m), 1.37-1.31 (4H, m), 0.92 (1H, dd, J = 12.1, 4.1 Hz), 0.85 (6H, t, J = 7.3 Hz). |

TABLE 25

| 226 | O |  | isomer-X Relative configuration |  | 544.3 | 1H-NMR (DMSO-D6) δ: 7.83-7.80 (1H, m), 7.70-7.67 (1H, m), 7.61-7.58 (1H, m), 7.53 (1H, d, J = 7.9 Hz), 7.41-7.38 (1H, m), 7.28 (1H, d, J = 6.7 Hz), 7.13 (1H, d, J = 7.9 Hz), 7.02 (1H, d, J = 10.1 Hz), 5.30 (1H, d, J = 8.9 Hz), 4.99-4.87 (2H, m), 4.44-3.53 (4H, m), 2.21-2.11 (2H, m), 1.92-1.88 (1H, m), 1.77-1.49 (4H, m), 1.23-1.18 (6H, m), 0.88 (1H, dd, J = 12.1, 4.7 Hz). |
| --- | --- | --- | --- | --- | --- | --- |
| 227 | O | | | | 518.2 | 1H-NMR (DMSO-D6) δ: 7.83-7.80 (1H, m), 7.70-7.67 (1H, m), 7.64-7.62 (1H, m), 7.52 (1H, dd, J = 7.9, 2.1 Hz), 7.37 (1H, d, J = 9.5 Hz), 7.29 (1H, d, J = 6.4 Hz), 7.11 (1H, dd, J = 7.9, 1.5 Hz), 7.01 (1H, d, J = 9.8 Hz), 5.30 (1H, d, J = 7.3 Hz), 4.99-4.88 (2H, m), 4.35-4.33 (1H, m), 3.67-3.50 (4H, m), 3.17-3.12 (1H, m), 2.01-1.88 (2H, m), 1.71-1.62 (2H, m), 1.22-1.19 (6H, m). |

TABLE 25-continued

| | | | | | |
|---|---|---|---|---|---|
| 228 | O | 4-cyano-2-fluorophenyl | bicyclic amine, isomer-X Relative configuration | fluoro-methyl-benzotriazole with 2-hydroxy-2-methylpropyl | 557.2 | 1H-NMR (DMSO-D6) δ: 7.87 (1H, d, J = 6.1 Hz), 7.79-7.68 (2H, m), 7.65-7.56 (2H, m), 7.46 (1H, d, J = 10.4 Hz), 7.15 (1H, dd, J = 8.2, 1.5 Hz), 4.78 (1H, s), 4.69 (2H, s), 4.49-3.87 (3H, m), 2.49 (3H, s), 2.24-2.11 (2H, m), 1.81-1.48 (3H, m), 1.20 (6H, s), 0.90 (1H, dd, J = 12.2, 4.3 Hz). |
| 229 | O | 4-cyano-2-fluorophenyl | pyrrolidinyl amine | fluoro-benzisoxazole with 2-hydroxy-2-methylpropyl | 517.2 | 1H-NMR (DMSO-D6) δ: 7.81-7.62 (6H, m), 7.44 (1H, d, J = 8.9 Hz), 7.16-7.13 (1H, m), 4.70 (1H, s), 3.73-3.51 (5H, m), 3.03 (2H, s), 2.03-1.93 (1H, m), 1.70-1.61 (1H, m), 1.18 (6H, s). |
| 230 | O | 4-cyano-2-fluorophenyl | bicyclic amine, Racemate Relative configuration | fluoro-indolyl-acetamide | 526.2 | 1H-NMR (DMSO-D6) δ: 8.34 (2H, s), 7.76 (1H, t, J = 7.5 Hz), 7.53 (3H, dd, J = 15.4, 7.5 Hz), 7.40 (1H, d, J = 10.4 Hz), 7.34 (1H, d, J = 3.1 Hz), 7.24 (1H, s), 7.14 (2H, dd, J = 12.8, 6.1 Hz), 6.47 (1H, d, J = 3.4 Hz), 4.75 (2H, s), 4.45-3.94 (3H, m), 2.26-2.14 (2H, m), 1.82-1.70 (1H, m), 1.66-1.46 (2H, m), 0.90 (1H, dd, J = 12.2, 4.6 Hz). |
| 231 | O | 4-cyano-2-fluorophenyl | bicyclic amine, Racemate Relative configuration | fluoro-indolyl-N-methylacetamide | 540.2 | 1H-NMR (DMSO-D6) δ: 8.03 (1H, d, J = 4.6 Hz), 7.91 (1H, d, J = 7.0 Hz), 7.76 (1H, t, J = 7.5 Hz), 7.56-7.48 (2H, m), 7.47-7.38 (2H, m), 7.34 (1H, d, J = 3.1 Hz), 7.20-7.09 (2H, m), 6.47 (1H, d, J = 2.7 Hz), 4.76 (2H, s), 4.48-3.92 (3H, m), 2.61 (3H, d, J = 4.6 Hz), 2.26-2.13 (2H, m), 1.82-1.72 (1H, m), 1.68-1.46 (2H, m), 0.90 (1H, dd, J = 12.1, 4.4 Hz). |
| 232 | O | 4-cyano-2-fluorophenyl | bicyclic amine, Racemate Relative configuration | fluoro-indolyl-N,N-dimethylacetamide | 554.2 | 1H-NMR (DMSO-D6) δ: 7.93 (1H, t, J = 4.1 Hz), 7.77 (1H, t, J = 7.6 Hz), 7.53 (2H, dd, J = 19.1, 7.5 Hz), 7.47 (1H, d, J = 7.9 Hz), 7.39 (1H, d, J = 10.4 Hz), 7.27 (1H, d, J = 3.1 Hz), 7.15 (2H, dt, J = 13.2, 6.0 Hz), 6.46 (1H, d, J = 3.4 Hz), 5.11 (2H, s), 4.46-3.87 (3H, m), 3.08 (3H, d, J = 12.2 Hz), 2.85 (3H, s), 2.25-2.15 (2H, m), 1.82-1.71 (1H, m), 1.67-1.50 (2H, m), 0.95-0.87 (1H, m). |
| 233 | O | 4-cyano-2-fluorophenyl | bicyclic amine, Racemate Relative configuration | fluoro-phenylacetamide | 487.2 | 1H-NMS (DMSO-D6) δ: 7.83 (1H, dd, J = 23.7, 7.2 Hz), 7.72-7.56 (1H, m), 7.52 (1H, t, J = 7.5 Hz), 7.33 (3H, ddd, J = 33.5, 19.8, 8.0 Hz), 7.05 (3H, dq, J = 53.3, 15.3 Hz), 4.40-3.87 (3H, m), 3.01 (2H, s), 2.22-2.14 (2H, m), 1.83-1.57 (3H, m), 0.91-0.85 (1H, m). |
| 234 | O | 4-cyano-2-fluorophenyl | bicyclic amine, Racemate Relative configuration | fluoro-phenyl-N-methylacetamide | 501.2 | 1H-NMR (DMSO-D6) δ: 7.83-7.79 (2H, m), 7.56-7.45 (2H, m), 7.38 (1H, d, J = 10.7 Hz), 7.27 (1H, t, J = 7.9 Hz), 7.12 (2H, td, J = 9.1, 3.7 Hz), 7.00 (1H, d, J = 11.0 Hz), 4.45-4.07 (3H, m), 3.02 (2H, s), 2.58 (3H, d, J = 4.6 Hz), 2.21-2.15 (2H, m), 1.79-1.72 (1H, m), 1.64-1.51 (2H, m), 0.93-0.85 (1H, m). |

TABLE 26

| | | | | | |
|---|---|---|---|---|---|
| 235 | O | 4-cyano-2-fluorophenyl | bicyclic amine, Racemate Relative configuration | fluoro-phenyl-N,N-dimethylacetamide | 515.2 | 1H-NMR (DMSO-D6) δ: 7.96-7.91 (1H, m), 7.82 (1H, t, J = 7.6 Hz), 7.54 (1H, d, J = 7.9 Hz), 7.49-7.44 (1H, m), 7.35 (1H, d, J = 10.7 Hz), 7.27 (1H, t, J = 7.9 Hz), 7.15 (1H, dd, J = 8.2, 1.5 Hz), 7.08 (1H, dd, J = 7.6 Hz), 6.97 (1H, d, J = 11.3 Hz), 4.47-3.89 (3H, m), 3.72 (2H, s), 3.00 (3H, s), 2.84 (3H, s), 2.22-2.13 (2H, m), 1.79-1.72 (1H, m), 1.67-1.48 (2H, m), 0.89 (1H, s). |

TABLE 26-continued

| | | | | | |
|---|---|---|---|---|---|
| 236 | O | 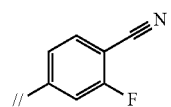 | 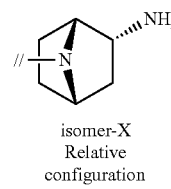<br>isomer-X<br>Relative configuration | 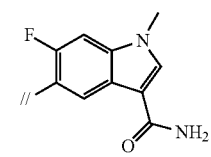 | 526.2 1H-NMR (DMSO-D6) δ: 8.14 (1H, d, J = 7.6 Hz), 8.01 (1H, s), 7.76 (1H, t, J = 7.6 Hz), 7.72-7.69 (1H, m), 7.60 (1H, s), 7.56 (1H, d, J = 7.9 Hz), 7.40 (1H, d, J = 10.4 Hz), 7.30 (1H, d, J = 10.7 Hz), 7.11 (1H, dd, J = 7.9, 1.5 Hz), 4.46-3.93 (3H, m), 3.77 (3H, s), 2.25-2.14 (2H, m), 1.81-1.72 (1H, m), 1.67-1.49 (2H, m), 0.93-0.86 (1H, m). |
| 237 | O | 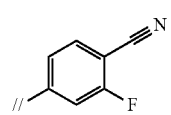 | 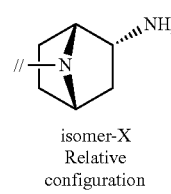<br>isomer-X<br>Relative configuration | 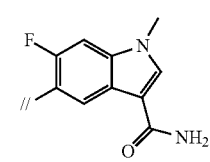 | 540.2 1H-NMR (DMSO-D6) δ: 8.13 (1H, d, J = 7.6 Hz), 7.94 (1H, s), 7.92-7.89 (1H, m), 7.78-7.55 (4H, m), 7.39 (1H, d, J = 9.2 Hz), 7.30 (1H, d, J = 10.7 Hz), 7.12 (1H, d, J = 7.9 Hz), 4.47-3.91 (3H, m), 3.77 (3H, s), 2.76 (3H, d, J = 4.6 Hz), 2.23-2.15 (2H, m), 1.80-1.74 (1H, m), 1.66-1.50 (2H, m), 0.90 (1H, dd, J = 12.1, 4.7 Hz). |
| 238 | O | 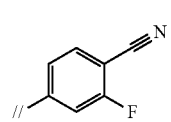 | 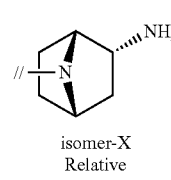<br>isomer-X<br>Relative configuration | 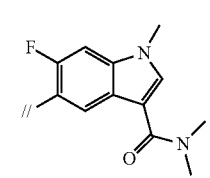 | 554.2 1H-NMR (DMSO-D6) δ: 7.83 (1H, s), 7.80-7.75 (2H, m), 7.73-7.68 (1H, m), 7.57 (2H, t, J = 18.3 Hz), 7.40 (1H, dd, J = 10.7, 1.5 Hz), 7.32 (1H, d, J = 11.0 Hz), 7.11 (1H, dd, J = 7.9, 1.5 Hz), 4.48-3.92 (3H, m), 3.80 (3H, d, J = 7.0 Hz), 3.06 (6H, s), 2.25-2.14 (2H, m), 1.80-1.70 (1H, m), 1.65-1.48 (2H, m), 0.90 (1H, t, J = 8.4 Hz). |
| 239 | O | 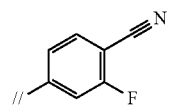 | 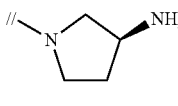 | 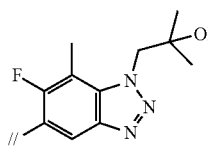 | 531.1 1H-NMR (DMSO-D6) δ: 7.87 (1H, d, J = 6.7 Hz), 7.80-7.64 (3H, m), 7.58 (1H, d, J = 7.9 Hz), 7.44 (1H, d, J = 10.4 Hz), 7.13 (1H, dd, J = 8.2, 1.5 Hz), 4.78 (1H, s), 4.69 (2H, s), 3.75-3.58 (5H, m), 2.49 (3H, s), 2.04-1.93 (1H, m), 1.74-1.64 (1H, m), 1.20 (6H, s). |
| 240 | O | 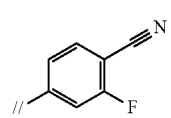 | 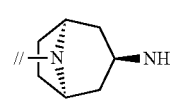 | 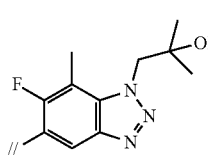 | 571.2 1H-NMR (DMSO-D6) δ: 7.87 (1H, d, J = 6.7 Hz), 7.75 (1H, t, J = 7.5 Hz), 7.63 (1H, d, J = 7.3 Hz), 7.60-7.55 (2H, m), 7.45 (1H, d, J = 10.4 Hz), 7.14 (1H, d, J = 7.9 Hz), 4.78 (1H, s), 4.69 (2H, s), 4.64-4.56 (1H, m), 4.11-4.04 (1H, m), 2.49 (3H, s), 2.34-2.20 (2H, m), 2.13-2.06 (1H, m), 1.99-1.85 (3H, m), 1.66-1.47 (3H, m), 1.20 (6H, s). |
| 241 | O | 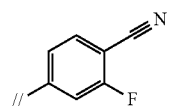 | 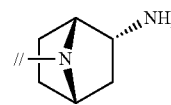<br>Racemate<br>Relative configuration | 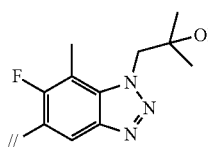 | 557.2 1H-NMR (DMSO-D6) δ: 7.87 (1H, d, J = 6.1 Hz), 7.79-7.68 (2H, m), 7.65-7.56 (2H, m), 7.46 (1H, d, J = 10.4 Hz), 7.15 (1H, dd, J = 8.2, 1.5 Hz), 4.78 (1H, s), 4.69 (2H, s), 4.49-3.87 (3H, m), 2.49 (3H, s), 2.24-2.11 (2H, m), 1.81-1.48 (3H, m), 1.20 (6H, s), 0.90 (1H, dd, J = 12.2, 4.3 Hz). |
| 242 | O | 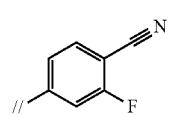 | 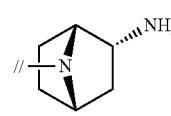<br>Racemate<br>Relative configuration | 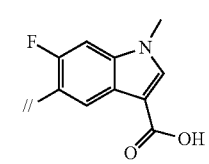 | 527.1 1H-NMR (DMSO-D6) δ: 8.07 (1H, s), 7.96 (1H, d, J = 7.3 Hz), 7.77-7.69 (2H, m), 7.62-7.55 (2H, m), 7.41 (1H, dd, J = 10.5, 1.4 Hz), 7.36 (1H, d, J = 10.7 Hz), 7.10 (1H, dd, J = 8.2, 1.5 Hz), 4.44-3.51 (6H, m), 2.20-2.13 (2H, m), 1.79-1.73 (1H, m), 1.60-1.50 (2H, m), 0.91 (1H, dd, J = 12.2, 4.6 Hz). |
| 243 | O | 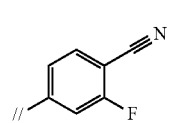 | 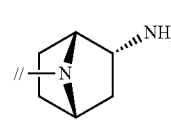<br>Racemate<br>Relative configuration | 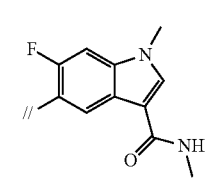 | 540.3 1H-NMR (DMSO-D6) δ: 8.13 (1H, d, J = 7.6 Hz), 7.94 (1H, s), 7.92-7.89 (1H, m), 7.78-7.55 (4H, m), 7.39 (1H, d, J = 9.2 Hz), 7.30 (1H, d, J = 10.7 Hz), 7.12 (1H, d, J = 7.9 Hz), 4.47-3.91 (3H, m), 3.77 (3H, s), 2.76 (3H, d, J = 4.6 Hz), 2.23-2.15 (2H, m), 1.80-1.74 (1H, m), 1.66-1.50 (2H, m), 0.90 (1H, dd, J = 12.1, 4.7 Hz). |

TABLE 27

| | | | | | |
|---|---|---|---|---|---|
| 244 | O | 4-cyano-2-fluorophenyl | 2-azabicyclic-NH2, Racemate Relative configuration | 5-fluoro-6-fluoro-1-methylindole-3-carboxamide N,N-dimethyl | 554.2 1H-NMR (DMSO-D6) δ: 7.83 (1H, s), 7.80-7.75 (2H, m), 7.73-7.58 (1H, m), 7.57 (2H, t, J = 18.3 Hz), 7.40 (1H, dd, J = 10.7, 1.5 Hz), 7.32 (1H, d, J = 11.0 Hz), 7.11 (1H, dd, J = 7.9, 1.5 Hz), 4.48-3.92 (3H, m), 3.80 (3H, d, J = 7.0 Hz), 3.06 (6H, s), 2.25-2.14 (2H, m), 1.80-1.70 (1H, m), 1.65-1.48 (2H, m), 0.90 (1H, t, J = 8.4 Hz). |
| 245 | O | 4-cyano-2-fluorophenyl | 2-azabicyclic-NH2, Racemate Relative configuration | 5-fluoro-6-fluoro-1-methylindole-3-carboxamide | 526.3 1H-NMR (DMSO-D6) δ: 8.14 (1H, d, J = 7.6 Hz), 8.01 (1H, s), 7.75 (1H, t, J = 7.6 Hz), 7.72-7.69 (1H, m), 7.60 (1H, s), 7.56 (1H, d, J = 7.9 Hz), 7.40 (1H, d, J = 10.4 Hz), 7.30 (1H, d, J = 10.7 Hz), 7.11 (1H, dd, J = 7.9, 1.5 Hz), 4.46-3.93 (3H, m), 3.77 (3H, s), 2.25-2.14 (2H, m), 1.81-1.72 (1H, m), 1.67-1.49 (2H, m), 0.93-0.86 (1H, m). |
| 246 | O | 4-cyano-2-fluorophenyl | 2-azabicyclic-NH2, isomer-X Relative configuration | 4-(difluoromethyl)-5-fluoro-benzotriazole-1-(2-hydroxy-2-methylpropyl) | 593.3 1H-NMR (DMSO-D6) δ: 8.40 (1H, d, J = 6.1 Hz), 7.80-7.52 (5H, m), 7.51-7.42 (1H, m), 7.15 (1H, dd, J = 8.1, 1.4 Hz), 5.03 (1H, s), 4.75 (2H, s), 4.48-3.87 (3H, m), 2.27-2.12 (2H, m), 1.81-1.72 (1H, m), 1.68-1.50 (2H, m), 1.16 (6H, s), 0.91-0.86 (1H, m). |
| 247 | O | 4-cyano-2-fluorophenyl | 2-azabicyclic-NH2, isomer-X Relative configuration | 4-cyano-5-fluoro-benzotriazole-1-(2-hydroxy-2-methylpropyl) | 568.3 1H-NMR (DMSO-D6) δ: 8.55 (1H, d, J = 6.7 Hz), 7.80-7.67 (4H, m), 7.53 (1H, d, J = 9.2 Hz), 7.19 (1H, dd, J = 8.2, 1.5 Hz), 4.83 (1H, s), 4.73 (2H, s), 4.52-3.87 (3H, m), 2.29-2.10 (2H, m), 1.83-1.72 (1H, m), 1.69-1.49 (2H, m), 1.22 (6H, s), 0.95-0.86 (1H, m). |
| 248 | O | 4-cyano-2-fluorophenyl | (3S)-pyrrolidin-3-amine | 4-(difluoromethyl)-5-fluoro-benzotriazole-1-(2-hydroxy-2-methylpropyl) | 567.3 1H-NMR (DMSO-D6) δ: 8.40 (1H, d, J = 5.5 Hz), 7.87-7.62 (5H, m), 7.43 (1H, d, J = 10.4 Hz), 7.14 (1H, dd, J = 8.1, 1.4 Hz), 5.03 (1H, s), 4.75 (2H, s), 3.79-3.60 (5H, m), 2.06-1.92 (1H, m), 1.75-1.62 (1H, m), 1.17 (6H, s). |
| 249 | O | 4-cyano-2-fluorophenyl | (3S)-pyrrolidin-3-amine | 4-cyano-5-fluoro-benzotriazole-1-(2-hydroxy-2-methylpropyl) | 542.3 1H-NMR (DMSO-D6) δ: 8.56 (1H, d, J = 6.4 Hz), 7.83-7.66 (4H, m), 7.51 (1H, d, J = 10.4 Hz), 7.22-7.14 (1H, m), 4.83 (1H, s), 4.73 (2H, s), 3.80-3.60 (5H, m), 2.06-1.92 (1H, m), 1.77-1.59 (1H, m), 1.22 (6H, s). |
| 250 | O | 4-cyano-2-fluorophenyl | 8-azabicyclic-NH2 | 4-(difluoromethyl)-5-fluoro-benzotriazole-1-(2-hydroxy-2-methylpropyl) | 607.3 1H-NMR (DMSO-D6) δ: 8.41 (1H, d, J = 6.1 Hz), 7.89-7.59 (5H, m), 7.45 (1H, d, J = 10.4 Hz), 7.15 (1H, dd, J = 7.9, 1.5 Hz), 5.03 (1H, s), 4.75 (2H, s), 4.64-4.56 (1H, m), 4.11-4.02 (1H, m), 2.33-1.84 (6H, m), 1.66-1.46 (3H, m), 1.17 (6H, s). |
| 251 | O | 4-cyano-2-fluorophenyl | 8-azabicyclic-NH2 | 4-cyano-5-fluoro-benzotriazole-1-(2-hydroxy-2-methylpropyl) | 582.3 1H-NMR (DMSO-D6) δ: 8.56 (1H, d, J = 6.4 Hz), 7.84-7.76 (1H, m), 7.68 (2H, s), 7.61 (1H, s), 7.52 (1H, d, J = 10.4 Hz), 7.19 (1H, dd, J = 8.1, 1.4 Hz), 4.83 (1H, s), 4.73 (2H, s), 4.63-4.55 (1H, m), 4.11-4.02 (1H, m), 2.33-1.82 (6H, m), 1.65-1.46 (3H, m), 1.22 (6H, s). |
| 252 | O | 4-cyano-2-fluorophenyl | 2-azabicyclic-NH2, Racemate Relative configuration | 4-(difluoromethyl)-5-fluoro-benzotriazole-1-(2-hydroxy-2-methylpropyl) | 593.3 1H-NMR (DMSO-D6) δ: 8.40 (1H, d, J = 6.1 Hz), 7.80-7.62 (5H, m), 7.51-7.42 (1H, m), 7.15 (1H, dd, J = 8.1, 1.4 Hz), 5.03 (1H, s), 4.75 (2H, s), 4.48-3.87 (3H, m), 2.27-2.12 (2H, m), 1.81-1.72 (1H, m), 1.68-1.50 (2H, m), 1.16 (6H, s), 0.91-0.86 (1H, m). |

TABLE 27-continued

| | | | | | |
|---|---|---|---|---|---|
| 253 | O | [4-cyano-3-fluorophenyl] | [azabicyclic-NH2, Racemate Relative configuration] | [fluoro-benzotriazole with 2-hydroxy-2-methylpropyl] | 568.3 | 1H-NMR (DMSO-D6) δ: 8.55 (1H, d, J = 6.7 Hz), 7.80-7.67 (4H, m), 7.53 (1H, d, J = 9.2 Hz), 7.19 (1H, dd, J = 8.2, 1.5 Hz), 4.83 (1H, s), 4.73 (2H, s), 4.52-3.87 (3H, m), 2.29-2.10 (2H, m), 1.83-1.72 (1H, m), 1.69-1.49 (2H, m), 1.22 (6H, s), 0.95-0.86 (1H, m). |

TABLE 28

| 254 | O | [4-cyano-3-fluorophenyl] | [azabicyclic-NH2, isomer-X Relative configuration] | [difluoro-benzotriazole with hydroxycyclobutylmethyl] | 573.2 | 1H-NMR (DMSO-D6) δ: 7.96 (1H, d, J = 5.5 Hz), 7.83-7.61 (4H, m), 7.50 (1H, d, J = 10.4 Hz), 7.17 (1H, d, J = 7.9 Hz), 5.43 (1H, s), 4.78 (2H, s), 4.49-3.87 (3H, m), 2.21-1.96 (6H, m), 1.82-1.50 (5H, m), 0.99-0.79 (1H, m). |
|---|---|---|---|---|---|---|
| 255 | O | [4-cyano-3-fluorophenyl] | [H2N-pyrrolidinyl] | [difluoro-benzotriazole with hydroxycyclobutylmethyl] | 547.3 | 1H-NMR (DMSO-D6) δ: 7.96 (1H, d, J = 4.9 Hz), 7.81-7.72 (2H, m), 7.70-7.63 (2H, m), 7.48 (1H, d, J = 10.7 Hz), 7.16 (1H, d, J = 8.5 Hz), 5.43 (1H, s), 4.78 (2H, s), 3.75-3.59 (5H, m), 2.26-2.17 (2H, m), 2.04-1.91 (3H, m), 1.77-1.59 (3H, m). |
| 256 | O | [4-cyano-3-fluorophenyl] | [azabicyclic-NH2] | [difluoro-benzotriazole with hydroxycyclobutylmethyl] | 587.2 | 1H-NMR (DMSO-D6) δ: 7.97 (1H, d, J = 5.2 Hz), 7.77 (1H, t, J = 7.5 Hz), 7.69-7.63 (2H, m), 7.59 (1H, s), 7.49 (1H, d, J = 10.7 Hz), 7.17 (1H, d, J = 8.5 Hz), 5.44 (1H, s), 4.78 (2H, s), 4.62-4.55 (1H, m), 4.07-4.01 (1H, m), 2.32-1.50 (15H, m). |
| 257 | O | [4-cyano-3-fluorophenyl] | [azabicyclic-NH2, isomer-X Relative configuration] | [chloro-fluoro-benzotriazole with hydroxycyclobutylmethyl] | 589.2 / 591.2 | 1H-NMR (DMSO-D6) δ: 8.14 (1H, d, J = 5.8 Hz), 7.79-7.63 (4H, m), 7.50 (1H, d, J = 9.8 Hz), 7.16 (1H, d, J = 8.5 Hz), 5.38 (1H, s), 4.97 (2H, s), 4.49-3.87 (3H, m), 2.25-1.97 (6H, m), 1.76-1.50 (5H, m), 0.95-0.33 (1H, m). |
| 258 | O | [4-cyano-3-fluorophenyl] | [H2N-pyrrolidinyl] | [chloro-fluoro-benzotriazole with hydroxycyclobutylmethyl] | 563.2 / 565.2 | 1H-NMR (DMSO-D6) δ: 8.14 (1H, d, J = 6.4 Hz), 7.78-7.73 (2H, m), 7.71-7.64 (2H, m), 7.47 (1H, d, J = 9.8 Hz), 7.14 (1H, d, J = 8.2 Hz), 5.38 (1H, s), 4.97 (2H, s), 3.68-3.59 (5H, m), 2.31-2.21 (2H, m), 2.10-1.93 (3H, m), 1.76-1.55 (3H, m). |
| 259 | O | [4-cyano-3-fluorophenyl] | [azabicyclic-NH2] | [chloro-fluoro-benzotriazole with hydroxycyclobutylmethyl] | 603.2 / 605.2 | 1H-NMR (DMSO-D6) δ: 8.14 (1H, d, J = 5.8 Hz), 7.77 (1H, d, J = 7.6 Hz), 7.69-7.59 (3H, m), 7.49 (1H, d, J = 10.4 Hz), 7.15 (1H, d, J = 8.2 Hz), 5.38 (1H, s), 4.97 (2H, s), 4.63-4.57 (1H, m), 4.08-4.02 (1H, m), 2.33-1.47 (15H, m). |
| 260 | O | [4-cyano-3-fluorophenyl] | [azabicyclic-NH2, isomer-X Relative configuration] | [difluoromethyl-fluoro-benzotriazole with hydroxycyclobutylmethyl] | 605.2 | 1H-NMR (DMSO-D6) δ: 8.40 (1H, d, J = 5.8 Hz), 7.85-7.59 (5H, m), 7.47 (1H, d, J = 10.4 Hz), 7.15 (1H, d, J = 7.9 Hz), 5.77 (1H, s), 4.92 (2H, s), 4.50-3.89 (3H, m), 2.17-1.45 (11H, m), 0.90 (1H, dd, J = 12.1, 4.4 Hz). |

TABLE 28-continued

| | | | | | |
|---|---|---|---|---|---|
| 261 | O | 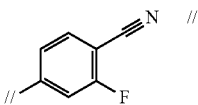 | 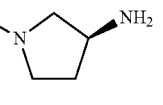 | 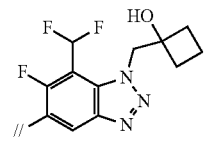 | 579.3 1H-NMR (DMSO-D6) δ: 8.40 (1H, d, J = 5.2 Hz), 7.82-7.62 (5H, m), 7.44 (1H, d, J = 10.7 Hz), 7.14 1H, d, J = 7.9 Hz), 5.77 (1H, s), 4.92 (2H, s), 3.63-3.39 (5H, m), 2.21-1.66 (8H, m). |
| 262 | O | 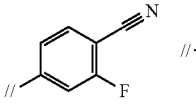 | 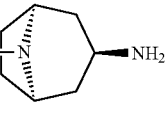 | 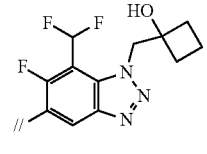 | 619.3 1H-NMR (DMSO-D6) δ: 8.40 (1H, d, J = 6.1 Hz), 7.84-7.59 (5H, m), 7.46 (1H, d, J = 10.7 Hz), 7.15 (1H, dd, J = 8.1, 1.4 Hz), 5.78 (1H, s), 4.92 (2H, s), 4.65-4.54 (1H, m), 4.11-4.02 (1H, m), 2.29-1.47 (15H, m). |
| 263 | O | 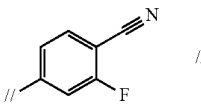 Racemate Relative configuration | 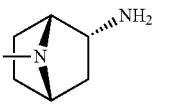 | | 605.2 1H-NMR (DMSO-D6) δ: 8.40 (1H, d, J = 5.8 Hz), 7.85-7.59 (5H, m), 7.47 (1H, d, J = 10.4 Hz), 7.15 (1H, d, J = 7.9 Hz), 5.77 (1H, s), 4.92 (2H, s), 4.50-3.89 (3H, m), 2.17-1.45 (11H, m), 0.90 (1H, dd, J = 12.1, 4.4 Hz). |
| 264 | O | 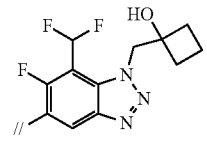 | 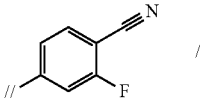 isomer-X Relative configuration | 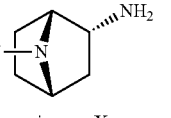 | 580.2 1H-NMR (DMSO-D6) δ: 8.54 (1H, d, J = 6.7 Hz), 7.91-7.38 (5H, m), 7.19 (1H, dd, J = 7.9, 1.5 Hz), 5.56 (1H, s), 4.89 (2H, s), 4.47-3.88 (3H, m), 2.27-1.48 (11H, m), 0.96-0.85 (1H, m). |

TABLE 29

| | | | | | |
|---|---|---|---|---|---|
| 265 | O | 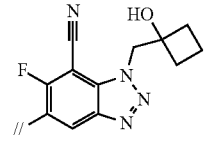 | 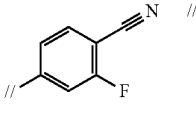 | 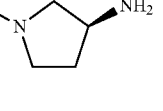 | 554.2 1H-NMR (DMSO-D6) δ: 8.55 (1H d, J = 6.4 Hz), 7.80-7.68 (4H, m), 7.57-7.49 (1H, m), 7.18 (1H, dd, J = 8.1, 1.4 Hz), 5.55 (1H, s), 4.89 (2H, s), 3.67-3.46 (5H, m), 2.26-1.67 (8H, m). |
| 266 | O | 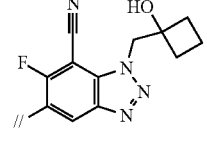 | 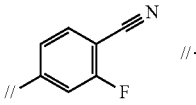 | 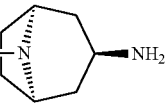 | 594.2 1H-NMR (DMSO-D6) δ: 8.55 (1H, d, J = 6.4 Hz), 7.78 (1H, t, J = 7.5 Hz), 7.70-7.60 (3H, m), 7.53 (1H, dd, J = 10.4, 1.5 Hz), 7.21-7.16 (1H, m), 5.55 (1H, s), 4.89 (2H, s), 4.61-4.55 (1H, m), 4.08-4.02 (1H, m), 2.31-1.50 (15H, m). |
| 267 | O | 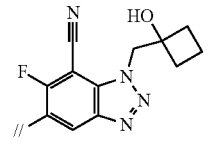 | 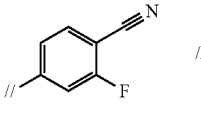 Racemate Relative configuration | 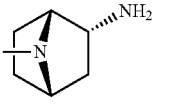 | 580.2 1H-NMR (DMSO-D6) δ: 8.54 (1H, d, J = 6.7 Hz), 7.91-7.38 (5H, m), 7.19 (1H, dd, J = 7.9, 1.5 Hz), 5.56 (1H, s), 4.89 (2H, s), 4.47-3.88 (3H, m), 2.27-1.48 (11H, m), 0.96-0.85 (1H, m). |
| 268 | O | 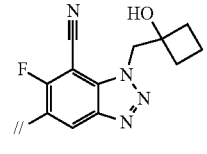 | 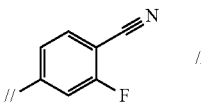 Racemate Relative configuration |  | 573.2 1H-NMR (DMSO-D6) δ: 7.96 (1H, d, J = 5.5 Hz), 7.83-7.61 (4H, m), 7.50 (1H, d, J = 10.4 Hz), 7.17 (1H, d, J = 7.9 Hz), 5.43 (1H, s), 4.78 (2H, s), 4.49-3.87 (3H, m), 2.21-1.96 (6H, m), 1.82-1.50 (5H, m), 0.99-0.75 (1H, m). |

TABLE 29-continued

| | | | | | |
|---|---|---|---|---|---|
| 269 | O | 4-cyano-2-fluorophenyl | 3-amino-azabicyclic (Racemate Relative configuration) | Cl,F-benzotriazole-CH2-cyclobutanol | 589.2 591.4 1H-NMR (DMSO-D6) δ: 8.14 (1H, d, J = 5.8 Hz), 7.79-7.63 (4H, m), 7.50 (1H, d, J = 9.8 Hz), 7.16 (1H, d, J = 8.5 Hz), 5.38 (1H, s), 4.97 (2H, s), 4.49-3.87 (3H, m), 2.25-1.97 (6H, m), 1.76-1.50 (5H, m), 0.95-0.83 (1H, m). |
| 270 | O | 4-cyano-2-fluorophenyl | 3-amino-azabicyclic (isomer-X Relative configuration) | F,Me-benzotriazole-CH2-cyclobutanol | 569.4 1H-NMR (DMSO-D6) δ: 7.86 (1H, d, J = 6.4 Hz), 7.79-7.57 (4H, m), 7.46 (1H, dd, J = 10.5, 1.4 Hz), 7.17-7.14 (1H, m), 5.52 (1H, s), 4.84 (2H, s), 4.45-3.89 (3H, m), 2.54 (3H, s), 2.30-1.96 (6H, m), 1.79-1.51 (5H, m), 0.89 (1H, dd, J = 11.9, 4.6 Hz). |
| 271 | O | 4-cyano-2-fluorophenyl | 3-aminopyrrolidine | F,Me-benzotriazole-CH2-cyclobutanol | 543.2 1H-NMR (DMSO-D6) δ: 7.86 (1H, d, J = 6.4 Hz), 7.76-7.69 (2H, m), 7.68-7.63 (1H, m), 7.60-7.56 (1H, m), 7.44 (1H, d, J = 10.7 Hz), 7.13 (1H, dd, J = 8.2, 1.5 Hz), 5.52 (1H, s), 4.84 (2H, s), 3.68-3.49 (5H, m), 2.52 (3H, s), 2.30-2.24 (2H, m), 2.02-1.93 (3H, m), 1.75-1.60 (3H, m). |
| 272 | O | 4-cyano-2-fluorophenyl | tropane-NH2 | F,Me-benzotriazole-CH2-cyclobutanol | 583.2 1H-NMR (DMSO-D6) δ: 7.87 (1H, d, J = 6.4 Hz), 7.75 (1H, t, J = 7.6 Hz), 7.63 (1H, dd, J = 7.8, 1.7 Hz), 7.60-7.53 (2H, m), 7.45 (1H, dd, J = 10.5, 1.4 Hz), 7.14 (1H, dd, J = 7.9, 1.5 Hz), 5.52 (1H, s), 4.84 (2H, s), 4.64-4.54 (1H, m), 4.11-4.01 (1H, m), 2.52 (3H, s), 2.28-1.50 (15H, m). |
| 273 | O | 4-cyano-2-fluorophenyl | 3-amino-azabicyclic (isomer-X Relative configuration) | Br,F-benzotriazole-CH2-C(CH3)2OH | 621.1 623.1 1H-NMR (DMSO-D6) δ: 8.17 (1H, d, J = 6.1 Hz), 7.80-7.62 (4H, m), 7.47 (1H, d, J = 9.5 Hz), 7.15 (1H, d, J = 8.2 Hz), 4.88 (2H, s), 4.74 (1H, s), 4.49-3.86 (3H, m), 2.27-2.12 (2H, m), 1.79-1.50 (3H, m), 1.18 (6H, s), 0.89 (1H, dd, J = 12.4, 4.4 Hz). |
| 274 | O | 4-cyano-2-fluorophenyl | 3-aminopyrrolidine | Br,F-benzotriazole-CH2-C(CH3)2OH | 595.1 597.1 1H-NMR (DMSO-D6) δ: 8.21-8.16 (1H, m), 7.78-7.65 (4H, m), 7.45 (1H, d, J = 10.7 Hz), 7.13 (1H, dd, J = 8.2, 1.5 Hz), 4.88 (2H, s), 4.74 (1H, s), 3.70-3.48 (5H, m), 2.03-1.94 (1H, m), 1.71-1.53 (1H, m), 1.18 (6H, s). |

TABLE 30

| | | | | | |
|---|---|---|---|---|---|
| 275 | O | 4-cyano-2-fluorophenyl | 3-amino-azabicyclic | Br,F-benzotriazole-CH2-C(CH3)2OH | 635.1 637.1 1H-NMR (DMSO-D6) δ: 8.18 (1H, d, J = 6.1 Hz), 7.76 (1H, t, J = 7.5 Hz), 7.68-7.59 (3H, m), 7.46 (1H, dd, J = 10.5, 1.4 Hz), 7.14 (1H, dd, J = 7.9, 1.5 Hz), 4.88 (2H, s), 4.74 (1H, s), 4.62-4.55 (1H, m), 4.10-4.02 (1H, m), 2.26-1.88 (6H, m), 1.65-1.47 (3H, m), 1.18 (6H, s). |
| 276 | O | 4-cyano-2-fluorophenyl | 3-amino-azabicyclic (Racemate Relative configuration) | F,Me-benzotriazole-CH2-cyclobutanol | 569.4 1H-NMR (DMSO-D6) δ: 7.86 (1H, d, J = 6.4 Hz), 7.79-7.57 (4H, m), 7.46 (1H, dd, J = 10.5, 1.4 Hz), 7.17-7.14 (1H, m), 5.52 (1H, s), 4.84 (2H, s), 4.45-3.89 (3H, m), 2.54 (3H, s), 2.30-1.96 (6H, m), 1.79-1.51 (5H, m), 0.89 (1H, dd, J = 11.9, 4.6 Hz). |

TABLE 30-continued

| 277 | O | 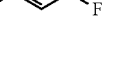 |  Racemate Relative configuration | 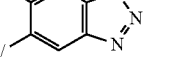 | 621.1 623.1 | 1H-NMR (DMSO-D6) δ: 8.17 (1H, d, J = 6.1 Hz), 7.80-7.62 (4H, m), 7.47 (1H, d, J = 9.5 Hz), 7.15 (1H, d, J = 8.2 Hz), 4.88 (2H, s), 4.74 (1H, s), 4.49-3.86 (3H, m), 2.27-2.12 (2H, m), 1.79-1.50 (3H, m), 1.18 (6H, s), 0.89 (1H, dd, J = 12.4, 4.4 Hz). |
| --- | --- | --- | --- | --- | --- | --- |
| 278 | O | 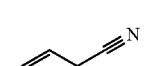 |  Racemate Relative configuration |  | 583.4 | 1H-NMR (DMSO-D6) δ: 7.99 (1H, d, J = 5.8 Hz), 7.83-7.58 (4H, m), 7.38 (1H, dd, J = 10.5, 1.4 Hz), 7.09 (1H, dd, J = 8.2, 1.5 Hz), 5.10-4.83 (2H, m), 4.72 (1H, s), 4.53-3.88 (3H, m), 2.29-2.13 (3H, m), 1.80-1.50 (3H, m), 1.15 (6H, s), 1.02-0.96 (2H, m), 0.89 (1H, dd, J = 11.9, 4.6 Hz), 0.53-0.12 (2H, m). |
| 279 | O |  |  isomer-X Relative configuration |  | 583.4 | 1H-NMR (DMSO-D6) δ: 7.99 (1H, d, J = 5.8 Hz), 7.83-7.58 (4H, m), 7.38 (1H, dd, J = 10.5, 1.4 Hz), 7.09 (1H, dd, J = 8.2, 1.5 Hz), 5.10-4.83 (2H, m), 4.72 (1H, s), 4.53-3.88 (3H, m), 2.29-2.13 (3H, m), 1.80-1.50 (3H, m), 1.15 (6H, s), 1.02-0.96 (2H, m), 0.89 (1H, dd, J = 11.9, 4.6 Hz), 0.53-0.12 (2H, m). |
| 280 | O |  | 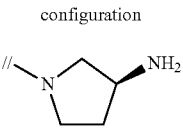 |  | 557.4 | 1H-NMR (DMSO-D6) δ: 7.99 (1H, d, J = 5.5 Hz), 7.76-7.64 (4H, m), 7.36 (1H, dd, J = 10.5, 2.9 Hz), 7.07 (1H, dd, J = 8.2, 1.5 Hz), 5.05-4.81 (2H, m), 4.72 (1H, s), 3.70-3.44 (5H, m), 2.26-2.17 (1H, m), 2.11-1.97 (1H, m), 1.78-1.67 (1H, m), 1.15 (6H, s), 1.03-0.95 (2H, m), 0.40-0.16 (2H, m). |
| 281 | O | 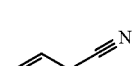 |  |  | 597.5 | 1H-NMR (DMSO-D6) δ: 7.99 (1H, d, J = 6.1 Hz), 7.74 (1H, t, J = 7.5 Hz), 7.68-7.56 (3H, m), 7.37 (1H, d, J = 10.7 Hz), 7.08 (1H, d, J = 7.9 Hz), 5.04-4.81 (2H, m), 4.72 (1H, s), 4.65-4.57 (1H, m), 4.13-4.05 (1H, m), 2.24-1.51 (10H, m), 1.15 (6H, s), 1.02-0.94 (2H, m), 0.42-0.16 (2H, m). |

TABLE 31

| Compound No. | Structural formula | MS m/z (M + 1) | NMR |
| --- | --- | --- | --- |
| Comp. Ex. 1 |  | 436.2 | 1H-NMR (DMSO-D6) δ: 8.55 (1H, d, J = 2.4 Hz), 8.32 (1H, s), 7.78 (2H, dd, J = 6.7, 1.5 Hz), 7.58-7.53 (3H, m), 7.48 (1H, d, J = 8.9 Hz), 6.82 (1H, dd, J = 8.9, 1.5 Hz), 4.77 (2H, s), 4.16 (3H, s), 3.64-3.50 (1H, m), 2.04 (2H, s), 1.86 (4H, dd, J = 28.4, 9.8 Hz), 1.68 (2H, d, J = 10.7 Hz). |

TABLE 31-continued

| Compound No. | Structural formula | MS m/z (M + 1) | NMR |
|---|---|---|---|
| Comp. Ex. 2 | | 376.2 | 1H-NMR (DMSO-D6) δ: 8.00-7.93 (2H, m), 7.55-7.49 (2H, m), 7.40-7.34 (2H, m), 7.32-7.25 (2H, m), 7.09-7.03 (1H, m), 4.11-3.57 (5H, m), 2.20-2.04 (1H, m), 1.93-1.74 (1H, m). |
| Comp. Ex. 3 | | 416.3 | 1H-NMR (DMSO-D6) δ: 7.97-7.92 (2H, m), 7.60-7.46 (2H, m), 7.41-7.33 (2H, m), 7.32-7.24 (2H, m), 6.99-6.95 (1H, m), 4.00-3.75 (4H, m), 3.60-3.46 (4H, m), 1.87-1.79 (2H, m), 1.59-1.48 (2H, m). |
| Comp. Ex. 4 | | 413.2 | 1H-NMR (DMSO-D6) δ: 8.62 (1H, s), 8.57 (1H, d, J = 4.4 Hz), 7.90-7.84 (3H, m), 7.73 (2H, d, J = 8.1 Hz), 7.49 (2H, t, J = 6.8 Hz), 7.44 (1H, s), 7.32 (1H, d, J = 8.4 Hz), 5.26 (2H, s), 4.13-3.96 (2H, m), 3.31-3.04 (3H, m), 2.04-1.92 (1H, m), 1.79-1.40 (3H, m). |
| Comp. Ex. 5 | | 425.1 | 1H-NMR (DMSO-D6) δ: 7.66-7.61 (3H, m), 7.54 (1H, d, J = 11.6 Hz), 7.48 (1H, d, J = 7.9 Hz), 7.36 (2H, d, J = 7.9 Hz), 7.09 (2H, d, J = 7.9 Hz), 7.02 (2H, d, J = 7.9 Hz), 3.70-3.42 (4H, m), 3.27-3.19 (1H, m), 2.27 (3H, s), 2.03-1.92 (1H, m), 1.72-1.60 (1H, m). |
| Comp. Ex. 6 | | 444.1 | 1H-NMR (DMSO-D6) δ: 8.61-8.52 (1H, m), 8.49-8.43 (1H, m), 7.84-7.68 (4H, m), 7.61-7.56 (1H, m), 7.54-7.47 (1H, m), 7.41-7.30 (3H, m), 7.10 (2H, t, J = 8.9 Hz), 7.05-6.97 (2H, m), 3.76-3.60 (5H, m), 2.50-2.49 (3H, m), 2.30-2.27 (2H, m). |

TABLE 31-continued

| Compound No. | Structural formula | MS m/z (M + 1) | NMR |
|---|---|---|---|
| Comp. Ex. 7 | | 386.0 | 1H-NMR (DMSO-D6) δ: 7.93 (2H, dd, J = 6.9, 2.0 Hz), 7.49 (2H, d, J = 8.9 Hz), 7.20 (4H, dd, J = 20.4, 8.2 Hz), 6.88 (1H, s), 4.45-4.29 (2H, m), 3.27-3.21 (1H, m), 3.00-2.82 (2H, m), 2.33 (3H, s), 1.85-1.72 (2H, m), 1.32-1.13 (2H, m). |

Test Example 1: Measurement of LSD1 Inhibitory Activity (In Vitro)

The conditions for measuring inhibitory activity of compounds against LSD1 activity were determined with reference to a document available from the website of PerkinElmer (U-TRF #38) and a patent of GlaxoSmithKline (WO2012135113).

To measure the inhibitory activity, first, the compound of the present invention was serially diluted in dimethylsulfoxide (DMSO). Sequentially, the solution of the compound of the present invention in DMSO (final concentration of DMSO: 5%) and human LSD1 protein (Abcam, ab80379) were added to a reaction buffer (25 mM Tris-HCl (pH 7.5), 50 mM KCl, 2 mM CHAPS, 1 mM DTT, 0.02% BSA). The mixture was preincubated at 25° C. for 30 minutes. Thereafter, a H3K4 (Me1)-biotin-labeled peptide (Anaspec #64355) (final concentration: 200 nM) was added thereto and reacted for 60 minutes. Tranylcypromine (final concentration: 3 mM) was then added thereto to terminate the reaction. Thereafter, a detection solution containing an Eu-labeled anti-H3K4 antibody (PerkinElmer, TRF0404) and Streptavidin Alexa Fluor 647 (Thermo Fisher Scientific, 521374) was added thereto, and the mixture was allowed to stand at room temperature for 1 hour. Finally, the intensity of fluorescence under the excitation light with a wavelength of 337 nm was measured with a PHERAstar FS (BMG Labtech) at two wavelengths: 620 nm and 665 nm. The demethylation level was calculated from the ratio of the fluorescence intensity at the two wavelengths, and the compound concentration at which demethylation was inhibited by 50% was defined as IC50 (nM). The following tables show the results.

TABLE 32

| Example No. | LSD1 Inhibitory activity IC50 (nM) |
|---|---|
| 1 | 7.02 |
| 3 | 10.6 |
| 4 | 4.93 |
| 5 | 1.59 |
| 6 | 10.7 |
| 7 | 0.78 |
| 8 | 5.92 |
| 9 | 4.45 |
| 10 | 3.74 |
| 11 | 17.4 |
| 12 | 5.83 |
| 13 | 14.9 |
| 14 | 11.0 |
| 15 | 2.41 |
| 16 | 1.97 |
| 17 | 3.51 |
| 18 | 0.40 |
| 19 | 2.67 |
| 20 | 1.31 |
| 21 | 0.87 |
| 22 | 1.18 |
| 23 | 0.18 |
| 24 | 0.29 |
| 25 | 1.83 |
| 26 | 0.45 |
| 27 | 11.4 |
| 28 | 0.57 |
| 29 | 19.8 |
| 30 | 4.31 |
| 31 | 16.0 |
| 32 | 17.7 |
| 33 | 11.0 |
| 34 | 15.1 |
| 35 | 10.0 |
| 36 | 1.04 |
| 37 | 2.40 |
| 38 | 16.0 |
| 39 | 1.91 |
| 40 | 5.96 |
| 41 | 1.57 |
| 42 | 11.6 |
| 45 | 7.71 |
| 46 | 19.7 |
| 47 | 9.15 |
| 48 | 17.9 |
| 49 | 5.51 |
| 51 | 11.0 |
| 52 | 8.31 |
| 53 | 10.9 |
| 54 | 4.58 |
| 55 | 20.0 |
| 56 | 11.3 |
| 57 | 3.42 |
| 58 | 13.5 |
| 59 | 6.78 |
| 60 | 13.8 |
| 61 | 15.5 |
| 62 | 6.34 |
| 63 | 3.48 |
| 64 | 6.69 |
| 65 | 2.80 |
| 66 | 6.99 |
| 67 | 10.4 |
| 68 | 17.3 |

TABLE 32-continued

| Example No. | LSD1 Inhibitory activity IC50 (nM) |
|---|---|
| 69 | 11.1 |
| 70 | 3.68 |
| 71 | 3.04 |
| 72 | 7.57 |
| 73 | 9.23 |
| 74 | 1.53 |
| 75 | 1.54 |
| 76 | 2.09 |
| 77 | 1.54 |
| 78 | 9.65 |
| 79 | 17.9 |
| 80 | 12.8 |
| 81 | 3.30 |
| 82 | 3.04 |
| 83 | 9.29 |
| 84 | 9.33 |
| 85 | 6.27 |
| 86 | 6.58 |
| 87 | 5.12 |
| 89 | 11.2 |
| 90 | 14.0 |
| 91 | 4.85 |
| 92 | 2.78 |
| 93 | 20.3 |
| 94 | 5.10 |
| 95 | 0.75 |
| 96 | 0.49 |
| 97 | 10.1 |
| 98 | 2.18 |
| 100 | 3.13 |
| 101 | 3.70 |
| 102 | 0.63 |
| 103 | 9.65 |
| 104 | 0.44 |
| 105 | 0.51 |
| 106 | 0.34 |
| 107 | 1.05 |
| 108 | 0.21 |
| 109 | 0.28 |
| 110 | 0.47 |
| 111 | 9.45 |
| 112 | 1.80 |
| 113 | 1.56 |
| 114 | 1.42 |
| 115 | 2.81 |
| 116 | 3.03 |
| 117 | 1.97 |
| 118 | 1.57 |
| 119 | 1.98 |
| 120 | 0.90 |
| 121 | 9.46 |
| 122 | 8.61 |
| 123 | 0.12 |
| 124 | 0.36 |
| 125 | 0.29 |
| 126 | 0.41 |
| 127 | 17.0 |
| 128 | 0.62 |
| 130 | 0.29 |
| 131 | 1.81 |
| 132 | 10.8 |
| 133 | 0.91 |
| 134 | 0.21 |
| 135 | 0.30 |
| 136 | 0.30 |
| 137 | 3.18 |
| 138 | 2.83 |
| 139 | 1.68 |
| 140 | 5.98 |
| 141 | 0.25 |
| 142 | 0.38 |
| 143 | 0.25 |
| 144 | 0.51 |
| 145 | 0.38 |
| 146 | 0.42 |

TABLE 32-continued

| Example No. | LSD1 Inhibitory activity IC50 (nM) |
|---|---|
| 147 | 0.35 |
| 148 | 19.8 |
| 150 | 2.99 |
| 151 | 5.02 |
| 155 | 0.51 |
| 156 | 12.8 |
| 158 | 6.35 |
| 159 | 17.7 |
| 160 | 0.92 |
| 161 | 0.74 |
| 162 | 1.09 |
| 164 | 12.8 |
| 165 | 11.2 |
| 166 | 0.63 |
| 167 | 1.79 |
| 168 | 1.05 |
| 169 | 0.90 |
| 170 | 0.72 |
| 171 | 0.35 |
| 172 | 0.55 |
| 173 | 1.84 |
| 174 | 13.8 |
| 175 | 0.33 |
| 176 | 0.30 |
| 177 | 0.23 |
| 178 | 1.24 |
| 179 | 0.69 |
| 180 | 0.88 |
| 181 | 2.70 |
| 182 | 17.6 |
| 183 | 0.67 |
| 184 | 0.25 |
| 185 | 0.14 |
| 186 | 0.43 |
| 187 | 0.26 |
| 188 | 0.61 |
| 189 | 0.33 |
| 190 | 0.16 |
| 191 | 0.22 |
| 192 | 0.40 |
| 193 | 2.35 |
| 194 | 0.34 |
| 195 | 0.20 |
| 196 | 0.14 |
| 197 | 0.11 |
| 198 | 0.18 |
| 199 | 1.00 |
| 200 | 0.91 |
| 201 | 0.40 |
| 202 | 0.09 |
| 203 | 0.24 |
| 204 | 0.45 |
| 205 | 1.28 |
| 206 | 0.30 |
| 207 | 6.89 |
| 208 | 16.8 |
| 209 | 0.06 |
| 210 | 0.16 |
| 211 | 0.14 |
| 213 | 0.15 |
| 214 | 0.10 |

TABLE 33

| Example No. | LSD1 Inhibitory activity IC50 (nM) |
|---|---|
| 215 | 0.25 |
| 216 | 0.50 |
| 217 | 0.21 |

TABLE 33-continued

| Example No. | LSD1 Inhibitory activity IC50 (nM) |
|---|---|
| 218 | 0.07 |
| 219 | 0.10 |
| 220 | 0.12 |
| 221 | 0.20 |
| 222 | 8.31 |
| 224 | 0.49 |
| 225 | 0.20 |
| 226 | 0.54 |
| 227 | 11.7 |
| 228 | 0.11 |
| 229 | 0.43 |
| 230 | 0.94 |
| 231 | 0.65 |
| 232 | 0.63 |
| 233 | 4.88 |
| 234 | 2.43 |
| 235 | 2.09 |
| 237 | 0.20 |
| 238 | 2.35 |
| 239 | 0.59 |
| 240 | 0.34 |
| 241 | 0.29 |
| 242 | 2.69 |
| 243 | 0.65 |
| 244 | 6.54 |
| 245 | 0.39 |
| 246 | 0.17 |
| 247 | 0.23 |
| 248 | 0.46 |
| 249 | 0.88 |
| 250 | 0.38 |
| 251 | 0.96 |
| 252 | 0.36 |
| 254 | 0.13 |
| 255 | 0.23 |
| 256 | 0.24 |
| 257 | 0.12 |
| 258 | 0.13 |
| 259 | 0.14 |
| 260 | 0.14 |
| 261 | 0.37 |
| 262 | 0.30 |
| 263 | 0.52 |
| 264 | 0.24 |
| 265 | 0.43 |
| 266 | 0.35 |
| 267 | 0.49 |
| 268 | 0.29 |
| 269 | 0.41 |
| 270 | 0.15 |
| 271 | 0.23 |
| 272 | 0.32 |
| 273 | 0.19 |
| 274 | 0.32 |
| 275 | 0.21 |
| 276 | 0.39 |
| 277 | 0.42 |
| 278 | 0.87 |
| 279 | 0.46 |
| 280 | 2.13 |
| 281 | 2.62 |
| Comp. Ex. 1 | 672 |
| Comp. Ex. 2 | 864 |
| Comp. Ex. 3 | >1000 |
| Comp. Ex. 4 | 2498 |
| Comp. Ex. 5 | 795 |
| Comp. Ex. 6 | >1000 |

The results of the test clarified that the compounds of the present invention exhibit LSD1 inhibitory activity.

Test Example 2: Cell-Growth Inhibition Test

Under the following conditions, an in vitro cell-growth inhibition test was performed with respect to HEL cells (human acute myelocytic leukemia cell lines), NCI-H1417 cells (human small-cell lung cancer cell lines), and NCI-H146 cells (human small-cell lung cancer cell lines).

HEL cells (JCRB, Cat #: JCRB0062), NCI-H1417 cells (ATCC, Cat #: CRL-5869), or NCI-H146 cells (ATCC, Cat #: HTB-173) cultured in a 10% FBS-containing RPMI1640 medium (Thermo Fisher Scientific, Cat #: A10491-01) were seeded in a 96-well flat-bottom microplate (Thermo Fisher Scientific, Cat #: 165305) so that each well contained 1500 HEL cells (100 µL), 5000 NCI-H1417 cells (100 µL), or 1200 NCI-H146 cells (100 µL). The compound of the present invention was serially diluted in dimethylsulfoxide (DMSO) to a concentration that was 500 times higher than the final concentration. The serially diluted compound of the present invention or dimethylsulfoxide alone was added to a 10% FBS-containing RPMI1640 medium to a concentration that was 2 times higher than the final concentration, and the resulting product was added in an amount of 100 µL to each well of the culture plate containing HEL cells, NCI-H1417 cells, or NCI-H146 cells, so that the final concentrations of the compound of the present invention were 3000, 1000, 300, 100, 30, 10, 3, 1, 0.3, 0.1, 0.03, and 0.01 nM. The final concentration of dimethylsulfoxide was adjusted to 0.2%. The cells with the compound of the present invention or with dimethylsulfoxide alone were cultured at 37° C. in a 5% carbon-dioxide-containing incubator for 5 days (HEL cells) or 10 days (NCI-H1417 cells and NCI-H146 cells). After culture, the plate was allowed to stand at room temperature for 30 minutes, and 100 µL of the supernatant was removed from each well to leave 100 µL of the cell culture solution. To each well containing the remaining 100 µL of the cell culture solution, the same amount of CellTiter-Glo 2.0 Assay (Promega, Cat #: G9242) was added. The microplate was shaken with a plate mixer for 1 minute and then allowed to stand in a dark place for 10 minutes. Thereafter, the luminescence intensity of viable cells in each well was measured using a microplate reader (PerkinElmer, EnSpire). The cell growth rate was determined in accordance with the following equation, and the concentration at which the cell growth rate was 50%, i.e.; the concentration of each compound of the present invention at which the cell growth was inhibited by 50% (IC50 (nM)) was determined.

Cell growth rate (%) = $T/C \times 100$

T: The luminescence intensity in a well to which the compound of the present invention was added (count per second)

C: The luminescence intensity in a well to which dimethylsulfoxide alone was added (count per second)

The tables below show the results.

TABLE 34

Cell-Growth Inhibition Test: HEL Cells

| Ex. No. | IC50 (nM) |
|---|---|
| 1 | 39.8 |
| 4 | 28.8 |
| 5 | 34.5 |
| 7 | 14.8 |
| 8 | 42.7 |
| 9 | 38.7 |
| 10 | 31.7 |

TABLE 34-continued

Cell-Growth Inhibition Test: HEL Cells

| Ex. No. | IC50 (nM) |
|---|---|
| 12 | 36.7 |
| 15 | 17.3 |
| 16 | 34.3 |
| 18 | 3.55 |
| 19 | 24.4 |
| 20 | 7.73 |
| 21 | 8.34 |
| 22 | 3.51 |
| 23 | 0.73 |
| 24 | 3.56 |
| 25 | 4.72 |
| 26 | 4.83 |
| 27 | 24.7 |
| 28 | 15.7 |
| 30 | 27.1 |
| 36 | 15.4 |
| 37 | 10.1 |
| 38 | 34.0 |
| 39 | 17.4 |
| 40 | 27.2 |
| 41 | 4.98 |
| 47 | 29.3 |
| 48 | 28.9 |
| 49 | 32.1 |
| 59 | 33.0 |
| 63 | 28.3 |
| 65 | 23.9 |
| 69 | 29.9 |
| 71 | 19.5 |
| 74 | 20.4 |
| 75 | 5.78 |
| 77 | 12.6 |
| 80 | 43.6 |
| 81 | 11.7 |
| 82 | 11.1 |
| 84 | 41.7 |
| 85 | 32.2 |
| 86 | 13.4 |
| 87 | 17.4 |
| 92 | 9.91 |
| 94 | 25.4 |
| 96 | 11.0 |
| 102 | 12.8 |
| 104 | 28.8 |
| 106 | 5.74 |
| 108 | 36.4 |
| 109 | 15.1 |
| 110 | 7.41 |
| 113 | 9.00 |
| 117 | 8.54 |
| 120 | 7.60 |
| 123 | 1.39 |
| 124 | 2.84 |
| 125 | 7.57 |
| 126 | 5.39 |
| 128 | 5.70 |
| 130 | 22.2 |
| 131 | 15.2 |
| 133 | 17.7 |
| 134 | 1.06 |
| 135 | 2.37 |
| 136 | 0.90 |
| 139 | 16.9 |
| 141 | 1.50 |
| 142 | 3.86 |
| 143 | 0.95 |
| 144 | 6.37 |
| 145 | 1.61 |
| 146 | 1.15 |
| 147 | 3.04 |
| 155 | 0.83 |
| 160 | 7.03 |
| 161 | 6.88 |
| 162 | 17.7 |
| 166 | 0.62 |
| 167 | 4.05 |
| 168 | 5.29 |
| 170 | 3.44 |
| 171 | 0.090 |
| 172 | 0.47 |
| 173 | 1.65 |
| 175 | 0.20 |
| 176 | 0.20 |
| 177 | 0.38 |
| 178 | 3.57 |
| 179 | 1.52 |
| 180 | 1.16 |
| 181 | 9.06 |
| 182 | 22.4 |
| 183 | 0.54 |
| 184 | 2.26 |
| 185 | 0.68 |
| 186 | 5.30 |
| 187 | 1.99 |
| 188 | 1.95 |
| 189 | 0.59 |
| 190 | 0.41 |
| 191 | 3.91 |
| 192 | 1.11 |
| 193 | 2.31 |
| 194 | 15.5 |
| 195 | 0.45 |
| 196 | 0.33 |
| 197 | 1.0 |
| 198 | 0.43 |
| 199 | 22.0 |
| 200 | 3.72 |
| 201 | 1.55 |
| 202 | 0.24 |
| 203 | 2.48 |
| 204 | 2.14 |
| 205 | 4.95 |
| 206 | 0.40 |

TABLE 35

Cell-Growth Inhibition Test: HEL Cells

| Ex. No. | IC50 (nM) |
|---|---|
| 209 | 0.24 |
| 210 | 3.30 |
| 211 | 1.41 |
| 213 | 0.65 |
| 214 | 0.44 |
| 215 | 4.91 |
| 216 | 4.19 |
| 217 | 0.86 |
| 218 | 0.22 |
| 219 | 1.70 |
| 220 | 1.09 |
| 221 | 0.49 |
| 222 | 38.0 |
| 224 | 46.2 |
| 225 | 0.69 |
| 226 | 2.56 |
| 227 | 23.6 |
| 228 | 0.68 |
| 229 | 2.55 |
| 231 | 13.4 |
| 232 | 2.04 |
| 234 | 42.6 |
| 235 | 8.42 |
| 237 | 28.5 |
| 238 | 26.1 |
| 239 | 12.5 |
| 240 | 4.20 |
| 241 | 2.54 |
| 246 | 0.37 |

TABLE 35-continued

Cell-Growth Inhibition Test: HEL Cells

| Ex. No. | IC50 (nM) |
|---|---|
| 247 | 3.02 |
| 248 | 6.94 |
| 249 | 41.6 |
| 250 | 2.36 |
| 251 | 23.9 |
| 252 | 0.77 |
| 253 | 6.11 |
| 254 | 0.20 |
| 255 | 2.73 |
| 256 | 1.31 |
| 257 | 0.13 |
| 258 | 1.27 |
| 259 | 0.58 |
| 260 | 0.13 |
| 261 | 2.67 |
| 262 | 0.93 |
| 263 | 0.39 |
| 264 | 0.84 |
| 265 | 17.6 |
| 266 | 4.63 |
| 267 | 1.98 |
| 268 | 0.40 |
| 269 | 0.29 |
| 270 | 0.26 |
| 271 | 4.29 |
| 272 | 1.52 |
| 273 | 0.27 |
| 274 | 3.15 |
| 275 | 0.99 |
| 276 | 0.62 |
| 277 | 0.65 |
| 278 | 3.76 |
| 279 | 1.59 |
| 280 | 36.6 |
| 281 | 23.9 |
| Comp. Ex. 3 | >3000 |
| Comp. Ex. 4 | >3000 |
| Comp. Ex. 5 | >3000 |
| Comp. Ex. 6 | >3000 |
| Comp. Ex. 7 | 1041 |

TABLE 36

Cell-Growth Inhibition Test: NCI-H1417 Cells

| Ex. No. | IC50 (nM) |
|---|---|
| 7 | 28.0 |
| 18 | 4.73 |
| 20 | 17.4 |
| 21 | 32.6 |
| 22 | 8.20 |
| 23 | 0.99 |
| 24 | 0.97 |
| 25 | 13.4 |
| 26 | 3.15 |
| 27 | 22.5 |
| 28 | 4.40 |
| 37 | 19.2 |
| 39 | 22.7 |
| 41 | 6.12 |
| 65 | 47.6 |
| 74 | 20.7 |
| 75 | 14.1 |
| 76 | 43.3 |
| 77 | 16.5 |
| 81 | 26.7 |
| 82 | 26.6 |
| 86 | 26.4 |
| 87 | 49.9 |
| 88 | 40.5 |
| 91 | 30.3 |
| 92 | 26.8 |
| 95 | 11.8 |
| 96 | 7.14 |
| 100 | 42.8 |
| 101 | 53.2 |
| 102 | 4.99 |
| 104 | 49.8 |
| 105 | 11.7 |
| 106 | 6.15 |
| 107 | 18.2 |
| 108 | 3.99 |
| 109 | 1.81 |
| 110 | 3.54 |
| 112 | 20.5 |
| 113 | 13.7 |
| 114 | 30.6 |
| 117 | 38.1 |
| 118 | 29.5 |
| 119 | 23.8 |
| 120 | 15.7 |
| 123 | 3.57 |
| 124 | 9.02 |
| 125 | 8.43 |
| 126 | 5.02 |
| 130 | 8.25 |
| 131 | 30.9 |
| 133 | 17.9 |
| 134 | 6.93 |
| 135 | 9.08 |
| 136 | 2.39 |
| 141 | 2.95 |
| 142 | 3.79 |
| 143 | 4.88 |
| 145 | 3.29 |
| 146 | 1.42 |
| 147 | 1.66 |
| 155 | 2.80 |
| 160 | 9.20 |
| 161 | 2.49 |
| 162 | 4.69 |
| 166 | 1.42 |
| 167 | 4.45 |
| 168 | 7.29 |
| 169 | 8.20 |
| 170 | 2.51 |
| 171 | 0.15 |
| 172 | 0.70 |
| 173 | 3.81 |
| 175 | 0.60 |
| 176 | 0.27 |
| 177 | 0.24 |
| 178 | 3.03 |
| 179 | 3.36 |
| 180 | 3.12 |
| 181 | 4.60 |
| 183 | 1.01 |
| 184 | 2.73 |
| 185 | 1.43 |
| 186 | 5.95 |
| 187 | 1.52 |
| 188 | 1.96 |
| 189 | 0.71 |
| 190 | 0.55 |
| 191 | 1.98 |
| 192 | 0.75 |
| 193 | 6.66 |
| 194 | 5.63 |
| 195 | 0.79 |
| 196 | 0.78 |
| 197 | 0.92 |
| 198 | 0.61 |
| 199 | 4.55 |
| 200 | 1.23 |
| 201 | 2.23 |
| 202 | 0.62 |
| 203 | 2.14 |
| 204 | 1.99 |

TABLE 36-continued

Cell-Growth Inhibition Test: NCI-H1417 Cells

| Ex. No. | IC50 (nM) |
| --- | --- |
| 205 | 6.25 |
| 206 | 0.95 |
| 209 | 0.18 |
| 210 | 1.27 |
| 211 | 0.79 |
| 213 | 0.57 |
| 214 | 0.47 |
| 215 | 2.67 |
| 216 | 4.40 |
| 217 | 1.10 |
| 218 | 0.21 |
| 219 | 1.11 |
| 220 | 1.03 |
| 221 | 0.64 |
| 222 | 41.8 |
| 225 | 1.99 |
| 226 | 5.36 |
| 227 | 26.5 |

TABLE 37

Cell-Growth Inhibition Test: NCI-H1417 Cells

| Ex. No. | IC50 (nM) |
| --- | --- |
| 228 | 0.30 |
| 229 | 1.30 |
| 230 | 16.4 |
| 231 | 7.11 |
| 232 | 1.55 |
| 233 | 36.5 |
| 234 | 14.8 |
| 235 | 6.99 |
| 236 | 11.0 |
| 237 | 6.63 |
| 238 | 10.8 |
| 239 | 3.8 |
| 240 | 2.55 |
| 241 | 2.89 |
| 246 | 0.81 |
| 247 | 1.4 |
| 248 | 6.06 |
| 249 | 16.1 |
| 250 | 1.2 |
| 251 | 2.7 |
| 252 | 0.5 |
| 253 | 1.47 |
| 254 | 0.18 |
| 255 | 1.52 |
| 256 | 0.94 |
| 257 | 0.12 |
| 258 | 0.65 |
| 259 | 0.46 |
| 260 | 0.13 |
| 261 | 1.30 |
| 262 | 0.70 |
| 263 | 0.38 |
| 264 | 0.30 |
| 265 | 4.40 |
| 266 | 1.85 |
| 267 | 0.86 |
| 268 | 0.30 |
| 269 | 0.27 |
| 270 | 0.18 |
| 271 | 1.42 |
| 272 | 0.81 |
| 273 | 0.19 |
| 274 | 1.25 |
| 275 | 0.59 |
| 276 | 0.50 |
| 277 | 0.53 |
| 278 | 2.68 |
| 279 | 0.90 |

TABLE 37-continued

Cell-Growth Inhibition Test: NCI-H1417 Cells

| Ex. No. | IC50 (nM) |
| --- | --- |
| 280 | 9.71 |
| 281 | 8.50 |
| Comp. Ex. 1 | >3000 |
| Comp. Ex. 2 | >3000 |
| Comp. Ex. 3 | >3000 |
| Comp. Ex. 4 | >3000 |
| Comp. Ex. 5 | >3000 |
| Comp. Ex. 6 | >3000 |
| Comp. Ex. 7 | 1962 |

TABLE 38

Cell-Growth Inhibition Test: NCI-H146 Cells

| Ex. No. | IC50 (nM) |
| --- | --- |
| 18 | 8.13 |
| 22 | 15.0 |
| 23 | 9.33 |
| 24 | 4.04 |
| 37 | 10.1 |
| 41 | 9.76 |
| 123 | 1.39 |
| 146 | 3.15 |
| 161 | 1.09 |
| 166 | 2.37 |
| 171 | 0.19 |
| 172 | 0.52 |
| 175 | 0.16 |
| 176 | 0.27 |
| 177 | 0.11 |
| 178 | 1.22 |
| 179 | 1.05 |
| 180 | 0.94 |
| 181 | 2.93 |
| 182 | 13.2 |
| 183 | 0.25 |
| 184 | 2.51 |
| 185 | 1.32 |
| 186 | 3.21 |
| 187 | 1.06 |
| 188 | 1.58 |
| 189 | 0.33 |
| 190 | 1.17 |
| 191 | 3.84 |
| 192 | 0.83 |
| 193 | 5.33 |
| 194 | 11.3 |
| 195 | 1.26 |
| 196 | 0.82 |
| 197 | 1.62 |
| 198 | 1.10 |
| 199 | 5.45 |
| 200 | 2.31 |
| 201 | 3.25 |
| 202 | 0.73 |
| 203 | 4.73 |
| 205 | 15.1 |
| 206 | 1.09 |
| 209 | 0.22 |
| 210 | 4.26 |
| 211 | 1.40 |
| 213 | 0.87 |
| 214 | 2.58 |
| 215 | 6.99 |
| 216 | 5.02 |
| 217 | 1.32 |
| 218 | 0.33 |
| 219 | 1.45 |
| 220 | 1.81 |
| 221 | 0.94 |
| 225 | 5.47 |
| 226 | 10.1 |

TABLE 38-continued

Cell-Growth Inhibition Test: NCI-H146 Cells

| Ex. No. | IC50 (nM) |
|---|---|
| 228 | 0.51 |
| 229 | 1.26 |
| 231 | 16.7 |
| 233 | 41.4 |
| 234 | 19.1 |
| 235 | 8.12 |
| 236 | 28.5 |
| 237 | 5.14 |
| 238 | 17.7 |
| 239 | 5.39 |
| 240 | 4.81 |
| 241 | 2.89 |
| 246 | 1.32 |
| 247 | 3.84 |
| 248 | 10.3 |
| 249 | 24.7 |
| 250 | 9.30 |
| 251 | 13.2 |
| 252 | 1.48 |
| 253 | 7.59 |
| 254 | 0.36 |
| 255 | 4.41 |
| 256 | 2.54 |
| 257 | 0.39 |
| 258 | 1.83 |
| 259 | 2.08 |
| 260 | 0.48 |
| 261 | 3.35 |
| 262 | 3.1 |
| 263 | 0.62 |
| 264 | 0.96 |
| 265 | 24.6 |
| 266 | 17.5 |
| 267 | 3.14 |
| 268 | 0.94 |
| 269 | 0.53 |
| 270 | 0.37 |
| 271 | 3.08 |
| 272 | 3.17 |
| 273 | 0.63 |
| 274 | 2.23 |
| 275 | 1.78 |
| 276 | 0.89 |
| 277 | 1.81 |
| 278 | 6.18 |
| 279 | 3.36 |
| 280 | 16.8 |
| 281 | 32.3 |

The results of this test revealed that the compound of the present invention exhibits in vitro cell growth inhibitory effects, and that the compound of the present invention not only inhibits the activity of recombinant human LSD1 protein but also inhibits cancer cell growth, suggesting that the compound of the present invention is useful as an antitumor agent.

Test Example 3: Antitumor Effect Test Using NCI-H146 Cells (Human Small-Cell Lung Cancer Cell Lines)

NCI-H146 cells, $3.5 \times 10^6$ cells (100 μL), were subcutaneously implanted into BALB/cAJcl-nu/nu mice, and mice with a tumor volume within a range of 100 to 300 mm³ were divided into groups so that the groups had a uniform average tumor volume. To 5 mice in each group, a vehicle (0.5% hydroxymethylpropylcellulose containing 0.1 N HCL) or each Example compound was orally administered. The administration was performed once a day for 21 consecutive days (Example compound 41) or 28 consecutive days (Example compounds 37, 161, 166, 175, 176, and 177). The major axis and the minor axis of each tumor were measured twice a week with an electric caliper to calculate the tumor volume (TV). According to the tumor volumes thus obtained, a relative tumor volume (RTV) and a relative tumor volume change (T/C (%)) were calculated. The TV, RTV, and T/C (%) were calculated using the following equations.

Tumor volume TV (mm³)=(major axis, mm)×(minor axis, mm)×(minor axis, mm)/2

Relative tumor volume RTV=TV/(TV on the grouping day) T/C (%)=(average RTV of administration group)/(average RTV of vehicle administration group)×100.

The table below shows the results.

TABLE 39

| Example compound No. | Dose (mg/kg) | T/C (%) |
|---|---|---|
| 37 | 50 | 22 |
| 41 | 25 | 19 |
| 161 | 40 | 14 |
| 166 | 20 | 19 |
| 175 | 2 | 41 |
| 176 | 20 | 27 |
| 177 | 10 | 22 |

The final measurement day was the day following the final administration day. The compound of the present invention showed an antitumor effect on the above models for efficacy evaluation, and the percentage of body weight reduction on the final measurement day was less than 20% of the body weight before administration (day 0).

The results revealed that the compound of the present invention or a salt thereof exhibits excellent LSD1 inhibitory activity, shows a cancer cell growth inhibitory effect, has low toxicity, and is orally administrable. Therefore, the compound of the present invention or a salt thereof is useful as an agent for preventing and/or treating cancer.

The invention claimed is:

1. A compound represented by Formula (I) or a salt thereof:

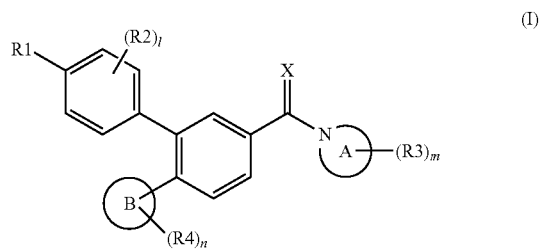

wherein
ring A represents a monocyclic, bridged cyclic, or spirocyclic 4- to 14-membered nitrogen-containing saturated heterocyclic group having 1 to 3 nitrogen atoms, 0 to 1 sulfur atoms, and 0 to 2 oxygen atoms as heteroatoms,
ring B represents monocyclic or bicyclic 5- to 14-membered unsaturated hydrocarbon or a monocyclic or bicyclic 5- to 14-membered unsaturated heterocyclic group that may be substituted with oxo, that has 0 to 4 nitrogen atoms, 0 to 2 sulfur atoms, and 0 to 3 oxygen atoms as heteroatoms, and that has at least one of nitrogen, sulfur, and oxygen, and X represents O or S,
R1 represents nitro or cyano,
R2 represents halogen,
R3 represents amino, mono- or di(C1-C6 alkyl)amino, (C3-C7 cycloalkyl)amino, or C1-C6 alkyl,
R4 is selected from the group consisting of halogen, nitro, cyano, carboxy, substituted or unsubstituted C1-C8 alkyl, substituted or unsubstituted C2-C6 alkenyl, substituted or unsubstituted C1-C6 alkoxy, substituted or unsubstituted C3-C7 cycloalkyl, mono- or di(C1-C6 alkyl)amino, and substituted or unsubstituted carbamoyl, wherein when two or more R4 are present they may be identical or different,
wherein when R4 is selected from the group consisting of substituted C1-C8 alkyl, substituted C2-C6 alkenyl, substituted C1-C6 alkoxy, substituted C3-C7 cycloalkyl, and substituted carbamoyl, the substituent is selected from the group consisting of halogen, carboxy, C1-C6 alkoxy, hydroxy, C1-C6 alkyl that is unsubstituted or substituted with hydroxy, monocyclic 5- to 10-membered unsaturated hydrocarbon, carbamoyl that is unsubstituted or substituted with C1-C6 alkyl or monocyclic 5- to 10-membered unsaturated hydrocarbon, (C2-C7 acyl)oxy, amino that is unsubstituted or substituted with C1-C6 alkyl or C2-C7 acyl, C3-C7 cycloalkyl that is unsubstituted or substituted with hydroxy, and (C1-C6 alkoxy)(C1-C6 alkyl), wherein when two or more of the substituents are present, the substituents may be identical or different,
l is an integer of 0 to 2,
m is an integer of 0 to 2, and
n is an integer of 0 to 5,
wherein when l is 2, two R2s may be identical or different, when m is 2, two R3s may be identical or different, and when n is 2 to 5, two to five R4s may be identical or different.

2. The compound or a salt thereof according to claim 1, which satisfies the following conditions in Formula (I):
ring A represents pyrrolidinyl, piperidinyl, piperazinyl, azepanyl, diazepanyl,

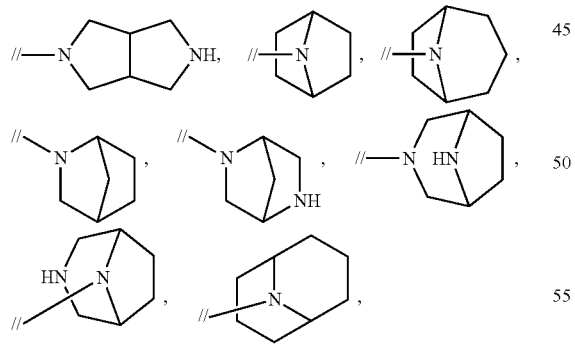

2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[4.5]decanyl, or 9-oxa-diazaspiro[3.5]nonanyl, and
R3 represents amino, methylamino, ethylamino, isopropylamino, dimethylamino, cyclobutylamino, or methyl, wherein when two or more R3s are present, R3s may be identical or different.

3. The compound or a salt thereof according to claim 1, which satisfies the following conditions in Formula (I):
R4 represents halogen, nitro, cyano, carboxy, C1-C8 alkyl that may be substituted with halogen, amino, hydroxyl, carboxy, carbamoyl, (C1-C6 alkyl)carbamoyl, (C1-C6 alkyl)carbonylamino, C1-C6 alkoxy, (C1-C6 alkyl)carbonyl, C3-C7 cycloalkyl, hydroxyl(C3-C7 cycloalkyl), or (C1-C6 alkyl)carbonyloxy, C2-C6 alkenyl, C1-C6 alkoxy that may be substituted with hydroxyl or monocyclic 5- to 10-membered unsaturated hydrocarbon, C3-C7 cycloalkyl that may be substituted with hydroxyl, hydroxyl(C1-C4 alkyl), (C1-C4 alkoxy)(C1-C4 alkyl), hydroxyl(C3-C7 cycloalkyl), or (C6-C14 aromatic hydrocarbon)-substituted carbamoyl, mono- or di(C1-C6 alkyl)amino, or carbamoyl that may be substituted with C1-C6 alkyl, wherein when two or more R4s are present, R4s may be identical or different.

4. The compound represented by Formula (I) or a salt thereof according to claim 1,
wherein
ring A represents pyrrolidinyl, piperidinyl, piperazinyl, azepanyl, diazepanyl,

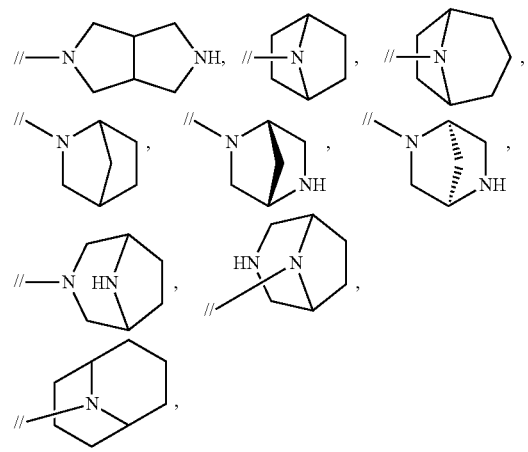

2,7-diazaspiro[3.4]octanyl, 3,7-diazaspiro[3.4]octanyl, 2,7-diazaspiro[3.5]nonanyl, 2,8-diazaspiro[3.5]nonanyl, 3,7-diazaspiro[3.5]nonanyl, 3,8-diazaspiro[4.4]nonanyl, 3,8-diazaspiro[4.5]decanyl, or 9-oxa-diazaspiro[3.5]nonanyl, ring B represents phenyl, naphthyl, pyridyl, pyrazolopyridyl, pyrazolopyrimidinyl, indolyl, indolinyl, 2-oxo-indolinyl, indazolyl, benzoimidazolyl, benzoisoxazolyl, benzothiazolyl, benzotriazolyl, imidazopyridinyl, quinolinyl, isoquinolinyl, quinoxalinyl, quinazolinyl, phthalazinyl, 2-oxo-2,3-dihydrobenzo[d]oxazolyl, 1,3-dihydroisobenzofuranyl, dihydrobenzooxazinyl, benzodioxolyl, dihydrobenzodioxynyl, or 2-oxo-2,3-dihydrobenzo[d]thiazolyl,
X represents O or S,
R1 represents nitro or cyano,
R2 represents fluorine, and is present at the ortho position relative to R1 on the phenyl,
R3 represents amino, methylamino, ethylamino, isopropylamino, dimethylamino, cyclobutylamino, or methyl, wherein when two or more R3s are present, R3s may be identical or different, and
R4 represents fluorine, chlorine, bromine, iodine, nitro, cyano, carboxy, methyl, ethyl, n-propyl, isopropyl, tert-butyl, difluoromethyl, trifluoromethyl, fluoroethyl, aminoethyl, hydroxymethyl, hydroxyethyl, hydroxypropyl, hydroxydimethylethyl, hydroxymethylpropyl, hydroxymethylbutyl, hydroxyethylbutyl, carboxymethyl, carbamoylmethyl, methylcarbamoylmethyl, di methylcarbamoylmethyl, acetylaminoethyl, methoxyethyl, hydroxycyclopropylmethyl, hydroxycyclopropylethyl, hydroxycyclobutylmethyl, methylcarbonyloxyethyl, isobutenyl, methoxy, hydroxypropoxy, cyclopropyl, hydroxymethyl cyclopropyl, methoxymethyl cyclopropyl, hydroxycyclopropyl cyclopropyl, phenylcarbamoyl cyclopropyl, benzyloxy, dimethylamino, carbamoyl, methylcarbamoyl, or dimethylcarbamoyl, wherein when two or more R4s are present, R4s may be identical or different, and n is an integer of 0 to 3, wherein when n is 2 to 3, two to three R4s may be identical or different.

5. A compound selected from the group consisting of compounds (1) (24) (1) 4-[5-[(3-exo)-3-amino-8-azabicyclo [3.2.1]octane-8-carbonyl]-2-[2-fluoro-4-(2-hydroxy-2-methyl-propyl)phenyl]phenyl]-2-fluoro-benzonitrile,
    (2) 4-[5-[(3S)-3-aminopyrrolidine-1-carbonyl]-2-[2-fluoro-4-(2-hydroxy-2-methyl-propyl)phenyl]phenyl]-2-fluoro-benzonitrile,
    (3) 4-[5-[(3-endo)-3-amino-8-azabicyclo[3.2.1]octane-8-carbonyl]-2-[2-fluoro-4-(2-hydroxy-2-methyl-propyl) phenyl]phenyl]-2-fluoro-benzonitrile,
    (4) (S)-5'-(3-aminopyrrolidine-1-carbonyl)-3-fluoro-2'-(6-fluoro-1-(2-hydroxy-2-methylpropyl)-1H-indol-5-yl)-[1,1'-biphenyl]-4-carbonitrile,
    (5) 5'-((3-endo)-3-amino-8-azabicyclo[3.2.1]octane-8-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile,
    (6) 5'-((1S,2S,4R)-rel-2-amino-7-azabicyclo[2.2.1]heptane-7-carbonyl)-2",3-difluoro-4"-(2-hydroxy-2-methylpropyl)-[1,1':2',1"-terphenyl]-4-carbonitrile-isomer-B,
    (7) 5'-((1S,2S,4R)-rel-2-amino-7-azabicyclo[2.2.1]heptane-7-carbonyl)-2'-(6,7-difluoro-1-methyl-1H-benzo [d][1,2,3]triazol-5-yl)-3-fluoro-[1,1'-biphenyl]-4-carbonitrile-isomer-B,
    (8) 5'-((1S,2S,4R)-rel-2-amino-7-azabicyclo[2.2.1]heptane-7-carbonyl)-3-fluoro-2'-(6-fluoro-1-(2-hydroxy-2-methylpropyl)-1H-indazol-5-yl)-[1,1'-biphenyl]-4-carbonitrile-isomer-B,
    (9) 5'-((1S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile-isomer-B,
    (10) 5'-((1 S,2S,4R)-rel-2-amino-7-azabicyclo[2.2.1]heptane-7-carbonyl)-2'-(6,7-difluoro-1-(2-hydroxy-2-methylpropyl)-1H-benzo[d][1,2,3]triazol-5-yl)-3-fluoro-[1,1'-biphenyl]-4-carbonitrile,
    (11) 5'-((1S,2S,4R)-rel-2-amino-7-azabicyclo[2.2.1]heptane-7-carbonyl)-2'-(7-chloro-6-fluoro-1-(2-hydroxy-2-methylpropyl)-1H-benzo[d][1,2,3]triazol-5-yl)-3-fluoro-[1,1'-biphenyl]-4-carbonitrile-isomer-X,
    (12) 5'-((1S,2S,4R)-rel-2-amino-7-azabicyclo[2.2.1]heptane-7-carbonyl)-2'-(7-chloro-6-fluoro-1-(2-hydroxy-2-methylpropyl)-1H-benzo[d][1,2,3]triazol-5-yl)-3-fluoro-[1,1'-biphenyl]-4-carbonitrile,
    (13) 5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1, 1'-biphenyl]-4-carbonitrile-isomer-X,
    (14) 5'-((1S,2S,4R)-rel-2-amino-7-azabicyclo[2.2.1]heptane-7-carbonyl)-2'-(1-(2-ethyl-2-hydroxybutyl)-6,7-difluoro-1H-benzo[d][1,2,3]triazol-5-yl)-3-fluoro-[1, 1'-biphenyl]-4-carbonitrile,
    (15) (S)-5'-(3-aminopyrrolidine-1-carbonyl)-3-fluoro-2'-(5-fluoro-3-(2-hydroxy-2-methylpropyl)benzo[d]isoxazol-6-yl)-[1,1'-biphenyl]-4-carbonitrile,
    (16) 5'-((1S,2S,4R)-rel-2-amino-7-azabicyclo[2.2.1]heptane-7-carbonyl)-2'-(7-(difluoromethyl)-6-fluoro-1-(2-hydroxy-2-methylpropyl)-1H-benzo[d][1,2,3]triazol-5-yl)-3-fluoro-[1,1'-biphenyl]-4-carbonitrile-isomer-X,
    (17) 5-(5-((1S,2S,4R)-rel-2-amino-7-azabicyclo[2.2.1] heptane-7-carbonyl)-4'-cyano-3'-fluoro-[1,1'-biphenyl]-2-yl)-6-fluoro-1-(2-hydroxy-2-methylpropyl)-1H-benzo[d][1,2,3]triazole-7-carbonitrile-isomer-X,
    (18) 5'-((1S,2S,4R)-rel-2-amino-7-azabicyclo[2.2.1]heptane-7-carbonyl)-2'-(7-(difluoromethyl)-6-fluoro-1-(2-hydroxy-2-methylpropyl)-1H-benzo[d][1,2,3]triazol-5-yl)-3-fluoro-[1,1'-biphenyl]-4-carbonitrile,
    (19) 5'-((3-endo)-3-amino-8-azabicyclo[3.2.1]octane-8-carbonyl)-2'-(7-chloro-6-fluoro-1-((1-hydroxycyclobutyl)methyl)-1H-benzo[d][1,2,3]triazol-5-yl)-3-fluoro-[1,1'-biphenyl]-4-carbonitrile,
    (20) 5'-((3-endo)-3-amino-8-azabicyclo[3.2.1]octane-8-carbonyl)-2'-(7-(difluoromethyl)-6-fluoro-1-((1-hydroxycyclobutyl)methyl)-1H-benzo[d][1,2,3]triazol-5-yl)-3-fluoro-[1,1'-biphenyl]-4-carbonitrile,
    (21) 5-(5-((1S,2S,4R)-rel-2-amino-7-azabicyclo[2.2.1] heptane-7-carbonyl)-4'-cyano-3'-fluoro-[1,1'-biphenyl]-2-yl)-6-fluoro-1-((1-hydroxycyclobutyl)methyl)-1H-benzo[d][1,2,3]triazole-7-carbonitrile-isomer-X,
    (22) 5-(5-((1S,2S,4R)-rel-2-amino-7-azabicyclo[2.2.1] heptane-7-carbonyl)-4'-cyano-3'-fluoro-[1,1'-biphenyl]-2-yl)-6-fluoro-1-((1-hydroxycyclobutyl)methyl)-1H-benzo[d][1,2,3]triazole-7-carbonitrile,
    (23) 5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile-isomer-X,
    (24) 5'-((1S,2S,4R)-rel-2-amino-7-azabicyclo[2.2.1]heptane-7-carbonyl)-2'-(7-bromo-6-fluoro-1-(2-hydroxy-2-methylpropyl)-1H-benzo[d][1,2,3]triazol-5-yl)-3-fluoro-[1,1'-biphenyl]-4-carbonitrile, and
salts thereof.

6. An LSD1 inhibitor comprising the compound or a salt thereof according to claim 1, as an active ingredient.

7. A pharmaceutical composition comprising the compound or a salt thereof according to claim 1.

8. The pharmaceutical composition according to claim 7, in combination with a carrier suitable for oral administration.

9. An antitumor agent comprising the compound or a salt thereof according to claim 1, as an active ingredient.

10. A method for treating a cancer patient, the method comprising administering an effective amount of the compound or a salt thereof according to claim 1 to the patient.

* * * * *